US011746129B2

(12) United States Patent
Hart et al.

(10) Patent No.: US 11,746,129 B2
(45) **Date of Patent: *Sep. 5, 2023**

(54) INSECTICIDAL PROTEINS

(71) Applicant: Syngenta Participations AG, Basel (CH)

(72) Inventors: Hope Hart, Durham, NC (US); Jeng Shong Chen, Durham, NC (US); Cheryl M. DeFontes, Riehen (CH)

(73) Assignee: Syngenta Participations AG, Basel (CH)

( * ) Notice: Subject to any disclaimer, the term of this patent is extended or adjusted under 35 U.S.C. 154(b) by 135 days.

This patent is subject to a terminal disclaimer.

(21) Appl. No.: 17/166,389

(22) Filed: Feb. 3, 2021

(65) Prior Publication Data

US 2021/0155661 A1 May 27, 2021

Related U.S. Application Data

(60) Continuation of application No. 16/212,892, filed on Dec. 7, 2018, now abandoned, which is a continuation of application No. 15/148,399, filed on May 6, 2016, now abandoned, which is a division of application No. 13/623,921, filed on Sep. 21, 2012, now Pat. No. 9,522,937, which is a division of application No. 12/529,246, filed as application No. PCT/US2008/058182 on Mar. 26, 2008, now Pat. No. 8,309,516.

(60) Provisional application No. 60/920,493, filed on Mar. 28, 2007.

(51) Int. Cl.

| | |
|---|---|
| *C07K 14/32* | (2006.01) |
| *C12N 15/82* | (2006.01) |
| *C07K 14/325* | (2006.01) |
| *A01N 63/50* | (2020.01) |

(52) U.S. Cl.
CPC ............ *C07K 14/325* (2013.01); *A01N 63/50* (2020.01); *C12N 15/8286* (2013.01); *C07K 2319/55* (2013.01); *Y02A 40/146* (2018.01)

(58) Field of Classification Search
CPC .................................................. C12N 15/8286
See application file for complete search history.

(56) References Cited

U.S. PATENT DOCUMENTS

| | | | | |
|---|---|---|---|---|
| 5,424,409 | A | 6/1995 | Ely et al. | |
| 5,659,123 | A | 8/1997 | Van Rie et al. | |
| 5,763,241 | A | 6/1998 | Fischhoff et al. | |
| 6,015,891 | A | 1/2000 | Adang et al. | |
| 6,063,597 | A | 5/2000 | English et al. | |
| 6,204,246 | B1 | 3/2001 | Bosch et al. | |
| 6,489,155 | B1 | 12/2002 | Takayama et al. | |
| 6,500,617 | B1 | 12/2002 | Stemmer et al. | |
| 6,720,488 | B2 | 4/2004 | Koziel et al. | |
| 7,030,295 | B2 | 4/2006 | Chen et al. | |
| 7,230,167 | B2 | 10/2007 | Chen et al. | |
| 8,309,516 | B2 * | 11/2012 | Hart .................. | C12N 15/8286 514/4.5 |
| 9,522,937 | B2 * | 12/2016 | Hart .................. | C12N 15/8286 |
| 2003/0120054 | A1 | 6/2003 | Chen et al. | |
| 2005/0216970 | A1 | 9/2005 | Steiner et al. | |
| 2005/0283857 | A1 | 12/2005 | Adang et al. | |

FOREIGN PATENT DOCUMENTS

| | | | |
|---|---|---|---|
| WO | 0213818 | A1 | 3/1987 |
| WO | 09117254 | A2 | 11/1991 |
| WO | 98/22595 | A1 | 5/1998 |
| WO | 1999/00407 | A2 | 1/1999 |
| WO | 1999/11797 | | 3/1999 |
| WO | 1999/31248 | A1 | 6/1999 |
| WO | 2001/14562 | A | 3/2001 |
| WO | 02/15701 | A2 | 2/2002 |
| WO | 2002/15701 | A2 | 2/2002 |
| WO | 03/018810 | A2 | 3/2003 |
| WO | 2003/0046726 | A1 | 6/2003 |

OTHER PUBLICATIONS

Spencer et al Plant Molecular Biology vol. 18, pp. 201-210 (Year: 1992).*
EPO Supplemental Search Report for EP Application No. 08732817.5 dated Mar. 25, 2010.

Shadenkov et al., “Construction of gene for the hybrid protein based on Bacillus thuringiensis delta-endotoxin CRYIA(a) and CRY IIIA sequences and expression of its derivatives in *E. coli*,” Molekulyarnaya Biologiya (Moscow), 1993, 27(4): 952-959; (Russian language).

Shadenkov et al., Construction of a hybride gene from CRYIIIA and CryIA(a) delta-Endotoxin genese of Bacillus thurgiensis and expression of its derivatives in *Escherichia coli* cells; 1993, 27(4): 586-591.
International Search Report dated Aug. 1, 2008 in International Patent Application No. PCT/US08/58182.

(Continued)

*Primary Examiner* — David H Kruse
(74) *Attorney, Agent, or Firm* — Katherine Seguin

(57) ABSTRACT

Compositions and methods for controlling plant pests are disclosed. In particular, novel engineered hybrid insecticidal proteins having toxicity to at least European corn borer are provided. By fusing unique combinations of complete or partial variable regions and conserved blocks of at least two different *Bacillus thuringiensis* (Bt) Cry proteins or a modified Cry proteins a hybrid insecticidal protein having activity against at least European corn borer is designed. Nucleic acid molecules encoding the novel hybrid proteins are also provided. Methods of making the hybrid proteins and methods of using the hybrid proteins and nucleic acids encoding the hybrid proteins of the invention, for example in transgenic plants to confer protection from insect damage are also disclosed.

20 Claims, 16 Drawing Sheets

Specification includes a Sequence Listing.

(56) References Cited

OTHER PUBLICATIONS

Hofte, Herman et al., "insceticidal Crystal Proteins fo Bacillus Thuringiensis", Microbiological Reviews, vol. 53, No. 2, Jun. 1989, pp. 242-255.
Carroll et al., "Proteolytic processing of a coleopteran-specific o-endotoxin produced by bacillus thuringiensis var tenebrionis", Biochemical Journal, vol. 26, 1989, pp. 99-105.
Carroll et al., Intramolecular protecolytic cleavage of bacuillus thuringiensis Cry3A o-endotoxin may facilitate its coleopteran toxicity, Journal of Invertebrate pathology, vol. 70, 1997, pp. 41-49.
Chen et al., Site-directed mutations in a highly conserved region of bacillus thuringiensis o-endotoxin affect inhibition of short circuit current across bombyx mori midguts, Proc. Natl. Acad. Sci., vol. 90, pp. 9041-9045, 1993.
Gazit et al., "The structure and organizaiton within the membrane of the helices composing the pore-forming domain of bacillus thuringiensis o-endotoxin are consistent with an "umbrella-like" structure of the pore", Proceedings of the National Academy of Sciences, USA, vol. 95, 1998, pp. 12289-12294.
Gazit et al., "The assembly and organization of the a5-a7 helices from the pore-forming domain of bacillus thuringiensis o-endotoxin", The Journal of Biological Chemistry, vol. 270, No. 6, 1995, pp. 2571-2578.
Gazit et al., "Structural and functional chracterization of the a5 segment of bacillus thuringiensis o-endotoxin", Biochemistry, 1993, vol. 32, pp. 3429-3436.
Ge et al., "Functional domains of bacillus thuringiensis insecticidal crystal proteins", The Journal of Biological Chemistry, vol. 266, No. 27, pp. 17954-17958, 1991.
Ge et al., "Location of the bombyx mori specificity domain of a bacillus thuringiensis o-endotoxin protein", Proc. Natl. Acad. Sci., vol. 86, pp. 4037-4047, 1989.
Gillikin et al., "Partial charaterization fo digestive tract proteinases from western corn rootworm larvae, diabrotica virgifera", Archives of Insect Biochemistry and Physiology, vol. 19, 1992, pp. 285-298.
Li et al., "C rystal structure of insecticidal o-endotoxin from bacillus thuringiensis at 2.5 a resolution", Nature, vol. 353, 1991, pp. 815-821.
Martinez-Ramirez et al., "Proteolytic processing of bacillus thuringiensis CryIIIA toxin and specific binding to brush-border membrane vesicles of *leptinotarsa decemlineata* (Colorado Potato Beetle)", Pesticide Biochemistry and Physiology, vol. 54, 1996, pp. 115-122, Article 0015.
McPherson et al, "Characterization of the Cleopteran-Specific Protein Gene of *Bacillus thuringiensis* Var. *tenebrionis*" Bio/ Technology, vol. 6 (1988), pp. 61-66.

Oppert B., "Protease Interactions With Bacillus thuringiensis Insecticidal Toxins", Archives of Insect Biochemistry and Physiology, vol. 42, pp. 1-12, 1999.
Sekar et al., "Molecular cloning and characterization of the insecticidal crystal protein gene of *Bacillus thuringiensis* var. *tenebrionis*" Proceedings of the National Academy of Sciences, USA, vol. 84 (Oct. 1987), pp. 7036-7040.
Wu S.J., Dean, D.H., "Functional Significance of Loops in The Receptor Binding Domain of Bacillus thuringiensis CryIIIA d-Endotoxin Journal of Molecular Biology", vol. 255 (1996), pp. 628-640.
Wu et al., Enhanced toxicity of Bacillus thuringiensis Cry3A d-Endotoxin in coleopterans by mutagenesis in a receptor binding loop:, Federation of European Biochemical Societies Letters, vol. 473 (2000), pp. 227-232.
Sutton et al., "Synthetic cryIIIA gene from Bacillus thuringiensis improved for high expression in plants", Transgenic Research, vol. 1 (1992), pp. 228-236.
Slaney et al.," Mode of Action of Bacillus Thuringiensis Toxin CryIIIA: An Analysis of Toxicity in *Leptinotarsa decemlineata* (Say) and Diabrotica Undecimpunctata Howardi Barber", Insect Biochemistry Molecular Biology, vol. 22, No. 1 (1992), pp. 9-18.
Haider et al., "Specificity of *Bacillus thuringiensis* Var. *colmeri* Insecticidal Delta-Endotoxin in Determined by Differential Proteolytic Processing of the Protoxin by Larval Gut Proteases", Eur. J. Biochem. 156, pp. 531-540, 1986.
Smedley et al., "Mutagenesis of three surface-exposed loops of a Bacillus thuringiensis insecticidal toxin reveals residues important for toxicity, receptor recognition and possibly membrane insertion", Microbiology, vol. 142, pp. 1617-1624, 1996.
Grochulski et al., Bacillus thuringiensis CryA(a) Insecticidal Toxin: Crystal Structure and Channel Formation, J. Mol. Biol., 1995, vol. 254, pp. 447-464.
Garczynski, et al., Identification of Putative Insect Brush Border Membrane-Binding Molecules Specific to Bacillus thuringiensis d-Endotoxin by Protein Blot Analysis, Applied and Enviromental Microbiology, 1991, pp. 2816-2820.
Naimov, S., et al., "Carboxy-Terminal Extension Effects on Crystal Formation and Insecticidal Properties of Colorado Potato Beetle-Active Bacillus thuringiensis d-Endotoxin", Microbiotechnology, 2006.
Naimov, S., et al., "Bacillus thuringiensis Delta-Endotoxin Cry1 Hybrid Proteins with Increased Activity against the Colorado Potato Beetle", Applied and Environmental Microbiology, 2001, pp. 5328-5330.
Chen et al., "The Cry3Aa gene of Bacillus thuringiensis Bt886 encodes a toxin against long-horned beetles", 2005, Applied Microbiology and Biotechnology, vol. 67:351-356.
Park et al., "Effect of specific mutations in helix-alpha 7 of domain I on the stability and crystallization of Cry3A in Bacillus thuringiensis", 2004, Molecular Biotechnology, vol. 27:89-100.

\* cited by examiner

Fig. 1A

Alignment:   Global Protein alignment against reference molecule
Parameters:  Scoring matrix: BLOSUM 62

Reference molecule: Cry3A055, Region 1-598
Number of sequences to align: 19

| Pos | Name | Sequence | Start | End | Length | Matches | %Identity |
|---|---|---|---|---|---|---|---|
| Ref 1 | Cry3A055 | (SEQ ID NO: 70) | 1 | 598 | 598 aa | | |
| 2 | moCry3A | (SEQ ID NO: 68) | 1 | 597 | 597 aa | 594 | 99 |
| 3 | Native Cry3A | (SEQ ID NO: 131) | 1 | 644 | 644 aa | 594 | 92 |
| 4 | 8AF | (SEQ ID NO: 64) | 1 | 640 | 640 aa | 524 | 81 |
| 5 | T7-8AF | (SEQ ID NO: 133) | 1 | 654 | 654 aa | 524 | 80 |
| 6 | 2OL-8A | (SEQ ID NO: 2) | 1 | 668 | 668 aa | 517 | 77 |
| 7 | FR8a | (SEQ ID NO: 4) | 1 | 653 | 653 aa | 518 | 79 |
| 8 | FRCG | (SEQ ID NO: 6) | 1 | 652 | 652 aa | 514 | 78 |
| 9 | FRD3 | (SEQ ID NO: 16) | 1 | 615 | 615 aa | 518 | 84 |
| 10 | FR-cg-dm3 | (SEQ ID NO: 18) | 1 | 614 | 614 aa | 514 | 83 |
| 11 | FR8a-12aa | (SEQ ID NO: 12) | 1 | 641 | 641 aa | 515 | 80 |
| 12 | WR-9mut | (SEQ ID NO: 14) | 1 | 599 | 599 aa | 589 | 98 |
| 13 | DM23A | (SEQ ID NO: 62) | 1 | 653 | 653 aa | 510 | 78 |
| 14 | FR8a-9F | (SEQ ID NO: 8) | 1 | 653 | 653 aa | 524 | 80 |
| 15 | FR-9F-cg-del6 | (SEQ ID NO: 20) | 1 | 646 | 646 aa | 520 | 80 |
| 16 | FR-9F-catg | (SEQ ID NO: 10) | 1 | 652 | 652 aa | 520 | 79 |
| 17 | V4F | (SEQ ID NO: 32) | 1 | 598 | 598 aa | 571 | 95 |
| 18 | 5+V4F | (SEQ ID NO: 34) | 1 | 611 | 611 aa | 565 | 92 |
| 19 | Cry1Ab | (SEQ ID NO: 72) | 1 | 648 | 648 aa | 213 | 31 |

Fig. 1B

```
Cry3A055        1                                                          MTADNNTEALDSSTTKDV
moCry3A         1                                                          MTADNNTEALDSSTTKDV
Cry3A           1  MNPNNRSEHDTIKTTENNEVPTNHVQYPLAETPNPTLEDLNYKEFLRMTADNNTEALDSSTTKDV
8AF             1                                                          MTADNNTEALDSSTTKDV
T7-8AF          1                                                  MASMTGGQQMGRGSMTADNNTEALDSSTTKDV
2OL-8A          1                                        MASMTGGQQMGRGSGSTSNGRQCAGIRPYDGRQQHRGLDSSTTKDV
FR8a            1                                                   MTSNGRQCAGIRPYDGRQQHRGLDSSTTKDV
FRCG            1                                                   MTSNGRQCAGIRPYDGRQQHRGLDSSTTKDV
FRD3            1                                                   MTSNGRQCAGIRPYDGRQQHRGLDSSTTKDV
FR-cg-dm3       1                                                   MTSNGRQCAGIRPYDGRQQHRGLDSSTTKDV
FR8a-12aa       1                                                            MYDGRQQHRGLDSSTTKDV
WR-9mut         1                                                            MYDGRQQHRGLDSSTTKDV
DM23A           1                                                   MTSNGRQCAGIRPYDGRQQHRGLDSSTTKDV
FR8a-9F         1                                                   MTSNGRQCAGIRPMTADNNTEALDSSTTKDV
FR-9F-cg-del6   1                                                        MCAGIRPMTADNNTEALDSSTTKDV
FR-9F-catg      1                                                   MTSNGRQCAGIRPMTADNNTEALDSSTTKDV
V4F             1                                                          MTADNNTEALDSSTTKDV
5*V4F           1                                                   MTSNGRQCAGIRPYDGRQQHRGLDSSTTKDV
Cry1Ab          1                                                        MDNNPNINECIPYNCLSNPEVEV Cry3A055       19 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
moCry3A        19 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
Cry3A          66 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
8AF            19 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
T7-8AF         33 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
2OL-8A         47 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR8a           32 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FRCG           32 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
FRD3           32 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR-cg-dm3 pr   32 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
FR8a-12aa      20 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
WR-9mut        20 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
DM23A          32 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR8a-9F        32 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
FR-9F-cg-del6  26 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
FR-9F-catg     32 -----IQKGISVVGDLLGVVGFPFGGAL--VSFYTNFLNTIWPSEDP--WKAFMEQVEALMDQKIADYAKNKALAELQGLQNNVEDYVSALSSWQKNPVSS-RNPHSQGR
V4F            19 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
5*V4F          32 -----IQKGISVVGDLLGVVGFPFGGAL--VSFYTNFLNTIWPSEDP--WKAFMEQVEALMDQKIADYAKNKALAELQGLQNNVEDYVSALSSWQKNPAAPFRNPHSQGR
Cry1Ab         24 LGGERIETGYTPIDISLSLTQFLLSEFVPGAGFVLGLVDIIWGIFGPSQWDAFLVQIEQLINQRIEEFARNQAISRLEGLSNLYQIYAESFREWEADPT----NPALREE
```

Fig. 1C

```
                              CB1
Cry3A055   120 IRELFSQAESHFRNSMPSFAISG NEVLFLTTYAQAANTHLFLLKDAQIYGEEW GYEKEDIAEFYKRQLKLTQE
moCry3A    119 IRELFSQAESHFRNSMPSFAISG NEVLFLTTYAQAANTHLFLLKDAQIYGEEW GYEKEDIAEFYKRQLKLTQE
Cry3A      166 IRELFSQAESHFRNSMPSFAISG NEVLFLTTYAQAANTHLFLLKDAQIYGEEW GYEKEDIAEFYKRQLKLTQE
8AF        120 IRELFSQAESHFRNSMPSFAISG NEVLFLTTYAQAANTHLFLLKDAQIYGEEW GYEKEDIAEFYKRQLKLTQE
T7-8AF pro 134 IRELFSQAESHFRNSMPSFAISG NEVLFLTTYAQAANTHLFLLKDAQIYGEEW GYEKEDIAEFYKRQLKLTQE
2OL-8A     148 IRELFSQAESHFRNSMPSFAISG NEVLFLTTYAQAANTHLFLLKDAQIYGEEW GYEKEDIAEFYKRQLKLTQE
FR8a       133 IRELFSQAESHFRNSMPSFAISG NEVLFLTTYAQAANTHLFLLKDAQIYGEEW GYEKEDIAEFYKRQLKLTQE
FRCG       132 IRELFSQAESHFRNSMPSFAISG NEVLFLTTYAQAANTHLFLLKDAQIYGEEW GYEKEDIAEFYKRQLKLTQE
FRD3       133 IRELFSQAESHFRNSMPSFAISG NEVLFLTTYAQAANTHLFLLKDAQIYGEEW GYEKEDIAEFYKRQLKLTQE
FR-cg-dm3  132 IRELFSQAESHFRNSMPSFAISG NEVLFLTTYAQAANTHLFLLKDAQIYGEEW GYEKEDIAEFYKRQLKLTQE
FR8a-12aa  121 IRELFSQAESHFRNSMPSFAISG NEVLFLTTYAQAANTHLFLLKDAQIYGEEW GYEKEDIAEFYKRQLKLTQE
WR-9mut    133 IRELFSQAESHFRNSMPSFAISG NEVLFLTTYAQAANTHLFLLKDAQIYGEEW GYEKEDIAEFYKRQLKLTQE
DM23A      133 IRELFSQAESHFRNSMPSFAISG NEVLFLTTYAQAANTHLFLLKDAQIYGEEW GYEKEDIAEFYKRQLKLTQE
FR8a-9F    126 IRELFSQAESHFRNSMPSFAISG NEVLFLTTYAQAANTHLFLLKDAQIYGEEW GYEKEDIAEFYKRQLKLTQE
FR-9F-cg-del6 132 IRELFSQAESHFRNSMPSFAISG NEVLFLTTYAQAANTHLFLLKDAQIYGEEW GYEKEDIAEFYKRQLKLTQE
FR-9F-catg 133 IRELFSQAESHFRNSMPSFAISG NEVLFLTTYAQAANTHLFLLKDAQIYGEEW GYEKEDIAEFYKROLKLTQE
V

Fig. 1D

```
Cry3A055      339 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
moCry3A       338 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
Cry3A         385 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
8AF           339 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
T7-8AF        353 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
2OL-8A        367 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR8a          352 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FRCG          351 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FRD3          352 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR-cg-dm3     351 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR8a-12aa     340 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
WR-9mut       340 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
DM23A         352 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR8a-9F       352 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR-9F-cg-del  345 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
FR-9F-catg    351 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
V4F           339 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
5*V4F         352 -SSEPVQNLEFN-GEKVYRAVANTNLAVWPSAVYSGVTKVEFSQYNDQTDEASTQTYDSKRNVGAVSW------DSIDQLPPETTDEPLEKGYSHQLNYVMCFLMQGSRG
Cry1Ab        342 GNAAPQQRIVAQLGQGVYRTLSST---LYRRPFNIGINNQQLSVL-DGTEFA----YGTSSNLPSAVYRKSGTVDSLDEIPPQNNNVPPRQGFSHRLSHVSMFRSGFSNS <----  Domain II | Domain III  ---->   CB3                                      CB4
Cry3A055      441 TI-----PV LTWTHKSVDEFNMIDSKKITQLPLVKAYKLQSGASVVAGPRFTGGDII QCTENGSAATIYVTPDVSYSQ KYRARIHYAS TSQITFTLSLDGAPFNQYYFDK
moCry3A       440 TI-----PV LTWTHKSVDEFNMIDSKKITQLPLVKAYKLQSGASVVAGPRFTGGDII QCTENGSAATIYVTPDVSYSQ KYRARIHYAS TSQITFTLSLDGAPFNQYYFDK
Cry3A         487 TI-----PV LTWTHKSVDEFNMIDSKKITQLPLVKAYKLQSGASVVAGPRFTGGDII QCTENGSAATIYVTPDVSYSQ KYRARIHYAS TSQITFTLSLDGAPFNQYYFDK
8AF           441 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
T7-8AF        455 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
2OL-8A        469 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FR8a          454 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FRCG          453 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FRD3          454 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FR-cg-dm3     453 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FR8a-12aa     442 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
WR-9mut       442 TI-----PV LTWTHKSVDEFNMIDSKKITQLPLVKAYKLQSGASVVAGPRFTGGDII QCTENGSAATIYVTPDVSYSQ KYRARIHYAS TSQITFTLSLDGAPFNQYYFDK
DM23A         454 TI-----PV LTWTHKSAEENNIIPSSQITQIPLTKSTNLGSGTSVVKGPGFTGGDIL RRTSPGQISTLRVNITAPLSQ RYRVRIRYAS TTNLQFHTSIDGRPINQGNFSA
FR8a-9F       454 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FR-9F-cg-del6 447 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
FR-9F-catg    453 TI-----PV LTWTHKSVDEFNMIDSKKITQLPLTKSTNLGSGTSVVKGPGFTGGDIL RRTSPGQISTLRVNITAPLSQ RYRVRIRYAS TTNLQFHTSIDGRPINQGNFSA
V4F           441 TI-----PV LTWTHKSVDEFNMIDSKKITQLALTKSTNLGSGTSVVKGPGFTGGDIL RRTSPGQISTLRVNITAPLSQ RYRVRIHYAS TSQITFTLSLDGAPFNQYYFDK
5*V4F         454 TI-----PV LTWTHKSVDEFNMIDSKKITQLALTKSTNLGSGTSVVKGPGFTGGDIL RRTSPGQISTLRVNITAPLSQ RYRVRIHYAS TSQITFTLSLDGAPFNQYYFDK
Cry1Ab        444 SVSIIRAPM FSWIHRSAEENNIIPSSQITQIPLTKSTNLGSGTSVVKGPGFTGGDIL RRTSPGQISTLRVNITAPLSQ RYRVRIRYAS TTNLQFHTSIDGRPINQGNFSA
```

Fig. 1E

```
                                                                           CB5
Cry3A055        546 TINKGDTLTYNSFNLASFSTPFELSGNNLQIGVTG--LSAGDK VYIDKIEFIPVN
moCry3A         545 TINKGDTLTYNSFNLASFSTPFELSGNNLQIGVTG--LSAGDK VYIDKIEFIPVN
Cry3A           592 TINKGDTLTYNSFNLASFSTPFELSGNNLQIGVTG--LSAGDK VYIDKIEFIPVN
8AF             546 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
T7-8AF          560 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
2OL-8A          574 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR8a            559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FRCG            558 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FRD3            559 TMSSGSNLQSGSFRTVGFTTPFNFSNGSSVFTLSAHVFNSGNE VYIDRIEFVPAE VT
FR-cg-dm3       558 TMSSGSNLQSGSFRTVGFTTPFNFSNGSSVFTLSAHVFNSGNE VYIDRIEFVPAE VT
FR8a-12aa       547 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
WR-9mut         547 TINKGDTLTYNSFNLASFSTPFELSGNNLQIGVTG--LSAGDK VYIDKIEFIPVN
DM23A           559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR8a-9F         559 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR-9F-cg-del6   552 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
FR-9F-catg      558 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
V4F             546 TINKGDTLTYNSFNLASFSTPFELSGNNLQIGVTG--LSAGDK VYIDKIEFIPVN
5*V4F           559 TINKGDTLTYNSFNLASFSTPFELSGNNLQIGVTG--LSAGDK VYIDKIEFIPVN
Cry1Ab          554 TMSSGSNLQSGSFRTVGFTTPFNFSNGSSVFTLSAHVFNSGNE VYIDRIEFVPAE VTFEAEYDLERAQKAVNELFTSSNQIGLKTDVTDYHIDQV
```

Fig. 2A

Alignment:   Global Protein alignment against reference molecule
Parameters:  Scoring matrix:  BLOSUM 62

Reference molecule:  8AF Protein, Amino acids 1-640
Number of sequences to align: 18

| Pos | Name | Sequence ID | Start | End | Length | Matches | %Identity |
|---|---|---|---|---|---|---|---|
| Ref 1 | 8AF | SEQ ID NO: 64 | 1 | 640 | 640 aa | | |
| 2 | 8AFdm3T | SEQ ID NO: 155 | 1 | 640 | 640 aa | 634 | 99 |
| 3 | -CatG8AF | SEQ ID NO: 147 | 1 | 639 | 639 aa | 636 | 99 |
| 4 | FR8a-9F | SEQ ID NO: 8 | 1 | 653 | 653 aa | 640 | 98 |
| 5 | FR8a-12 AA | SEQ ID NO: 12 | 1 | 641 | 641 aa | 631 | 98 |
| 6 | FR8a | SEQ ID NO: 4 | 1 | 653 | 653 aa | 634 | 97 |
| 7 | FR-9F-catg | SEQ ID NO: 10 | 1 | 653 | 653 aa | 636 | 97 |
| 8 | cap8AFdm3T | SEQ ID NO: 159 | 1 | 653 | 653 aa | 628 | 96 |
| 9 | FRCG | SEQ ID NO: 16 | 1 | 652 | 652 aa | 630 | 96 |
| 10 | DM23A | SEQ ID NO: 62 | 1 | 653 | 653 aa | 626 | 95 |
| 11 | 2OL-8A | SEQ ID NO: 2 | 1 | 668 | 668 aa | 633 | 94 |
| 12 | 8AFdm3 | SEQ ID NO: 149 | 1 | 602 | 602 aa | 596 | 93 |
| 13 | FR8a +34 | SEQ ID NO: 160 | 1 | 687 | 687 aa | 634 | 92 |
| 14 | FR-12-cg-dm3 | SEQ ID NO: 18 | 1 | 603 | 603 aa | 589 | 91 |
| 15 | 9F-cg-dm3 | SEQ ID NO: 24 | 1 | 614 | 614 aa | 598 | 91 |
| 16 | Cap8AFdm3 | SEQ ID NO: 153 | 1 | 615 | 615 aa | 590 | 90 |
| 17 | 5*V4F | SEQ ID NO: 34 | 1 | 611 | 611 aa | 545 | 83 |
| 18 | V3A | SEQ ID NO: 30 | 1 | 596 | 596 aa | 368 | 56 |

Fig. 2B

| Label | | Sequence |
|---|---|---|
| 8AF | 1 | MTADNNTEALDSSTTKDVIQKGISVVGD |
| 8AFdm3T | 1 | MTADNNTEALDSSTTKDVIQKGISVVGD |
| -CatG8AF | 1 | MTADNNTEALDSSTTKDVIQKGISVVGD |
| FR8a-9F | 1 | MTSNGRQCAGIRPMTADNNTEALDSSTTKDVIQKGISVVGD |
| FR8a-12 AA | 1 | MYDGRQQHRGLDSSTTKDVIQKGISVVGD |
| FR8a | 1 | MTSNGRQCAGIRPYDGRQQHRGLDSSTTKDVIQKGISVVGD |
| FR-9F-catg | 1 | MTSNGRQCAGIRPMTADNNTEALDSSTTKDVIQKGISVVGD |
| cap8AFdm3T | 1 | MTSNGRQCAGIRPYDGRQQHRGLDSSTTKDVIQKGISVVGD |
| FRCG | 1 | MTSNGRQCAGIRPYDGRQQHRGLDSSTTKDVIQKGISVVGD |
| DM23A | 1 | MTSNGRQCAGIRPYDGRQQHRGLDSSTTKDVIQKGISVVGD |
| 2OL-8A | 1 | MTSNGRQCAGIRPYDGRQQHRGLDSSTTKDVIQKGISVVGD |
| 8AFdm3 | 1 | MTADNNTEALDSSTTKDVIQKGISVVGD |
| FR8a +34 | 1 | MASMTGGQQMGRGSGSTSNGRQCAGIRPYDGRQQHRGLDSSTMTSNGRQCAGIRPYDGRQQHRGLDSSTTKDVIQKGISVVGD |
| FR-12-cg-dm3 | 1 | MYDGRQQHRGLDSSTTKDVIQKGISVVGD |
| 9F-cg-dm3 | 1 | MTSNGRQCAGIRPMTADNNTEALDSSTTKDVIQKGISVVGD |
| Cap8AFdm3 | 1 | MTSNGRQCAGIRPYDGRQQHRGLDSSTTKDVIQKGISVVGD |
| 5*V4F | 1 | MTSNGRQCAGIRPYDGRQQHRGLDSSTTKDVIQKGISVVGD |
| V3A | 1 | MKETAAAKERQHMDSPDLGTLVPRGSMADIGSTMTADNNTEALDSSTTKDVIQKGISVVGD |

| Label | | Sequence |
|---|---|---|
| 8AF | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 8AFdm3T | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| -CatG8AF | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a-9F | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a-12 AA | 30 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| FR8a | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR-9F-catg | 42 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| cap8AFdm3T | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FRCG | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| DM23A | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 2OL-8A | 57 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 8AFdm3 | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR8a +34 | 76 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| FR-12-cg-dm3 | 30 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| 9F-cg-dm3 | 42 | LLGVVGFPFGGALVSFYTNFLNTIWPSEDPWKAFMEQVEALMDQKIADYAKNKALAELQGLQNNVEDYVSALSSWQKNPVSS-RNPHSQGRIRELFSQAE |
| Cap8AFdm3 | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| 5*V4F | 42 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |
| V3A | 29 | LLGVVGFPFGGALVSFYTNFLNTIWPSEDPWKAFMEQVEALMDQKIADYAKNKALAELQGLQNNVEDYVSALSSWQKNPAAPFRNPHSQGRIRELFSQAE |

Fig. 2C

```
                                                              CB1                                                        CB2
8AF           129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
8AFdm3T       129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
-CatG8AF      128 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a-9F       142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a-12 AA    130 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a          142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR-9F-catg    141 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
cap8AFdm3T    142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FRCG          141 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
DM23A         142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
2OL-8A        157 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
8AFdm3        129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR8a +34      176 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
FR-12-cg-dm3  129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
9F-cg-dm3     141 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
Cap8AFdm3     142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
5'V4F         142 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL
V3A           129 SHFRNSMPSFAISG YEVLFLTTYAQAANTHLFLLKDAQIYGEEW GYEKEDIAEFYKRQLKLTQE YTDHCVKWYNVGLDKLRGSSYESWVNFNRYRREMTL <----- Domain I ----->|<----- Domain II ----->
8AF           229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
8AFdm3T       229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
-CatG8AF      228 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a-9F       242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a-12 AA    230 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a          242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR-9F-catg    241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
cap8AFdm3T    242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FRCG          241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
DM23A         242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
2OL-8A        257 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
8AFdm3        229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR8a +34      276 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
FR-12-cg-dm3  229 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
9F-cg-dm3     241 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
Cap8AFdm3     242 TVLDLIALFPLYDVRLYPKEVKTELTRDVLT DPIVGVNNLRG-YGTTFSNIENYIRKPHLFDYLHRIQFHTRFQPGYYGNDSFNYWSGNYVSTRPSIGSN
5'V4F         242 TVLDLIALFPLYDVRLYPKEVKTELTRDVLT NPVL--ENFDGSFRGSAQGIEGSIRSPHLMDJLNSITITDAHRGEY------YWSGHQIMASPVGFSG
V3A           229 TVLDIVSLFPNYDSRTYPIRTVSQLTREIYI
```

Fig. 2D

```
8AF          328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
8AFdm3T      328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
-CatG8AF     327 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a-9F      341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a-12 AA   329 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a         341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR-9F-catg   340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
cap8AFdm3T   341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FRCG         340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
DM23A        341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
2OL-8A       356 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
8AFdm3       328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR8a +34     375 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
FR-12-cg-dm3 328 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
9F-cg-dm3    340 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
Cap8AFdm3    341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
5*V4F        341 DIITSPFYGNK-SSEPVQNLEFN-GEKVYRAVANTNLAVWPSAVYSGVTKVEFSQYNDQTDEASTQTYDSKRNVGAVSW------DSIDQLPPETTDEPL
V3A          321 PEFTFPLYGTMGNAAPQQRIVAQLGQGVYRTLSST---LYRFPFNIGINNQQLSVL-DGTEFA----YGTSNLPSAVYRKSGTVDSLDEIPPQNNVPP Domain II    Domain III 8AF          420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
8AFdm3T      420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
-CatG8AF     419 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a-9F      433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a-12 AA   421 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a         433 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR-9F-catg   432 EKGYSHQLNYVMCFLMQGSRGTI------PV LTWTHKSVDFFNMIDSKKITQIPSSQITQIPLTKSTNLGSGTSVVKGPGFTGGDII RRTSPGQISTLRVNITAPLSQ
cap8AFdm3T   433 EKGYSHQLNYVMCFLMQGSRGTI------PV LTWTHKSVDFFNMIDSKKITQIPSSQITQIPLTKSTNLGSGTSVVKGPGFTGGDII RRTSPGQISTLRVNITAPLSQ
FRCG         432 EKGYSHQLNYVMCFLMQGSRGTI------PV LTWTHKSVDFFNMIDSKKITQIPSSQITQIPLTKSTNLGSGTSVVKGPGFTGGDII RRTSPGQISTLRVNITAPLSQ
DM23A        433 EKGYSHQLNYVMCFLMQGSRGTI------PV LTWTHKSAEFNNIIPSSQITQIPLTKSTNLGSGTSVVKGPGFTGGDII RRTSPGQISTLRVNITAPLSQ
2OL-8A       448 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
8AFdm3       420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
FR8a +34     467 EKGYSHQLNYVMCFLMQGSRGTI------PV LTWTHKSVDFFNNIIPSSQITQIPLTKSTNLGSGTSVVKGPGFTGGDII RRTSPGQISTLRVNITAPLSQ
FR-12-cg-dm3 420 EKGYSHQLNYVMCFLMQGSRGTI------PV LTWTHKSVDFFNMIDSKKITQLPLTKSTNLGSGTSVVKGPGFTGGDII RRTSPGQISTLRVNITAPLSQ
9F-cg-dm3    432 EKGYSHQLNYVMCFLMQGSRGTI------PV LTWTHKSVDFFNMIDSKKITQIPSSQITQIPLTKSTNLGSGTSVVKGPGFTGGDII RRTSPGQISTLRVNITAPLSQ
Cap8AFdm3    433 EKGYSHQLNYVMCFLMQGSRGTI------PV LTWTHKSVDFFNNIIPSSQITQIPLTKSTNLGSGTSVVKGPGFTGGDII RRTSPGQISTLRVNITAPLSQ
5*V4F        433 EKGYSHQLNYVMCFLMQGSRGTI------PV LTWTHKSVDFFNMIDSKKITQLALTKSTNLGSGTSVVKGPGFTGGDII RRTSPGQISTLRVNITAPLSQ
V3A          413 RQGFSHRLSHVSMFRSGFSNSSVSIIRAPL FSWIHRSAEFNNIIPSSQITQIPLVKAYKLQSGASVVAGPRFTGGDII QCTENGSAATIYVTPDVSYSQ
```

Fig. 2E

```
                       CB4                                                                                                              CB5
8AF              514   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
8AFdm3T          514   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
-CatG8AF         513   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
FR8a-9F          527   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
FR8a-12 AA       515   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
FR8a             527   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
FR-9F-catg       526   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
cap8AFdm3T       527   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
FRCG             526   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
DM23A            527   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
2OL-8A           542   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
8AFdm3           514   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VT------------
FR8a +34         561   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VT------------
FR-12-cg-dm3     514   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VTFEAEYDLERAQK
9F-cg-dm3        526   RYRVRIRYAS  TTNLQFHTSIDGRPINQGNFSATMSSGSNLQSGSFRTVGFTTPFNFSNGSSVFTLSAHVFNSGNE  VYIDRIEFVPAE  VT------------
Cap8AFdm3        527   RYRVRIHYAS  TSQITFTLSLDGAPFNQYYFDKTINKGDTLTYNSFNLASFSTPFELSGNN--LQIGVTGLSAGDK  VYIDKIEFIPVN  --------------
5*V4F            527   RYRVRIHYAS  TSQITFTLSLDGAPFNQYYFDKTINKGDTLTYNSFNLASFSTPFELSGNN--LQIGVTGLSAGDK  VYIDKIEFIPVN  --------------
V3A              512   KYRARIHYAS                                                                VYIDKIEFIPVN  --------------

8AF              615   AVNELFTSSNQIGLKTDVTDYHIDQV
8AFdm3T          615   AVNELFTSSNQIGLKTDVTDYHIDQV
-CatG8AF         614   AVNELFTSSNQIGLKTDVTDYHIDQV
FR8a-9F          628   AVNELFTSSNQIGLKTDVTDYHIDQV
FR8a-12 AA       616   AVNELFTSSNQIGLKTDVTDYHIDQV
FR8a             628   AVNELFTSSNQIGLKTDVTDYHIDQV
FR-9F-catg       627   AVNELFTSSNQIGLKTDVTDYHIDQV
cap8AFdm3T       628   AVNELFTSSNQIGLKTDVTDYHIDQV
FRCG             627   AVNELFTSSNQIGLKTDVTDYHIDQV
DM23A            628   AVNELFTSSNQIGLKTDVTDYHIDQV
2OL-8A           643   AVNELFTSSNQIGLKTDVTDYHIDQV
8AFdm3           603   --------------------------
FR8a +34         662   AVNELFTSSNQIGLKTDVTDYHIDQV
FR-12-cg-dm3     603   --------------------------
9F-cg-dm3        615   --------------------------
Cap8AFdm3        628   --------------------------
5*V4F            610   --------------------------
V3A              595   --------------------------
```

INSECTICIDAL PROTEINS

CROSS-REFERENCE

This application is a continuation of U.S. patent application Ser. No. 16/212,892, filed Dec. 7, 2018, which is a continuation of U.S. patent application Ser. No. 15/148,399, filed May 6, 2016 and now abandoned, which is a divisional of U.S. patent application Ser. No. 13/623,921, now U.S. Pat. No. 9,522,937, filed Sep. 21, 2012, which is a divisional of U.S. patent application Ser. No. 12/529,246, now U.S. Pat. No. 8,309,516, filed Sep. 25, 2009, which is a § 371 of PCT/US08/58182, filed Mar. 26, 2008, which claims priority to U.S. Provisional Application No. 60/920,493, filed Mar. 28, 2007, all of which are incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "70231_C_seglisting.txt", created on Feb. 3, 2021, and having a size of 423 kilobytes and is filed concurrently with the specification. The sequence listing contained in this ASCII formatted document is part of the specification and is herein incorporated by reference in its entirety.

BACKGROUND

The present invention relates to the fields of protein engineering, plant molecular biology and pest control. More particularly the invention relates to novel engineered hybrid proteins having insecticidal activity, nucleic acids whose expression results in the insecticidal proteins, and methods of making and methods of using the insecticidal proteins and corresponding nucleic acids to control insects.

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm, *D. longicornis barberi*, the northern corn rootworm and *D. undecimpunctata howardi*, the southern corn rootworm. Only western and northern corn rootworms are considered primary pests of corn in the US Corn Belt. An important corn rootworm pest in the Southern US is the Mexican corn rootworm, *Diabrotica virgifera zeae*. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have also been applied to crop plants with satisfactory results against primarily lepidopteran insect pests. The δ-endotoxins are proteins held within a crystalline matrix that are known to possess insecticidal activity when ingested by certain insects. The various δ-endotoxins have been classified based upon their spectrum of activity and sequence homology. Prior to 1990, the major classes were defined by their spectrum of activity with the Cry1 proteins active against Lepidoptera (moths and butterflies), Cry2 proteins active against both Lepidoptera and Diptera (flies and mosquitoes), Cry3 proteins active against Coleoptera (beetles) and Cry4 proteins active against Diptera (Hofte & Whitely, 1989, Microbiol. Rev. 53:242-255). A new nomenclature was developed in 1998 which systematically classifies the Cry proteins based on amino acid sequence homology rather than insect target specificities (Crickmore et al. 1998, Microbiol. Molec. Biol. Rev. 62:807-813).

The spectrum of insecticidal activity of an individual δ-endotoxin from Bt is quite narrow, with a given δ-endotoxin being active against only a few species within an Order. For instance, a Cry3A toxin is known to be very toxic to the Colorado potato beetle, *Leptinotarsa decemlineata*, but has very little or no toxicity to related beetles in the genus *Diabrotica* (Johnson et al., 1993, J. Econ. Entomol. 86:330-333). According to Slaney et al. (1992, Insect Biochem. Molec. Biol. 22:9-18) a Cry3A toxin is at least 2000 times less toxic to southern corn rootworm larvae than to the Colorado potato beetle. It is also known that Cry3A has little or no toxicity to the western corn rootworm or northern corn rootworm.

Specificity of the δ-endotoxins is the result of the efficiency of the various steps involved in producing an active toxic protein and its subsequent interaction with the epithelial cells in an insect mid-gut. To be insecticidal, most known δ-endotoxins must first be ingested by the insect and proteolytically activated to form an active toxin. Activation of the insecticidal crystal (Cry) proteins is a multi-step process. After ingestion, the crystals must first be solubilized in the insect gut. Once solubilized, the δ-endotoxins are activated by specific proteolytic cleavages. The proteases in the insect gut can play a role in specificity by determining where the δ-endotoxin is processed. Once the δ-endotoxin has been solubilized and processed it binds to specific receptors on the surface of the insects' mid-gut epithelium and subsequently integrates into the lipid bilayer of the brush border membrane. Ion channels then form disrupting the normal function of the midgut eventually leading to the death of the insect.

In Lepidoptera, which have alkaline pH guts, gut proteases process δ-endotoxins for example, Cry1Aa, Cry1Ab, Cry1Ac, Cry1B and Cry1F, from 130-140 kDa protoxins to toxic proteins of approximately 60-70 kDa. Processing of the protoxin to toxin has been reported to proceed by removal of both N- and C-terminal amino acids with the exact location of processing being dependent on the specific δ-endotoxin and the specific insect gut fluids involved (Ogiwara et al., 1992, J. Invert. Pathol. 60:121-126). Thus activation requires that the entire C-terminal protoxin tail region be cleaved off. This proteolytic activation of a δ-endotoxin can play a significant role in determining its specificity.

Coleopteran insects have guts that are more neutral to acidic and coleopteran-specific δ-endotoxins are similar to the size of the activated lepidopteran-specific toxins. Therefore, the processing of coleopteran-specific δ-endotoxins was formerly considered unnecessary for toxicity. However, data suggests that coleopteran-active δ-endotoxins are solubilized and proteolyzed to smaller toxic polypeptides. A 73 kDa Cry3A δ-endotoxin protein produced by *B. thuringiensis* var. *tenebrionis* is readily processed in the bacterium at the N-terminus, losing 49-57 residues during or after crystal formation to produce the commonly isolated 67 kDa form (Carroll et al., 1989, Biochem. J. 261:99-105). McPherson et al., (1988, Biotechnology 6:61-66) also demonstrated that a native cry3A coding sequence contains two functional translational initiation codons in the same reading frame, one coding for a 73 kDa protein and the other coding for a 67 kDa protein starting at Met-1 and Met-48 respectively, of the deduced amino acid sequence. Both proteins then can be considered naturally occurring full-length Cry3A proteins.

As more knowledge has been gained as to how the δ-endotoxins function, attempts to engineer δ-endotoxins to have new activities have increased. Engineering δ-endotoxins was made more possible by solving the three dimensional structure of Cry3A in 1991 (Li et al., 1991, Nature 353:815-821). Li et al. determined that a Cry3A protein has three structural domains: the N-terminal domain I, from residues 58-290, consists of 7 α-helices, domain II, from residues 291-500, contains three β-sheets in a so-called Greek key-conformation, and the C-terminal domain III, from residues 501-644, is a β-sandwich in a so-called jellyroll conformation. The three dimensional structure for the lepidopteran active Cry1Aa toxin has also been solved (Grochulski et al., 1995, J. Mol. Biol. 254:447-464). The Cry1Aa toxin also has three domains: the N-terminal domain I, from residues 33-253, domain II from residues 265-461, and domain III from residues 463-609 with an additional outer strand in one of the β-sheets from by residues 254-264. If the Cry3A and Cry1Aa structures are projected on other Cry1 sequences, domain I runs from about amino acid residue 28 to 260, domain II from about 260 to 460 and domain III from about 460 to 600. See, Nakamura et al., Agric. Biol. Chem. 54(3): 715-724 (1990); Li et al., Nature 353: 815-821 (1991); Ge et al., J. Biol. Chem. 266(27): 17954-17958 (1991); and Honee et al., Mol. Microbiol. 5(11): 2799-2806 (1991); each of which are incorporated herein by reference. Thus, it is now known that based on amino acid sequence homology, known Bt δ-endotoxins have a similar three-dimensional structure comprising three domains.

The toxin portions of Bt Cry proteins are also characterized by having five conserved blocks across their amino acid sequence numbered CB1 to CB5 from N-terminus to C-terminus, respectively (Hofte & Whiteley, supra). Conserved block 1 (CB1) comprises approximately 29 amino acids, conserved block 2 (CB2) comprises approximately 67 amino acids, conserved block 3 (CB3) comprises approximately 48 amino acids, conserved block 4 (CB4) comprises approximately 10 amino acids and conserved block 5 (CB5) comprises approximately 12 amino acids. The sequences before and after these five conserved blocks are highly variable and thus are designated the "variable regions," V1-V6. Domain I of a Bt δ-endotoxin typically comprises variable region 1, conserved block 1, variable region 2, and the N-terminal 52 amino acids of conserved block 2. Domain II typically comprises approximately the C-terminal 15 amino acids of conserved block 2, variable region 3, and approximately the N-terminal 10 amino acids of conserved block 3. Domain III typically comprises approximately the C-terminal 38 amino acids of conserved block 3, variable region 4, conserved block 4, variable region 5, and conserved block 5. The Cry1 lepidopteran active toxins, among other delta-endotoxins, have a variable region 6 with approximately 1-3 amino acids lying within domain III.

Many Bt strains and δ-endotoxins are active against different insect species and nematodes. However, relatively few of these strains and toxins have activity against coleopteran insects. Further, most of the now known native coleopteran-active δ-endotoxins, for example Cry3A, Cry3B, Cry3C, Cry7A, Cry8A, Cry8B, and Cry8C, have insufficient oral toxicity against corn rootworm to provide adequate field control if delivered, for example, through microbes or transgenic plants. Therefore, other approaches for producing novel toxins active against corn rootworm need to be explored.

Lepidopteran-active δ-endotoxins have been engineered in attempts to improve specific activity or to broaden the spectrum of insecticidal activity. For example, the silk moth (*Bombyx mori*) specificity domain from a Cry1Aa protein was moved to a Cry1Ac protein, thus imparting a new insecticidal activity to the resulting hybrid Bt protein (Ge et al. 1989, PNAS 86: 4037-4041). Also, Bosch et al. 1998 (U.S. Pat. No. 5,736,131, incorporated herein by reference) describes *Bacillus thuringiensis* hybrid toxins comprising at their C-terminus domain III of a first Cry protein and at its N-terminus domains I and II of a second Cry protein. Such hybrid toxins were shown to have altered insecticidal specificity against lepidopteran insects. For example, the H04 hybrid toxin, which is also described in De Maagd et al., *Appl. Environ. Microbiol.* 62(5): 1537-1543 (1996), comprises at its N-terminus domains I and II of a Cry1Ab and at its C-terminus domain III of a Cry1C. H04 is reportedly highly toxic to the lepidopteran insect *Spodoptera exigua* (beet armyworm) compared with the parental Cry1Ab toxin and significantly more toxic than the Cry1C parental toxin. It has also been shown that substitution of domain III of toxins, which are not active against the beet armyworm such as Cry1E and Cry1Ab, by domain III of Cry1C, which is active against beet armyworm, can produce hybrid toxins that are active against this insect. All of the hybrids disclosed in Bosch et al. use domains from lepidopteran active Cry proteins to make new toxins with lepidopteran activity. The results do suggest that domain III of Cry1C is an important determinant of specificity for beet armyworm. See also, Bosch et al., *FEMS Microbiology Letters* 118: 129-134 (1994); Bosch et al., Bio/Technology 12: 915-918 (1994); De Maagd et al., Appl. Environ. Microbiol. 62(8): 2753-2757 (1996); and De Maagd et al., *Mol. Microbiol.* 31(2): 463-471 (1999); each of which is incorporated herein by reference.

Several attempts at engineering the coleopteran-active δ-endotoxins have been reported. Chen and Stacy (U.S. Pat. No. 7,030,295, herein incorporated by reference) successfully created a corn rootworm active toxin by inserting a non-naturally occurring protease recognition site in domain I, domain III, or both domains I and III of a Cry3A protein. One of the resulting modified Cry3A proteins, designated Cry3A055, having a protease recognition site inserted in domain I, was active against several species of *Diabrotica*. Van Rie et al., 1997, (U.S. Pat. No. 5,659,123) engineered Cry3A by randomly replacing amino acids, thought to be important in solvent accessibility, in domain II with the amino acid alanine. Several of these random replacements confined to domain II were reportedly involved in increased western corn rootworm toxicity. However, others have shown that some alanine replacements in domain II of Cry3A result in disruption of receptor binding or structural instability (Wu and Dean, 1996, J. Mol. Biol. 255: 628-640). English et al., 1999, (Intl. Pat. Appl. Publ. No. WO 99/31248) reported amino acid substitutions in Cry3Bb that caused increases in toxicity to southern and western corn rootworm. However, of the 35 reported Cry3Bb mutants, only three, with mutations primarily in domain II and the domain I-domain II interface, were active against western corn rootworm. Further, the variation in toxicity of wild-type Cry3Bb against western corn rootworm in the same assays appear to be greater than any of the differences between the mutated Cry3Bb toxins and the wild-type Cry3Bb. Shadenkov et al. (1993, Mol. Biol. 27:586-591), made a hybrid protein by fusing amino acids 48-565 of a Cry3A protein to amino acids 526-725 of a Cry1Aa protein. Therefore, the cross-over between Cry3A and Cry1Aa sequence was in conserved block 4 located in domain III. Cry3A is very active against the Colorado potato beetle (*Leptinotarsa decemlineata*). However, the hybrid protein disclosed by Shadenkov et al. was not active against Colorado potato beetle even though more than 75% of the hybrid protein was made up of Cry3A sequence. Thus, the addition of only 25% of Cry1Aa sequence destroyed activity against a coleopteran insect that the parent Cry3A was active against. This suggests that hybrid proteins made by fusing portions of a coleopteran-active Cry protein, e.g. Cry3A, and a lepidopteran-active Cry protein, e.g. Cry1A, would not have activity against coleopteran insects, particularly a coleopteran insect that is not naturally susceptible to Cry3A like corn rootworm.

In view of the above discussion, there remains a need to design new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of control agents through products that minimize the burden on the environment, as through transgenic plants, are desirable.

SUMMARY

In view of these needs, it is an object of the present invention to provide novel engineered hybrid insecticidal proteins (eHIPs). Such novel eHIPs are made by fusing unique combinations of variable regions and conserved blocks of at least two different Cry proteins and optionally including a protoxin tail region from a Bt Cry protein at the C-terminus or an N-terminal peptidyl fragment or both. For example, without limitation, by combining complete or partial variable regions and conserved blocks from a first Cry protein that has coleopteran activity with complete or partial variable regions and conserved blocks from a second Cry protein that has lepidopteran activity, and is different from the first Cry protein, and optionally including a protoxin tail region from a lepidopteran active Bt Cry protein, or an N-terminal peptidyl fragment or both, new engineered hybrid insecticidal proteins are created that have activity against a spectrum of insects different from the first or second parent Cry proteins or both. Such novel eHIPs may comprise complete or partial variable regions, conserved blocks or domains from a modified Cry3A protein and a Cry protein different from the modified Cry3A protein. The peptidyl fragment may confer insecticidal activity upon the eHIP, or may increase the insecticidal activity of the eHIP over an eHIP without the peptidyl fragment, or make the eHIP more stable than an eHIP without the peptidyl fragment. The eHIPs of the invention have surprising and unexpected toxicity to corn rootworm (*Diabrotica* sp.). The invention is further drawn to nucleic acids that encode the eHIPs or which is complementary to one which hybridizes under stringent conditions with the recombinant hybrid nucleic acids according to the invention.

Also included in the invention are vectors containing such recombinant (or complementary thereto) nucleic acids; a plant or micro-organism which includes, and enables expression of such nucleic acids; plants transformed with such nucleic acids, for example transgenic corn plants; the progeny of such plants which contain the nucleic acids stably incorporated and hereditable in a Mendelian manner, and/or the seeds of such plants and such progeny.

The invention also includes compositions and formulations containing the eHIPs, which are capable of inhibiting the ability of insect pests to survive, grow and reproduce, or of limiting insect-related damage or loss to crop plants, for example applying the eHIPs or compositions or formulations to insect-infested areas, or to prophylactically treat insect-susceptible areas or plants to confer protection against the insect pests.

The invention is further drawn to a method of making the eHIPs and to methods of using the nucleic acids, for example in microorganisms to control insects or in transgenic plants to confer protection from insect damage.

The novel eHIPs described herein are highly active against insects. For example, the eHIPs of the present invention can be used to control economically important insect pests such as western corn rootworm (*Diabrotica virgifera virgifera*) northern corn rootworm (*D. longicornis barberi*) and Mexican corn rootworm (*D. virgifera zeae*). Certain eHIPs may also be used to control European corn borer (*Ostrinia nubilais*) and other lepidopteran insects. The eHIPs can be used singly or in combination with other insect control strategies to confer maximal pest control efficiency with minimal environmental impact.

Other aspects and advantages of the present invention will become apparent to those skilled in the art from a study of the following description of the invention and non-limiting examples.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-1E shows a sequence alignment of some eHIP embodiments with parental Cry proteins or modified Cry 3A used to construct the eHIPs, including, a Cry3A, Cry1Ab, and Cry3A055, and indicates percent identity. N-terminal peptidyl fragments are underlined. The 5 conserved blocks are labeled CB1-CB5. Location of junctions between domains I, II and III are designated by a vertical dashed line. A cathepsin G protease recognition sequence, AAPF, is in bold.

FIG. 2A-2E shows an alignment of eHIP embodiments that are active against at least western corn rootworm and indicates percent identity compared to the 8AF eHIP. N-terminal peptidyl fragments are single underlined. C-terminal protoxin tail regions are double underlined. The 5 conserved blocks are labeled CB1-CB5. Locations of junctions between domains I, II and III are indicated by "↓" and labeled accordingly. Locations of crossover positions are indicted by a "♦". A cathepsin G protease recognition sequence, AAPF, is in bold.

FIG. 3 shows a map of recombinant vector 12207 used to transform corn comprising an expression cassette with a maize ubiquitin promoter operably linked to a FRCG coding sequence operably linked to a NOS terminator.

FIG. 4 shows a map of recombinant vector 12161 used to transform corn comprising an expression cassette with a maize ubiquitin promoter operably linked to a FR8a coding sequence operably linked to a NOS terminator.

FIG. 5 shows a map of recombinant vector 12208 used to transform corn comprising an expression cassette with a cestrum yellow leaf curling virus promoter (cmp) operably linked to a FRCG coding sequence operably linked to a NOS terminator.

FIG. 6 shows a map of recombinant vector 12274 used to transform corn comprising an expression cassette with a cestrum yellow leaf curling virus promoter (cmp) operably linked to a FR8a coding sequence operably linked to a NOS terminator.

FIG. 7 shows a map of recombinant vector 12473 used to transform corn comprising an expression cassette with a maize ubiquitin promoter (ubi) operably linked to a FRD3 coding sequence operably linked to a NOS terminator.

FIG. 8 shows a map of recombinant vector 12474 used to transform corn comprising an expression cassette with a cestrum yellow leaf curling virus promoter (cmp) operably linked to a FRD3 coding sequence operably linked to a NOS terminator.

BRIEF DESCRIPTION OF THE SEQUENCES IN THE SEQUENCE LISTING

SEQ ID NO: 1 is the 2OL-8a nucleotide sequence.
SEQ ID NO: 2 is the 2OL-8a encoded by SEQ ID NO: 1.
SEQ ID NO: 3 is the FR8a nucleotide sequence.
SEQ ID NO: 4 is the FR8a encoded by SEQ ID NO: 3.
SEQ ID NO: 5 is the FRCG nucleotide sequence.
SEQ ID NO: 6 is the FRCG encoded by SEQ ID NO: 5.
SEQ ID NO: 7 is the FR8a-9F nucleotide sequence.
SEQ ID NO: 8 is the FR8a-9F encoded by SEQ ID NO: 7.
SEQ ID NO: 9 is the FR-9F-catg nucleotide sequence.
SEQ ID NO: 10 is the FR-9F-catg encoded by SEQ ID NO: 9.
SEQ ID NO: 11 is the FR8a-12AA nucleotide sequence.
SEQ ID NO: 12 is the FR8a-12AA encoded by SEQ ID NO: 11.
SEQ ID NO: 13 is the WR-9mut nucleotide sequence.
SEQ ID NO: 14 is the WR-9mut encoded by SEQ ID NO: 13.
SEQ ID NO: 15 is the FRD3 nucleotide sequence.
SEQ ID NO: 16 is the FRD3 encoded by SEQ ID NO: 15.
SEQ ID NO: 17 is the FR-12-cg-dm3 nucleotide sequence.
SEQ ID NO: 18 is the FR-12-cg-dm3 encoded by SEQ ID NO: 17.
SEQ ID NO: 19 is the 9F-cg-del6 nucleotide sequence.
SEQ ID NO: 20 is the 9F-cg-del6 encoded by SEQ ID NO: 19.
SEQ ID NO: 21 is the FR-cg-dm3 nucleotide sequence.
SEQ ID NO: 22 is the FR-cg-dm3 encoded by SEQ ID NO: 21.
SEQ ID NO: 23 is the 9F-cg-dm3 nucleotide sequence.
SEQ ID NO: 24 is the 9F-cg-dm3 encoded by SEQ ID NO:23.
SEQ ID NO: 25 is the B8a nucleotide sequence.
SEQ ID NO: 26 is the B8a encoded by SEQ ID NO: 25.
SEQ ID NO: 27 is the 5*B8a nucleotide sequence.
SEQ ID NO: 28 is the 5*B8a encoded by SEQ ID NO: 27.
SEQ ID NO: 29 is the V3A nucleotide sequence.
SEQ ID NO: 30 is the V3A encoded by SEQ ID NO: 29.
SEQ ID NO: 31 is the V4F nucleotide sequence.
SEQ ID NO: 32 is the V4F encoded by SEQ ID NO: 31.
SEQ ID NO: 33 is the 5*V4F nucleotide sequence.
SEQ ID NO: 34 is the 5*V4F encoded by SEQ ID NO: 33.
SEQ ID NO: 35 is the 2OL-7 nucleotide sequence.
SEQ ID NO: 36 is the 2OL-7 encoded by SEQ ID NO: 35.
SEQ ID NO: 37 is the T7-2OL-7 nucleotide sequence.
SEQ ID NO: 38 is the T7-2OL-7 encoded by SEQ ID NO: 37.
SEQ ID NO: 39 is the 5*2OL-7 nucleotide sequence.
SEQ ID NO: 40 is the 5*2OL-7 encoded by SEQ ID NO: 39.
SEQ ID NO: 41 is the 2OL-10 nucleotide sequence.
SEQ ID NO: 42 is the 2OL-10 encoded by SEQ ID NO: 41.
SEQ ID NO: 43 is the 5*2OL-10 nucleotide sequence.
SEQ ID NO: 44 is the 5*2OL-10 encoded by SEQ ID NO: 43.
SEQ ID NO: 45 is the 2OL-12A nucleotide sequence.
SEQ ID NO: 46 is the 2OL-12A encoded by SEQ ID NO: 45.
SEQ ID NO: 47 is the 2OL-13 nucleotide sequence.
SEQ ID NO: 48 is the 2OI-13 encoded by SEQ ID NO: 47.
SEQ ID NO: 49 is the V5&6 nucleotide sequence.
SEQ ID NO: 50 is the V5&6 encoded by SEQ ID NO: 49.
SEQ ID NO: 51 is the 5*V5&6 nucleotide sequence.
SEQ ID NO: 52 is the 5*V5&6 encoded by SEQ ID NO: 51.
SEQ ID NO: 53 is the 88A-dm3 nucleotide sequence.
SEQ ID NO: 54 is the 88A-dm3 encoded by SEQ ID NO: 53.
SEQ ID NO: 55 is the FR(1Fa) nucleotide sequence.
SEQ ID NO: 56 is the FR(1Fa) encoded by SEQ ID NO: 55.
SEQ ID NO: 57 is the FR(Ac) nucleotide sequence.
SEQ ID NO: 58 is the FR(1Ac) encoded by SEQ ID NO: 57.
SEQ ID NO: 59 is the FR(1Ia) nucleotide sequence.
SEQ ID NO: 60 is the FR(1Ia) encoded by SEQ ID NO: 59.
SEQ ID NO: 61 is the DM23A nucleotide sequence.
SEQ ID NO: 62 is the DM23A encoded by SEQ ID NO: 61.
SEQ ID NO: 63 is the 8AF nucleotide sequence.
SEQ ID NO: 64 is the 8AF encoded by SEQ ID NO: 63.
SEQ ID NO: 65 is the 5*cry3A055 nucleotide sequence.
SEQ ID NO: 66 is the 5*Cry3A055 encoded by SEQ ID NO: 65.
SEQ ID NO: 67 is a maize optimized cry3A nucleotide sequence.
SEQ ID NO: 68 is the Cry3A encoded by SEQ ID NO: 67.
SEQ ID NO: 69 is the cry3A055 nucleotide sequence.
SEQ ID NO: 70 is the Cry3A055 encoded by SEQ ID NO: 69.
SEQ ID NO: 71 is a maize optimized cry1Ab nucleotide sequence.
SEQ ID NO: 72 is the Cry1Ab encoded by SEQ ID NO: 71.
SEQ ID NO: 73 is a maize optimized cry1Ba nucleotide sequence.
SEQ ID NO: 74 is the Cry1Ba encoded by SEQ ID NO: 73.

SEQ ID NO: 75 is a maize optimized cry1Fa nucleotide sequence.
SEQ ID NO: 76 is the Cry1Fa encoded by SEQ ID NO: 75.
SEQ ID NO: 77 is a cry8Aa nucleotide sequence.
SEQ ID NO: 78 is the Cry8Aa encoded by SEQ ID NO: 77.
SEQ ID NO: 79 is a cry1Ac nucleotide sequence.
SEQ ID NO: 80 is the Cry1Ac encoded by SEQ ID NO: 79.
SEQ ID NO: 81 is a cry1Ia nucleotide sequence.
SEQ ID NO: 82 is the Cry1Ia encoded by SEQ ID NO: 81.
SEQ ID NOs 83-125 are primer sequences useful in the present invention.
SEQ ID NOs 126-134 are N-terminal peptidyl fragments.
SEQ ID NO: 135 is a full-length Cry3A protein.
SEQ ID NO: 136-143 are primer sequences useful in the present invention.
SEQ ID NO: 144 is the T7-8AF coding sequence.
SEQ ID NO: 145 is the T7-8AF encoded by ASEQ ID NO: 144.
SEQ ID NO: 146 is the -catG8AF coding sequence.
SEQ ID NO: 147 is the -CatG8AF encoded by SEQ ID NO: 146.
SEQ ID NO: 148 is the 8AFdm3 coding sequence.
SEQ ID NO: 149 is the 8AFdm3 encoded by SEQ ID NO: 148.
SEQ ID NO: 150 is the 8AFlongdm3 coding sequence.
SEQ ID NO: 151 is the 8AFlongdm3 encoded by SEQ ID NO: 150.
SEQ ID NO: 152 is the cap8AFdm3 coding sequence.
SEQ ID NO: 153 is the cap8AFdm3 encoded by SEQ ID NO: 152.
SEQ ID NO: 154 is the 8AFdm3T coding sequence.
SEQ ID NO: 155 is the 8AFdm3T encoded by SEQ ID NO: 154.
SEQ ID NO: 156 is the 8AFlongdm3T coding sequence.
SEQ ID NO: 157 is the 8AFlongdm3T encoded by SEQ ID NO: 156.
SEQ ID NO: 158 is the cap8AFdm3T coding sequence.
SEQ ID NO: 159 is the cap8AFdm3T encoded by SEQ ID NO: 158.
SEQ ID NO: 160 is the FR8a+34 eHIP.

Definitions

Figure 3:
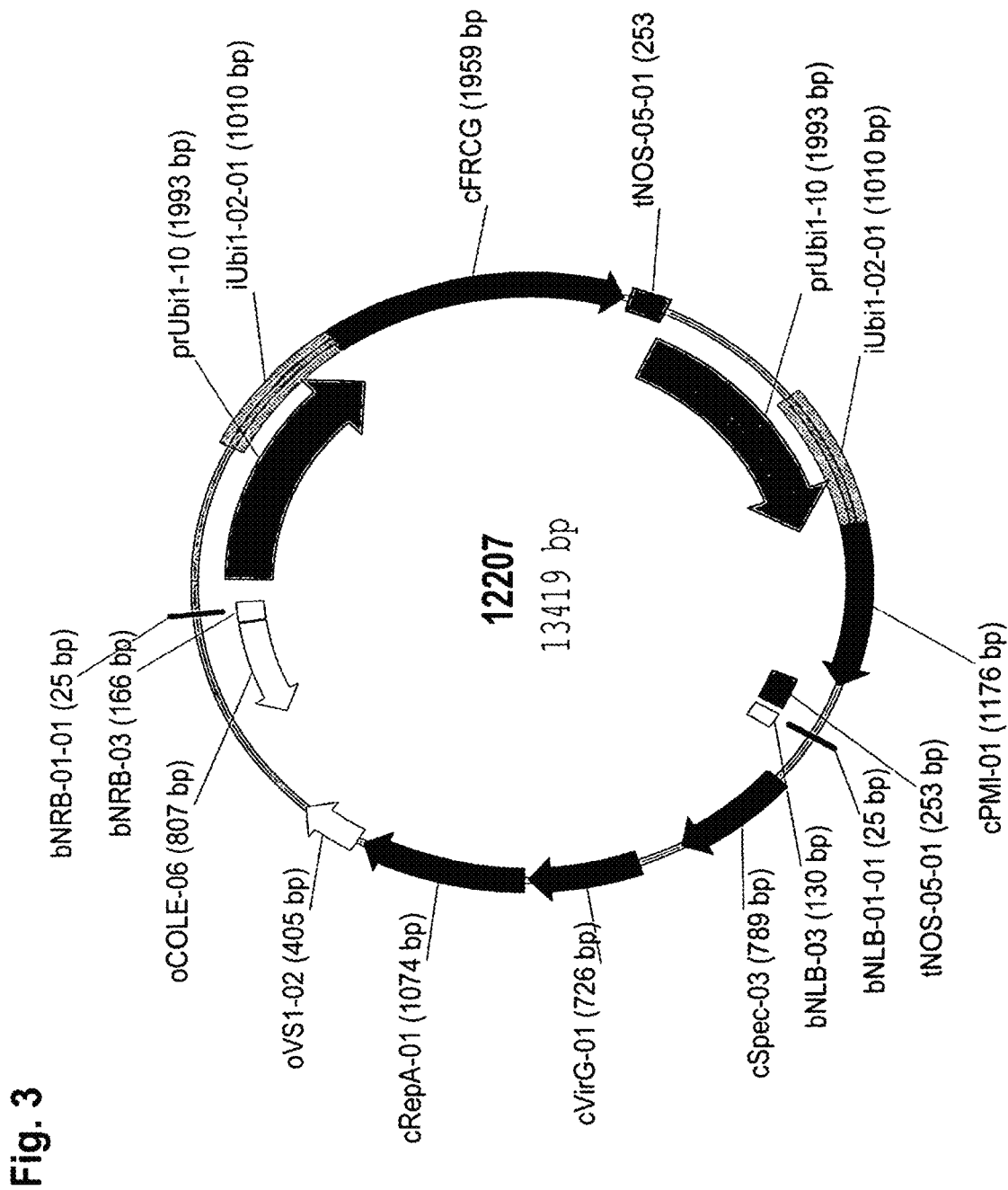

For clarity, certain terms used in the specification are defined and presented as follows:

"Activity" of the eHIPs of the invention is meant that the eHIPs function as orally active insect control agents, have a toxic effect, or are able to disrupt or deter insect feeding, which may or may not cause death of the insect. When an eHIP of the invention is delivered to the insect, the result is typically death of the insect, or the insect does not feed upon the source that makes the eHIP available to the insect.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

In the context of the present invention, a "chimeric insecticidal protein" (CIP) is an insecticidal protein comprising a peptidyl fragment fused to the N-terminus of an eHIP. The peptidyl fragment may confer insecticidal activity upon the eHIP, may increase the insecticidal activity of the eHIP over an eHIP without the peptidyl fragment, or may make the eHIP more stable than an eHIP without the peptidyl fragment, particularly against at least western corn rootworm. The peptidyl fragment is an amino acid sequence that is typically heterologus to (not derived from) a Bt Cry protein but may be derived from a Bt Cry protein. Such peptidyl fragments extend from the N-terminus of the insecticidal protein and do not naturally occur at the N-terminus of Bt Cry proteins. One example of an N-terminal peptidyl fragment has the amino acid sequence MTSNGRQCAGIRP (SEQ ID NO: 129) which is not derived from a Bt Cry protein.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

In the context of the present invention, "connecting" nucleic acids means to join two or more nucleic acids together using any means known in the art. For example, without limitation, the nucleic acids may be ligated together using for example, DNA ligase, or may be annealed using PCR. The nucleic acids may also be joined by chemically synthesizing a nucleic acid using the sequence of two or more separate nucleic acids.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

In the context of the present invention, "corresponding to" means that when the amino acid sequences of certain proteins (for example Bt Cry proteins or modified Cry3A proteins) are aligned with each other, the amino acids that align with certain enumerated positions in for example, but not limited to, a Cry3A toxin (either SEQ ID NO: 68 or SEQ ID NO: 134); a Cry3A055 toxin (SEQ ID NO: 70); or a Cry1Ab toxin (SEQ ID NO: 72), but that are not necessarily in these exact numerical positions relative to the reference amino acid sequence, particularly as it relates to identification of domains I, II and III, and/or the conserved blocks and variable regions, these amino acid positions "correspond to" each other. For example, in delineating Domain I of a hybrid protein, amino acids 11-244 of a Cry3A055 protein (SEQ ID NO: 70) correspond to amino acids 58-290 of a native Cry3A toxin (SEQ ID NO: 135) or to amino acids 11-243 of a native Cry3A toxin (SEQ ID NO: 68) or to amino acids 33-254 of a native Cry1Ab toxin.

In the context of the present invention the words "Cry protein" can be used interchangeably with the words "delta-endotoxin" or "δ-endotoxin."

In the context of the present invention, an "engineered hybrid insecticidal protein" (eHIP) is an insecticidal protein created by fusing unique combinations of variable regions and conserved blocks of at least two different Cry proteins. Such novel eHIPs may comprise complete or partial variable regions, conserved blocks or domains from a modified Cry3A protein and a Cry protein different from the modified Cry3A protein. The eHIPs of the invention may optionally include a protoxin tail region from a Bt Cry protein or an N-terminal peptidyl fragment or both. For example without limitation, an eHIP is created by combining in an N-terminal to C-terminal direction, amino acids 1-468 of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of a Cry1Ab protoxin tail. An eHIP that comprises an N-terminal peptidyl fragment may also be designated as a "chimeric insecticidal protein (CIP)."

To "deliver" an eHIP means that the eHIP comes in contact with an insect, resulting in a toxic effect and control of the insect. The eHIP may be delivered in many recognized ways, e.g., through a transgenic plant expressing the eHIP, formulated protein composition(s), sprayable protein composition(s), a bait matrix, or any other art-recognized toxin delivery system.

"Effective insect-controlling amount" means that concentration of an eHIP that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence. A heterologous amino acid sequence is one that is not naturally associated with a native amino acid sequence, for example an amino acid sequence of a Cry protein.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleic acid or protein sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1× SSC, 0.1% SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example without limitation, a recombinant microbial cell, plant cell, plant tissue, or plant.

A "modified Cry3A toxin" or "Cry3A055" of this invention refers to a Cry3A-derived toxin having at least one additional protease recognition site that is recognized by a gut protease of a target insect, which does not naturally occur in a Cry3A toxin, as described in U.S. Pat. No. 7,030,295, herein incorporated by reference.

A "modified cry3A coding sequence" according to this invention can be derived from a native cry3A coding sequence or from a synthetic cry3A coding sequence and comprises the coding sequence of at least one additional protease recognition site that does not naturally occur in an unmodified cry3A gene.

A "nucleic acid molecule" or "nucleic acid sequence" is a segment of single- or double-stranded DNA or RNA that can be isolated from any source. In the context of the present invention, the nucleic acid molecule is typically a segment of DNA.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DESCRIPTION

This invention relates to novel engineered hybrid insecticidal proteins (eHIPS), created to have activity against at least western corn rootworm, and may further include northern corn rootworm, Mexican corn rootworm, and/or Colorado potato beetle. Some eHIPs have activity against the lepidopteran pest, European corn borer. Such novel eHIPs are made by fusing unique combinations of complete or partial variable regions and conserved blocks of at least two different Cry proteins and optionally include a protoxin tail region from a Bt Cry protein at the C-terminus or an N-terminal peptidyl fragment or both. For example, without limitation, by combining complete or partial variable regions and conserved blocks from a first Cry protein that has coleopteran activity with complete or partial variable regions and conserved blocks from a second Cry protein that has lepidopteran activity and is different from the first Bt Cry protein, and optionally including a protoxin tail region from a Bt Cry protein at the C-terminus or an N-terminal peptidyl fragment or both, new engineered hybrid insecticidal proteins that have activity against a spectrum of insects that is different from the first or second parent Cry protein, or both, is created. Such novel eHIPs may also comprise complete or partial variable regions, conserved blocks or domains from a modified Cry3A protein and a Cry protein different from the modified Cry3A protein. The N-terminal peptidyl fragment or protoxin tail region may confer insecticidal activity upon the eHIP, may increase the insecticidal activity of an eHIP over an eHIP without the peptidyl fragment or protoxin tail region, and/or may make the eHIP more stable than an eHIP without the peptidyl fragment or protoxin tail region, particularly against at least western corn rootworm. The amino acid sequence of the peptidyl fragment typically is heterologous to (i.e. not derived from) a Bt Cry protein. However, based on the teaching disclosed herein, the skilled person will recognize that an N-terminal peptidyl fragment may be generated using an amino acid sequence derived from a Bt Cry protein. The eHIPs of the invention have surprising and unexpected toxicity to corn rootworm, particularly to western, northern and Mexican corn rootworm. The present invention also relates to nucleic acids whose expression results in eHIPs, and to the making and using of the eHIPs to control insect pests. The expression of the nucleic acids results in eHIPs that can be used to control coleopteran insects such as western, northern or Mexican corn rootworm, or used to control lepidopteran insects such as European corn borer, particularly when expressed in a transgenic plant such as a transgenic corn plant.

In one embodiment, the invention encompasses an engineered hybrid insecticidal protein comprising an amino acid sequence from a first *Bacillus thuringiensis* (Bt) Cry protein comprising complete or partial variable regions and conserved blocks of the first Cry protein fused to an amino acid sequence from a second Bt Cry protein different from the first Bt Cry protein comprising complete or partial variable regions and conserved blocks of the second Cry protein, and optionally comprising: (a) a protoxin tail region of a Bt Cry protein located at the C-terminus; or (b) an N-terminal peptidyl fragment; or both (a) and (b), wherein the eHIP has activity against at least western corn rootworm.

In another embodiment, the present invention encompasses an eHIP comprising an N-terminal region of a first Bt Cry protein fused to a C-terminal region of a second Bt Cry protein different from the first Bt Cry protein, wherein at least one crossover position between the first and the second Bt Cry protein is located in conserved block 2, conserved block 3, variable region 4 or conserved block 4, and optionally comprising: (a) a protoxin tail region of a Bt Cry protein located at the C-terminus; or (b) an N-terminal peptidyl fragment; or both (a) and (b), wherein the eHIP has insecticidal activity against at least western corn rootworm.

In another embodiment, an eHIP according to the invention comprises from N-terminus to C-terminus variable region 1 or a C-terminal portion of variable region 1, conserved block 1, variable region 2, conserved block 2, variable region 3, and an N-terminal portion of conserved block 3 of a first Bt Cry protein fused to a C-terminal portion of conserved block 3, variable region 4, conserved block 4, variable region 5, conserved block 5, and variable region 6 of a second Bt Cry protein.

In another embodiment, an eHIP of the invention comprises at least two crossover positions between an amino acid sequence from the first Bt Cry protein and an amino acid sequence from the second Bt Cry protein. In one embodiment, a first crossover position is located in conserved block 2 and a second crossover position is located in conserved block 3. In another embodiment, a first crossover junction is located in conserved block 3 and a second crossover position is located in conserved block 4.

In another embodiment, an eHIP of the invention comprises at the C-terminus a protoxin tail region of a Bt Cry protein. The protoxin tail region may confer insecticidal activity upon the eHIP, meaning that without the protoxin tail region the eHIP would not be active, may increase activity of the eHIP over an eHIP without the protoxin tail region, or may make the eHIP more stable than an eHIP without the protoxin tail region. In one embodiment, the protoxin tail region is from a lepidopteran active Bt Cry protein. In another embodiment, the protoxin tail region is from a Cry1A protein. In yet another embodiment, the protoxin tail region is from a Cry1Aa or a Cry1Ab protein. The protoxin tail region of the invention may comprise an entire protoxin tail of a Bt Cry protein or any fragment thereof. In one aspect of this embodiment, the protoxin tail region of an eHIP comprises at least 38 amino acids from the N-terminus of a protoxin tail of a Cry1Ab protein. In another aspect of this embodiment, the protoxin tail region comprises an amino acid sequence corresponding to amino acids 611-648 of SEQ ID NO: 72. In still another aspect of this embodiment, the protoxin tail region comprises amino acids 611-648 of SEQ ID NO: 72.

In still another embodiment, an eHIP comprises an N-terminal peptidyl fragment. The N-terminal peptidyl fragment may confer insecticidal activity upon the eHIP, meaning that without the N-terminal peptidyl fragment the protein does not have insecticidal activity, or the N-terminal peptidyl fragment may increase the insecticidal activity of the eHIP over an eHIP without the N-terminal peptidyl fragment, or the N-terminal peptidyl fragment may make the eHIP more stable than an eHIP without an N-terminal peptidyl fragment. In one aspect of this embodiment, the peptidyl fragment comprises an amino acid sequence that is heterologous to (i.e. not derived from) a Bt Cry protein. In another aspect of this embodiment, the N-terminal peptidyl fragment comprises at least 9 amino acids. In yet another aspect of this embodiment, the peptidyl fragment comprises at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90 or 100 amino acids. In another aspect of this embodiment, the peptidyl fragment comprises greater than 100 amino acids. In still another aspect of this embodiment, the N-terminal peptidyl fragment comprises the amino acid sequence YDGRQQHRG (SEQ ID NO: 133) or TSNGRQCAGIRP (SEQ ID NO: 134). In yet another aspect of this embodiment, the N-terminal peptidyl fragment comprises an amino acid sequence selected from the group consisting of SEQ ID NO: 126, SEQ ID NO: 127, SEQ ID NO: 128, SEQ ID NO: 129, SEQ ID NO: 130, SEQ ID NO: 131, and SEQ ID NO: 132.

In yet another embodiment, the variable regions and conserved blocks of a first Cry protein active against coleopteran insects are used to make the eHIP of the invention in combination with variable regions and conserved blocks of a second Cry protein active against a lepidopteran insect. Coleopteran active Cry proteins include but are not limited to Cry3, Cry7, Cry8, and Cry34/Cry35. The lepidopteran active Cry proteins include but are not limited to Cry 1 and Cry9. In one aspect of this embodiment, the first Cry protein is a Cry3A and the second Cry protein is a Cry1A. In another aspect, the Cry3A protein can be replaced with a modified Cry3A, for example without limitation, the Cry3A055 protein disclosed in U.S. Pat. No. 5,659,123, which is herein incorporated by reference. In still another aspect of this embodiment, the Cry3A protein is a Cry3Aa and the Cry1A protein is a Cry1Aa or a Cry1Ab. In another aspect of this embodiment, the Cry3Aa is selected from the following group and has the indicated GenBank Accession Number: Cry3Aa1 (M22472), Cry3Aa2 (J02978), Cry3Aa3 (Y00420), Cry3Aa4 (M30503), Cry3Aa5 (M37207), Cry3Aa6 (U10985), Cry3Aa7 (AJ237900), Cry3Aa8 (AAS79487), Cry3Aa9 (AAW05659), Cry3Aa10 (AAU29411), and Cry3Aa11 (AY882576). In another aspect of this embodiment the Cry1Aa is selected from the following group and has the indicated GenBank Accession Number: Cry1Aa1 (M11250), Cry1Aa2 (M10917), Cry1Aa3 (D00348), Cry1Aa4 (X13535), Cry1Aa5 (D17518), Cry1Aa6 (U43605), Cry1Aa7 (AF081790), Cry1Aa8 (126149), Cry1Aa9 (AB026261), Cry1Aa0 (AF154676), Cry1Aa11 (Y09663), Cry1Aa12 (AF384211), Cry1Aa13 (AF510713), Cry1Aa14(AY197341), and Cry1Aa15 (DQ062690). In still another aspect of this embodiment, the Cry1Ab is selected from the following group and has the indicated GenBank Accession Number: Cry1Ab1 (M13898), Cry1Ab2 (M12661), Cry1Ab3 (M15271), Cry1Ab4 (D00117), Cry1Ab5 (X04698), Cry1Ab6 (M37263), Cry1Ab7 (X13233), Cry1Ab8 (M16463), Cry1Ab9 (X54939), Cry1Ab10 (A29125), Cry1Ab1 (I12419), Cry1Ab12 (AF059670), Cry1Ab13 (AF254640), Cry1Ab14 (U94191), Cry1Ab15 (AF358861), Cry1Ab16 (AF37560), Cry1Ab17 (AAT46415), Cry1Ab18 (AAQ88259), Cry1Ab19 (AY847289), Cry1Ab20

(DQ241675), Cry1Ab21 (EF683163), and Cry1Ab22 (ABW87320). In yet another aspect of this embodiment, the first Cry protein comprises an amino acid sequence selected from the group consisting of SEQ ID NO: 68, SEQ ID NO: 70, and SEQ ID NO: 135, and the second Cry protein comprises an amino acid sequence set forth in SEQ ID NO: 72.

In one embodiment, the present invention encompasses an eHIP of the invention comprising at least one crossover position between the N-terminal region of the first Cry protein and the C-terminal region of the second Cry protein located in conserved block 3, variable region 4, or conserved block 4. In one aspect of this embodiment, the crossover position in conserved block 3 is located immediately following an amino acid corresponding to Ser451, Phe454, or Leu468 of SEQ ID NO: 70. In another aspect of this embodiment, the crossover position is located in conserved block 3 immediately following Ser451, Phe454, or Leu468 of SEQ ID: 70 or Ser450, Phe453, or Leu467 of SEQ ID NO: 68; or Ser497, Phe100, Leu114 of SEQ ID NO: 135. The crossover positions in certain Cry3A/Cry1Ab eHIP embodiments or modified Cry3A/Cry1Ab eHIP embodiments according to the invention are indicated on FIG. 2, which indicates percent identity.

In another embodiment, an eHIP of the invention comprises at least two crossover positions between an amino acid sequence from a first Bt Cry protein and an amino acid sequence from the second Bt Cry protein. In one aspect of this embodiment, a crossover position between a Cry3A or modified Cry3A and a Cry1Ab or a Cry1Aa is located in conserved block 2 immediately following an amino acid corresponding to Asp232 of SEQ ID NO: 70 and a second crossover position between Cry1Ab and Cry3A or modified Cry3A is located in conserved block 3 immediately following an amino acid corresponding to Leu476 of SEQ ID NO: 72. In another aspect of this embodiment, a crossover position between a Cry3A or modified Cry3A and a Cry1Ab or a Cry1Aa is located in conserved block 2 immediately following Asp232 of SEQ ID NO: 70, or Asp231 of SEQ ID NO: 68, or Asp278 of SEQ ID NO: 135, and a second crossover position between Cry1Ab and Cry3A or modified Cry3A is located in conserved block 3 immediately following Leu476 of SEQ ID NO: 72.

In still another aspect of this embodiment, a first crossover position between a Cry3A or modified Cry3A and a Cry1Ab is located in conserved block 3 immediately following an amino acid corresponding to Leu468 of SEQ ID NO: 70 and a second crossover position between a Cry1Ab and a Cry3A or modified Cry3A is located in conserved block 4 immediately following an amino acid corresponding to Ile527 of SEQ ID NO: 72. In another aspect of this embodiment, the first crossover position between a Cry3A or modified Cry3Aa and a Cry1Ab is located in conserved block 3 immediately following an Leu468 of SEQ ID NO: 70, or Leu467 of SEQ ID NO: 68, or Leu114 of SEQ ID NO: 135, and the second crossover position between a Cry1Ab and a Cry3A or modified Cry3A is located in conserved block 4 immediately following Ile527 of SEQ ID NO: 72. In yet another aspect of this embodiment, the eHIP comprises the amino acid sequence of SEQ ID NO: 28 or SEQ ID NO: 34.

In one embodiment, the present invention encompasses an eHIP wherein the first Cry protein is a Cry3A or a modified Cry3A and the second Cry protein is a Cry1Aa or Cry1Ab and wherein the eHIP comprises an amino acid sequence that has at least 80% identity to SEQ OD NO: 64. In another embodiment the eHIP comprises an amino acid sequence that has at least 81, 82, 83, 84, 85, 86, 87, 88, 89, 90, 91, 92, 93, 94, 95, 96, 97, 98 or 99% identity to SEQ ID NO: 64. An alignment of certain eHIP embodiments of the invention with SEQ ID NO: 64 is shown in FIG. 2, which indicates percent identity.

In another embodiment, the present invention encompasses an eHIP wherein the first Cry protein is a Cry3A or a modified Cry3A and the second Cry protein is a Cry1Aa or Cry1Ab and wherein the eHIP comprises an amino acid sequence that has at least 75% identity to SEQ OD NO: 70. In another embodiment the eHIP comprises an amino acid sequence that has at least 76, 77, 78, 79, 80, 81, 82, 83, 84, 85, 86, 87, 88, 89, 90, 91, 92, 93, 94, 95, 96, 97, 98 or 99% identity to SEQ ID NO: 70. An alignment of certain eHIP embodiments of the invention with SEQ ID NO: 70 is shown in FIG. 1, which indicates percent identity.

In another embodiment, the present invention encompasses an eHIP having a first crossover position between Cry3A or modified Cry3A and Cry1Aa or Cry1Ab in conserved block 2 and a second crossover position between Cry1Aa or Cry1Ab and Cry3A or modified Cry3A in conserved block 3 and wherein the eHIP comprises an amino acid sequence that has at least 56% identity to SEQ OD NO: 64. In one aspect of this embodiment, the eHIP has at least 60, 70 or 80% identity to SEQ ID NO: 64. In another aspect of this embodiment, the eHIP has at least 81, 82, 83, 84, 85, 86, 87, 88, 89, 90, 91, 92, 93, 94, 95, 96, 97, 98 or 99% identity to SEQ ID NO: 64.

In yet another embodiment, the present invention encompasses an eHIP comprising an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 16, SEQ ID NO: 18, SEQ ID NO: 22, SEQ ID NO: 24, SEQ ID NO: 30, SEQ ID NO: 34, SEQ ID NO: 62; SEQ ID NO: 64, SEQ ID NO: 147, SEQ ID NO: 153, SEQ ID NO: 155, SEQ ID NO: 159 and SEQ ID NO: 160.

In one embodiment, the eHIPs of the invention have activity against other insect pests including but not limited to northern corn rootworm, Mexican corn rootworm, Colorado potato beetle, and/or European corn borer.

In another embodiment, the present invention encompasses a nucleic acid molecule comprising a nucleotide sequence that encodes an eHIP of the invention. In one aspect of this embodiment, the nucleic acid molecule comprises a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 15, SEQ ID NO: 17, SEQ ID NO: 21, SEQ ID NO: 23, SEQ ID NO: 29, SEQ ID NO: 33, SEQ ID NO: 61; SEQ ID NO: 63, SEQ ID NO: 146, SEQ ID NO: 152, SEQ ID NO: 154 and SEQ ID NO: 158. Specifically exemplified teachings of methods to make nucleic acid molecules that encode eHIPs can be found in Examples 1-41. Those skilled in the art will recognize that modifications can be made to the exemplified methods to make eHIPs encompassed by the present invention.

The present invention further encompasses expression cassettes comprising the nucleic acid molecules, and recombinant vectors and transgenic non-human host cells, such as bacterial cells or plant cells, comprising the expression cassettes of the invention.

The present invention also encompasses recombinant vectors comprising the nucleic acids of this invention. In such vectors, the nucleic acids are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acids of the present invention. Vectors comprising the nucleic acids are may be capable of replication in particular host cells, preferably as extrachromosomal molecules, and are therefore used to amplify the nucleic acids of this invention in the host cells. In one embodiment, host cells for such vectors are microorganisms, such as bacteria, in particular *Bacillus thuringiensis* or *E. coli*. In another embodiment, host cells for such recombinant vectors are endophytes or epiphytes. In yet another embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of a transgenic host. In one embodiment, the transgenic host is plant such as corn plant.

The eHIPs of the present invention have insect control activity when tested against insect pests in bioassays. In one embodiment, the eHIPs of the invention are active against coleopteran insects or lepidopteran insects or both. In one aspect of this embodiment, the eHIPs of the invention are active against western corn rootworm, northern corn rootworm, Mexican corn rootworm and/or Colorado potato beetle. In another aspect of this embodiment, the eHIPs of the invention are active against European corn borer. The insect controlling properties of the eHIPs of the invention are further illustrated in Examples 43, 45 and 46.

The present invention also encompasses a composition comprising an effective insect-controlling amount of an eHIP according to the invention.

In another embodiment, the invention encompasses a method of producing a eHIP that is active against insects, comprising: (a) obtaining a host cell comprising a gene, which itself comprises a heterologous promoter sequence operatively linked to a nucleic acid molecule of the invention; and (b) growing the transgenic host cell in such a manner to express an eHIP that is active against insects.

In yet another embodiment, the invention encompasses a method of producing an insect-resistant transgenic plant, comprising introducing a nucleic acid molecule of the invention into the transgenic plant, wherein the nucleic acid molecule causes the expression of an eHIP in the transgenic plant in an effective amount to control insects. In one aspect of this embodiment, the insects are coleopteran insects or lepidopteran insects. In another aspect of this embodiment, the coleopteran insects are western corn rootworm, northern corn rootworm, Mexican corn rootworm and/or Colorado potato beetle. In still another aspect of this embodiment, the lepidopteran insects are European corn borer.

In yet a further embodiment, the invention encompasses a method of controlling insects, comprising delivering to the insects an effective amount of an eHIP of the invention. In one aspect of this embodiment, the insects are coleopteran insects or lepidopteran insects. In another aspect of this embodiment, the coleopteran insects are western corn rootworm, northern corn rootworm, Mexican corn rootworm and/or Colorado potato beetle. In still another aspect of this embodiment, the lepidopteran insects are European corn borer. Typically, the eHIP is delivered to the insects orally. In one aspect, the eHIP is delivered orally through a transgenic plant comprising a nucleic acid sequence that expresses an eHIP of the present invention.

The present invention further encompasses a method of controlling insects wherein the transgenic plant further comprises a second nucleic acid molecule or groups of nucleic acid molecules that encode a second pesticidal principle. Examples of such second nucleic acids are those that encode a Bt Cry protein, those that encode a Vegetative Insecticidal Protein, disclosed in U.S. Pat. Nos. 5,849,870 and 5,877,012, incorporated herein by reference, or those that encode a pathway for the production of a non-proteinaceous principle.

The present invention also encompasses a method of making an engineered hybrid insecticidal protein (eHIP), comprising: (a) obtaining a first Bt Cry protein or modified Bt Cry protein; (b) obtaining a second Bt Cry protein which is different from the first Bt Cry protein or modified Bt Cry protein; (c) combining complete or partial variable regions and conserved blocks of the first Bt Cry protein or modified Bt Cry protein with complete or partial variable regions and conserved blocks of the second Bt Cry protein to make an eHIP that has activity against at least western corn rootworm; and optionally (d) inserting a peptidyl fragment at the N-terminus or a protoxin tail region of a Bt Cry protein at the C-terminus of the eHIP, or both, wherein the N-terminal peptidyl fragment or the C-terminal protoxin region or both confers activity upon the eHIP, or increases the insecticidal activity of the eHIP or makes the eHIP more stable than an eHIP without the peptidyl fragment or protoxin tail region or both.

In another embodiment, the present invention encompasses a method of making an engineered hybrid insecticidal protein (eHIP) comprising: (a) obtaining a first nucleic acid encoding a first Bt Cry protein or modified Bt Cry protein and a second nucleic acid encoding a second Cry protein different from the first Cry protein or modified Bt Cry protein; (b) isolating from the first and second nucleic acids, a nucleotide sequence that encodes complete or partial variable regions and conserved blocks of the first Bt Cry protein or modified Bt Cry protein and the second Bt Cry protein; (c) connecting together the resulting isolated nucleic acids of step (b) in such a way as to make a new hybrid nucleic acid that encodes a protein, and optionally fusing to a 5' end of said hybrid nucleic acid a nucleic acid that encodes a peptidyl fragment resulting in a 5' extension or fusing to a 3' end of said hybrid nucleic acid a nucleic acid that encodes a protoxin tail region of a Bt Cry protein resulting in a 3' extension, or both; (d) inserting the hybrid nucleic acid with or without one or both of the 5' or 3' extensions into an expression cassette; (e) transforming the expression cassette into a host cell, resulting in said host cell producing an eHIP; and (f) bioassaying the eHIP against at least western corn rootworm, which results in insecticidal activity against western corn rootworm.

In further embodiments of the methods of the invention, the first Bt Cry protein or modified Bt Cry protein is a Cry3A or modified Cry3A and the second Bt Cry protein is A Cry1Aa or Cry1Ab.

In another embodiment of the methods of the invention, the N-terminal peptidyl fragment comprises at 9 amino acids. In one aspect of this embodiment the N-terminal peptidyl fragment comprises the amino acid sequence YDGRQQHRG (SEQ ID NO: 132) or the amino acid sequence TSNGRQCAGIRP (SEQ ID NO: 133). In another aspect of this embodiment the N-terminal peptidyl fragment is selected from the group consisting of SEQ ID NO: 126, SEQ ID NO: 127, SEQ ID NO: 128, SEQ ID NO: 129, SEQ ID NO: 130, SEQ ID NO: 131, and SEQ ID NO: 132.

In still another embodiment of the methods of the invention, the protoxin tail region is from a Cry1Aa or Cry1Ab. In one aspect of this embodiment, the protoxin tail region comprises at least 38 amino acids. In another aspect of this embodiment, the protoxin tail region comprises an amino acid sequence that corresponds to amino acids 611-648 of SEQ ID NO: 72. In yet another aspect of this embodiment, the protoxin tail region comprises amino acids 611-648 of SEQ ID NO: 72.

Specifically exemplified teachings of the methods of making the hybrid nucleic acids and the eHIPs of the invention can be found in Examples 1-41.

In further embodiments, the nucleotide sequences of the invention, particularly a sequence encoding the peptidyl fragment, the protoxin tail, and/or conserved blocks 2, 3, and 4, can be further modified by incorporation of random mutations in a technique known as in vitro recombination or DNA shuffling. This technique is described in Stemmer et al., Nature 370:389-391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or ranges of target-insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

As biological insect control agents, the eHIPs are produced by expression of the nucleic acids in heterologous host cells capable of expressing the nucleic acids. In one embodiment, *B. thuringiensis* cells comprising modifications of a nucleic acid of this invention are made. Such modifications encompass mutations or deletions of existing regulatory elements, thus leading to altered expression of the nucleic acid, or the incorporation of new regulatory elements controlling the expression of the nucleic acid. In another embodiment, additional copies of one or more of the nucleic acids are added to *Bacillus thuringiensis* cells either by insertion into the chromosome or by introduction of extrachromosomally replicating molecules containing the nucleic acids.

In another embodiment, at least one of the nucleic acids of the invention is inserted into an appropriate expression cassette, comprising a promoter and termination signal. Expression of the nucleic acid is constitutive, or an inducible promoter responding to various types of stimuli to initiate transcription is used. In another embodiment, the cell in which the eHIP is expressed is a microorganism, such as a virus, bacteria, or a fungus. In yet another embodiment, a virus, such as a baculovirus, contains a nucleic acid of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In:Industrial microorganisms:basic and applied molecular genetics, Baltz, Hegeman, and Skatrud eds., American Society for Microbiology, Washington (1993); Dequin & Barre, Biotechnology L2:173-177 (1994); van den Berg et al., Biotechnology 8:135-139 (1990)).

In one embodiment, at least one of the eHIPs of the invention is expressed in a higher organism such as a plant. In this case, transgenic plants expressing effective amounts of the eHIP protect themselves from insect pests. When the insect starts feeding on such a transgenic plant, it also ingests the expressed eHIP. This will deter the insect from further biting into the plant tissue or may even harm or kill the insect. A nucleic acid of the present invention is inserted into an expression cassette, which may then be stably integrated in the genome of the plant. In another embodiment, the nucleic acid is included in a non-pathogenic self-replicating virus. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, *papaya*, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleic acid has been transformed into a particular plant species, it may be propagated in that species or moved into other varieties of the same species, particularly including commercial varieties, using traditional breeding techniques.

A nucleic acid of this invention is preferably expressed in transgenic plants, thus causing the biosynthesis of the corresponding eHIP in the transgenic plants. In this way, transgenic plants with enhanced resistance to insects, particularly corn rootworm, are generated. For their expression in transgenic plants, the nucleic acids of the invention may require other modifications and optimization. Although in many cases genes from microbial organisms can be expressed in plants at high levels without modification, low expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above are made using well known techniques of site directed mutagenesis, PCR, and synthetic gene construction using the methods described in the published patent applications EP 0 385 962, EP 0 359 472, and WO 93/07278.

In one embodiment of the invention an eHIP coding sequence and/or a parent Bt Cry protein coding sequence is/are made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference.

In this manner, the nucleotide sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleic acids of this invention. The sequences are incorporated into constructions comprising the nucleic acids, up to and including the ATG (whilst leaving the second amino acid unmodified), or alternatively up to and including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In one embodiment promoters are used that are expressed constitutively including the actin or ubiquitin or cmp promoters or the CaMV 35S and 19S promoters. The nucleic acids of this invention can also be expressed under the regulation of promoters that are chemically regulated. This enables the eHIPs to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

In another embodiment a category of promoters which is wound inducible can be used. Numerous promoters have been described which are expressed at wound sites and also at the sites of phytopathogen infection. Ideally, such a promoter should only be active locally at the sites of infection, and in this way the eHIPs only accumulate in cells that need to synthesize the eHIPs to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding eHIPs in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U. S. patents are herein incorporated by reference in their entirety.

Further embodiments are transgenic plants expressing the nucleic acids in a wound-inducible or pathogen infection-inducible manner.

In addition to promoters, a variety of transcriptional terminators are also available for use in hybrid nucleic acid construction using the eHIP genes of the present invention. Transcriptional terminators are responsible for the termination of transcription beyond the transgene and its correct polyadenylation. Appropriate transcriptional terminators and those that are known to function in plants include the CaMV 35S terminator, the tml terminator, the nopaline synthase (NOS) terminator, the pea rbcS E9 terminator and others known in the art. These can be used in both monocotyledons and dicotyledons. Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the eHIP genes of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In another embodiment, a nucleic acid of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

The eHIPs of the invention can be used in combination with other pesticidal principles (e.g. Bt Cry proteins) to increase pest target range. Furthermore, the use of the eHIPs of the invention in combination with modified Cry3A toxins, Bt Cry proteins, or other CRW-active principles, such as an RNAi, which have a different mode of action or target a different receptor in the insect gut, has particular utility for the prevention and/or management of corn rootworm resistance. Other insecticidal principles include, but are not limited to, lectins, α-amylase, peroxidase, and cholesterol oxidase. Vip genes, as disclosed in U.S. Pat. No. 5,889,174 and herein incorporated by reference, are also useful in combination with the eHIPs of the present invention.

This co-expression of more than one insecticidal principle in the same transgenic plant can be achieved by making a single recombinant vector comprising coding sequences of more than one insecticidal principle in a so called molecular stack and genetically engineering a plant to contain and express all the insecticidal principles in the transgenic plant. Such molecular stacks may be also be made by using mini-chromosomes as described, for example in U.S. Pat. No. 7,235,716. Alternatively, a transgenic plant comprising one nucleic acid encoding a first insecticidal principle can be re-transformed with a different nucleic acid encoding a second insecticidal principle and so forth. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2.

Transgenic seed of the present invention can also be treated with an insecticidal seed coating as described in U.S. Pat. Nos. 5,849,320 and 5,876,739, herein incorporated by reference. Where both the insecticidal seed coating and the transgenic seed of the invention are active against the same target insect, the combination is useful (i) in a method for enhancing activity of a eHIP of the invention against the target insect and (ii) in a method for preventing development of resistance to a eHIP of the invention by providing a second mechanism of action against the target insect. Thus, the invention provides a method of enhancing activity against or preventing development of resistance in a target insect, for example corn rootworm, comprising applying an insecticidal seed coating to a transgenic seed comprising one or more eHIPs of the invention.

Even where the insecticidal seed coating is active against a different insect, the insecticidal seed coating is useful to expand the range of insect control, for example by adding an insecticidal seed coating that has activity against lepidopteran insects to the transgenic seed of the invention, which has activity against coleopteran insects, the coated transgenic seed produced controls both lepidopteran and coleopteran insect pests.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., Molecular Cloning: *A Laboratory Manual, 3d Ed.*, Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1. Parental Coding Sequences

Maize optimized cry3Aa, cry1Ab, cry1Ba, and cry1Fa coding sequences; designated herein mocry3Aa, mocry1Ab, mocry1Ba and mocry1Fa, respectively, were made according to the procedure disclosed in U.S. Pat. No. 5,625,136, herein incorporated by reference in its entirety.

The cry3A055 (SEQ ID NO: 67) coding sequence, which encodes a Cry3A055 protein (SEQ ID NO: 68) was made by modifying the mocry3A coding sequence by inserting a nucleotide sequence that encodes a Cathepsin G protease recognition site into domain I according to U.S. Pat. No. 7,030,295, herein incorporated by reference in its entirety.

The mocry3Aa (SEQ ID NO: 67), which encodes the protein set forth in SEQ ID NO: 68, cry3A055 (SEQ ID NO: 69), which encodes the protein set forth in SEQ ID NO: 70, mocry1Ab (SEQ ID NO: 71), which encodes the protein set forth in SEQ ID NO: 72, mocry1Ba (SEQ ID NO: 73), which encodes the protein set forth in SEQ ID NO: 74, mocry1Fa (SEQ ID NO: 75), which encodes the protein set forth in SEQ ID NO: 76, cry8Aa (SEQ ID NO: 77), which encodes the protein set forth in SEQ ID NO: 78, cry1Ac (SEQ ID NO: 79), which encodes the protein set forth in SEQ ID NO: 80, and cry1Ia (SEQ ID NO: 81), which encodes the protein set forth in SEQ ID NO: 82, were used in the construction of the hybrid nucleic acids and the proteins which they encode and described in the following Examples.

Example 2. Use of PCR Primers to Construct Hybrid Nucleic Acids

Polymerase Chain Reaction (PCR) is a repetitive, enzymatic, primed synthesis of a nucleic acid sequence. This procedure is well known and commonly used by those skilled in this art (See Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of .beta.-Globin Genomic Sequences and Restriction Site Analysis for Diagnosis of Sickle Cell Anemia," Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The chimeric coding sequences described in the following examples were constructed using various combinations of the exemplified primers shown in Table 1. The PCR reaction mixes and PCR thermocycling protocols used in the experiments are listed in Tables 2 and 3, respectively. In each of the examples that follow, the PCR primers are referred to by name and "SEQ ID NO:" and the PCR reaction mixes and PCR thermocycling protocols are referred to by their respective numbers. It will be recognized by the skilled person that other PCR primers and PCR reaction conditions can be used to construct the chimeric coding sequences of the invention and by listing the exemplified primers and PCR conditions that were used in the instant invention is not meant to be limiting in any way.

TABLE 1

Primers used to construct the coding sequences encoding eHIPs.

| Primer Name | Sequence | SEQ ID NO: |
|---|---|---|
| 5'3A-1-bam | 5'-CCGGATCCATGACGGCC GACAACAACACCGAGGC-3' | SEQ ID NO: 83 |
| C3-3A-6 | 5'-CAGGGGCAGCTGGGTG ATCT-3' | SEQ ID NO: 84 |
| C3-1Ab-3 | 5'-AGATCACCCAGATCCC CCTG-3' | SEQ ID NO: 85 |
| 1Ab-6-sac | 5'-CCGAGCTCAGCTCCTAC ACCTGATCGATGTGGTAGTC GG-3' | SEQ ID NO: 86 |
| 8A-atg-delRI | 5'-CCGGATCCACCATGACT AGTAACGGCCGCCAGTGTGC TGGTATTCGCCCTTATGAC-3' | SEQ ID NO: 87 |
| C2-3A-4 | 5'-GTCCAGCACGGTCAGGGT CA-3' | SEQ ID NO: 88 |
| reverse | 5'-GCGTGCAGTCAAGTCAGA TC-3' | SEQ ID NO: 89 |
| FR8a-OL-1 | 5'-GGTGTTGTTGTCGGCCGT CATAGGGCGAATACCAGCAC-3' | SEQ ID NO: 90 |
| FR8a-OL-2 | 5'-GCCGACAACAACACCGAG GCCCTGGACAGCAGCACCACC-3' | SEQ ID NO: 91 |
| C1-3A-2 | 5'-CAGGTGGGTGTTGGCGGC CTGGGCGTA-3' | SEQ ID NO: 92 |
| 5'FR8a | 5'-GGATCCACCATGACTAG TAAC-3' | SEQ ID NO: 93 |
| 5'FR8a-12aa | 5'-CCGGATCCACCATGTATG ACGGCCGACAACAACACC-3' | SEQ ID NO: 94 |
| C2-3A-3 | 5'-TGACCCTGACCGTGCTGG AC-3' | SEQ ID NO: 95 |
| 3'1Ab-dm3 | 5'-GAGCTCCTAGGTCACCT CGGCGGGCAC-3' | SEQ ID NO: 96 |
| 5'FR-del6 | 5'-GGATCCACCATGTGTGC TGGTATTCGCCCTAT-3' | SEQ ID NO: 97 |
| 5'1Ab-bam | 5'-CCGGATCCATGGACAAC AACCCAACATCAAC-3' | SEQ ID NO: 98 |
| C3-3A-8 | 5'-GATGTCGCCGCCGGTGA AGC-3' | SEQ ID NO: 99 |
| C3-3A-7 | 5'-GCTTCACCGGCGGCGAC ATC-3' | SEQ ID NO: 100 |
| 1B-5 | 5'-CCGCCGCGACCTGACCC TGGGCGTGCTGGAC-3' | SEQ ID NO: 101 |
| 1B-10 | 5'-CCGAGCTCCTAGAACAG GGCGTTCAC-3' | SEQ ID NO: 102 |
| 3A-22 | 5'-GGCCTTCACCAGGGGCA GCTGGGTGAT-3' | SEQ ID NO: 103 |
| 1B-7 | 5'-ATCACCCAGATCCCCAT GGTGAAGGCC-3' | SEQ ID NO: 104 |
| C3-1Ab-2 | 5'-CAGGGGGATCTGGGTGA TCT-3' | SEQ ID NO: 105 |
| C3-3A-5 | 5'-AGATCACCCAGCTGCCC CTG-3' | SEQ ID NO: 106 |
| 3A-12-sac | 5'-CCGAGCTCAGCTCAGATC TAGTTCACGGGGATGAACTCG ATCTT-3' | SEQ ID NO: 107 |
| C4-3A-10 | 5'-TGGTGCTGGCGTAGTGGA TGCGG-3' | SEQ ID NO: 108 |
| C4-3A-9 | 5'-CCGCATCCACTACGCCAG CACCA-3' | SEQ ID NO: 109 |
| C1-1Ab-1 | 5'-TACGTGCAGGCCGCCAAC CTGCACCTG-3' | SEQ ID NO: 110 |
| 5'8Aa-dm3 | 5'-AGATCACCCAGCTGCCCC TGGTAAAGGGAGACATGTTAT ATC-3' | SEQ ID NO: 111 |
| 3'8Aa-dm3 | 5'-GAGCTCCTATGT CTCATCTACTGGGAT GAA-3' | SEQ ID NO: 112 |
| tant-OL-2 | 5'-GAGGGTGTGGGCC TTCACCAGGGGCAGCT GGGT-3' | SEQ ID NO: 113 |
| tant-OL-1 | 5'-ACCCAGCTGCCCC TGGTGAAGGCCCACAC CCTC-3' | SEQ ID NO: 114 |
| tant-3'sac | 5'-GAGCTCTAGCTTA AGCAGTCCACGAGGT T-3' | SEQ ID NO: 115 |
| 1Ac-OL-2 | 5'-TAAAAAGAAAGTT TCCCTTCACCAGGGGC AGCTGGGT-3' | SEQ ID NO: 116 |
| 1Ac-OL-1 | 5'-ACCCAGCTGCCCC TGGTGAAGGGAAACTT TCTTTTTA-3' | SEQ ID NO: 117 |
| 1Ac-3'sac | 5'-GAGCTCCTATGTT GCAGTAACTGGAATAA A-3' | SEQ ID NO: 118 |
| 1Ia-OL-2 | 5'-AAGACAGATTGAA AGCTTTTACTCAGGGG CAGCTGGGT-3' | SEQ ID NO: 119 |
| 1Ia-OL-1 | 5'-ACCCAGCTGCCCC TGAGTAAAAGCTTTCA ATCTGTCTT-3' | SEQ ID NO: 120 |
| 1Ia-3'sac | 5'-GAGCTCCTACATG TTACGCTCAATATGGA GT-3' | SEQ ID NO: 121 |
| FR-1Ab-2 | 5'-GATGTTGTTGAAC TCGCCGCTCTTGTGGC TCCA-3' | SEQ ID NO: 122 |
| FR-1Ab-1 | 5'-TGGACCCACAAGA GCGCCGAGTTCAACAA CATC-3' | SEQ ID NO: 123 |

TABLE 1-continued

Primers used to construct the coding sequences encoding eHIPs.

| Primer Name | Sequence | SEQ ID NO: |
|---|---|---|
| FR-1Ab-4 | 5'-GGCTCGTGGGGAT GATGTTGTTGAAGTCG ACGCTCTTGTGG-3' | SEQ ID NO: 124 |
| FR-1Ab-3 | 5'-CCACAAGAGCGTC GACTTCAACACATCAT CCCCAGCAGCC-3' | SEQ ID NO: 125 |
| CMS94 | 5'-GGCGCGCCACCAT GGCTAGCATGACTGGT GG-3' | SEQ ID NO: 136 |
| CMS95 | 5'-GCAGGAACAGGTG GGTGTTG-3' | SEQ ID NO: 137 |
| CMS96 | 5'-CCTGAACACCATC TGGCCCA-3' | SEQ ID NO: 138 |
| CMS97 | 5'-CTGGCTGCTGGGG ATGATGTTGTTGAAGT CGACGCTCTT-3' | SEQ ID NO: 139 |
| CMS98 | 5'-GAGCTCTTAGGTC ACCTCGGC-3' | SEQ ID NO: 140 |
| CMS99 | 5'-AAGAGCGTCGACT TCAACAACATCATCCC CAGCAGCCAG-3' | SEQ ID NO: 141 |
| CMS100 | 5'-GAAGTACCGCGCC CGCATCCGCTACGCCA GCACCACCAAC-3' | SEQ ID NO: 142 |
| CMS101 | 5'-GTTGGTGGTGCTG GCGTAGCGGATGCGGG CGCGGTACTTC-3' | SEQ ID NO: 143 |

TABLE 2

PCR reaction mixes.

| Mix 1 | Mix 2 |
|---|---|
| 50-100 ng template DNA<br>0.8 µM primer 1<br>0.8 µM primer 2<br>1X Pfu buffer<br>0.4 mM dNTPs<br>2% formamide<br>1.25 units Pfu Polymerase (Stratagene)<br>2.5 units Taq Polymerase (Qiagen)<br>water to a total volume of 50 µl | 50-100 ng template DNA<br>0.8 µM primer 1<br>0.8 µM primer 2<br>1X Taq buffer<br>0.4 mM dNTPs<br>2% formamide<br>2.5 units Taq Polymerase (Qiagen)<br>water to a total volume of 50 µl |

| Mix 3 | Mix 4 |
|---|---|
| 50-100 ng template DNA<br>0.8 µM primer 1<br>0.8 µM primer 2<br>1X cDNA Advantage buffer<br>0.4 mM dNTPs<br>x units cDNA Advantage Polymerase (Clontech)<br>water to a total volume of 50 µl | 50-100 ng template DNA<br>0.4 µM primer 1<br>0.4 µM primer 2<br>1X PCR buffer (Invitrogen)<br>0.4 mM dNTPs<br>2.5 units HotStart Taq Polymerase<br>water to a total volume of 50 µl |

TABLE 2-continued

PCR reaction mixes.

| Mix 5 |
|---|
| 50-100 ng template DNA<br>0.4 µM primer 1<br>0.4 µM primer 2<br>1X Pfu buffer (Stratagene)<br>0.2 mM dNTPs<br>1.25 units Pfu Turbo Polymerase<br>water to a total volume of 50 µl |

TABLE 3

PCR thermocycling profiles.

| Thermocycle Profile 1 | Thermocycle Profile 2 | Thermocycle Profile 3 |
|---|---|---|
| 94° C. –5 minutes<br>20 cycles:<br>94° C. –30 seconds<br>65° C. –30 seconds<br>72° C. –30 seconds<br>72° C. –7 minutes<br>hold at 4° C. | 94° C. –5 minutes<br>20 cycles:<br>94° C. –30 seconds<br>55° C. –30 seconds<br>72° C. –30 seconds<br>72° C. –7 minutes<br>hold at 4° C. | 94° C. –5 minutes<br>20 cycles:<br>94° C. –30 seconds<br>55° C. –30 seconds<br>68° C. –30 seconds<br>68° C. –7 minutes<br>hold at 4° C. |

| Thermocycle Profile 4 | Thermocycle Profile 5 | Thermocycle Profile 6 |
|---|---|---|
| 94° C. –15 minutes<br>20 cycles:<br>94° C. –30 seconds<br>50-70° C. –30 seconds<br>72° C. –30 seconds<br>72° C. –7 minutes<br>hold at 4° C. | 94° C. –5 minutes<br>20 cycles:<br>94° C. –30 seconds<br>55-75° C. –30 seconds<br>72° C. –1 minute<br>72° C. –15 minutes<br>hold at 4° C. | 94° C. –5 minutes<br>20 cycles:<br>94° C. –30 seconds<br>55-75° C. –30 seconds<br>72° C. –2 minutes<br>72° C. –15 minutes<br>hold at 4° C. |

Table 4 shows the relationship between the three domains of Cry3A055, Cry1Ab and Cry3A with their respective variable regions and conserved blocks. The amino acids comprised in the domains, conserved blocks and variable regions are shown for each protein.

TABLE 4

| DOMAIN | REGION | Cry3A055 (SEQ ID NO: 70) | Cry1Ab (SEQ ID NO: 72) | Cry3A (SEQ ID NO: 68) | Cry3A (SEQ ID NO: 131) |
|---|---|---|---|---|---|
| I | V1 | 1-10 | 1-32 | 1-10 | 1-57 |
|  | V1 | 11-142 | 33-152 | 11-141 | 58-188 |
|  | CB1 | 143-172 | 153-182 | 142-171 | 189-218 |
|  | V2 | 173-192 | 183-202 | 172-191 | 219-238 |
|  | CB2 | 193-244 | 203-254 | 192-243 | 239-290 |
| II |  | 245-259 | 255-269 | 244-258 | 291-305 |
|  | V3 | 260-444 | 270-452 | 259-443 | 306-490 |
|  | CB3 | 445-454 | 453-462 | 444-453 | 491-500 |
| III |  | 455-492 | 463-500 | 454-491 | 501-538 |
|  | V4 | 493-513 | 501-520 | 492-512 | 539-559 |
|  | CB4 | 514-523 | 521-531 | 513-522 | 560-569 |
|  | V5 | 524-586 | 532-596 | 523-585 | 570-632 |
|  | CB5 | 587-598 | 597-606 | 586-597 | 633-644 |
|  | V6 |  | 607-610 |  |  |
|  | Protoxin |  | 611-648 |  |  |

Example 3. Construction of 2OL-8a

A first nucleic acid fragment encoding an N-terminal portion of a Cry3A055 protein (SEQ ID NO: 70) was PCR amplified from a plasmid comprising cry3A055 (SEQ ID NO: 69) using primers 5'3A-1-bam (SEQ ID NO: 83) and C3-3A-6 (SEQ ID NO: 84) and PCR reaction Mix 1 and thermocycle Profile 1. This PCR reaction introduced a point mutation by deleting nucleotide 28 of SEQ ID NO: 69 (cry3A055), which caused a frame shift in the cry3A055 reading frame, and deleted the BamHI site and Kozak sequence (Kozak, M., 1986. Cell 44:283-92) at the 5' end of the resulting amplicon.

A second nucleic acid fragment encoding a C-terminal portion of a Cry1Ab protein (SEQ ID NO: 72) was PCR amplified from a plasmid comprising mocry1Ab (SEQ ID NO: 71) using primers C3-1Ab-3 (SEQ ID NO: 85) and 1Ab-6-Sac (SEQ ID NO: 86) and PCR reaction Mix 1 and thermocycle Profile 1.

The first and second nucleic acids described above were connected by using them as templates in an overlap PCR reaction (Horton et al., 1989. Gene 77: 61-68) with the primers 5'3A-1-bam (SEQ ID NO: 83) and 1Ab-6-Sac (SEQ ID NO: 86) using PCR reaction Mix 2 and thermocycle Profile 1, except a 45-65° C. gradient was used for the annealing temperature.

The resulting amplicon was ligated as a blunt ended fragment to a pCR2.1-TOPO vector (Invitrogen, Carlsbad, Calif.) cut with SmaI to form plasmid p2OL8a/CR2.1. A BamHI-SacI fragment from p2OL8a/CR2.1 was then ligated to pET21a (EMD Biosciences, Inc., San Diego, Calif.), which was cut with BamHI-SacI, and transformed into E. coli. The BamHI-SacI fragment from p2OL8a/CR2.1 comprised 40 nucleotides derived from the pCR2.1-TOPO vector adjacent to the out of frame amplicon from the first PCR reaction. Ligating this BamHI-SacI fragment to pET21a created an open reading frame starting with the start codon (ATG) of a T7 tag and ending with the SacI site of the inserted DNA. This open reading frame was designated 2OL-8a (SEQ ID NO: 1) and encodes the 2OL-8a chimeric insecticidal protein (SEQ ID NO: 2). Thus, the 2OL-8a chimeric insecticidal protein comprises, from N-terminus to C-terminus, a peptidyl fragment comprising the amino acid sequence MASMTGGQQMGRGSTSNGRQCA-GIRPYDGRQQHRG (SEQ ID NO: 126), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The nucleotides that encode amino acids 1-14 of the peptidyl fragment are derived from the T7-tag and the BamHI cleavage site of the pET21a vector. The nucleotides that encode amino acids 15-26 of the peptidyl fragment are derived from the pCR2.1-TOPO vector. And the nucleotides that encode amino acids 27-35 of the peptidyl fragment are derived from cry3A055 which are out of frame with the remainder of the cry3A055 coding sequence.

Example 4. Construction of FR8a

The FR8a coding sequence was constructed by placing a Kozak sequence (ACC) and a start codon (ATG) just downstream of an N-terminal BamHI site in 2OL-8a (See Example 3). In addition, an EcoRI site in 2OL-8a was disrupted to aid in future vectoring of FR8a. All of these changes were made using one PCR reaction with 2OL-8a as the template and the primers: 8a-atg-delRI (SEQ ID NO: 87) and C2-3A-4 (SEQ ID NO: 88) using PCR reaction Mix 2 and thermocycle Profile 2.

The resulting amplicon was ligated to a pCR2.1-TOPO vector (Invitrogen). A BamHI-PpuMI fragment from the cloned PCR product was then ligated to a PpuMI-NcoI fragment from 2OL8a/pCR2.1 (See Example 3) and a NcoI-BamHI fragment from 2OL8a/pCR2.1 to create FR8a (SEQ ID NO: 3) which encodes the FR8a chimeric insecticidal protein (SEQ ID NO: 4). Thus, the FR8a chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a eHIP was very active against western corn rootworm as shown in Table 5. Therefore, elimination of the T7 amino acid sequence from the N-terminal peptidyl fragment from the 2OL-8a eHIP did not have a negative impact on insecticidal activity.

Adding an additional 34 amino acids to the N-terminus of FR8a created a eHIP, designated FR8a+34 (SEQ ID NO: 160), with an N-terminal peptidyl fragment of 56 amino acids (SEQ ID NO: 131). The 56 amino acid N-terminal prptidyl fragment had no negative effect on activity of FR8a against western corn rootworm (See Table 5).

Example 5. Construction of FRCG

In order to determine if a cathepsin G protease recognition site was necessary for the insecticidal activity of a hybrid protein comprising an N-terminal fragment of Cry3A055, a construct was made which eliminated the cathepsin G site from the FR8a hybrid protein (Example 4). A first MluI-PpuMI nucleic acid fragment from a plasmid comprising FR8a (SEQ ID NO: 3) and a second PpuMI/MuI nucleic acid fragment from a plasmid comprising mocry3Aa (SEQ ID NO: 67) were ligated using standard molecular biology techniques to create FRCG (also designated FR8a-catg) (SEQ ID NO: 5) which encodes the FRCG hybrid protein (SEQ ID NO: 6). Thus, the FRCG chimeric insecticidal protein comprises, from N-terminus to C-terminus, a peptidyl fragment comprising the amino acid sequence MTSN-GRQCAGIRPYDGRQQHRG (SEQ ID NO: 127), amino acids 10-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FRCG protein was as active against western corn rootworm as the FR8a protein (See Table 5) suggesting that a cathepsin G protease site is not required for insecticidal activity of a eHIP.

Example 6. Construction of FR8a-9F

A first approximately 323 bp nucleic acid fragment was PCR amplified from a plasmid comprising FR8a (SEQ ID NO: 3) using primers reverse (SEQ ID NO: 89) and FR8a-

OL-1 (SEQ ID NO: 90) and PCR reaction Mix 2 and thermocycle Profile 2. A second approximately 470 bp nucleic acid fragment was PCR amplified from a plasmid comprising FR8a using primers FR8a-OL-2 (SEQ ID NO: 91) and C1-3A-2 (SEQ ID NO: 92) and PCR reaction Mix 2 and thermocycle Profile 2. The two resulting amplicons were connected by using them as templates in an overlap PCR reaction with primers 5'FR8a (SEQ ID NO: 93) and C1-3A-2 (SEQ ID NO: 92) using PCR reaction Mix 2 and thermocycle Profile 2 to amplify the 5' end of FR8a-9F. The overlap PCR product was cloned into a pCR2.1-TOPO vector (Invitrogen) designated 5'FR-9F/pCR2.1. A BamHI/PpuMI fragment of 5'FR-9F/pCR2.1 was then ligated to a PpuMI/BamHI fragment of FR8a to create FR8a-9F (SEQ ID NO: 7) which encodes the FR8a-9F chimeric protein (SEQ ID NO: 8). Thus, the FR8a-9F chimeric insecticidal protein comprises, from N-terminus to C-terminus, a peptidyl fragment comprising the amino acid sequence MTSNGRQCAGIRP (SEQ ID NO: 129), amino acids 1-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-9F eHIP was slightly less active against western corn rootworm than the FR8a eHIP (See Table 5) suggesting that the C-terminal 9 amino acids of the peptidyl fragment of SEQ ID NO: 127 play a role in conferring full insecticidal activity to FR8a.

Example 7. Construction of FR-9F-Catg

The FR-9F-catg coding sequence was created to place the out-of-frame cry3A055 derived nucleotides of FR8a back in frame and to eliminate the cathepsin G protease recognition site. A BamHI/PpuMI fragment of 5'FR-9F/pCR2.1 (See Example 6) was ligated with a PpuMI/BamHI fragment of FRCG (See Example 5) to create the FR-9F-catg coding sequence (SEQ ID NO: 9) which encodes the FR-9F-catg chimeric protein (SEQ ID NO: 10). Thus, the FR-9F-catg chimeric protein comprises, from N-terminus to C-terminus, a peptidyl fragment comprising the amino acid sequence MTSNGRQCAGIRP (SEQ ID NO: 129), amino acids 1-467 of a Cry3Aa protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-9F-catg eHIP provided the same level of activity as FR8a against western corn rootworm (See Table 5) confirming that an eHIP can be made from either a modified Cry3A or a native Cry3 sequence.

Example 8. Construction of FR8a-12Aa

The nucleotides encoding amino acids 2-13 of the peptidyl fragment comprised in FR8a (SEQ ID NO: 4) were removed using PCR. A fragment was PCR amplified from a plasmid comprising FR8a (SEQ ID NO: 3) using primers 5'FR8a-12aa (SEQ ID NO: 94) and C1-3A-2 (SEQ ID NO: 90) and PCR reaction Mix 1 and thermocycle Profile 1. The resulting amplicon was cloned into pCR2.1-TOPO (Invitrogen). A BamHI-PpuMI fragment from the pCR2.1-TOPO clone was then ligated with a PpuMI-BamHI fragment from a plasmid comprising FR8a to create FR8a-12aa (SEQ ID NO: 11) which encodes the FR8a-12aa chimeric insecticidal protein (SEQ ID NO: 12). Thus, the FR8a-12aa chimeric insecticidal protein comprises, from N-terminus to C-terminus, a peptidyl fragment comprising the amino acid sequence MYDGRQQHRG (SEQ ID NO: 128), amino acids 10-468 of a Cry3A055 protein (SEQ ID NO: 70), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region.

The FR8a-12aa eHIP provided the same level of activity as FR8a against western corn rootworm (See Table 5) suggesting that the N-terminal 12 amino acids of the peptidyl fragment of SEQ ID NO: 127 are not necessary for full insecticidal activity of FR8a.

Example 9. Construction of Wr-9Mut

A nucleic acid fragment was PCR amplified from FR8a/pCR2.1 (Example 2) using primers 5'FR8a-12aa (SEQ ID NO: 94) and C1-3A-2 (SEQ ID NO: 92) and PCR reaction Mix 1 and thermocycle Profile 2. The resulting amplicon was cloned into pCR2.1-TOPO (Invitrogen). A BamHI/PpuMI fragment was then ligated to a PpuMI/BamHI fragment of FR8a (SEQ ID NO: 3) to create Wr-9mut (SEQ ID NO: 13) which encodes the WR-9mut protein (SEQ ID NO: 14), which comprises, from N-terminus to C-terminus, a peptidyl fragment comprising the amino acid sequence MYDGRQQHRG (SEQ ID NO: 128), and amino acids 10-598 of a Cry3A055 protein (SEQ ID NO: 70). Thus the WR-9mut protein is Cry3A055 with an N-terminal peptidyl fragment of the invention.

The WR-9mut protein was not active against western corn rootworm. Therefore, the addition of an N-terminal peptidyl fragment to a non-hybrid modified Cry3a protein destroyed insecticidal activity. This suggests that there may be some interaction between the Cry1Ab C-terminal portion of FR8a and the N-terminal peptidyl fragment that confers full insecticidal activity to FR8a.

Example 10. Construction of FRD3

The 3' end of this coding sequence was made by PCR amplifying a fragment from a plasmid comprising FR8a (SEQ ID NO: 3) using primers C2-3A-3 (SEQ ID NO: 95) and 3'1Ab-dm3 (SEQ ID NO: 96) and PCR reaction Mix 2 and thermocycle Profile 2. The resulting amplicon was cloned into pCR2.1-TOPO (Invitrogen). A 364 bp ApaI/SacI fragment of the cloned amplicon, designated 3'FRD3/pCR2.1, was ligated with a SacI/ApaI fragment of FR8a to create FRD3 (SEQ ID NO: 15) which encodes the FRD3 chimeric protein (SEQ ID NO: 16). The FRD3 chimeric protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70), which comprises complete variable region 1, conserved block 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6. Thus, the FRD3 chimeric insecticidal protein is a variant of an FR8a chimeric insecticidal protein with the 38 amino acid region of the Cry1Ab protoxin tail deleted.

The FRD3 eHIP provided the same level of activity as FR8a against western corn rootworm (See Table 5) suggesting that the 38 amino acid protoxin tail region of FR8a is not necessary for full insecticidal activity.

Example 11. Construction of FR-12-cg-dm3

A 3082 bp SacI/PpuMI fragment from a plasmid comprising FR8a-12 (See Example 8), a 721 bp PpuMI/MluI fragment of FRCG (See Example 5) and a 923 bp MluI/SacI fragment of FRD3 (See Example 10) were combined to create the FR-12-cg-dm3 coding sequence (SEQ ID NO: 17) which encodes the FR-12-cg-dm3 chimeric protein (SEQ ID NO: 18). The FR-12-cg-dm3 chimeric protein comprises, from N-terminus to C-terminus, a peptidyl fragment comprising the amino acid sequence MYDGRQQHRG (SEQ ID NO: 129), amino acids 10-467 of a Cry3Aa protein (SEQ ID NO: 70), which comprises complete variable region 1, conserved block 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6. Thus, the FR-12-cg-dm3 chimeric protein is a variant of FR8a with 12 N-terminal amino acids of the peptidyl fragment, the cathepsin G protease recognition site, and the 38 amino acid region of the Cry1Ab protoxin tail deleted.

The FR-12-cg-dm3 eHIP was not as active against western corn rootworm as FR8a (See Table 5) suggesting that some interaction between the C-terminal portion of FR8a and the N-terminal peptidyl fragment is required for full insecticidal activity.

Example 12. Construction of 9F-cg-del6

The 5' end of this coding sequence was made by PCR amplifying a fragment from a plasmid comprising FR-9F-catg (See Example 7) using primers 5'FR-del6 (SEQ ID NO: 97) and C1-3A-2 (SEQ ID NO: 92) and PCR reaction Mix 3 and thermocycle Profile 3. The resulting amplicon was cloned into pCR2.1-TOPO. A 215 bp BamHI/PpuMI fragment was then ligated with a 4668 bp PpuMI/BamHI fragment of FR-9F-catg to create FR-9F-cg-del6 (SEQ ID NO: 19) which encodes the FR-9F-cg-del6 chimeric protein (SEQ ID NO: 20). The FR-9F-cg-del6 chimeric protein comprises, from N-terminus to C-terminus, a peptidyl fragment comprising the amino acid sequence MCAGIRP (SEQ ID NO: 130), amino acids 1-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5, and variable region 6; and 38 amino acids of the Cry1Ab protoxin tail region. Thus, the FR-9F-cg-del6 chimeric protein is a variant of FR8a-9F-catg with amino acids 2 to 7 of the peptidyl fragment deleted.

The FR-9F-cg-del6 was not active against western corn rootworm suggesting that the N-terminal peptidyl fragment needs at least 7 amino acids of the C-terminal 9 amino acids of SEQ ID NO: 127 to be active against western corn rootworm.

Example 13. Construction of FR-cg-dm3

A 3839 bp MluI/SacI fragment of FRCG (Example 5) and a 923 bp MluI/SacI fragment of FRD3 (Example 10) were ligated to create FR-cg-dm3 (SEQ ID NO: 21) which encodes the FR-cg-dm protein (SEQ ID NO: 22). The FR-cg-dm3 chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6.

The FRD3 eHIP the same level of activity against western corn rootworm as FR8a (See Table 5) confirming that the cathepsin G site and the protoxin tail region of FR8a were not required for full insecticidal activity against western corn rootworm.

Example 14. Construction of 9F-cg-dm3

A MluI/SacI fragment from a plasmid comprising FR-9F-cg (See Example 7) was ligated with a 923 bp MluI/SacI fragment from a plasmid comprising FRD3 (See Example 10) to create 9F-cg-dm3 (SEQ ID NO: 23) which encodes the 9F-cg-dm3 chimeric protein (SEQ ID NO: 24). The 9F-cg-dm3 protein comprises, from N-terminus to C-terminus, a peptidyl fragment comprising the amino acid sequence MTSNGRQCAGIRP (SEQ ID NO: 129), amino acids 1-467 of a Cry3A protein (SEQ ID NO: 68), which comprises variable regions 1, conserved block 1, variable region 2, conserved block 2, variable region 3, and the N-terminal 24 amino acids of conserved block 3, and amino acids 477-610 of a Cry1Ab protein (SEQ ID NO: 72), which comprises the C-terminal 24 amino acids of conserved block 3, variable region 4, conserved block 4, variable region 5, conserved block 5, and variable region 6.

The 9F-cg-dm3 eHIP provided the same level of activity against western corn rootworm (See Table 5) confirming that the C-terminal 9 amino acids of the peptidyl fragment could confer activity when domain I of the eHIP was comprised of either modified Cry3A (Cry3A055) variable regions and conserved blocks or Cry3A variable regions and conserved blocks.

Example 15. Construction of B8a

A nucleic acid fragment encoding an N-terminal portion of a Cry3A055 protein (SEQ ID NO: 70), was PCR amplified from a plasmid comprising cry3A055 (SEQ ID NO: 69) using primers 5'3A-1-bam (SEQ ID NO: 83) and C3-3A-8 (SEQ ID NO: 99) and PCR reaction Mix 1 and thermocycling Profile 1. A nucleic acid fragment encoding a C-terminal portion of a Cry1Ab protein (SEQ ID NO: 72), comprising variable regions 4-6, was amplified from a plasmid comprising mocry1Ab (SEQ ID NO: 71) using primers C3-3A-7 (SEQ ID NO: 100) and 1Ab-6-sac (SEQ ID NO: 86) and PCR reaction Mix 1 and thermocycling Profile 1. The resulting amplicon was designated 2OL-8b.

A nucleic acid fragment encoding an N-terminal portion of the Cry3A055 protein (SEQ ID NO: 70), was PCR amplified from a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1.

A nucleic acid fragment encoding a C-terminal portion of a Cry1Ba protein (SEQ ID NO: 74) was PCR amplified from a plasmid comprising mocry1Ba (SEQ ID NO: 73) using primers 1B-5 (SEQ ID NO: 101) and 1B-10 (SEQ ID NO: 102) and PCR reaction Mix 1 and thermocycling Profile 1, except a 60° C. annealing temperature was used.

The two above-described PCR products were then used as the templates in an overlap PCR reaction with primers 5'3A-1-bam (SEQ ID NO: 83) and 1B-10 (SEQ ID NO: 102) using PCR reaction Mix 1 and thermocycling Profile 2. The resulting amplicon was designated B10.

Next, a nucleic acid fragment of cry3A055 (SEQ ID NO: 69) was PCR amplified using 2OL-8b (see above) as the template and primers 5'3A-1-bam (SEQ ID NO: 83) and 3A-22 (SEQ ID NO: 103) with the following PCR conditions: Mix 1, thermocycling profile: 94° C.—45 seconds, 50° C.-70° C. gradient—45 seconds, 72° C.-90 seconds for 30 cycles. Another nucleic acid fragment was PCR amplified using B10 (see above) as the template and primers 1B-7 (SEQ ID NO: 104) and 1B-10 (SEQ ID NO: 102) using PCR reaction Mix 1 and thermocycling Profile 2, except a 60° C. annealing temperature was used. The two resulting PCR products were then used as templates in an overlap PCR reaction with primers 5'3A-1-bam (SEQ ID NO: 83) and 1B-10 (SEQ ID NO: 102) using the following PCR conditions: Mix 2, thermocycling profile: 94° C.—30 seconds, 40° C.-60° C. gradient—30 seconds, 72° C.—60 seconds for 30 cycles.

The resulting PCR product was ligated to a pCR2.1-TOPO vector (Invitrogen) and designated B10/pCR2.1. A BamHi-SacI fragment from B8a/pCR2.1 was then ligated to pET21a (Novagen), which was cut with BamHI/SacI, to create the B8a coding sequence (SEQ ID NO: 25), which encodes a B8a hybrid toxin (SEQ ID NO: 26). The B8a hybrid protein comprises, from N-terminus to C-terminus, amino acids 1-468 of a Cry3A055 protein (SEQ ID NO: 70), and amino acids 505-656 of a Cry1Ba protein (SEQ ID NO: 74).

Example 16. Construction of 5*B8a

A BamHI-XbaI fragment from a plasmid comprising 2OL-8a (See Example 3) and a XbaI-SacI fragment from a plasmid comprising B8a (See Example 15) were ligated to create 5*B8a (SEQ ID NO: 27), which encodes the 5*B8a chimeric protein (SEQ ID NO: 28). The 5*B8a protein comprises, from N-terminus to C-terminus, a peptidyl fragment comprising the amino acid sequence MTSNGRQCAGIRPYDGRQQHRG (SEQ ID NO: 127), amino acids 10-467 of a Cry3A055 protein (SEQ ID NO: 70) and amino acids 505-656 of a Cry1Ba protein (SEQ ID NO: 74). Thus, the 5*B8a chimeric protein is the B8a hybrid protein to which an N-terminal peptidyl fragment has been added.

Example 17. Construction of V3A

This gene was PCR amplified using 3 fragments together as templates: the first fragment was amplified from a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1; the second fragment was amplified from a plasmid comprising mocry1Ab (SEQ ID NO: 71) using primers C2-3A-3 (SEQ ID NO: 95) and C3-1Ab-2 (SEQ ID NO: 105) and PCR reaction Mix 1 and thermocycling Profile 1; and the third fragment was amplified from a plasmid comprising cry3A055 (SEQ ID NO: 69) using primers C3-3A-5 (SEQ ID NO: 106) and 3A-12-sac (SEQ ID NO: 107) and PCR reaction Mix 1 and thermocycling Profile 1. These 3 PCR products were then used as templates in an overlap PCR reaction with primers 5'3A-1-bam (SEQ ID NO: 83) and 3A-12-sac (SEQ ID NO: 107) using PCR reaction Mix 1 and thermocycling Profile 1, to produce the v3A coding sequence (SEQ ID NO: 29), which encodes the V3A hybrid protein (SEQ ID NO: 30). The V3A hybrid protein comprises, from N-terminus to C-terminus, amino acids 1-226 of a Cry3A055 protein (SEQ ID NO: 70), which comprises variable region 1, conserved block 1, variable region 2, and the N-terminal 34 amino acids of conserved block 2, amino acids 237-474 of a Cry1Ab protein (SEQ ID NO: 72), which comprises the C-terminal 33 amino acids of conserved block 2, variable region 3, and the N-terminal 20 amino acids of conserved block 3, and amino acids 467-598 of a Cry3A055 protein (SEQ ID NO: 70), which comprises the C-terminal 28 amino acids of conserved block 3, variable region 4, conserved block 4, variable region 5, and conserved block 5.

The V3A eHIP comprises two crossover positions. The first crossover between Cry3A055 and Cry1Ab is located in conserved block 2 and the second crossover between Cry1Ab and Cry3A055 is located in conserved block 3. Therefore, V3A is a variant of Cry3A055 in which all of variable region 3 has been replaced with variable region 3 of a Cry1Ab protein. The V3A eHIP was not as active against western corn rootworm as FR8a, suggesting that having Cry1Ab sequence in conserved block 3, variable region 4, conserved block 4, variable region 5, conserved block 5 and/or variable region 6 is important for full insecticidal activity of FR8a.

The v3A coding sequence was ligated to a pCR2.1-TOPO vector and then subcloned into pET21a using a BamHI/SacI fragment. The V3A protein expressed by the pET21a vector has a T7 tag on the N-terminus. This protein was designated T7-V3A.

Example 18. Construction of V4F

A first nucleic acid fragment encoding variable regions 1-3 of a Cry3A055 was PCR amplified from a plasmid comprising cry3A055 (SEQ ID NO: 69) using primers 5'3A-1-bam (SEQ ID NO: 83) and C3-3A-6 (SEQ ID NO: 84) and PCR reaction Mix 1 and thermocycling Profile 1.

A second nucleic acid fragment encoding variable region 4 of a Cry1Ab was PCR amplified from a plasmid comprising mocry1Ab (SEQ ID NO: 71) using primers C3-1Ab-3 (SEQ ID NO: 85) and C4-3A-10 (SEQ ID NO: 108) and PCR reaction Mix 1 and thermocycling Profile 1.

A third nucleic acid fragment encoding variable regions 5-6 of Cry3A055 was PCR amplified from a plasmid comprising cry3A055 (SEQ ID NO: 69) using primers C4-3A-9 (SEQ ID NO: 109) and 3A-12-sac (SEQ ID NO: 107) and PCR reaction Mix 1 and thermocycling Profile 1.

All three PCR amplicons were combined and used as the template in an overlap PCR reaction with primers 5'3A-1-bam (SEQ ID NO: 83) and 3A-12-sac (SEQ ID NO: 107) using the following PC conditions: Mix 1 and thermocycling profile: 94° C.—30 seconds, 50° C.-70° C. gradient—30 seconds, 72° C.—30 seconds for 20 cycles. The resulting amplicon, designated the v4F coding sequence (SEQ ID NO: 31) which encodes the V4F hybrid toxin (SEQ ID NO: 32), was cloned into a pCR2.1-TOPO vector and designated v4F/pCR2.1. The V4F hybrid protein comprises, from N-terminus to C-terminus, amino acids 1-468 of a Cry3A055 protein (SEQ ID NO: 70), amino acids 477-520, comprising variable region 4, of a Cry1Ab protein (SEQ ID NO: 72), and amino acids 512-598 of a Cry3A055 protein (SEQ ID NO: 70).

The V4F protein has two crossover positions. The first crossover between Cry3A055 and Cry1Ab is in conserved block 3 and the second crossover between Cry1Ab and Cry3A055 is located in conserved block 4. Therefore, V4F is a variant of Cry3A055 in which all of variable region 4 has been replaced with variable region 4 of a Cry1Ab protein. The V4F hybrid protein was not active against western corn rootworm suggesting that Cry1Ab sequence at the C-terminal portion of FR8a contributes to the insecticidal activity of FR8a.

A BamHI-SacI fragment of v4F/pCR2.1 was subcloned into pET21. The protein expressed by the resulting plasmid was designated T7-V4F.

Example 19. Construction of 5*V4F

A BamHI-XbaI fragment from a plasmid comprising FR8a (See Example 4) and a XbaI-SacI fragment from V4F/pCR2.1 (See Example 18) were ligated to pET21 cut with BamHI-SacI to form 5*V4F/pET21. The 5*V4F coding sequence (SEQ ID NO: 33) encodes the 5*V4F chimeric protein (SEQ ID NO: 34). The 5*V4F chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-491 of a Cry3A055 protein (SEQ ID NO: 70), amino acids 501-520, comprising variable region 4, of a Cry1Ab protein (SEQ ID NO: 72), and amino acids 512-598 of a Cry3A055 protein (SEQ ID NO: 70).

The 5*V4F eHIP is the V4F hybrid protein with an N-terminal peptidyl fragment (SEQ ID NO: 127) added. The 5*V4F eHIP provided insecticidal activity against western corn rootworm although not at the same level as FR8a. Thus, the N-terminal conferred insecticidal activity to V4F confirming that there may be some contributory interaction between the C-terminal portion and the N-terminal peptidyl fragment of FR8a.

The protein expressed by the 5*V4F/pET21 plasmid was designated T7-5*V4F and has a T7 tag N-terminal to the 5*V4F peptidyl fragment.

Example 20. Construction of 2OL-7

A nucleic acid fragment encoding variable region 1 of Cry3A055 was PCR amplified from a plasmid comprising cry3A055 (SEQ ID NO: 69) using primers 5'3A-1-bam (SEQ ID NO: 83) and C1-3A-2 (SEQ ID NO: 92) and PCR reaction Mix 1 and thermocycling Profile 1.

A nucleic acid fragment encoding variable regions 2-6 of Cry1Ab was PCR amplified from a plasmid comprising mocry1Ab (SEQ ID NO: 71) using primers C1-1Ab-1 (SEQ ID NO: 110) and 1Ab-6-sac (SEQ ID NO: 86) and PCR reaction Mix 1 and thermocycling Profile 1.

The resulting two amplicons were used as templates in an overlap PCR reaction with primers 5'3A-1-bam (SEQ ID NO: 83) and 1Ab-6-sac (SEQ ID NO: 86) using PCR reaction Mix 2 and thermocycling Profile 1, to create the 2OL-7 coding sequence (SEQ ID NO: 35) which encodes the 2OL-7 hybrid protein (SEQ ID NO: 36). The 2OL-7 hybrid protein comprises, from N-terminus to C-terminus, amino acids 1-156 of a Cry3A055 protein (SEQ ID NO: 70), which comprises variable region 1 and the N-terminal 14 amino acids of conserved block 1, and amino acids 167-648 of a Cry1Ab protein (SEQ ID NO: 72), which comprises the C-terminal 15 amino acids of conserved block 1, variable region 2, conserved block 2, variable region 3, conserved block 3, variable region 4, conserved block 4, variable region 5, conserved block 5 and variable region 6, and 38 amino acids of the Cry1Ab protoxin tail region Thus, 2OL-7 is a variant of a Cry1Ab protein with variable region 1 replaced by variable region 1 from a Cry3A055 protein.

The 2OL-7 coding sequence was cloned into pCR2.1-TOPO (Invitrogen) and then moved into pET21a using BamHI/SacI which was designated 2OL-7/pET21a. The coding sequence in 2OL-7/pET21a was designated T7-2OL-7 (SEQ ID NO: 37). The protein expressed by the 2OL-7/pET21a vector was designated T7-2OL-7 (SEQ ID NO: 38).

Example 21. Construction of 5*2OL-7

A BamHI/XbaI fragment of FR8a (See Example 4), a PpuMI/SacI fragment of 2OL-7 (See Example 20) and a BamHI/SacI fragment of pET21a were ligated to produce 5*2OL-7/pET21a. The 5*2OL-7 coding sequence (SEQ ID NO: 39) encodes the 5*2OL-7 chimeric protein (SEQ ID NO: 40). The 5*2OL-7 protein comprises, from N-terminus to C-terminus, a peptidyly fragment comprising the amino acid sequence MTSNGRQCAGIRPYDGRQQHRG (SEQ ID NO: 127), amino acids 10-156 of a Cry3A055 protein (SEQ ID NO: 70), and amino acids 167-643 of a Cry1Ab protein (SEQ ID NO: 72). Thus, the 5*2OL-7 hybrid protein is the 2OL-7 hybrid protein with a N-terminal peptidyl fragment added.

Example 22. Construction of 2OL-10

A nucleic acid fragment encoding an N-terminal portion of a Cry3A055 protein was PCR amplified from a plasmid comprising cry3A055 (SEQ ID NO: 69) using primers 5'3A-1-bam (SEQ ID NO: 83) and C2-3A-4 (SEQ ID NO: 88) and PCR reaction Mix 1 and thermocycling Profile 1. A nucleic acid fragment encoding a C-terminal portion of a Cry1Ab protein was PCR amplified from a plasmid comprising mocry1Ab (SEQ ID NO: 71) using primers C2-3A-3 (SEQ ID NO: 95) and 1Ab-6-sac (SEQ ID NO: 86) and PCR reaction Mix 1 and thermocycling Profile 1. These 2 PCR products were then used as the templates in an overlap PCR reaction with primers 5'3A-1-bam (SEQ ID NO: 83) and 1Ab-6-sac (SEQ ID NO: 86) using the following PCR conditions: Mix 2, thermocycling profile: 94° C.—30 seconds, 45° C.-65° C. gradient—30 seconds, 72° C.—30 seconds for 20 cycles, resulting in the 2OL-10 coding sequence (SEQ ID NO: 41) which encodes the 2OL-10 hybrid toxin (SEQ ID NO: 42). The 2OL-10 protein comprises, from N-terminus to C-terminus, amino acids 1-232 of a Cry3A055 protein (SEQ ID NO: 70) and amino acids 243-648 of a Cry1Ab protein (SEQ ID NO: 72). Thus, the 2OL-10 hybrid protein is substantially Domain I of a Cry3A055 protein and Domains II and III of a Cry1Ab protein.

The 2OL-10 coding sequence was cloned into pCR2.1-TOPO (Invitrogen) then moved to pET21a using BamHI/SacI. The protein expressed by 2OL-10/pET21a was designated T7-2OL-10.

Example 23. Construction of 5*2OL-10

A BamHI-XbaI fragment from a plasmid comprising FR8a (See Example 4) and a XbaI-SacI fragment from 2OL-10/pCR2.1 (See Example 22) were ligated to pET21 cut with BamHI-SacI to form 5*2OL-10/pET21. The 5*2OL-10 coding sequence (SEQ ID NO: 43) encodes the 5*2OL-10 chimeric protein (SEQ ID NO: 44). The 5*2OL-10 protein comprises, from N-terminus to C-terminus, a peptidyl fragment comprising the amino acid sequence MTSNGRQCAGIRPYDGRQQHRG (SEQ ID NO: 127), amino acids 10-232 of a Cry3A055 protein (SEQ ID NO: 70) and amino acids 243-648 of a Cry1Ab protein (SEQ ID NO: 72). Thus, the 5*2OL-10 chimeric protein is the 2OL-10 hybrid protein with a N-terminal peptidyl fragment added.

Example 24. Construction of 2OL-12A

A first nucleic acid fragment encoding an N-terminal portion of Cry1Ab was PCR amplified from a plasmid comprising mocry1Ab (SEQ ID NO: 71) using primers 5'1Ab-bam (SEQ ID NO: 98) and C3-1Ab-2 (SEQ ID NO: 105) and PCR reaction Mix 1 and thermocycling Profile 1.

A second nucleic acid fragment encoding a C-terminal portion of Cry3A055 was PCR amplified from a plasmid comprising cry3A055 (SEQ ID NO: 69) using primers C3-3A-5 (SEQ ID NO: 106) and 3A-12-sac (SEQ ID NO: 107) and PCR reaction Mix 1 and thermocycling Profile 1.

The first and second nucleic acid fragment described above were connected by using them as templates in an overlap PCR reaction with primers 5'1Ab-bam (SEQ ID NO: 98) and 3A-12-sac (SEQ ID NO: 107) using Mix 1 and thermocycling Profile 1 to create the 2OL-12A coding sequence (SEQ ID NO: 45) which encodes the 2OL-12A eHIP (SEQ ID NO: 46). The 2OL-12A protein comprises, from N-terminus to C-terminus, amino acids 1-476 of a Cry1Ab protein (SEQ ID NO: 72) and amino acids 469-598 of a Cry3A055 protein (SEQ ID NO: 70).

The 2OL-12A eHIP was not active against western corn rootworm but was active against European corn borer (See Table 6). This demonstrates that eHIP can be constructed using lepidopteran active and coleopteran active Cry proteins without loss of activity against a lepidopteran insect species.

The 2OL-12A coding sequence was cloned into pCR2.1-TOPO (Invitrogen) then moved to pET21a with BamHI/SacI. The protein expressed by the 2OL-12A/pET21a vector was designated T7-2OL-12A. The Example 25. Construction of 2OL-13

Four nucleic acid fragments were generated as follows: fragment 1 was PCR amplified from a plasmid comprising cry3A055 (SEQ ID NO: 69) using primers 5'3A-1-bam (SEQ ID NO: 83) and C1-3A-2 (SEQ ID NO: 92) and PCR reaction Mix 1 and thermocycling Profile 1; fragment 2 was PCR amplified from a plasmid comprising mocry1Ab (SEQ ID NO: 71) using primers C2-3A-3 (SEQ ID NO: 95) and C3-1Ab-2 (SEQ ID NO: 105) and PCR reaction Mix 1 and thermocycling Profile 1; fragment 3 was PCR amplified from a plasmid comprising mocry1Ab (SEQ ID NO: 71) using primers C3-1Ab-3 (SEQ ID NO: 85) and C4-3A-10 (SEQ ID NO: 108) and PCR reaction Mix 1 and thermocycling Profile 1; and fragment 4 was PCR amplified from a plasmid comprising cry3A055 (SEQ ID NO: 69) using primers C4-3A-9 (SEQ ID NO: 109) and 3A-12-sac (SEQ ID NO: 107) and PCR reaction Mix 1 and thermocycling Profile 1.

All four fragments were then used as templates in an overlap PCR reaction using primers 5'3A-bam (SEQ ID NO: 83) and 3A-12-sac (SEQ ID NO: 107) using PCR reaction Mix 1 and thermocycling Profile 1 to create the 2OL-13 coding sequence (SEQ ID NO: 47) which encodes the 2OL-13 hybrid toxin (SEQ ID NO: 48). The 2OL-13 protein comprises, from N-terminus to C-terminus, amino acids 1-159 of a Cry3A055 protein (SEQ ID NO: 70), amino acids 170-522 of a Cry1Ab protein (SEQ ID NO: 72), and amino acids 515-598 of a Cry3A055 protein (SEQ ID NO: 70). Thus, the 2OL-13 hybrid toxin is comprised of V1 and the N-terminal portion of CB1 from a Cry3A055 protein; the C-terminal portion of CB1, V2, CB2, V3, CB3, and V4 from a Cry1Ab protein; and CB4, V5, and CB5 from a Cry3A055 protein.

The 2OL-13 coding sequence was cloned into pCR2.1-TOPO (Invitrogen) then moved to pET21a using BamHI/SacI. The protein expressed by the 2OL-13/pET21a vector was designated T7-2OL-13.

Example 26. Construction of 2OL-20

A BamHI/NspI fragment from a plasmid comprising mocry3A (SEQ ID NO: 67), a NspI/HindIII fragment from a plasmid comprising 2OL-8A (SEQ ID NO: 1), and a HindIII/BamHI fragment from pET21a were ligated to make 2OL-20/pET21a.

Example 27. Construction of V5&6

A nucleic acid fragment encoding an N-terminal portion of Cry3A055 was PCR amplified from a plasmid comprising cry3A055 (SEQ ID NO: 69) using primers 5'3A-1-bam (SEQ ID NO: 83) and C4-3A-10 (SEQ ID NO: 108) and PCR reaction Mix 1 and thermocycling Profile 1.

A nucleic acid fragment encoding a C-terminal portion of Cry1Ab was PCR amplified from a plasmid comprising mocry1Ab (SEQ ID NO: 71) using primers C4-3A-9 (SEQ ID NO: 109) and 1Ab-6-sac (SEQ ID NO: 86) and PCR reaction Mix 1 and thermocycling Profile 1.

These two PCR products were then used as the templates in an overlap PCR reaction with primers 5'3A-1-bam (SEQ ID NO: 83) and 1Ab-6-sac (SEQ ID NO: 86) using PCR reaction Mix 1 and thermocycling Profile 2 to create the V5&6 coding sequence (SEQ ID NO: 49), which encodes the V5&6 hybrid toxin (SEQ ID NO: 50). The V5&6 protein comprises, from N-terminus to C-terminus, amino acids 1-524 of a Cry3A055 protein (SEQ ID NO: 70), which comprises V1, CB1, V2, CB2, V3, CB3, V4, and CB4, and amino acids 533-648 of a Cry1Ab protein (SEQ ID NO: 72), which comprises V5, CB5 and V6, and 38 amino acids of a Cry1Ab protoxin tail region.

The V5&6 coding sequence was cloned into pCR2.1-TOPO then moved to pET21 with BamHI/SacI. The protein expressed by V5&6/pET21a was designated T7-V5&6.

Example 28. Construction of 5*V5&6

A BamHI/XbaI fragment of FR8a (See Example 4), a XbaI/SacI fragment of V5&6 (See Example 27) and a BamHI/SacI fragment of pET21a were ligated to form 5*V5&6/pET21. The 5*V5&6 coding sequence (SEQ ID NO: 51) encodes the 5*V5&6 chimeric protein (SEQ ID NO: 52). The 5*V5&6 chimeric insecticidal protein comprises, from N-terminus to C-terminus, a peptidyl fragment comprising the amino acid sequence MTSNGRQCA-GIRPYDGRQQHRG (SEQ ID NO: 127), amino acids 10-524 of a Cry3A055 protein (SEQ ID NO: 70), which comprises V1, CB1, V2, CB2, V3, CB3, V4, and CB4, and amino acids 533-648 of a Cry1Ab protein (SEQ ID NO: 72), which comprises V5, CB5 and V6, and 38 amino acids of a Cry1Ab protoxin tail region. Thus, the 5*V5&6 chimeric insecticidal protein is the V5&6 hybrid protein with an N-terminal peptidyl fragment added.

Example 29. Construction of 88A-dm3

A nucleic acid fragment encoding a C-terminal portion of a Cry8Aa protein (SEQ ID NO: 78) was PCR amplified from a plasmid comprising cry8Aa (SEQ ID NO: 77) using primers 5'8Aa-dm3 (SEQ ID NO: 111) and 3'8Aa-dm3 (SEQ ID NO: 112) and PCR reaction Mix 2 and thermocycling Profile 2. The resulting amplicon was cloned into pCR2.1-TOPO (Invitrogen) and designated 88A-dm3/pCR2.1.

A MluI/SacI fragment from 88A-dm3/pCR2.1 and a SacI/MluI fragment from a plasmid comprising FR8a (See Example 4) were ligated to create the 88A-dm3 coding sequence (SEQ ID NO: 53) which encodes the 88A-dm3 hybrid protein (SEQ ID NO: 54). The 88A-dm3 protein comprises, from N-terminus to C-terminus, a peptidyl fragment comprising the amino acid sequence MTSNGRQCA-GIRPYDGRQQHRG (SEQ ID NO: 127), amino acids 10-468 of a Cry3A055 protein (SEQ ID NO: 70) and amino acids 532-664 of a Cry8Aa protein (SEQ ID NO: 78).

The 88A-dm3 coding sequence was also transformed into pET21a using a BamHI/SacI restriction digest and ligation. The protein expressed by 88A-dm3/pET21a was designated T7-88A-dm3.

Example 30. Construction of FR(1Fa)

A nucleic acid fragment encoding an N-terminal portion of FR8a (See Example 3) was PCR amplified from a plasmid comprising FR8a (SEQ ID NO: 1) using primers C2-3A-3 (SEQ ID NO: 95) and tant-OL-2 (SEQ ID NO: 113) and PCR reaction Mix 3 and thermocycling Profile 3.

A nucleic acid fragment encoding a C-terminal portion of a Cry1Fa protein (SEQ ID NO: 76) was PCR amplified from a plasmid comprising mocry1Fa (SEQ ID NO: 75) using primers tant-OL-1 (SEQ ID NO: 114) and tant-3'sac (SEQ ID NO: 115) and PCR reaction Mix 3 and thermocycling Profile 3.

These two PCR products were then used as templates in an overlap PCR reaction with primers C2-3A-3 (SEQ ID NO: 95) and tant-3'sac (SEQ ID NO: 115) using PCR reaction Mix 3 and thermocycling Profile 3. The resulting PCR product was cloned into pCR2.1-TOPO (Invitrogen). A BamHI/MluI fragment from a plasmid comprising FR8a, a MluI/SacI fragment from the overlap PCR product in pCR2.1 and a BamHI/SacI fragment of pET21a were then ligated to create FR(1Fa)/pET21a. The FR(1Fa) coding sequence (SEQ ID NO: 55) encodes the FR(1Fa) chimeric protein (SEQ ID NO: 56). The FR(1Fa) protein comprises, from N-terminus to C-terminus, a peptidyl fragment comprising the amino acid sequence MTSNGRQCA-GIRPYDGRQQHRG (SEQ ID NO: 127), amino acids 10-468 of a Cry3A055 protein (SEQ ID NO: 70) and amino acids 470-649 of a Cry1Fa protein (SEQ ID NO: 76).

Example 31. Construction of FR(1Ac)

Domains I & II of FR8a were PCR amplified from a plasmid comprising FR8a (SEQ ID NO: 1) using primers C2-3A-3 (SEQ ID NO: 95) and Ac-OL-2 (SEQ ID NO: 116) and PCR reaction Mix 3 and thermocycling Profile 3. Domain III of Cry1Ac (SEQ ID NO: 80) was PCR amplified from a plasmid comprising cry1Ac (SEQ ID NO: 79) using primers 1Ac-OL-1 (SEQ ID NO: 117) and 1Ac-3'sac (SEQ ID NO: 118) and PCR reaction Mix 3 and thermocycling Profile 3.

These 2 PCR products were used as templates in an overlap PCR reaction with primers C2-3A-3 (SEQ ID NO: 95) and 1Ac-3'sac (SEQ ID NO: 118) and the following conditions: Mix 3 and thermocycling profile: 94° C.—30 seconds, 68° C.—30 seconds, 68° C.—30 seconds for 20 cycles. The overlap PCR product was cloned into pCR2.1-TOPO (Invitrogen). A BamHI/MluI fragment from a plasmid comprising FR8a, the MluI/SacI fragment from the overlap PCR product in pCR2.1 and BamHI/SacI fragment of pET21a were ligated to create FR(1Ac)/pET21a. The FR(1Ac) protein comprises, from N-terminus to C-terminus, a peptidyl fragment comprising the amino acid sequence MTSNGRQCAGIRPYDGRQQHRG (SEQ ID NO: 127), amino acids 10-468 of a Cry3A055 protein (SEQ ID NO: 70) and amino acids 477-608 of a Cry1Ac protein (SEQ ID NO: 80).

Example 32. Construction of FR(1Ia)

A nucleotide fragment encoding Domains I and II of FR8a was PCR amplified from a plasmid comprising FR8a (SEQ ID NO: 3) using primers C2-3A-3 (SEQ ID NO: 95) and Ia-OL-2 (SEQ ID NO: 119) and PCR reaction Mix 3 and thermocycling Profile 3. A second nucleotide fragment encoding Domain III of a Cry1Ia protein (SEQ ID NO: 82) was PCR amplified from a plasmid comprising cry1Ia (SEQ ID NO: 81) using primers Ia-OL-1 (SEQ ID NO: 120) and Ia-3'sac (SEQ ID NO: 121) and PCR reaction Mix 3 and thermocycling Profile 3. These two PCR products were used as templates in an overlap PCR reaction with primers C2-3A-3 (SEQ ID NO: 95) and Ia-3'sac (SEQ ID NO: 121) and PCR reaction Mix 3 and thermocycling profile: 94° C.—30 seconds, 68° C. —45 seconds for 20 cycles. The overlap PCR product was cloned into pCR2.1-TOPO (Invitrogen). The BamHI/MluI fragment from a plasmid comprising FR8a, the MluI/SacI fragment from the overlap PCR product in pCR2.1 and BamHI/SacI fragment of pET21a were ligated to create FR(1Ia)/pET21a. The FR(1Ia) protein comprises, from N-terminus to C-terminus, a peptidyl fragment comprising the amino acid sequence MTSNGRQCA-GIRPYDGRQQHRG (SEQ ID NO: 127), amino acids 10-468 of a Cry3A055 protein (SEQ ID NO: 70) and amino acids 513-719 of a Cry1Ia protein (SEQ ID NO: 82).

Example 33. Construction of Dm2-3A

Part of the 5' end of this coding sequence was PCR amplified from a plasmid comprising cry3A055 (SEQ ID NO: 69) using primers C2-3A-3 (SEQ ID NO: 95) and FR-1Ab-2 (SEQ ID NO: 122) and PCR reaction Mix 3 and thermocycling Profile 2. A nucleotide fragment encoding Domain III of Cry1Ab was PCR amplified from a plasmid comprising mocry1Ab (SEQ ID NO: 71) using primers FR1Ab-1 (SEQ ID NO: 123) and 1Ab-6-sac (SEQ ID NO: 86) and PCR reaction Mix 3 and thermocycling Profile 2. These two PCR products were used as the templates in an overlap PCR reaction with primers C2-3A-3 (SEQ ID NO: 95) and 1Ab-6-sac (SEQ ID NO: 86) and PCR reaction Mix 3 and thermocycling Profile 2. The resulting amplicon was cloned into pCR2.1-TOPO (Invitrogen). FR8a BamHI/MluI, and the above PCR product in pCR2.1-TOPO AflIII, FR8a AflIII/SacI were ligated into pET21a BamHI/SacI. The entire coding sequence (BamHI/SacI) was then moved to 1454. The DM2-3A chimeric insecticidal protein comprises, from N-terminus to C-terminus, a peptidyl fragment comprising the amino acid sequence MTSNGRQCAGIRPYDGRQQHRG (SEQ ID NO: 127), amino acids 10-451 of a Cry3A055 protein (SEQ ID NO: 70), which comprises variable region 1, conserved block 1, variable region 2, conserved block 2, variable region 3, and the N-terminal 7 amino acids of conserved block 3, and amino acids 460-648 of a Cry1Ab protein (SEQ ID NO: 72), which comprises the C-terminal 41 amino acids of conserved block 3, variable region 4, conserved block 4, variable region 5, conserved block 5, and variable region 6. Thus, the DM2-3A eHIP has a cross-over junction between Cry3A055 and Cry1Ab located in conserved block 3 immediately following Ser451 which is upstream of the domain II domain III junction. DM2-3A has insecticidal activity against western corn rootworm but the activity was less than that of the 8AF and FR8a eHIPs as shown in Table 5.

Example 34. Construction of T7-8AF

A nucleic acid fragment encoding an N-terminal portion of a Cry3A055 protein (SEQ ID NO: 70) was PCR amplified from a plasmid comprising cry3A055 (SEQ ID NO: 69) using primers 5'3A-1-bam (SEQ ID NO: 83) and C3-3A-6 (SEQ ID NO: 84) and PCR reaction Mix 1 and thermocycling Profile 1.

A nucleic acid fragment encoding a C-terminal portion of a Cry1Ab protein (SEQ ID NO: 72) was PCR amplified from a plasmid comprising mocry1Ab (SEQ ID NO: 71) using primers C3-1Ab-3 (SEQ ID NO: 85) and 1Ab-6-Sac (SEQ ID NO: 86) and PCR reaction Mix 1 and thermocycle Profile 1.

The two above-described PCR products were next used as templates in an overlap PCR reaction with the primers 5'3A-1-bam (SEQ ID NO: 83) and 1Ab-6-Sac (SEQ ID NO: 86) using PCR reaction Mix 2 and thermocycling Profile 1.

The resulting amplicon was ligated as a blunt ended fragment to a pCR2.1-TOPO vector (Invitrogen, Carlsbad, Calif.) cut with SmaI to form plasmid p8AF/CR2.1. A BamHI-SacI fragment from p8AF/CR2.1 was then ligated to pET21a (EMD Biosciences, Inc., San Diego, Calif.), which was cut with BamHI-SacI, and transformed into *E. coli*. The open reading frame was designated T7-8AF (SEQ ID NO: 144) and encodes the T7-8AF hybrid protein (SEQ ID NO: 145). The T7-8AF hybrid protein comprises, from N-terminus to C-terminus, a peptidyl fragment comprising the amino acid sequence MASMTGGQQMGRGS (amino acids 1-14 of SEQ ID NO: 126), amino acids 1-468 of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of the Cry1Ab protoxin tail. The T7-8AF hybrid protein had little or no insecticidal activity against western corn rootworm.

Example 35. Construction of 8AF

A BamHI-SacI fragment from plasmid p8AF/CR2.1 (See Example 34) was ligated to a plasmid containing a constitutive Cry1Ac promoter that has been modified from that described by Schnepf et al. (1985. J. Biol. Chem. 260:6264-6272) to correct an internal ATG start codon which exists in the promoter of Schnepf et al. to an ATC codon, which was cut with BamHI-SacI, and transformed into *E. coli*. The open reading frame was designated 8AF (SEQ ID NO: 63) and encodes the 8AF eHIP (SEQ ID NO: 64). The 8AF eHIP is similar to the FR8a eHIP but does not contain the optional N-terminal peptidyl fragment. The 8AF eHIP comprises, from N-terminus to C-terminus, amino acids 1-468 of a Cry3A055 protein (SEQ ID NO: 70), which comprises variable region 1, conserved block 1, variable region 2, conserved block 2, variable region 3, and the N-terminal 24 amino acids of conserved block 3, and amino acids 477-648 of a Cry1Ab protein (SEQ ID NO: 72), which comprises the C-terminal 24 amino acids of conserved block 3, variable region 4, conserved block 4, variable region 5, conserved block 5 and variable region 6, and a 38 amino acid region of a Cry1Ab protoxin tail. Thus, the 8AF eHIP has a cross-over junction between Cry3A055 and Cry1Ab located in conserved block 3 immediately following Leu468 of SEQ ID NO: 70 which is downstream of the domain II domain III junction. The 8AF eHIP had high activity against western corn rootworm.

Example 36. Construction of -catG8AF

A construct was made without the Cathepsin G (Cat G) site to determine whether the Cat G site in domain I of the 8AF eHIP was necessary for rootworm activity. A 1359 bp BamHI/SalI fragment from a plasmid comprising moCry3A (SEQ ID NO: 67) and a 3483 bp BamHI/SalI fragment from a plasmid comprising 2OL-8a (SEQ ID NO: 1) were ligated to create -catG8AF (SEQ ID NO: 146) which encodes the -catG8AF eHIP (SEQ ID NO: 147).

The -catG8AF eHIP was very active against western corn rootworm demonstrating that the Cathepsin G protease recognition site in the 8AF eHIP is not required for insecticidal activity.

Example 37. Construction of 8AFdm3

The 8AF eHIP described in Example 35 has a cross-over point between Cry3A055 and Cry1Ab located in CB3 downstream of the domain II/III junction, resulting in domain III of the 8AF eHIP having a small N-terminal region of domain III of Cry3A055 and the remainder of domain III being Cry1Ab domain III sequence. To determine whether the small N-terminal region of domain III of Cry3A055 was required for insecticidal activity in 8AF, another construct was made having the cross-over between Cry3A055 and Cry1Ab located in CB3 exactly at the domain II-domain III junction.

A nucleic acid fragment encoding part of domain I and domain II of Cry3A055 was PCR amplified from a plasmid comprising FR8a (SEQ ID NO: 3) using primers CMS96 (SEQ ID NO: 138) and CMS97 (SEQ ID NO: 139) and PCR reaction Mix 5 and thermocycle Profile 5.

A nucleic acid fragment encoding domain III of moCry1Ab was PCR amplified from a plasmid comprising mocry1Ab (SEQ ID NO: 71) using primers CMS98 (SEQ ID NO: 140) and CMS99 (SEQ ID NO: 141) and PCR reaction Mix 5 and thermocycle Profile 5.

The resulting two amplicons were used as templates in an overlap PCR reaction with primers CMS96 (SEQ ID NO: 138) and CMS98 (SEQ ID NO: 140) using PCR reaction Mix 5 and thermocycle Profile 6. The resulting amplicon was cloned into pCR4 Blunt (Invitrogen, Carlsbad, Calif.). A 1633 bp StuI/SacI fragment of the cloned amplicon, designated pCR4Blunt-OLWrdm3, and a approximately 3089 bp StuI/SacI fragment of a plasmid comprising cry3A055 (SEQ ID NO: 69) were combined to create 8AFdm3 (SEQ ID NO: 148) which encodes the 8AFdm3 hybrid protein (SEQ ID NO: 149).

The 8AFdm3 hybrid protein comprises, from N-terminus to C-terminus, amino acids 1-454 of a Cry3A055 protein (SEQ ID NO: 70), which comprises domains I and II, which comprise variable region 1, conserved block 1, variable region 2, conserved block 2, variable region 3, and the N-terminal 10 amino acids of conserved block 3, and amino acids 463-610 of a Cry1Ab protein (SEQ ID NO: 72), which comprises all of domain III, comprising the C-terminal 38 amino acids of conserved block 3, variable region 4, conserved block 4, variable region 5, conserved block 5 and variable region 6.

Thus, the 8AFdm3 protein has a cross-over junction between Cry3A055 and Cry1Ab immediately after Phe454 of SEQ ID NO: 70, which is at the domain II-domain III junction. The 8AFdm3 protein had no activity against western corn rootworm. This suggests that the 24 amino acid N-terminal region of CB3 of Cry3A055 or Cry3A, since they have the same sequence in this region, are necessary for activity of an 8AF eHIP.

Example 38. Construction of 8AFlongdm3

To determine if the location of the cross-over junction in CB3 between Cry3A or Cry3A005 and Cry1Ab was critical for rootworm activity a construct was made wherein the cross-over junction was placed in CB4 immediately after amino acid 519 of a Cry3A055 protein.

A nucleic acid fragment encoding part of domain I and all of domain II and part of domain III of Cry3A055 was PCR amplified from a plasmid comprising cry3A055 (SEQ ID NO: 69) using primers CMS96 (SEQ ID NO: 138) and CMS101 (SEQ ID NO: 143) and PCR reaction Mix 5 and thermocycle Profile 5.

A nucleic acid fragment encoding part of domain III of Cry1Ab was PCR amplified from a plasmid comprising mocry1Ab(SEQ ID NO: 71) using primers CMS98 (SEQ ID NO: 140) and CMS100 (SEQ ID NO: 142) and PCR reaction Mix 5 and thermocycle Profile 5.

The resulting two amplicons were used as templates in an overlap PCR reaction with primers CMS96 (SEQ ID NO: 138) and CMS98 (SEQ ID NO: 140) using PCR reaction Mix 5 and thermocycle Profile 6. The resulting amplicon was cloned into pCR4 Blunt (Invitrogen, Carlsbad, Calif.). A approximately 460 bp SalI/SacI fragment of the cloned amplicon, designated pCR4Blunt-OL8AFlongdm3, and a approximately 4265 bp SalI/SacI fragment of a plasmid comprising 8AFdm3 (SEQ ID NO: 147) were combined to create 8AFlongdm3 (SEQ ID NO: 150) which encodes the 8AFlongdm3 hybrid protein (SEQ ID NO: 151).

The 8AFlongdm3 hybrid protein comprises, from N-terminus to C-terminus, amino acids 1-519 of a Cry3A055 protein (SEQ ID NO: 70), which comprises domains I and II, which comprise variable region 1, conserved block 1, variable region 2, conserved block 2, variable region 3, conserved block 3, variable region 4, and the N-terminal 6 amino acids of conserved block 4, and amino acids 528-610 of a Cry1Ab protein (SEQ ID NO: 72), which comprises a C-terminal region of domain III, comprising the C-terminal 4 amino acids of conserved block 4, variable region 5, conserved block 5, and variable region 6.

Thus, the 8AFlongdm3 protein has a cross-over junction between Cry3A055 and Cry1Ab in conserved block 4 immediately after Ile519 of SEQ ID NO: 70. The 8AFlongdm3 hybrid Cry protein had no activity against western corn rootworm. This suggests that a critical region for corn rootworm activity of a Cry3A-Cry1A eHIP lies in a region between amino acids corresponding to amino acid 6 of CB3 to amino acid 7 of CB4.

Example 39. Construction of cap8AFdm3

A approximately 1363 bp BamHI/SalI fragment from a plasmid comprising 8AFdm3 (SEQ ID NO: 148) and a approximately 3362 bp BamHI/SalI fragment from a plasmid comprising FR8a (SEQ ID NO: 3) were ligated to create cap8AFdm3 (SEQ ID NO: 152) which encodes the cap8AFdm3 eHIP (SEQ ID NO: 153).

The cap8AFdm3 protein had some activity against western corn rootworm as indicated in Table 5. The only difference between the 8AFdm3 hybrid protein, which was not insecticidal, and the cap8AFdm3 eHIP is the presence of an N-terminal peptidyl fragment (SEQ ID NO: 127). Thus, adding a peptidyl fragment to a non-active hybrid Cry protein created a rootworm active engineered hybrid insecticidal protein.

Example 40. Construction of 8AFdm3T

A approximately 4654 bp PmlI/SacI fragment from a plasmid comprising 8AFdm3 (SEQ ID NO: 148) and a approximately 190 bp PmlI/SacI fragment from a plasmid comprising FR8a (SEQ ID NO: 3) were ligated to create 8AFdm3T (SEQ ID NO: 154) which encodes the 8AFdm3T eHIP (SEQ ID NO: 155). The 8AFdm3T eHIP comprises from N-terminus to C-terminus, amino acids 1-454 of a Cry3A055 protein (SEQ ID NO: 70), which comprises domains I and II, which comprise variable region 1, conserved block 1, variable region 2, conserved block 2, variable region 3, and the N-terminal 10 amino acids of conserved block 3, and amino acids 463-610 of a Cry1Ab protein (SEQ ID NO: 72), which comprises all of domain III, comprising the C-terminal 38 amino acids of conserved block 3, variable region 4, conserved block 4, variable region 5, conserved block 5, variable region 6, and a 38 amino acid region of a Cry1Ab protoxin tail.

The only difference between the 8AFdm3 hybrid protein and the 8AFdm3T eHIP is the addition of the 38 amino acid Cry1Ab protoxin tail region indicating that addition of a protoxin tail region can change a non-active hybrid Cry protein into an active eHIP.

Example 41. Construction of 8AFlongdm3T

A approximately 4693 bp PmlI/SacI fragment from a plasmid comprising 8AFlongdm3 (SEQ ID NO: 150) and a approximately 190 bp PmlI/SacI fragment from a plasmid comprising FR8a (SEQ ID NO: 3) were ligated to create 8AFlongdm3T (SEQ ID NO: 156) which encodes the 8AFlongdmT hybrid Cry protein (SEQ ID NO: 157).

The only difference between the 8AFlongdm3 hybrid Cry protein and the 8AFlongdm3T hybrid Cry protein, which was not active against western corn rootworm, is the addition of a 38 amino acid Cry1Ab protoxin tail region indicating that the protoxin region was not itself sufficient to confer insecticidal activity to the 8AFlongdm3 hybrid Cry protein. This indicates that a combination of variable regions and conserved blocks in addition to a protoxin tail region and/or an N-terminal peptidyl fragment may be necessary to create some eHIPs.

Example 42. Construction of cap8AFdm3 T

A approximately 4693 bp PmlI/SacI fragment from a plasmid comprising cap8AFdm3 (SEQ ID NO: 152) and a approximately 190 bp PmlI/SacI fragment from a plasmid comprising FR8A (SEQ ID NO: 3) were ligated to create cap8AFdm3T (SEQ ID NO: 158) which encodes the cap8AFdm3T eHIP (SEQ ID NO: 159).

The cap8AFdm3T protein had increased activity against western corn rootworm over the cap8AFdm3 eHIP as indicated in Table 5. The only difference between the cap8AFdm3 eHIP, which had some insecticidal activity against corn rootworm, and the cap8AFdm3T eHIP is the presence of a 38 amino acid protoxin tail region from Cry1Ab. Thus, some hybrid Cry proteins can be made active by adding an N-terminal peptidyl fragment and a protoxin tail region.

Example 43. Testing Hybrid Proteins for Insecticidal Activity

Western Corn Rootworm

Hybrid proteins generated in the above described Examples were tested for insecticidal activity against western corn rootworm in laboratory bioassays. Bioassays were performed using a diet incorporation method. *E. coli* clones that express one of the proteins were grown overnight. 500 μl of an overnight culture was sonicated and the amount of protein to be tested was determined. The protein solution was then mixed with 500 μl of molten artificial diet similar to that described in Marrone et al. (1985, J. of Economic Entomology 78:290-293). After the diet solidified, it was dispensed in a petri-dish and 20 neonate corn rootworm were placed on the diet. The petri-dishes were held at approximately 30° C. Mortality was recorded after 6 days.

Results of the bioassays are shown in Table 5. Column 1 indicates the names of the hybrid Cry proteins, engineered hybrid insecticidal proteins and chimeric insecticidal proteins. Column 2 indicates relative levels of western corn rootworm activity ("−"=<40% mortality; "+"=40-49% mortality; "++"=50-59% mortality; "+++"=60-80% mortality; and "++++"=>80% mortality). Column 3 indicates relative levels of the appropriate protein detected by Western blot. Column 4 indicates presence of a peptidyl fragment ("−"=No peptidyl fragment; #1=SEQ ID NO: 126; #2=SEQ ID NO:127, #3=SEQ ID NO: 128; #4=SEQ ID NO: 129; #5=SEQ ID NO: 130; #6=SEQ ID NO: 131; #7=SEQ ID NO:132). Columns 5-7 show the combinations and arrangement of the variable regions (V1-V6), conserved blocks (C1-C5) and associated domains (Domain I-III) from a first Bt Cry protein or modified Cry protein and a second Bt Cry protein different from the first Cry protein or modified Cry protein that make up a core hybrid protein, which are not active against western corn rootworm and eHIPs, which have activity against western corn rootworm. Column 8 indicates the number of amino acids in a protoxin tail region if present and the Cry protein from which the tail region is derived ("1Ab-38"=38 amino acids from a Cry1Ab protoxin tail; "1Ba-18"=18 amino acids from a Cry1Ba protoxin tail).

TABLE 5

Results of western corn rootworm bioassays.

| Proteins | CRW | Protein | Peptidyl | Domain I | | | Domain II | | Domain III | | | | | | Protoxin |
|---|---|---|---|---|---|---|---|---|---|---|---|---|---|---|---|
| Tested | Activity | Expressed | Fragment | VI | C1 | V2 | C2 | V3 | C3 | V4 | C4 | V5 | C5 | V6 | Region |
| 8AF | ++++ | ++ | — | | 3A055 | | 3A055 | | 3A055 | | | 1Ab | | | 1Ab-38 |
| T7-8AF | − | + | #7 | | 3A055 | | 3A055 | | 3A055 | | | 1Ab | | | 1Ab-38 |
| -CatG8AF | ++++ | ++ | — | | 3A | | 3A | | 3A | | | 1Ab | | | 1Ab-38 |
| 8AFdm3 | − | + | — | | 3A055 | | 3A055 | | | | 1Ab | | | | — |
| 8AFdm3T | +++ | ++ | — | | 3A055 | | 3A055 | | | | 1Ab | | | | 1Ab-38 |
| 8AFlongdm3 | − | + | — | | 3A055 | | 3A055 | | | 3A055 | | | 1Ab | | — |
| 8AFlongdm3T | − | + | — | | 3A055 | | 3A055 | | | 3A055 | | | 1Ab | | 1Ab-38 |
| Cap8AFdm3 | + | + | #2 | | 3A055 | | 3A055 | | | | 1Ab | | | | — |
| Cap8AFdm3T | ++ | ++ | #2 | | 3A055 | | 3A055 | | | | 1Ab | | | | 1Ab-38 |
| 2OL-8a | ++++ | ++ | #1 | | 3A055 | | 3A055 | | 3A055 | | | 1Ab | | | 1Ab-38 |
| FR8a +34 | ++++ | ++ | #6 | | 3A055 | | 3A055 | | 3A055 | | | 1Ab | | | 1Ab-38 |
| FR8a | ++++ | ++ | #2 | | 3A055 | | 3A055 | | 3A055 | | | 1Ab | | | 1Ab-38 |
| FRCG | ++++ | ++ | #2 | | 3A | | 3A | | 3A | | | 1Ab | | | 1Ab-38 |
| FR8a-9F | +++ | ++ | #5 | | 3A055 | | 3A055 | | 3A055 | | | 1Ab | | | 1Ab-38 |
| FR8a-9F-catg | ++++ | ++ | #5 | | 3A | | 3A | | 3A | | | 1Ab | | | 1Ab-38 |
| FR8a-12aa | ++++ | ++ | #3 | | 3A055 | | 3A055 | | 3A055 | | | 1Ab | | | 1Ab-38 |
| Cry3A055 | ++++ | ++ | — | | 3A055 | | 3A055 | | | | 3A055 | | | | — |
| 5*Cry3A055 | − | ++ | #2 | | 3A055 | | 3A055 | | | | 3A055 | | | | — |
| Wr-9mut | − | ++ | #3 | | 3A055 | | 3A055 | | | | 3A055 | | | | — |
| FRD3 | ++++ | ++ | #2 | | 3A055 | | 3A055 | | 3A055 | | | 1Ab | | | — |
| FR-12-cg-dm3 | ++ | ++ | #3 | | 3A055 | | 3A055 | | 3A055 | | | 1Ab | | | — |
| 9F-cg-del6 | − | ++ | #5 | | 3A | | 3A | | 3A | | | 1Ab | | | 1Ab-38 |
| FR-cg-dm3 | ++++ | ++ | #2 | | 3A | | 3A | | 3A | | | 1Ab | | | — |
| 9F-cg-dm3 | ++++ | ++ | #5 | | 3A | | 3A | | 3A | | | 1Ab | | | — |
| B8a | − | + | — | | 3A055 | | 3A055 | | 3A055 | | | 1Ba | | | 1Ba-18 |
| 5*B8a | − | + | #2 | | 3A055 | | 3A055 | | 3A055 | | | 1Ba | | | 1Ba-18 |
| V3A | ++ | + | — | | 3A055 | | | 1Ab | | | | 3A055 | | | — |
| V4F | − | ++ | — | | 3A055 | | 3A055 | | | 1Ab | | | 3A055 | | — |
| 5*V4F | ++ | + | #2 | | 3A055 | | 3A055 | | | 1Ab | | | 3A055 | | — |

TABLE 5-continued Results of western corn rootworm bioassays.

| Proteins Tested | CRW Activity | Protein Expressed | Peptidyl Fragment | Domain I | Domain II | Domain III | Protoxin Region |
|---|---|---|---|---|---|---|---|
| 2OL-7 | − | ++ | — | 3A055  1Ab | 1Ab | 1Ab | 1Ab-38 |
| 5*2OL-7 | − | + | #2 | 3A055  1Ab | 1Ab | 1Ab | 1Ab-38 |
| 2OL-10 | − | + | — | 3A055 | 1Ab | 1Ab | 1Ab-38 |
| 5*2OL40 | +/− | +/− | #2 | 3A055 | 1Ab | 1Ab | 1Ab-38 |
| 2OL-12A | − | ++ | — | 1Ab | 1Ab | 3A | — |
| 2OL-13 | − | − | — | 3A055 | 1Ab | 1Ab         3A055 | — |
| 2OL-20 | − | + | — | 3A | 3A | 3A       1Ab | 1Ab-38 |
| V5&6 | − | ++ | — | 3A055 | 3A055 | 3A055      1Ab | 1Ab-38 |
| 5*V5&6 | − | ++ | #2 | 3A055 | 3A055 | 3A055      1Ab | 1Ab-38 |
| 88A-dm3 | − | ++ | #2 | 3A055 | 3A055 | 3A055   8Aa | — |
| FR(1Fa) | − | ++ | #2 | 3A055 | 3A055 | 3A055   1Fa | — |
| FR(1Ac) | − | + | #2 | 3A055 | 3A055 | 3A055   1Ac | — |
| FR(1Ia) | − | − | #2 | 3A055 | 3A055 | 3A055   1Ia | — |
| DM23A | + | + | #2 | 3A055 | 3A055 | 3A055   1Ab | 1Ab-38 |

The chimeric insecticidal proteins, 2OL-8a and FR8a, and the 2OL-12A eHIP, were tested against several insect species to determine spectrum of activity. The insects tested included western corn rootworm (WCR), northern corn rootworm (NCR), southern corn rootworm (SCR), Colorado potato beetle (CPB), and European corn borer (ECB). Results of the assays are shown in Table 6. A "+" indicates insecticidal activity. A "−" indicates no activity. The 2OL-8a and FR8a CIPs were active against WCR, NCR and CPB. The 2OL-12A eHIP was surprisingly active against ECB.

TABLE 6

Activity spectrum of CIPs.

| Protein | WCR | NCR | SCR | CPB | ECB |
|---|---|---|---|---|---|
| 2OL-8a | + | + | − | + | − |
| FR8a | + | + | − | + | − |
| 2OL-12A | − | nt | nt | nt | + |
| Cry3A055 | + | + | − | + | − |
| Cry3A | − | − | − | + | − |
| Cry1Ab | − | − | − | − | + |

Example 44. Insertion of Genes Encoding eHIPs into Plants

Figure 4:
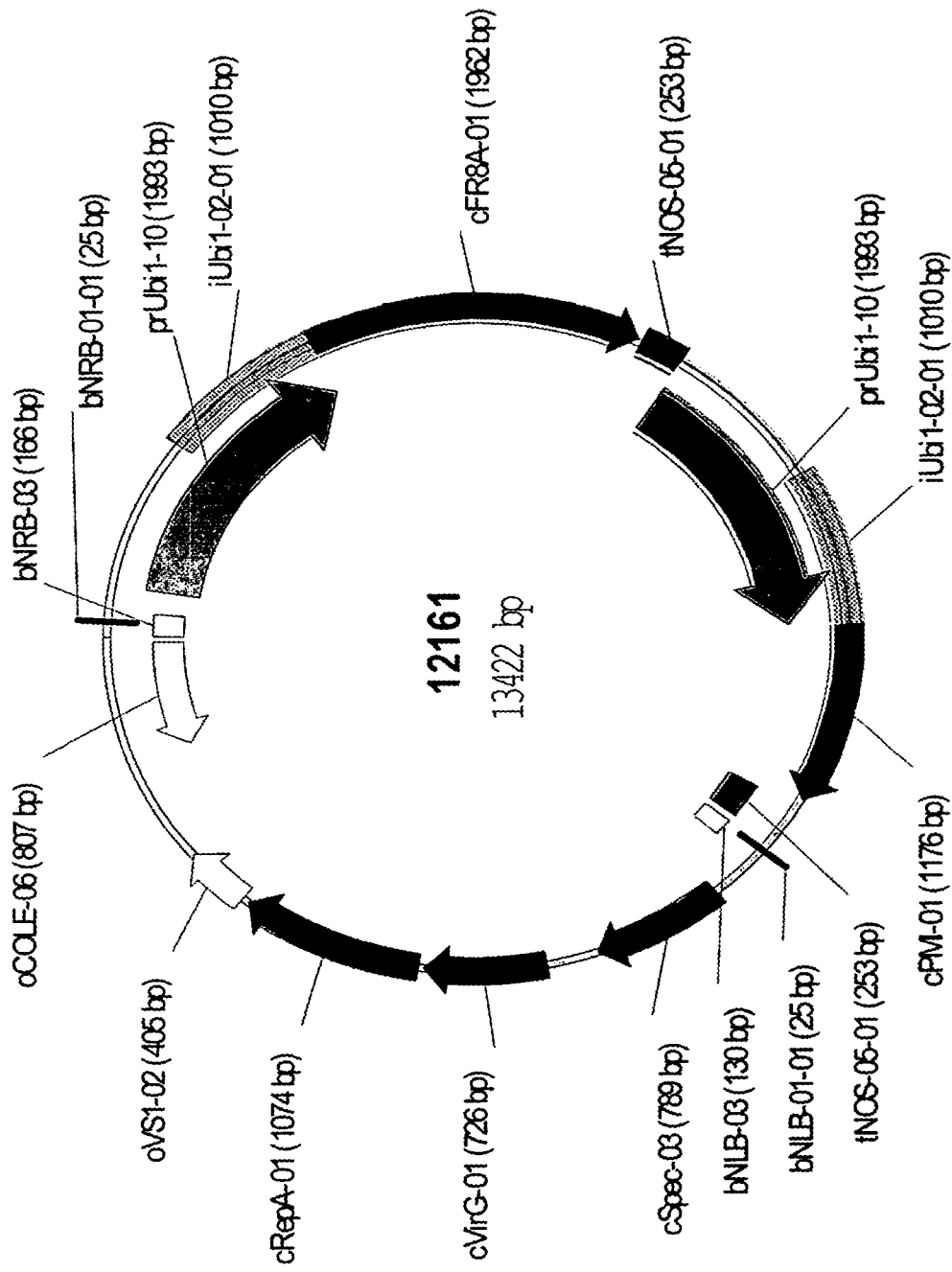
Figure 5:
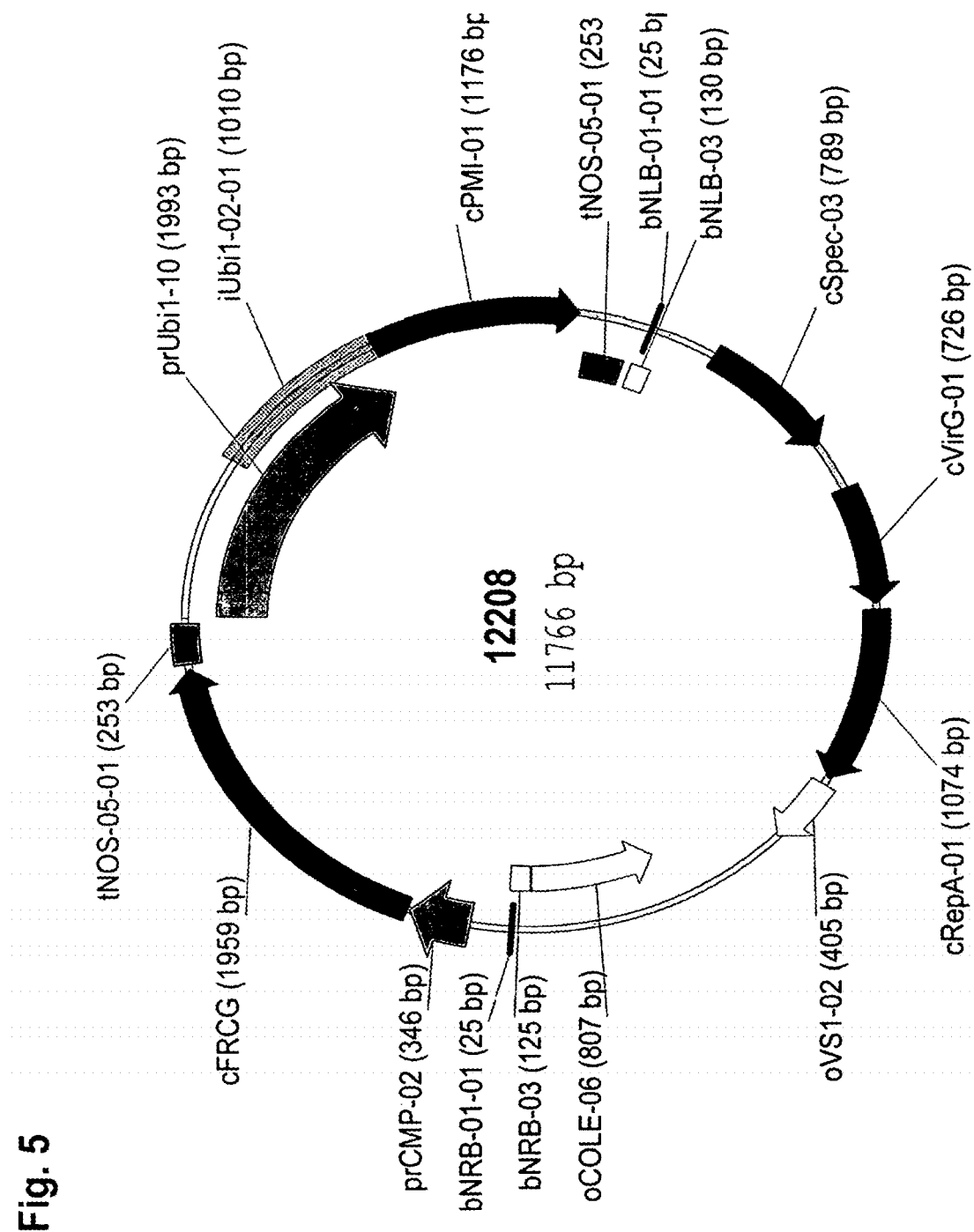
Figure 6:
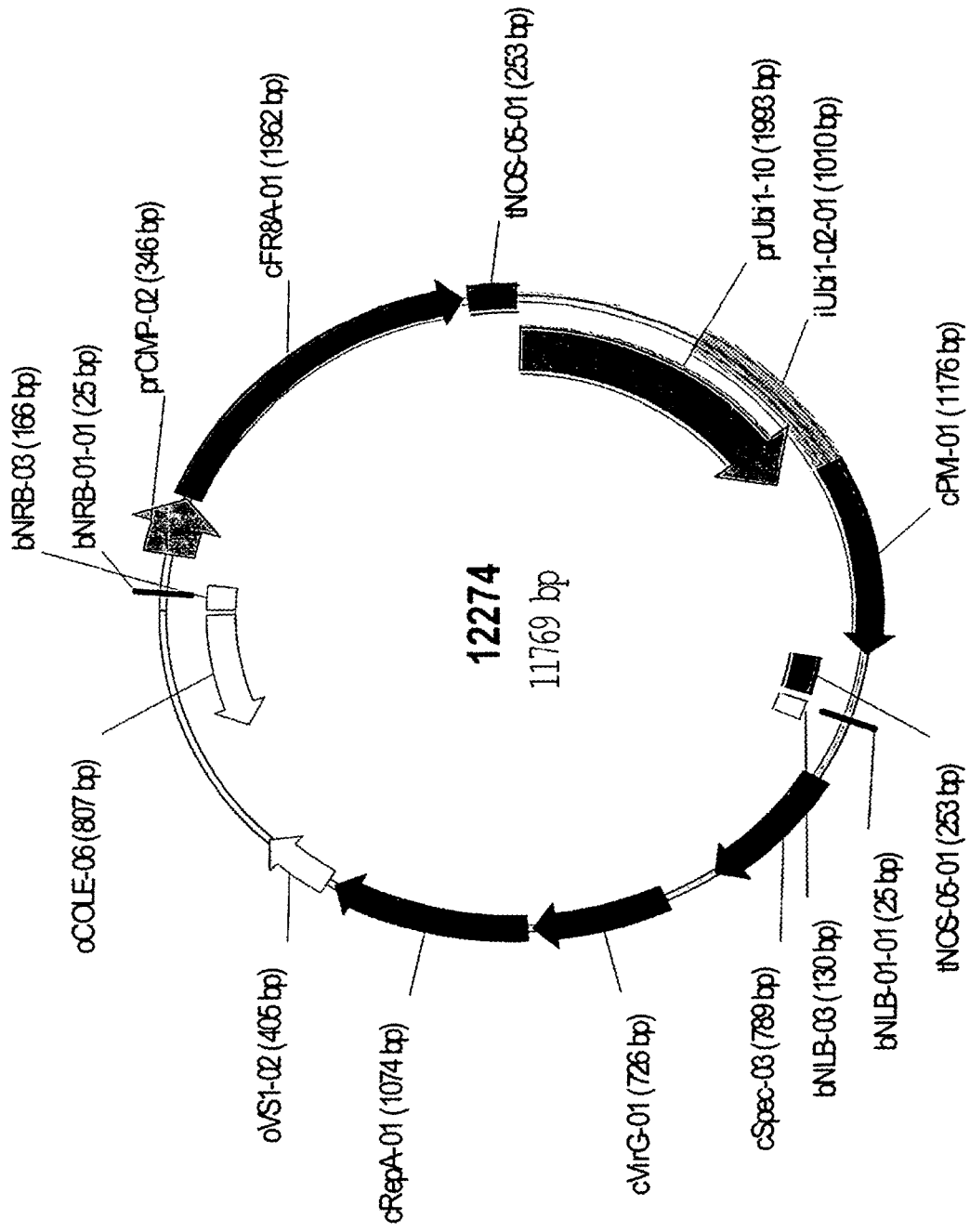
Figure 7:
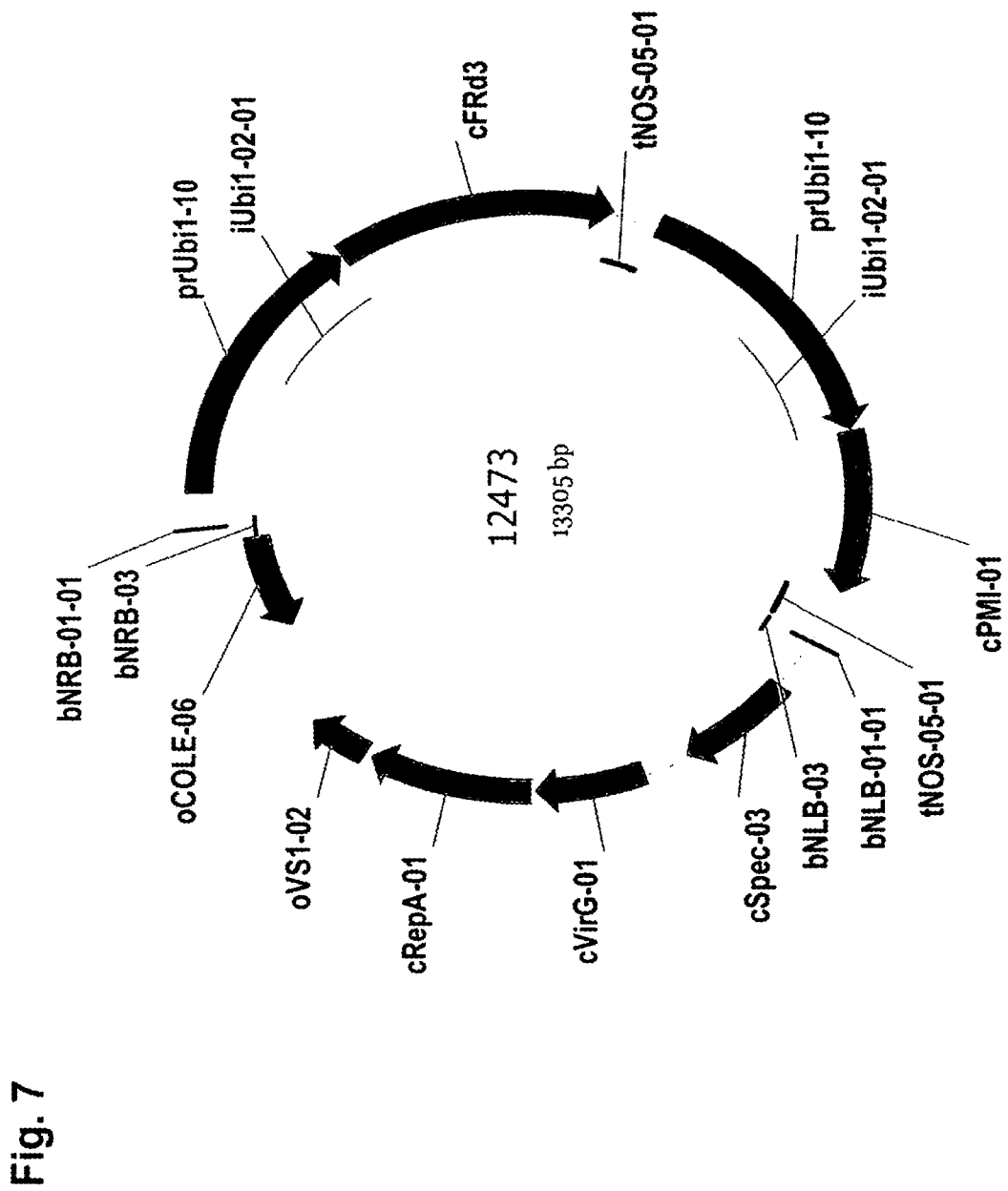
Figure 8:
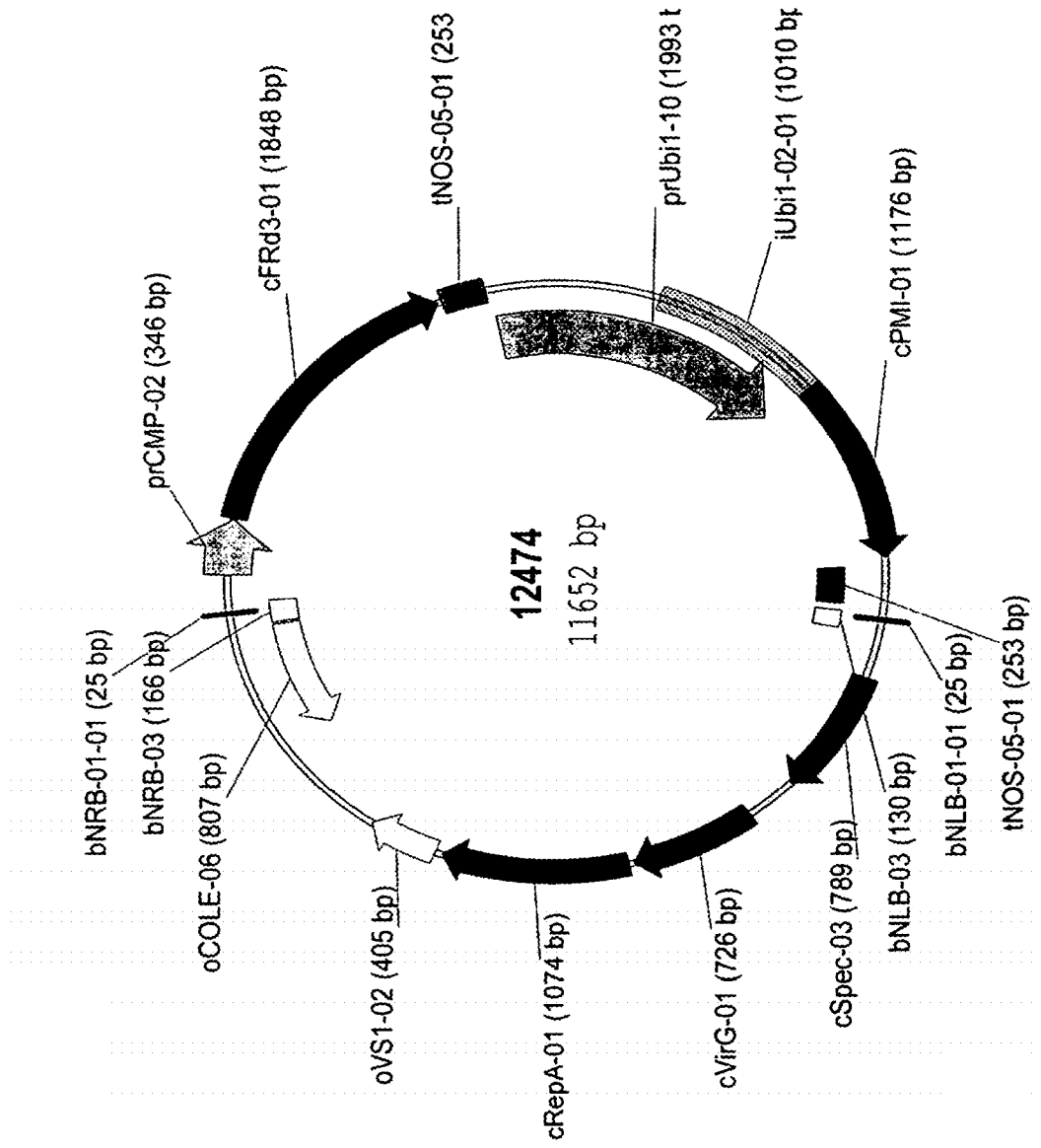

Three genes encoding the chimeric insecticidal proteins FR8a, FRCG and FRD3 were chosen for transformation into maize plants. An expression cassette comprising the FR8a or FRCG or FRD3 coding sequence was transferred to a suitable vector for Agrobacterium-mediated maize transformation. For this example, the following vectors were used in the transformation experiments: 12207 (FIG. 3), 12161 (FIG. 4), 12208 (FIG. 5), 12274 (FIG. 6), 12473 (FIG. 7) and 12474 (FIG. 8).

Transformation of immature maize embryos was performed essentially as described in Negrotto et al., 2000, Plant Cell Reports 19: 798-803. For this example, all media constituents were essentially as described in Negrotto et al., supra. However, various media constituents known in the art may be substituted.

The genes used for transformation were cloned into a vector suitable for maize transformation. Vectors used in this example contain the phosphomannose isomerase (PMI) gene for selection of transgenic lines (Negrotto et al., supra).

Briefly, Agrobacterium strain LBA4404 (pSB1) containing a plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ Agrobacterium were suspended in LS-inf media supplemented with 100 μM As (Negrotto et al., supra). Bacteria were pre-induced in this medium for 30-60 minutes.

Immature embryos from A188 or other suitable genotype are excised from 8-12 day old ears into liquid LS-inf+100 μM As. Embryos are rinsed once with fresh infection medium. Agrobacterium solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days.

Immature embryos, producing embryogenic callus were transferred to LSD1M0.5S medium. The cultures were selected on this medium for about 6 weeks with a subculture step at about 3 weeks. Surviving calli were transferred to Reg1 medium supplemented with mannose. Following culturing in the light (16 hour light/8 hour dark regiment), green tissues were then transferred to Reg2 medium without growth regulators and incubated for about 1-2 weeks. Plantlets were transferred to Magenta GA-7 boxes (Magenta Corp, Chicago Ill.) containing Reg3 medium and grown in the light. After about 2-3 weeks, plants were tested for the presence of the pmi gene and the FR8a or FRCG genes by PCR. Positive plants from the PCR assay were transferred to the greenhouse and tested for resistance to corn rootworm.

Example 45. Analysis of Transgenic Maize Plants for Corn Rootworm Efficacy: Root Excision Bioassay Typically, corn plants are sampled as they are being transplanted from Magenta GA-7 boxes into soil. This allows the roots to be sampled from a reasonably sterile environment relative to soil conditions. Sampling consists of cutting a small piece of root (ca. 2-4 cm long) and placing it onto enriched phytagar (phytagar, 12 g., sucrose, 9 g., MS salts, 3 ml., MS vitamins, 3 ml., Nystatin (25 mg/ml), 3 ml., Cefotaxime (50 mg/ml), 7 ml., Aureomycin (50 mg/ml), 7 ml., Streptomycin (50 mg/ml), 7 ml., dH₂O, 600 ml) in a small petri-dish. Negative controls are either transgenic plants that are PCR negative for the FR8a or FRCG gene from the same transformation experiment, or from non-transgenic plants (of a similar size to test plants) that were being grown in the phytotron.

Roots are also sampled after plants have been growing in soil. If sampling roots from soil, the root pieces are washed with water to remove soil residue, dipped in Nystatin solution (5 mg/ml), removed from the dip, blotted dry with paper toweling, and placed into a phytagar dish as above.

Root samples are inoculated with western corn rootworms by placing about 10 first instar larvae onto the inside surface of the lid of each phytagar dish and the lids then tightly resealed over the exposed root piece. Larvae are handled using a fine tip paintbrush. After all dishes were inoculated, the tray of dishes was placed in the dark at room temperature until data collection.

At about 2-4 days after root inoculation, data were collected. The percent mortality of the larvae was calculated along with a visual damage rating of the root. Feeding damage was scored by observing the number of feeding holes (FH) in the root piece caused by the rootworm larvae and was rated as high, moderate, low, or absent and given a numerical value of category 3, 2, or 1, respectively (with Category 1 including damage ratings of absent and/or low). Category 1 plants typically have 0-FH to 2-FH; Category 2 plants have 3 to 4-FH; and Category 3 plants have >5-FH. Root samples having a damage rating in Category 1 were considered excellent performers, category 2: average performers and category 3: poor performers. Category 1 plants were selected for further testing in the greenhouse and field.

Results in Table 7 show that plants expressing a the FR8a and FRCG eHIPs protected roots from feeding damage caused by western corn rootworm. A majority of events expressing the chimeric insecticidal protein were considered category 1 plants, whereas control plants not expressing a chimeric insecticidal protein were in category 3. Plants expressing the FRD3 eHIP provided comparable levels of control of western corn rootworm.

TABLE 7

Efficacy of transgenic plants expressing FR8a and FRCG against WCR.

| Vector | Event | Damage Rating (No. FH) | Category |
|---|---|---|---|
| 12161 | 1 | 1 | 1 |
|  | 2 | 1 | 1 |
|  | 3 | 0 | 1 |
|  | 4 | 3 | 2 |
|  | 5 | 2 | 1 |
|  | 6 | 0 | 1 |
|  | 7 | 0 | 1 |
|  | 8 | 0 | 1 |
|  | 9 | 1 | 1 |
|  | 10 | 1 | 1 |
|  | 11 | 4 | 2 |
|  | 12 | 0 | 1 |
| Control | 1 | 6 | 3 |
|  | 2 | 6 | 3 |
|  | 3 | 6 | 3 |
|  | 4 | 18 | 3 |
| 12208 | 1 | 0 | 1 |
|  | 2 | 0 | 1 |
|  | 3 | 3 | 2 |
|  | 4 | 4 | 2 |
|  | 5 | 1 | 1 |
|  | 6 | 4 | 2 |
|  | 7 | 0 | 1 |
|  | 8 | 4 | 2 |
|  | 9 | 4 | 2 |
|  | 10 | 1 | 1 |
|  | 11 | 1 | 1 |
|  | 12 | 1 | 1 |
|  | 13 | 0 | 1 |
| Control | 1 | 10 | 3 |
|  | 2 | 5 | 3 |
|  | 3 | 7 | 3 |
|  | 4 | 7 | 3 |
|  | 5 | 8 | 3 |
|  | 6 | 8 | 3 |
| 12207 | 1 | 0 | 1 |
|  | 2 | 2 | 1 |
|  | 3 | 1 | 1 |
|  | 4 | 2 | 1 |
|  | 5 | 1 | 1 |
|  | 6 | 2 | 1 |
|  | 7 | 4 | 2 |
|  | 8 | 3 | 2 |
|  | 9 | 4 | 2 |
| Control | 1 | 7 | 3 |
|  | 2 | 9 | 3 |
|  | 3 | 8 | 3 |
|  | 4 | 11 | 3 |
|  | 5 | 7 | 3 |
|  | 6 | 12 | 3 |
| 12274 | 1 | 3 | 2 |
|  | 2 | 0 | 1 |
|  | 3 | 3 | 2 |
|  | 4 | 3 | 2 |
|  | 5 | 0 | 1 |
|  | 6 | 3 | 2 |
|  | 7 | 3 | 2 |
|  | 8 | 0 | 1 |
|  | 9 | 3 | 2 |
|  | 10 | 3 | 2 |
|  | 11 | 0 | 1 |
| Control | 1 | 10 | 3 |
|  | 2 | 10 | 3 |
|  | 3 | 10 | 3 |
|  | 4 | 7 | 3 |
|  | 5 | 8 | 3 |
|  | 6 | 6 | 3 |

Example 46. Analysis of Transgenic Maize Plants for Corn Rootworm Efficacy in the Field Some positive plants identified using the root excision bioassay described above were evaluated in the field. Eighteen plants from each event were removed from field plots and evaluated for damage to the roots. Root damage was rated using the Iowa State 0 to 3 linear root damage scale (Oleson, J. D. et al., 2005. J. Econ Entomol. 98(1): 1-8), where 0.00=no feeding damage (lowest rating that can be given); 1.00=one node (circle of roots), or the equivalent of an entire node, eaten back to within approximately 1½ inches of the stalk (soil line on the 7th node); 2.00=two complete nodes eaten; 3.00=three or more nodes eaten (highest rating that can be given); and damage in between complete nodes eaten is noted as the percentage of the node missing, i.e. 1.50=1½ nodes eaten, 0.25=¼ of one node eaten, etc.

Results of the field trials against western and northern corn rootworm are shown in Table 8 and against Mexican corn rootworm in Table 9. All transgenic corn expressing the FR8a chimeric insecticidal protein performed better than a standard commercial chemical insecticide against western, northern and Mexican corn rootworm.

TABLE 8

Results of western and northern corn rootworm field trials.

| Event | Plasmid | Root Rating |
|---|---|---|
| 1 | 12161 (ubi: FR8a) | 0.08 |
| 2 | 12161 | 0.05 |
| 3 | 12161 | 0.09 |
| 4 | 12161 | 0.04 |
| 5 | 12274 (cmp:FR8a) | 0.04 |
| 6 | 12274 | 0.08 |

TABLE 8-continued

Results of western and northern corn rootworm field trials.

| Event | Plasmid | Root Rating |
|---|---|---|
| 7 | 12274 | 0.05 |
| Chemical | | 0.15 |
| Neg Check | | 0.87 |

TABLE 9

Results of Mexican corn rootworm field trials.

| Event | Plasmid | Root Rating |
|---|---|---|
| 1 | 12161 (ubi: FR8a) | 0.04 |
| 5 | 12274 (cmp: FR8a) | 0.22 |
| 6 | 12274 | 0.05 |
| Chemical | | 0.15 |
| Neg Check | | 1.04 |

SEQUENCE LISTING

```
<160> NUMBER OF SEQ ID NOS: 160

<210> SEQ ID NO 1
<211> LENGTH: 2001
<212> TYPE: DNA
<213> ORGANISM: Artificial Sequence
<220> FEATURE:
<223> OTHER INFORMATION: 2OL-8a coding sequence

<400> SEQUENCE: 1
atggctagca tgactggtgg acagcaaatg ggtcgcggat ccactagtaa cggccgccag     60
tgtgctggaa ttcgccctta tgacggccga caacaacacc gaggcctgga cagcagcacc    120
accaaggacg tgatccagaa gggcatcagc gtggtgggcg acctgctggg cgtggtgggc    180 ttcccctcg gcggcgccct ggtgagcttc tacaccaact tcctgaacac catctggccc    240
agcgaggacc cctggaaggc cttcatggag caggtggagg ccctgatgga ccagaagatc    300
gccgactacg ccaagaacaa ggcactggcc gagctacagg gcctccagaa caacgtggag    360
gactatgtga gcgccctgag cagctggcag aagaaccccg ctgcaccgtt ccgcaacccc    420
cacagccagg gccgcatccg cgagctgttc agccaggccg agagccactt ccgcaacagc    480
atgcccagct cgccatcag cggctacgag gtgctgttcc tgaccaccta cgcccaggcc    540
gccaacaccc acctgttcct gctgaaggac gcccaaatct acggagagga gtggggctac    600
gagaaggagg acatcgccga gttctacaag cgccagctga agctgaccca ggagtacacc    660
gaccactgcg tgaagtggta caacgtgggt ctagacaagc tccgcggcag cagctacgag    720
agctgggtga acttcaaccg ctaccgccgc gagatgaccc tgaccgtgct ggacctgatc    780
gccctgttcc ccctgtacga cgtgcgcctg taccccaagg aggtgaagac cgagctgacc    840
cgcgacgtgc tgaccgaccc catcgtgggc gtgaacaacc tgcgcggcta cggcaccacc    900
ttcagcaaca tcgagaacta catccgcaag ccccacctgt cgactacct gcaccgcatc    960 cagttccaca cgcgtttcca gcccggctac tacggcaaca acagcttcaa ctactggagc   1020
ggcaactacg tgagcacccg ccccagcatc ggcagcaacg acatcatcac cagccccttc   1080
tacggcaaca agagcagcga gcccgtgcag aaccttgagt tcaacggcga gaaggtgtac   1140
cgcgccgtgg ctaacaccaa cctggccgtg tggccctctg cagtgtacag cggcgtgacc   1200
```

```
aaggtggagt tcagccagta caacgaccag accgacgagg ccagcaccca gacctacgac    1260
agcaagcgca acgtgggcgc cgtgagctgg gacagcatcg accagctgcc ccccgagacc    1320
accgacgagc ccctggagaa gggctacagc caccagctga actacgtgat gtgcttcctg    1380
atgcagggca gccgcggcac catccccgtg ctgacctgga cccacaagag cgtcgacttc    1440
ttcaacatga tcgacagcaa gaagatcacc cagctgcccc tgaccaagag caccaacctg    1500
ggcagcggca ccagcgtggt gaagggcccc ggcttcaccg gcggcgacat cctgcgccgc    1560
accagccccg gccagatcag caccctgcgc gtgaacatca ccgccccccct gagccagcgc    1620 taccgcgtcc gcatccgcta cgccagcacc accaacctgc agttccacac cagcatcgac    1680
ggccgcccca tcaaccaggg caacttcagc gccaccatga gcagcggcag caacctgcag    1740
agcggcagct tccgcaccgt gggcttcacc accccccttca acttcagcaa cggcagcagc    1800
gtgttcaccc tgagcgccca cgtgttcaac agcggcaacg aggtgtacat cgaccgcatc    1860
gagttcgtgc cgccgaggt gaccttcgag gccgagtacg acctggagag ggctcagaag    1920
gccgtgaacg agctgttcac cagcagcaac cagatcggcc tgaagaccga cgtgaccgac    1980
taccacatcg atcaggtgta g                                              2001
```

<210> SEQ ID NO 2
<211> LENGTH: 668
<212> TYPE: PRT
<213> ORGANISM: Artificial Sequence
<220> FEATURE:
<223> OTHER INFORMATION: 2OL-8a protein

<400> SEQUENCE: 2

```
Met Ala Ser Met Thr Gly Gly Gln Gln Met Gly Arg Gly Ser Gly Ser
1               5                   10                  15

Thr Ser Asn Gly Arg Gln Cys Ala Gly Ile Arg Pro Tyr Asp Gly Arg
            20                  25                  30

Gln Gln His Arg Gly Leu Asp Ser Ser Thr Thr Lys Asp Val Ile Gln
        35                  40                  45

Lys Gly Ile Ser Val Val Gly Asp Leu Leu Gly Val Val Gly Phe Pro
    50                  55                  60

Phe Gly Gly Ala Leu Val Ser Phe Tyr Thr Asn Phe Leu Asn Thr Ile
65                  70                  75                  80

Trp Pro Ser Glu Asp Pro Trp Lys Ala Phe Met Glu Gln Val Glu Ala
                85                  90                  95

Leu Met Asp Gln Lys Ile Ala Asp Tyr Ala Lys Asn Lys Ala Leu Ala
            100                 105                 110

Glu Leu Gln Gly Leu Gln Asn Asn Val Glu Asp Tyr Val Ser Ala Leu
        115                 120                 125

Ser Ser Trp Gln Lys Asn Pro Ala Ala Pro Phe Arg Asn Pro His Ser
    130                 135                 140

Gln Gly Arg Ile Arg Glu Leu Phe Ser Gln Ala Glu Ser His Phe Arg
145                 150                 155                 160

Asn Ser Met Pro Ser Phe Ala Ile Ser Gly Tyr Glu Val Leu Phe Leu
                165                 170                 175

Thr Thr Tyr Ala Gln Ala Ala Asn Thr His Leu Phe Leu Leu Lys Asp
            180                 185                 190

Ala Gln Ile Tyr Gly Glu Glu Trp Gly Tyr Glu Lys Glu Asp Ile Ala
        195                 200                 205

Glu Phe Tyr Lys Arg Gln Leu Lys Leu Thr Gln Glu Tyr Thr Asp His
    210                 215                 220
```

```
Cys Val Lys Trp Tyr Asn Val Gly Leu Asp Lys Leu Arg Gly Ser Ser
225                 230                 235                 240

Tyr Glu Ser Trp Val Asn Phe Asn Arg Tyr Arg Arg Glu Met Thr Leu
            245                 250                 255

Thr Val Leu Asp Leu Ile Ala Leu Phe Pro Leu Tyr Asp Val Arg Leu
        260                 265                 270

Tyr Pro Lys Glu Val Lys Thr Glu Leu Thr Arg Asp Val Leu Thr Asp
    275                 280                 285

Pro Ile Val Gly Val Asn Asn Leu Arg Gly Tyr Gly Thr Thr Phe Ser
290                 295                 300

Asn Ile Glu Asn Tyr Ile Arg Lys Pro His Leu Phe Tyr Leu His
305                 310                 315                 320

Arg Ile Gln Phe His Thr Arg Phe Gln Pro Gly Tyr Tyr Gly Asn Asp
                325                 330                 335

Ser Phe Asn Tyr Trp Ser Gly Asn Tyr Val Ser Thr Arg Pro Ser Ile
            340                 345                 350

Gly Ser Asn Asp Ile Ile Thr Ser Pro Phe Tyr Gly Asn Lys Ser Ser
        355                 360                 365

Glu Pro Val Gln Asn Leu Glu Phe Asn Gly Glu Lys Val Tyr Arg Ala
    370                 375                 380

Val Ala Asn Thr Asn Leu Ala Val Trp Pro Ser Ala Val Tyr Ser Gly
385                 390                 395                 400

Val Thr Lys Val Glu Phe Ser Gln Tyr Asn Asp Gln Thr Asp Glu Ala
                405                 410                 415

Ser Thr Gln Thr Tyr Asp Ser Lys Arg Asn Val Gly Ala Val Ser Trp
            420                 425                 430

Asp Ser Ile Asp Gln Leu Pro Pro Glu Thr Thr Asp Glu Pro Leu Glu
        435                 440                 445

Lys Gly Tyr Ser His Gln Leu Asn Tyr Val Met Cys Phe Leu Met Gln
    450                 455                 460

Gly Ser Arg Gly Thr Ile Pro Val Leu Thr Trp Thr His Lys Ser Val
465                 470                 475                 480

Asp Phe Phe Asn Met Ile Asp Ser Lys Lys Ile Thr Gln Leu Pro Leu
                485                 490                 495

Thr Lys Ser Thr Asn Leu Gly Ser Gly Thr Ser Val Val Lys Gly Pro
            500                 505                 510

Gly Phe Thr Gly Gly Asp Ile Leu Arg Arg Thr Ser Pro Gly Gln Ile
        515                 520                 525

Ser Thr Leu Arg Val Asn Ile Thr Ala Pro Leu Ser Gln Arg Tyr Arg
    530                 535                 540

Val Arg Ile Arg Tyr Ala Ser Thr Thr Asn Leu Gln Phe His Thr Ser
545                 550                 555                 560

Ile Asp Gly Arg Pro Ile Asn Gln Gly Asn Phe Ser Ala Thr Met Ser
                565                 570                 575

Ser Gly Ser Asn Leu Gln Ser Gly Ser Phe Arg Thr Val Gly Phe Thr
            580                 585                 590

Thr Pro Phe Asn Phe Ser Asn Gly Ser Ser Val Phe Thr Leu Ser Ala
        595                 600                 605

His Val Phe Asn Ser Gly Asn Glu Val Tyr Ile Asp Arg Ile Glu Phe
    610                 615                 620

Val Pro Ala Glu Val Thr Phe Glu Ala Glu Tyr Asp Leu Glu Arg Ala
625                 630                 635                 640
```

Gln Lys Ala Val Asn Glu Leu Phe Thr Ser Ser Asn Gln Ile Gly Leu
            645                 650                 655

Lys Thr Asp Val Thr Asp Tyr His Ile Asp Gln Val
            660                 665

<210> SEQ ID NO 3
<211> LENGTH: 1962
<212> TYPE: DNA
<213> ORGANISM: Artificial Sequence
<220> FEATURE:
<223> OTHER INFORMATION: FR8a coding sequence

<400> SEQUENCE: 3

| | |
|---|---|
| atgactagta acggccgcca gtgtgctggt attcgccctt atgacggccg acaacaacac | 60 |
| cgaggcctgg acagcagcac caccaaggac gtgatccaga agggcatcag cgtggtgggc | 120 |
| gacctgctgg gcgtggtggg cttccccttc ggcggcgccc tggtgagctt ctacaccaac | 180 |
| ttcctgaaca ccatctggcc cagcgaggac ccctggaagg ccttcatgga gcaggtggag | 240 |
| gccctgatgg accagaagat cgccgactac gccaagaaca aggcactggc cgagctacag | 300 |
| ggcctccaga caacgtggaa ggactatgtg agcgccctga gcagctggca gaagaacccc | 360 |
| gctgcaccgt tccgcaaccc ccacagccag ggccgcatcc gcgagctgtt cagccaggcc | 420 |
| gagagccact ccgcaacag catgcccagc ttcgccatca gcggctacga ggtgctgttc | 480 |
| ctgaccacct acgccaggc cgccaacacc cacctgttcc tgctgaagga cgcccaaatc | 540 |
| tacggagagg agtggggcta cgagaaggag gacatcgccg agttctacaa cgccagctg | 600 |
| aagctgaccc aggagtacac cgaccactgc gtgaagtggt acaacgtggg tctagacaag | 660 |
| ctccgcggca gcagctacga gagctgggtg aacttcaacc gctaccgccg cgagatgacc | 720 |
| ctgaccgtgc tggacctgat cgccctgttc cccctgtacg acgtgcgcct gtaccccaag | 780 |
| gaggtgaaga ccgagctgac ccgcgacgtg ctgaccgacc ccatcgtggg cgtgaacaac | 840 |
| ctgcgcggct acggcaccac cttcagcaac atcgagaact acatccgcaa gccccacctg | 900 |
| ttcgactacc tgcaccgcat ccagttccac acgcgtttcc agcccggcta ctacggcaac | 960 |
| gacagcttca actactggag cggcaactac gtgagcaccc gccccagcat cggcagcaac | 1020 |
| gacatcatca ccagccccctt ctacggcaac aagagcagcg agcccgtgca gaaccttgag | 1080 |
| ttcaacggcg agaaggtgta ccgcgccgtg gctaacacca acctggccgt gtggccctct | 1140 |
| gcagtgtaca gcggcgtgac caaggtggag ttcagccagt acaacgacca gaccgacgag | 1200 |
| gccagcaccc agacctacga cagcaagcgc aacgtgggcg ccgtgagctg ggacagcatc | 1260 |
| gaccagctgc cccccgagac caccgacgag cccctggaga agggctacag ccaccagctg | 1320 |
| aactacgtga tgtgcttcct gatgcagggc agccgcggca ccatcccgt gctgacctgg | 1380 |
| acccacaaga gcgtcgactt cttcaacatg atcgacagca gaagatcac ccagctgccc | 1440 |
| ctgaccaaga gcaccaacct gggcagcggc accagcgtgg tgaagggccc cggcttcacc | 1500 |
| ggcggcgaca tcctgcgccg caccagcccc ggccagatca gcaccctgcg cgtgaacatc | 1560 |
| accgccccc tgagccagcg ctaccgcgtc cgcatccgct acgccagcac caccaacctg | 1620 |
| cagttccaca ccagcatcga cggccgcccc atcaaccagg caacttcag cgccaccatg | 1680 |
| agcagcggca gcaacctgca gagcggcagc ttccgcaccg tgggcttcac caccccttc | 1740 |
| aacttcagca acggcagcag cgtgttcacc ctgagcgccc acgtgttcaa cagcggcaac | 1800 |
| gaggtgtaca tcgaccgcat cgagttcgtg cccgccgagg tgaccttcga ggccgagtac | 1860 |
| gacctggaga gggctcagaa ggccgtgaac gagctgttca ccagcagcaa ccagatcggc | 1920 | ctgaagaccg acgtgaccga ctaccacatc gatcaggtgt ag        1962

<210> SEQ ID NO 4
<211> LENGTH: 653
<212> TYPE: PRT
<213> ORGANISM: Artificial Sequence
<220> FEATURE:
<223> OTHER INFORMATION: FR8a protein

<400> SEQUENCE: 4

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350
```

Ser Glu Pro Val Gln Asn Leu Glu Phe Asn Gly Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
                500                 505                 510

Ile Ser Thr Leu Arg Val Asn Ile Thr Ala Pro Leu Ser Gln Arg Tyr
            515                 520                 525

Arg Val Arg Ile Arg Tyr Ala Ser Thr Thr Asn Leu Gln Phe His Thr
        530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
                580                 585                 590

Ala His Val Phe Asn Ser Gly Asn Glu Val Tyr Ile Asp Arg Ile Glu
            595                 600                 605

Phe Val Pro Ala Glu Val Thr Phe Glu Ala Glu Tyr Asp Leu Glu Arg
        610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650

<210> SEQ ID NO 5
<211> LENGTH: 1959
<212> TYPE: DNA
<213> ORGANISM: Artificial Sequence
<220> FEATURE:
<223> OTHER INFORMATION: FRCG coding sequence

<400> SEQUENCE: 5
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttcccctcc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca ggcactggcc gagctacag      300 ggcctccaga caacgtgga ggactatgtg agcgccctga cagctggca aagaacccc        360

```
gtctcgagcc gcaaccccca cagccagggc cgcatccgcg agctgttcag ccaggccgag    420
agccacttcc gcaacagcat gcccagcttc gccatcagcg gctacgaggt gctgttcctg    480
accacctacg cccaggccgc caacacccac ctgttcctgc tgaaggacgc ccaaatctac    540
ggagaggagt ggggctacga gaaggaggac atcgccgagt tctacaagcg ccagctgaag    600
ctgacccagg agtacaccga ccactgcgtg aagtggtaca acgtgggtct agacaagctc    660
cgcggcagca gctacgagag ctgggtgaac ttcaaccgct accgccgcga gatgaccctg    720
accgtgctgg acctgatcgc cctgttcccc ctgtacgacg tgcgcctgta ccccaaggag    780
gtgaagaccg agctgacccg cgacgtgctg accgacccca tcgtgggcgt gaacaacctg    840
cgcggctacg caccaccttt cagcaacatc gagaactaca tccgcaagcc ccacctgttc    900
gactacctgc accgcatcca gttccacacg cgtttccagc ccggctacta cggcaacgac    960
agcttcaact actggagcgg caactacgtg agcacccgcc ccagcatcgg cagcaacgac   1020
atcatcacca gcccctttcta cggcaacaag agcagcgagc ccgtgcagaa ccttgagttc   1080
aacggcgaga aggtgtaccg cgccgtggct aacaccaacc tggccgtgtg gccctctgca   1140
gtgtacagcg gcgtgaccaa ggtggagttc agccagtaca acgaccagac cgacgaggcc   1200
agcacccaga cctacgacag caagcgcaac gtgggcgccg tgagctggga cagcatcgac   1260
cagctgcccc ccgagaccac cgacgagccc ctggagaagg gctacagcca ccagctgaac   1320
tacgtgatgt gcttcctgat gcagggcagc cgcggcacca tccccgtgct gacctggacc   1380
cacaagagcg tcgacttctt caacatgatc gacagcaaga agatcaccca gctgcccctg   1440
accaagagca ccaacctggg cagcggcacc agcgtggtga agggcccccgg cttcaccggc   1500 ggcgacatcc tgcgccgcac cagccccggc cagatcagca ccctgcgcgt gaacatcacc   1560
gcccccctga ccagcgcta ccgcgtccgc atccgctacg ccagcaccac caacctgcag   1620
ttccacacca gcatcgacgg ccgccccatc aaccagggca cttcagcgc caccatgagc   1680 agcggcagca acctgcagag cggcagcttc gcaccgtgg gcttcaccac ccccttcaac   1740
ttcagcaacg gcagcagcgt gttcaccctg agcgcccacg tgttcaacag cggcaacgag   1800
gtgtacatcg accgcatcga gttcgtgccc gccgagtga ccttcgaggc cgagtacgac   1860
ctggagaggg ctcagaaggc cgtgaacgag ctgttcacca gcagcaacca gatcggcctg   1920
aagaccgacg tgaccgacta ccacatcgat caggtgtag                          1959
```

<210> SEQ ID NO 6
<211> LENGTH: 652
<212> TYPE: PRT
<213> ORGANISM: Artificial Sequence
<220> FEATURE:
<223> OTHER INFORMATION: FRCG protein

<400> SEQUENCE: 6

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80
```

```
Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Val Ser Ser Arg Asn Pro His Ser
            115                 120                 125

Gln Gly Arg Ile Arg Glu Leu Phe Ser Gln Ala Glu Ser His Phe Arg
            130                 135                 140

Asn Ser Met Pro Ser Phe Ala Ile Ser Gly Tyr Glu Val Leu Phe Leu
145                 150                 155                 160

Thr Thr Tyr Ala Gln Ala Ala Asn Thr His Leu Phe Leu Leu Lys Asp
                165                 170                 175

Ala Gln Ile Tyr Gly Glu Glu Trp Gly Tyr Glu Lys Glu Asp Ile Ala
                180                 185                 190

Glu Phe Tyr Lys Arg Gln Leu Lys Leu Thr Gln Glu Tyr Thr Asp His
                195                 200                 205

Cys Val Lys Trp Tyr Asn Val Gly Leu Asp Lys Leu Arg Gly Ser Ser
                210                 215                 220

Tyr Glu Ser Trp Val Asn Phe Asn Arg Tyr Arg Arg Glu Met Thr Leu
225                 230                 235                 240

Thr Val Leu Asp Leu Ile Ala Leu Phe Pro Leu Tyr Asp Val Arg Leu
                245                 250                 255

Tyr Pro Lys Glu Val Lys Thr Glu Leu Thr Arg Asp Val Leu Thr Asp
                260                 265                 270

Pro Ile Val Gly Val Asn Asn Leu Arg Gly Tyr Gly Thr Thr Phe Ser
                275                 280                 285

Asn Ile Glu Asn Tyr Ile Arg Lys Pro His Leu Phe Asp Tyr Leu His
290                 295                 300

Arg Ile Gln Phe His Thr Arg Phe Gln Pro Gly Tyr Tyr Gly Asn Asp
305                 310                 315                 320

Ser Phe Asn Tyr Trp Ser Gly Asn Tyr Val Ser Thr Arg Pro Ser Ile
                325                 330                 335

Gly Ser Asn Asp Ile Ile Thr Ser Pro Phe Tyr Gly Asn Lys Ser Ser
                340                 345                 350

Glu Pro Val Gln Asn Leu Glu Phe Asn Gly Glu Lys Val Tyr Arg Ala
                355                 360                 365

Val Ala Asn Thr Asn Leu Ala Val Trp Pro Ser Ala Val Tyr Ser Gly
                370                 375                 380

Val Thr Lys Val Glu Phe Ser Gln Tyr Asn Asp Gln Thr Asp Glu Ala
385                 390                 395                 400

Ser Thr Gln Thr Tyr Asp Ser Lys Arg Asn Val Gly Ala Val Ser Trp
                405                 410                 415

Asp Ser Ile Asp Gln Leu Pro Pro Glu Thr Thr Asp Glu Pro Leu Glu
                420                 425                 430

Lys Gly Tyr Ser His Gln Leu Asn Tyr Val Met Cys Phe Leu Met Gln
                435                 440                 445

Gly Ser Arg Gly Thr Ile Pro Val Leu Thr Trp Thr His Lys Ser Val
450                 455                 460

Asp Phe Phe Asn Met Ile Asp Ser Lys Lys Ile Thr Gln Leu Pro Leu
465                 470                 475                 480

Thr Lys Ser Thr Asn Leu Gly Ser Gly Thr Ser Val Val Lys Gly Pro
                485                 490                 495

Gly Phe Thr Gly Gly Asp Ile Leu Arg Arg Thr Ser Pro Gly Gln Ile
```

```
                500             505             510
Ser Thr Leu Arg Val Asn Ile Thr Ala Pro Leu Ser Gln Arg Tyr Arg
            515             520             525

Val Arg Ile Arg Tyr Ala Ser Thr Thr Asn Leu Gln Phe His Thr Ser
            530             535             540

Ile Asp Gly Arg Pro Ile Asn Gln Gly Asn Phe Ser Ala Thr Met Ser
545             550             555             560

Ser Gly Ser Asn Leu Gln Ser Gly Ser Phe Arg Thr Val Gly Phe Thr
            565             570             575

Thr Pro Phe Asn Phe Ser Asn Gly Ser Ser Val Phe Thr Leu Ser Ala
            580             585             590

His Val Phe Asn Ser Gly Asn Glu Val Tyr Ile Asp Arg Ile Glu Phe
            595             600             605

Val Pro Ala Glu Val Thr Phe Glu Ala Glu Tyr Asp Leu Glu Arg Ala
            610             615             620

Gln Lys Ala Val Asn Glu Leu Phe Thr Ser Ser Asn Gln Ile Gly Leu
625             630             635             640

Lys Thr Asp Val Thr Asp Tyr His Ile Asp Gln Val
            645             650
```

<210> SEQ ID NO 7
<211> LENGTH: 1962
<212> TYPE: DNA
<213> ORGANISM: Artificial Sequence
<220> FEATURE:
<223> OTHER INFORMATION: FR8a-9F coding sequence

<400> SEQUENCE: 7

```
atgactagta acggccgcca gtgtgctggt attcgcccta tgacggccga caacaacacc      60
gaggccctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtggag ggactatgtg agcgccctga gcagctggca agaaccccc      360 gctgcaccgt tccgcaaccc ccacagccag ggccgcatcc gcgagctgtt cagccaggcc     420
gagagccact tccgcaacag catgcccagc ttcgccatca cgggctacga ggtgctgttc     480
ctgaccacct acgcccaggc cgccaacacc cacctgttcc tgctgaagga cgcccaaatc     540 tacgagagg agtggggcta cgagaaggag gacatcgccg agttctacaa cgccagctg      600 aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca ctactggag cggcaactac gtgagcaccc gccccagcat cggcagcaac    1020
gacatcatca ccagcccctt ctacggcaac aagagcagcg agccgtgca gaaccttgag    1080 ttcaacggcg agaaggtgta ccgcgccgtg gctaacacca acctggccgt gtggccctct    1140
gcagtgtaca gcggcgtgac caaggtggag ttcagccagt acaacgacca gaccgacgag    1200
```

```
gccagcaccc agacctacga cagcaagcgc aacgtgggcg ccgtgagctg ggacagcatc    1260
gaccagctgc cccccgagac caccgacgag cccctggaga agggctacag ccaccagctg    1320
aactacgtga tgtgcttcct gatgcagggc agccgcggca ccatcccgt gctgacctgg     1380 acccacaaga gcgtcgactt cttcaacatg atcgacagca gaagatcac ccagctgccc     1440 ctgaccaaga gcaccaacct gggcagcggc accagcgtgg tgaagggccc cggcttcacc    1500
ggcggcgaca tcctgcgccg caccagcccc ggccagatca gcaccctgcg cgtgaacatc    1560 accgccccc tgagccagcg ctaccgcgtc cgcatccgct acgccagcac caccaacctg     1620
cagttccaca ccagcatcga cggccgcccc atcaaccagg gcaacttcag cgccaccatg    1680
agcagcggca gcaacctgca gagcggcagc ttccgcaccg tgggcttcac cacccccttc    1740
aacttcagca acggcagcag cgtgttcacc ctgagcgccc acgtgttcaa cagcggcaac    1800
gaggtgtaca tcgaccgcat cgagttcgtg cccgccgagg tgaccttcga ggccgagtac    1860
gacctggaga gggctcagaa ggccgtgaac gagctgttca ccagcagcaa ccagatcggc    1920
ctgaagaccg acgtgaccga ctaccacatc gatcaggtgt ag                       1962
```

<210> SEQ ID NO 8
<211> LENGTH: 653
<212> TYPE: PRT
<213> ORGANISM: Artificial Sequence
<220> FEATURE:
<223> OTHER INFORMATION: FR8a-9F protein

<400> SEQUENCE: 8

```
Met Thr Ser Asn Gly Arg Gln Cys Ala Gly Ile Arg Pro Met Thr Ala
1               5                   10                  15

Asp Asn Asn Thr Glu Ala Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Gly Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
```

```
            225                 230                 235                 240
Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Asn Leu Arg Gly Tyr Gly Thr Thr Phe
                275                 280                 285

Ser Asn Ile Glu Asn Tyr Ile Arg Lys Pro His Leu Phe Asp Tyr Leu
                290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
                355                 360                 365

Ala Val Ala Asn Thr Asn Leu Ala Val Trp Pro Ser Ala Val Tyr Ser
                370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
                435                 440                 445

Gln Gly Ser Arg Gly Thr Ile Pro Val Leu Thr Trp Thr His Lys Ser
                450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
                500                 505                 510

Ile Ser Thr Leu Arg Val Asn Ile Thr Ala Pro Leu Ser Gln Arg Tyr
                515                 520                 525

Arg Val Arg Ile Arg Tyr Ala Ser Thr Thr Asn Leu Gln Phe His Thr
                530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
                580                 585                 590

Ala His Val Phe Asn Ser Gly Asn Glu Val Tyr Ile Asp Arg Ile Glu
                595                 600                 605

Phe Val Pro Ala Glu Val Thr Phe Glu Ala Glu Tyr Asp Leu Glu Arg
                610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650
```

<210> SEQ ID NO 9
<211> LENGTH: 1959
<212> TYPE: DNA
<213> ORGANISM: Artificial Sequence
<220> FEATURE:
<223> OTHER INFORMATION: FR-9F-catg coding sequence

<400> SEQUENCE: 9

| | |
|---|---|
| atgactagta acggccgcca gtgtgctggt attcgcccta tgacggccga caacaacacc | 60 |
| gaggccctgg acagcagcac caccaaggac gtgatccaga agggcatcag cgtggtgggc | 120 |
| gacctgctgg gcgtggtggg cttccccttc ggcggcgccc tggtgagctt ctacaccaac | 180 |
| ttcctgaaca ccatctggcc cagcgaggac ccctggaagg ccttcatgga gcaggtggag | 240 |
| gccctgatgg accagaagat cgccgactac gccaagaaca aggcactggc cgagctacag | 300 |
| ggcctccaga caacgtggag ggactatgtg agcgccctga gcagctggca agaaccccc | 360 |
| gtctcgagcc gcaacccca cagccagggc cgcatccgcg agctgttcag ccaggccgag | 420 |
| agccacttcc gcaacagcat gcccagcttc gccatcagcg gctacgaggt gctgttcctg | 480 |
| accacctacg cccaggccgc caacacccac ctgttcctgc tgaaggacgc ccaaatctac | 540 |
| ggagaggagt ggggctacga gaaggaggac atcgccgagt tctacaagcg ccagctgaag | 600 |
| ctgacccagg agtacaccga ccactgcgtg aagtggtaca cgtgggtct agacaagctc | 660 |
| cgcggcagca gctacgagag ctgggtgaac ttcaaccgct accgccgcga gatgaccctg | 720 |
| accgtgctgg acctgatcgc cctgttcccc ctgtacgacg tgcgcctgta ccccaaggag | 780 |
| gtgaagaccg agctgacccg cgacgtgctg accgacccca tcgtgggcgt gaacaacctg | 840 |
| cgcggctacg gcaccacctt cagcaacatc gagaactaca tccgcaagcc ccacctgttc | 900 |
| gactacctgc accgcatcca gttccacacg cgtttccagc ccggctacta cggcaacgac | 960 |
| agcttcaact actggagcgg caactacgtg agcacccgcc ccagcatcgg cagcaacgac | 1020 |
| atcatcacca gccccttcta cggcaacaag agcagcgagc ccgtgcagaa ccttgagttc | 1080 |
| aacggcgaga aggtgtaccg cgccgtggct aacaccaacc tggccgtgtg gccctctgca | 1140 |
| gtgtacagcg gcgtgaccaa ggtggagttc agccagtaca cgaccagac cgacgaggcc | 1200 |
| agcacccaga cctacgacag caagcgcaac gtgggcgccg tgagctggga cagcatcgac | 1260 |
| cagctgcccc ccgagaccac cgacgagccc tggagaaggg ctacagcca ccagctgaac | 1320 |
| tacgtgatgt gcttcctgat gcagggcagc cgcggcacca tccccgtgct gacctggacc | 1380 |
| cacaagagcg tcgacttctt caacatgatc gacagcaaga gatcaccca gctgccctg | 1440 |
| accaagagca ccaacctggg cagcggcacc agcgtggtga agggccccgg cttcaccggc | 1500 |
| ggcgacatcc tgcgccgcac cagccccggc cagatcagca cctgcgcgt gaacatcacc | 1560 |
| gccccctga ccagcgcta ccgcgtccgc atccgctacg ccagcaccac caacctgcag | 1620 |
| ttccacacca gcatcgacgg ccgccccatc aaccagggca acttcagcgc caccatgagc | 1680 |
| agcggcagca acctgcagag cggcagcttc gcaccgtgg gcttcaccac ccccttcaac | 1740 |
| ttcagcaacg gcagcagcgt gttcaccctg agcgcccacg tgttcaacag cggcaacgag | 1800 |
| gtgtacatcg accgcatcga gttcgtgccc gccgaggtga ccttcgaggc cgagtacgac | 1860 |
| ctggagaggg ctcagaaggc cgtgaacgag ctgttcacca gcagcaacca gatcggcctg | 1920 |
| aagaccgacg tgaccgacta ccacatcgat caggtgtag | 1959 |

<210> SEQ ID NO 10

<211> LENGTH: 652
<212> TYPE: PRT
<213> ORGANISM: Artificial Sequence
<220> FEATURE:
<223> OTHER INFORMATION: FR-9F-catg protein

<400> SEQUENCE: 10

```
Met Thr Ser Asn Gly Arg Gln Cys Ala Gly Ile Arg Pro Met Thr Ala
 1               5                  10                  15

Asp Asn Asn Thr Glu Ala Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
 50                  55                  60

Ile Trp Pro Ser Glu Asp Pro Trp Lys Ala Phe Met Glu Gln Val Glu
 65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Val Ser Ser Arg Asn Pro His Ser
        115                 120                 125

Gln Gly Arg Ile Arg Glu Leu Phe Ser Gln Ala Glu Ser His Phe Arg
130                 135                 140

Asn Ser Met Pro Ser Phe Ala Ile Ser Gly Tyr Glu Val Leu Phe Leu
145                 150                 155                 160

Thr Thr Tyr Ala Gln Ala Ala Asn Thr His Leu Phe Leu Leu Lys Asp
                165                 170                 175

Ala Gln Ile Tyr Gly Glu Glu Trp Gly Tyr Glu Lys Glu Asp Ile Ala
            180                 185                 190

Glu Phe Tyr Lys Arg Gln Leu Lys Leu Thr Gln Glu Tyr Thr Asp His
        195                 200                 205

Cys Val Lys Trp Tyr Asn Val Gly Leu Asp Lys Leu Arg Gly Ser Ser
210                 215                 220

Tyr Glu Ser Trp Val Asn Phe Asn Arg Tyr Arg Arg Glu Met Thr Leu
225                 230                 235                 240

Thr Val Leu Asp Leu Ile Ala Leu Phe Pro Leu Tyr Asp Val Arg Leu
                245                 250                 255

Tyr Pro Lys Glu Val Lys Thr Glu Leu Thr Arg Asp Val Leu Thr Asp
            260                 265                 270

Pro Ile Val Gly Val Asn Asn Leu Arg Gly Tyr Gly Thr Thr Phe Ser
        275                 280                 285

Asn Ile Glu Asn Tyr Ile Arg Lys Pro His Leu Phe Asp Tyr Leu His
290                 295                 300

Arg Ile Gln Phe His Thr Arg Phe Gln Pro Gly Tyr Tyr Gly Asn Asp
305                 310                 315                 320

Ser Phe Asn Tyr Trp Ser Gly Asn Tyr Val Ser Thr Arg Pro Ser Ile
                325                 330                 335

Gly Ser Asn Asp Ile Ile Thr Ser Pro Phe Tyr Gly Asn Lys Ser Ser
            340                 345                 350

Glu Pro Val Gln Asn Leu Glu Phe Asn Gly Glu Lys Val Tyr Arg Ala
        355                 360                 365

Val Ala Asn Thr Asn Leu Ala Val Trp Pro Ser Ala Val Tyr Ser Gly
370                 375                 380
```

| | | | | | | | | | | | | | | |
|---|---|---|---|---|---|---|---|---|---|---|---|---|---|---|
| Val | Thr | Lys | Val | Glu | Phe | Ser | Gln | Tyr | Asn | Asp | Gln | Thr | Asp | Glu | Ala |
| 385 | | | | 390 | | | | 395 | | | | 400 | | |

Val Thr Lys Val Glu Phe Ser Gln Tyr Asn Asp Gln Thr Asp Glu Ala
385                 390                 395                 400

Ser Thr Gln Thr Tyr Asp Ser Lys Arg Asn Val Gly Ala Val Ser Trp
            405                 410                 415

Asp Ser Ile Asp Gln Leu Pro Pro Glu Thr Thr Asp Glu Pro Leu Glu
            420                 425                 430

Lys Gly Tyr Ser His Gln Leu Asn Tyr Val Met Cys Phe Leu Met Gln
            435                 440                 445

Gly Ser Arg Gly Thr Ile Pro Val Leu Thr Trp Thr His Lys Ser Val
        450                 455                 460

Asp Phe Phe Asn Met Ile Asp Ser Lys Lys Ile Thr Gln Leu Pro Leu
465                 470                 475                 480

Thr Lys Ser Thr Asn Leu Gly Ser Gly Thr Ser Val Val Lys Gly Pro
                485                 490                 495

Gly Phe Thr Gly Gly Asp Ile Leu Arg Arg Thr Ser Pro Gly Gln Ile
            500                 505                 510

Ser Thr Leu Arg Val Asn Ile Thr Ala Pro Leu Ser Gln Arg Tyr Arg
            515                 520                 525

Val Arg Ile Arg Tyr Ala Ser Thr Thr Asn Leu Gln Phe His Thr Ser
        530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr
                565                 570                 575

Thr Pro Phe Asn Phe Ser Asn Gly Ser Ser Val Phe Thr Leu Ser Ala
            580                 585                 590

His Val Phe Asn Ser Gly Asn Glu Val Tyr Ile Asp Arg Ile Glu Phe
            595                 600                 605

Val Pro Ala Glu Val Thr Phe Glu Ala Glu Tyr Asp Leu Glu Arg Ala
        610                 615                 620

Gln Lys Ala Val Asn Glu Leu Phe Thr Ser Ser Asn Gln Ile Gly Leu
625                 630                 635                 640

Lys Thr Asp Val Thr Asp Tyr His Ile Asp Gln Val
                645                 650

<210> SEQ ID NO 11
<211> LENGTH: 1926
<212> TYPE: DNA
<213> ORGANISM: Artificial Sequence
<220> FEATURE:
<223> OTHER INFORMATION: FR8a-12AA coding sequence

<400> SEQUENCE: 11
atgtatgacg gccgacaaca acaccgaggc ctggacagca gcaccaccaa ggacgtgatc        60
cagaagggca tcagcgtggt gggcgacctg ctgggcgtgg tgggcttccc cttcggcggc       120
gccctggtga gcttctacac caacttcctg aacaccatct ggcccagcga ggaccccctgg      180 aaggccttca tggagcaggt ggaggccctg atggaccaga gatcgccga ctacgccaag        240 aacaaggcac tggccgagct acagggcctc cagaacaacg tggaggacta tgtgagcgcc      300
ctgagcagct ggcagaagaa ccccgctgca ccgttccgca accccacag ccagggccgc       360 atccgcgagc tgttcagcca ggccgagagc cacttccgca acagcatgcc cagcttcgcc      420
atcagcggct acgaggtgct gttcctgacc acctacgccc aggccgccaa cacccacctg      480
ttcctgctga aggacgccca aatctacgga gaggagtggg gctacgagaa ggaggacatc      540

```
gccgagttct acaagcgcca gctgaagctg acccaggagt acaccgacca ctgcgtgaag    600
tggtacaacg tgggtctaga caagctccgc ggcagcagct acgagagctg ggtgaacttc    660
aaccgctacc gccgcgagat gaccctgacc gtgctggacc tgatcgccct gttccccctg    720
tacgacgtgc gcctgtaccc caaggaggtg aagaccgagc tgacccgcga cgtgctgacc    780
gacccccatcg tgggcgtgaa caacctgcgc ggctacggca ccaccttcag caacatcgag    840
aactacatcc gcaagcccca cctgttcgac tacctgcacc gcatccagtt ccacacgcgt    900
ttccagcccg gctactacgg caacgacagc ttcaactact ggagcggcaa ctacgtgagc    960
acccgcccca gcatcggcag caacgacatc atcaccagcc ccttctacgg caacaagagc   1020
agcgagcccg tgcagaacct tgagttcaac ggcgagaagg tgtaccgcgc cgtggctaac   1080
accaacctgg ccgtgtggcc ctctgcagtg tacagcggcg tgaccaaggt ggagttcagc   1140
cagtacaacg accagaccga cgaggccagc acccagacct acgacagcaa gcgcaacgtg   1200
ggcgccgtga gctgggacag catcgaccag ctgcccccccg agaccaccga cgagcccctg   1260
gagaagggct acagccacca gctgaactac gtgatgtgct tcctgatgca gggcagccgc   1320
ggcaccatcc ccgtgctgac ctggacccac aagagcgtcg acttcttcaa catgatcgac   1380
agcaagaaga tcacccagct gccccctgacc aagagcacca acctgggcag cggcaccagc   1440
gtggtgaagg ccccggcttt caccggcggc gacatcctgc cgcaccag ccccggccag      1500
atcagcaccc tgcgcgtgaa catcaccgcc ccctgagcc agcgctaccg cgtccgcatc     1560
cgctacgcca gcaccaccaa cctgcagttc cacaccagca tcgacggccg cccatcaac     1620
cagggcaact tcagcgccac catgagcagc ggcagcaacc tgcagagcgg cagcttccgc    1680
accgtgggct tcaccacccc cttcaacttc agcaacggca gcagcgtgtt caccctgagc    1740
gcccacgtgt tcaacagcgg caacgaggtg tacatcgacc gcatcgagtt cgtgcccgcc    1800
gaggtgaccct tcgaggccga gtacgacctg gagagggctc agaaggccgt gaacgagctg   1860
ttcaccagca gcaaccagat cggcctgaag accgacgtga ccgactacca catcgatcag   1920
gtgtag                                                              1926
```

<210> SEQ ID NO 12
<211> LENGTH: 641
<212> TYPE: PRT
<213> ORGANISM: Artificial Sequence
<220> FEATURE:
<223> OTHER INFORMATION: FR8a-12AA protein

<400> SEQUENCE: 12

```
Met Tyr Asp Gly Arg Gln Gln His Arg Gly Leu Asp Ser Ser Thr Thr
1               5                   10                  15
Lys Asp Val Ile Gln Lys Gly Ile Ser Val Val Gly Asp Leu Leu Gly
            20                  25                  30
Val Val Gly Phe Pro Phe Gly Gly Ala Leu Val Ser Phe Tyr Thr Asn
        35                  40                  45
Phe Leu Asn Thr Ile Trp Pro Ser Glu Asp Pro Trp Lys Ala Phe Met
    50                  55                  60
Glu Gln Val Glu Ala Leu Met Asp Gln Lys Ile Ala Asp Tyr Ala Lys
65                  70                  75                  80
Asn Lys Ala Leu Ala Glu Leu Gln Gly Leu Gln Asn Asn Val Glu Asp
                85                  90                  95
Tyr Val Ser Ala Leu Ser Ser Trp Gln Lys Asn Pro Ala Ala Pro Phe
            100                 105                 110
```

```
Arg Asn Pro His Ser Gln Gly Arg Ile Arg Glu Leu Phe Ser Gln Ala
        115                 120                 125

Glu Ser His Phe Arg Asn Ser Met Pro Ser Phe Ala Ile Ser Gly Tyr
    130                 135                 140

Glu Val Leu Phe Leu Thr Thr Tyr Ala Gln Ala Ala Asn Thr His Leu
145                 150                 155                 160

Phe Leu Leu Lys Asp Ala Gln Ile Tyr Gly Glu Glu Trp Gly Tyr Glu
                165                 170                 175

Lys Glu Asp Ile Ala Glu Phe Tyr Lys Arg Gln Leu Lys Leu Thr Gln
            180                 185                 190

Glu Tyr Thr Asp His Cys Val Lys Trp Tyr Asn Val Gly Leu Asp Lys
        195                 200                 205

Leu Arg Gly Ser Ser Tyr Glu Ser Trp Val Asn Phe Asn Arg Tyr Arg
    210                 215                 220

Arg Glu Met Thr Leu Thr Val Leu Asp Leu Ile Ala Leu Phe Pro Leu
225                 230                 235                 240

Tyr Asp Val Arg Leu Tyr Pro Lys Glu Val Lys Thr Glu Leu Thr Arg
                245                 250                 255

Asp Val Leu Thr Asp Pro Ile Val Gly Val Asn Asn Leu Arg Gly Tyr
            260                 265                 270

Gly Thr Thr Phe Ser Asn Ile Glu Asn Tyr Ile Arg Lys Pro His Leu
        275                 280                 285

Phe Asp Tyr Leu His Arg Ile Gln Phe His Thr Arg Phe Gln Pro Gly
    290                 295                 300

Tyr Tyr Gly Asn Asp Ser Phe Asn Tyr Trp Ser Gly Asn Tyr Val Ser
305                 310                 315                 320

Thr Arg Pro Ser Ile Gly Ser Asn Asp Ile Ile Thr Ser Pro Phe Tyr
                325                 330                 335

Gly Asn Lys Ser Ser Glu Pro Val Gln Asn Leu Glu Phe Asn Gly Glu
            340                 345                 350

Lys Val Tyr Arg Ala Val Ala Asn Thr Asn Leu Ala Val Trp Pro Ser
        355                 360                 365

Ala Val Tyr Ser Gly Val Thr Lys Val Glu Phe Ser Gln Tyr Asn Asp
    370                 375                 380

Gln Thr Asp Glu Ala Ser Thr Gln Thr Tyr Asp Ser Lys Arg Asn Val
385                 390                 395                 400

Gly Ala Val Ser Trp Asp Ser Ile Asp Gln Leu Pro Pro Glu Thr Thr
                405                 410                 415

Asp Glu Pro Leu Glu Lys Gly Tyr Ser His Gln Leu Asn Tyr Val Met
            420                 425                 430

Cys Phe Leu Met Gln Gly Ser Arg Gly Thr Ile Pro Val Leu Thr Trp
        435                 440                 445

Thr His Lys Ser Val Asp Phe Phe Asn Met Ile Asp Ser Lys Lys Ile
    450                 455                 460

Thr Gln Leu Pro Leu Thr Lys Ser Thr Asn Leu Gly Ser Gly Thr Ser
465                 470                 475                 480

Val Val Lys Gly Pro Gly Phe Thr Gly Gly Asp Ile Leu Arg Arg Thr
                485                 490                 495

Ser Pro Gly Gln Ile Ser Thr Leu Arg Val Asn Ile Thr Ala Pro Leu
            500                 505                 510

Ser Gln Arg Tyr Arg Val Arg Ile Arg Tyr Ala Ser Thr Thr Asn Leu
        515                 520                 525
```

```
Gln Phe His Thr Ser Ile Asp Gly Arg Pro Ile Asn Gln Gly Asn Phe
            530                 535                 540

Ser Ala Thr Met Ser Ser Gly Ser Asn Leu Gln Ser Gly Ser Phe Arg
545                 550                 555                 560

Thr Val Gly Phe Thr Thr Pro Phe Asn Phe Asn Gly Ser Ser Val
                565                 570                 575

Phe Thr Leu Ser Ala His Val Phe Asn Ser Gly Asn Glu Val Tyr Ile
                580                 585                 590

Asp Arg Ile Glu Phe Val Pro Ala Glu Val Thr Phe Glu Ala Glu Tyr
            595                 600                 605

Asp Leu Glu Arg Ala Gln Lys Ala Val Asn Glu Leu Phe Thr Ser Ser
        610                 615                 620

Asn Gln Ile Gly Leu Lys Thr Asp Val Thr Asp Tyr His Ile Asp Gln
625                 630                 635                 640

Val

<210> SEQ ID NO 13
<211> LENGTH: 1800
<212> TYPE: DNA
<213> ORGANISM: Artificial Sequence
<220> FEATURE:
<223> OTHER INFORMATION: WR-9mut coding sequence

<400> SEQUENCE: 13
atgtatgacg ccgacaaca cacccgaggc ctggacagca gcaccaccaa ggacgtgatc      60
cagaagggca tcagcgtggt gggcgacctg ctgggcgtgg tgggcttccc cttcggcggc     120
gccctggtga gcttctacac caacttcctg aacaccatct ggcccagcga ggacccctgg     180
aaggccttca tggagcaggt ggaggccctg atggaccaga gatcgccga ctacgccaag      240 aacaaggcac tggccgagct acagggcctc cagaacaacg tggaggacta tgtgagcgcc     300
ctgagcagct ggcagaagaa ccccgctgca ccgttccgca accccacag ccagggccgc      360 atccgcgagc tgttcagcca ggccgagagc cacttccgca cagcatgcc cagcttcgcc      420 atcagcggct acgaggtgct gttcctgacc acctacgccc aggccgccaa cacccacctg     480
ttcctgctga aggacgccca aatctacgga gaggagtggg gctacgagaa ggaggacatc     540
gccgagttct acaagcgcca gctgaagctg acccaggagt acaccgacca ctgcgtgaag     600
tggtacaacg tgggtctaga caagctccgc ggcagcagct acgagagctg ggtgaacttc     660
aaccgctacc gccgcgagat gaccctgacc gtgctggacc tgatcgccct gttccccctg     720
tacgacgtgc gcctgtaccc caaggaggtg aagaccgagc tgacccgcga cgtgctgacc     780
gaccccatcg tgggcgtgaa caacctgcgc ggctacggca ccaccttcag caacatcgag     840
aactacatcc gcaagcccca cctgttcgac tacctgcacc gcatccagtt ccacacgcgt     900
ttccagcccg gctactacgg caacgacagc ttcaactact ggagcggcaa ctacgtgagc     960
acccgcccca gcatcggcag caacgacatc atcaccagcc ccttctacgg caacaagagc    1020
agcgagcccg tgcagaacct tgagttcaac ggcgagaagg tgtaccgcgc cgtggctaac    1080
accaacctgg ccgtgtggcc ctctgcagtg tacagcggcg tgaccaaggt ggagttcagc    1140
cagtacaacg accagaccga cgaggccagc acccagacct acgacagcaa gcgcaacgtg    1200
ggcgccgtga gctgggacag catcgaccag ctgccccccg agaccaccga cgagcccctg    1260
gagaagggct acagccacca gctgaactac gtgatgtgct cctgatgca gggcagccgc    1320 ggcaccatcc ccgtgctgac ctggacccac aagagcgtcg acttcttcaa catgatcgac    1380
```

```
agcaagaaga tcacccagct gccccctggtg aaggcctaca agctccagag cggcgccagc    1440
gtggtggcag ccccccgctt caccggcggc gacatcatcc agtgcaccga gaacggcagc    1500
gccgccacca tctacgtgac ccccgacgtg agctacagcc agaagtaccg cgcccgcatc    1560
cactacgcca gcaccagcca gatcaccttc accctgagcc tggacggggc ccccttcaac    1620
caatactact tcgacaagac catcaacaag ggcgacaccc tgacctacaa cagcttcaac    1680
ctggccagct tcagcacccc tttcgagctg agcggcaaca acctccagat cggcgtgacc    1740
ggcctgagcg ccggcgacaa ggtgtacatc gacaagatcg agttcatccc cgtgaactag    1800
```

<210> SEQ ID NO 14
<211> LENGTH: 599
<212> TYPE: PRT
<213> ORGANISM: Artificial Sequence
<220> FEATURE:
<223> OTHER INFORMATION: WR-9mut protein

<400> SEQUENCE: 14

```
Met Tyr Asp Gly Arg Gln Gln His Arg Gly Leu Asp Ser Ser Thr Thr
1               5                   10                  15

Lys Asp Val Ile Gln Lys Gly Ile Ser Val Val Gly Asp Leu Leu Gly

```
                    290                 295                 300
Tyr Tyr Gly Asn Asp Ser Phe Asn Tyr Trp Ser Gly Asn Tyr Val Ser
305                 310                 315                 320

Thr Arg Pro Ser Ile Gly Ser Asn Asp Ile Ile Thr Ser Pro Phe Tyr
                325                 330                 335

Gly Asn Lys Ser Ser Glu Pro Val Gln Asn Leu Glu Phe Asn Gly Glu
            340                 345                 350

Lys Val Tyr Arg Ala Val Ala Asn Thr Asn Leu Ala Val Trp Pro Ser
        355                 360                 365

Ala Val Tyr Ser Gly Val Thr Lys Val Glu Phe Ser Gln Tyr Asn Asp
    370                 375                 380

Gln Thr Asp Glu Ala Ser Thr Gln Thr Tyr Asp Ser Lys Arg Asn Val
385                 390                 395                 400

Gly Ala Val Ser Trp Asp Ser Ile Asp Gln Leu Pro Pro Glu Thr Thr
                405                 410                 415

Asp Glu Pro Leu Glu Lys Gly Tyr Ser His Gln Leu Asn Tyr Val Met
            420                 425                 430

Cys Phe Leu Met Gln Gly Ser Arg Gly Thr Ile Pro Val Leu Thr Trp
        435                 440                 445

Thr His Lys Ser Val Asp Phe Phe Asn Met Ile Asp Ser Lys Lys Ile
    450                 455                 460

Thr Gln Leu Pro Leu Val Lys Ala Tyr Lys Leu Gln Ser Gly Ala Ser
465                 470                 475                 480

Val Val Ala Gly Pro Arg Phe Thr Gly Gly Asp Ile Ile Gln Cys Thr
                485                 490                 495

Glu Asn Gly Ser Ala Ala Thr Ile Tyr Val Thr Pro Asp Val Ser Tyr
            500                 505                 510

Ser Gln Lys Tyr Arg Ala Arg Ile His Tyr Ala Ser Thr Ser Gln Ile
        515                 520                 525

Thr Phe Thr Leu Ser Leu Asp Gly Ala Pro Phe Asn Gln Tyr Tyr Phe
    530                 535                 540

Asp Lys Thr Ile Asn Lys Gly Asp Thr Leu Thr Tyr Asn Ser Phe Asn
545                 550                 555                 560

Leu Ala Ser Phe Ser Thr Pro Phe Glu Leu Ser Gly Asn Asn Leu Gln
                565                 570                 575

Ile Gly Val Thr Gly Leu Ser Ala Gly Asp Lys Val Tyr Ile Asp Lys
            580                 585                 590

Ile Glu Phe Ile Pro Val Asn
        595

<210> SEQ ID NO 15
<211> LENGTH: 1848
<212> TYPE: DNA
<213> ORGANISM: Artificial Sequence
<220> FEATURE:
<223> OTHER INFORMATION: FRD3 coding sequence

<400> SEQUENCE: 15
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
```

```
ggcctccaga caacgtgga ggactatgtg agcgccctga gcagctggca gaagaacccc    360
gctgcaccgt tccgcaaccc ccacagccag ggccgcatcc gcgagctgtt cagccaggcc    420
gagagccact tccgcaacag catgcccagc ttcgccatca gcggctacga ggtgctgttc    480
ctgaccacct acgcccaggc cgccaacacc cacctgttcc tgctgaagga cgcccaaatc    540
tacggagagg agtggggcta cgagaaggag gacatcgccg agttctacaa cgccagctg     600 aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc ccctgtacg acgtgcgcct gtaccccaag     780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagcccctt ctacggcaac aagagcagcg agcccgtgca gaaccttgag   1080
ttcaacggcg agaaggtgta ccgcgccgtg gctaacacca acctggccgt gtggccctct   1140
gcagtgtaca cgcgcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag ccccctggaga agggctacag ccaccagctg   1320
aactacgtga tgtgcttcct gatgcagggc agccgcggca ccatcccgt gctgacctgg    1380 acccacaaga gcgtcgactt cttcaacatg atcgacagca gaagatcac ccagctgccc    1440 ctgaccaaga gcaccaacct gggcagcggc accagcgtgg tgaagggccc cggcttcacc   1500
ggcggcgaca tcctgcgccg caccagcccc ggccagatca gcaccctgcg cgtgaacatc   1560 accgccccc tgagccagcg ctaccgcgtc cgcatccgct acgccagcac caccaacctg   1620
cagttccaca ccagcatcga cggccgcccc atcaaccagg gcaacttcag cgccaccatg   1680
agcagcggca gcaacctgca gagcggcagc ttccgcaccg tgggcttcac cacccccttc   1740
aacttcagca acggcagcag cgtgttcacc ctgagcgccc acgtgttcaa cagcggcaac   1800
gaggtgtaca tcgaccgcat cgagttcgtg cccgccgagg tgacctag              1848
```

<210> SEQ ID NO 16
<211> LENGTH: 615
<212> TYPE: PRT
<213> ORGANISM: Artificial Sequence
<220> FEATURE:
<223> OTHER INFORMATION: FRD3 protein

<400> SEQUENCE: 16

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

```
Ala Glu Leu Gln Gly Leu Gln Asn Asn Val Glu Asp Tyr Val Ser Ala
                100                 105                 110

Leu Ser Ser Trp Gln Lys Asn Pro Ala Ala Pro Phe Arg Asn Pro His
            115                 120                 125

Ser Gln Gly Arg Ile Arg Glu Leu Phe Ser Gln Ala Glu Ser His Phe
        130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
    450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
            500                 505                 510
```

```
Ile Ser Thr Leu Arg Val Asn Ile Thr Ala Pro Leu Ser Gln Arg Tyr
        515                 520                 525

Arg Val Arg Ile Arg Tyr Ala Ser Thr Thr Asn Leu Gln Phe His Thr
        530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
            580                 585                 590

Ala His Val Phe Asn Ser Gly Asn Glu Val Tyr Ile Asp Arg Ile Glu
        595                 600                 605

Phe Val Pro Ala Glu Val Thr
        610             615

<210> SEQ ID NO 17
<211> LENGTH: 1809
<212> TYPE: DNA
<213> ORGANISM: Artificial Sequence
<220> FEATURE:
<223> OTHER INFORMATION: FR-12-cg-dm3 coding sequence

<400> SEQUENCE: 17
atgtatgacg gccgacaaca acaccgaggc ctggacagca gcaccaccaa ggacgtgatc      60
cagaagggca tcagcgtggt gggcgacctg ctgggcgtgg tgggcttccc cttcggcggc     120
gccctggtga gcttctacac caacttcctg aacaccatct ggcccagcga ggaccctgg      180 aaggccttca tggagcaggt ggaggccctg atggaccaga agatcgccga ctacgccaag     240
aacaaggcac tggccgagct acagggcctc cagaacaacg tggaggacta tgtgagcgcc     300
ctgagcagct ggcagaagaa ccccgtctcg agccgcaacc ccacagcca gggccgcatc      360 cgcgagctgt tcagccaggc cgagagccac ttccgcaaca gcatgccag cttcgccatc      420 agcggctacg aggtgctgtt cctgaccacc tacgcccagg ccgccaacac ccacctgttc     480
ctgctgaagg acgcccaaat ctacggagag gagtggggct acgagaagga ggacatcgcc     540
gagttctaca gcgccagct gaagctgacc caggagtaca ccgaccactg cgtgaagtgg      600
tacaacgtgg gtctagacaa gctccgcggc agcagctacg agagctgggt gaacttcaac     660
cgctaccgcc gcgagatgac cctgaccgtg ctggacctga tcgccctgtt cccccctgtac    720 gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcgcaacta cgtgagcacc    960 cgccccagca tcggcagcaa cgacatcatc accagcccct tctacggcaa caagagcagc  1020
gagcccgtgc agaaccttga gttcaacggc gagaaggtgt accgcgccgt ggctaacacc  1080
aacctggccg tgtggccctc tgcagtgtac agcggcgtga ccaaggtgga gttcagccag  1140
tacaacgacc agaccgacga ggccagcacc cagacctacg acagcaagcg caacgtgggc  1200
gccgtgagct gggacagcat cgaccagctg cccccgaga ccaccgacga gcccctggag   1260
aagggctaca gccaccagct gaactacgtg atgtgcttcc tgatgcaggg cagccgcggc  1320
accatccccg tgctgacctg gacccacaag agcgtcgact tcttcaacat gatcgacagc  1380
aagaagatca cccagctgcc cctgaccaag agcaccaacc tgggcagcgg caccagcgtg  1440
```

-continued

```
gtgaagggcc ccggcttcac cggcggcgac atcctgcgcc gcaccagccc cggccagatc    1500
agcaccctgc gcgtgaacat caccgccccc ctgagccagc gctaccgcgt ccgcatccgc    1560
tacgccagca ccaccaacct gcagttccac accagcatcg acggccgccc catcaaccag    1620
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca acagcggcaa cgaggtgtac atcgaccgca tcgagttcgt gcccgccgag    1800
gtgacctag                                                           1809

<210> SEQ ID NO 18
<211> LENGTH: 602
<212> TYPE: PRT
<213> ORGANISM: Artificial Sequence
<220> FEATURE:
<223> OTHER INFORMATION: FR-12-cg-dm3 protein

<400> SEQUENCE: 18

Met Tyr Asp Gly Arg Gln Gln His Arg Gly Leu Asp Ser Ser Thr Thr
1               5                   10                  15

Lys Asp Val Ile Gln Lys Gly Ile Ser Val Val Gly Asp Leu Leu Gly
            20                  25                  30

Val Val Gly Phe Pro Phe Gly Ala Leu Val Ser Phe Tyr Thr Asn
        35                  40                  45

Phe Leu Asn Thr Ile Trp Pro Ser Glu Asp Pro Trp Lys Ala Phe Met
    50                  55                  60

Glu Gln Val Glu Ala Leu Met Asp Gln Lys Ile Ala Asp Tyr Ala Lys
65                  70                  75                  80

Asn Lys Ala Leu Ala Glu Leu Gln Gly Leu Gln Asn Asn Val Glu Asp
                85                  90                  95

Tyr Val Ser Ala Leu Ser Ser Trp Gln Lys Asn Pro Val Ser Ser Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
```

```
                290                 295                 300
Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
                355                 360                 365

Val Tyr Ser Gly Val Thr Lys Val Glu Phe Ser Gln Tyr Asn Asp Gln
                370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
                435                 440                 445

His Lys Ser Val Asp Phe Phe Asn Met Ile Asp Ser Lys Lys Ile Thr
                450                 455                 460

Gln Leu Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
                500                 505                 510

Gln Arg Tyr Arg Val Arg Ile Arg Tyr Ala Ser Thr Thr Asn Leu Gln
                515                 520                 525

Phe His Thr Ser Ile Asp Gly Arg Pro Ile Asn Gln Gly Asn Phe Ser
                530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
                580                 585                 590

Arg Ile Glu Phe Val Pro Ala Glu Val Thr
                595                 600
```

<210> SEQ ID NO 19
<211> LENGTH: 1941
<212> TYPE: DNA
<213> ORGANISM: Artificial Sequence
<220> FEATURE:
<223> OTHER INFORMATION: 9F-cg-del6 coding sequence

<400> SEQUENCE: 19

```
atgtgtgctg gtattcgccc tatgacggcc gacaacaaca ccgaggccct ggacagcagc      60
accaccaagg acgtgatcca agagggcatc agcgtggtgg cgacctgct gggcgtggtg     120 ggcttcccct tcggcggcgc cctggtgagc ttctacacca acttcctgaa caccatctgg     180
cccagcgagg acccctggaa ggccttcatg gagcaggtgg aggccctgat ggaccagaag     240
atcgccgact acgccaagaa caaggcactg gccgagctac agggcctcca gaacaacgtg     300
```

```
gaggactatg tgagcgccct gagcagctgg cagaagaacc ccgtctcgag ccgcaacccc    360
cacagccagg gccgcatccg cgagctgttc agccaggccg agagccactt ccgcaacagc    420
atgcccagct tcgccatcag cggctacgag gtgctgttcc tgaccaccta cgcccaggcc    480
gccaacaccc acctgttcct gctgaaggac gcccaaatct acggagagga gtggggctac    540
gagaaggagg acatcgccga gttctacaag cgccagctga agctgaccca ggagtacacc    600
gaccactgcg tgaagtggta caacgtgggt ctagacaagc tccgcggcag cagctacgag    660
agctgggtga acttcaaccg ctaccgccgc gagatgaccc tgaccgtgct ggacctgatc    720
gccctgttcc ccctgtacga cgtgcgcctg taccccaagg aggtgaagac cgagctgacc    780
cgcgacgtgc tgaccgaccc catcgtgggc gtgaacaacc tgcgcggcta cggcaccacc    840
ttcagcaaca tcgagaacta catccgcaag ccccacctgt tcgactacct gcaccgcatc    900
cagttccaca cgcgtttcca gcccggctac tacggcaaca cagcttcaa ctactggagc    960 ggcaactacg tgagcacccg ccccagcatc ggcagcaacg acatcatcac cagccccttc    1020
tacggcaaca agagcagcga gccgtgcag aaccttgagt tcaacggcga aaggtgtac    1080 cgcgccgtgg ctaacaccaa cctggccgtg tggccctctg cagtgtacag cggcgtgacc    1140
aaggtggagt tcagccagta caacgaccag accgacgagg ccagcaccca gacctacgac    1200
agcaagcgca acgtgggcgc cgtgagctgg acagcatcg accagctgcc ccccgagacc    1260
accgacgagc cctggagaa gggctacagc caccagctga actacgtgat gtgcttcctg    1320
atgcagggca gccgcggcac catccccgtg ctgacctgga cccacaagag cgtcgacttc    1380
ttcaacatga tcgacagcaa gaagatcacc cagctgcccc tgaccaagag caccaacctg    1440
ggcagcggca ccagcgtggt gaagggcccc ggcttcaccg gcggcgacat cctgcgccgc    1500
accagccccg gccagatcag caccctgcgc gtgaacatca ccgcccccct gagccagcgc    1560
taccgcgtcc gcatccgcta cgccagcacc accaacctgc agttccacac cagcatcgac    1620
ggccgcccca tcaaccaggg caacttcagc gccaccatga gcagcggcag caacctgcag    1680
agcggcagct tccgcaccgt gggcttcacc acccccttca acttcagcaa cggcagcagc    1740
gtgttcaccc tgagcgccca cgtgttcaac agcggcaacg aggtgtacat cgaccgcatc    1800
gagttcgtgc ccgccgaggt gaccttcgag gccgagtacg acctggagag ggctcagaag    1860
gccgtgaacg agctgttcac cagcagcaac cagatcggcc tgaagaccga cgtgaccgac    1920
taccacatcg atcaggtgta g                                             1941
```

<210> SEQ ID NO 20
<211> LENGTH: 646
<212> TYPE: PRT
<213> ORGANISM: Artificial Sequence
<220> FEATURE:
<223> OTHER INFORMATION: 9F-cg-del6 protein

<400> SEQUENCE: 20

```
Met Cys Ala Gly Ile Arg Pro Met Thr Ala Asp Asn Asn Thr Glu Ala
1               5                   10                  15

Leu Asp Ser Ser Thr Thr Lys Asp Val Ile Gln Lys Gly Ile Ser Val
                20                  25                  30

Val Gly Asp Leu Leu Gly Val Gly Phe Pro Phe Gly Gly Ala Leu
                35                  40                  45

Val Ser Phe Tyr Thr Asn Phe Leu Asn Thr Ile Trp Pro Ser Glu Asp
        50                  55                  60

Pro Trp Lys Ala Phe Met Glu Gln Val Glu Ala Leu Met Asp Gln Lys
```

```
                65                  70                  75                  80
Ile Ala Asp Tyr Ala Lys Asn Lys Ala Leu Ala Glu Leu Gln Gly Leu
                    85                  90                  95

Gln Asn Asn Val Glu Asp Tyr Val Ser Ala Leu Ser Ser Trp Gln Lys
                100                 105                 110

Asn Pro Val Ser Ser Arg Asn Pro His Ser Gln Gly Arg Ile Arg Glu
                115                 120                 125

Leu Phe Ser Gln Ala Glu Ser His Phe Arg Asn Ser Met Pro Ser Phe
                130                 135                 140

Ala Ile Ser Gly Tyr Glu Val Leu Phe Leu Thr Thr Tyr Ala Gln Ala
145                 150                 155                 160

Ala Asn Thr His Leu Phe Leu Leu Lys Asp Ala Gln Ile Tyr Gly Glu
                165                 170                 175

Glu Trp Gly Tyr Glu Lys Glu Asp Ile Ala Glu Phe Tyr Lys Arg Gln
                180                 185                 190

Leu Lys Leu Thr Gln Glu Tyr Thr Asp His Cys Val Lys Trp Tyr Asn
                195                 200                 205

Val Gly Leu Asp Lys Leu Arg Gly Ser Ser Tyr Glu Ser Trp Val Asn
210                 215                 220

Phe Asn Arg Tyr Arg Arg Glu Met Thr Leu Thr Val Leu Asp Leu Ile
225                 230                 235                 240

Ala Leu Phe Pro Leu Tyr Asp Val Arg Leu Tyr Pro Lys Glu Val Lys
                245                 250                 255

Thr Glu Leu Thr Arg Asp Val Leu Thr Asp Pro Ile Val Gly Val Asn
                260                 265                 270

Asn Leu Arg Gly Tyr Gly Thr Thr Phe Ser Asn Ile Glu Asn Tyr Ile
                275                 280                 285

Arg Lys Pro His Leu Phe Asp Tyr Leu His Arg Ile Gln Phe His Thr
                290                 295                 300

Arg Phe Gln Pro Gly Tyr Tyr Gly Asn Asp Ser Phe Asn Tyr Trp Ser
305                 310                 315                 320

Gly Asn Tyr Val Ser Thr Arg Pro Ser Ile Gly Ser Asn Asp Ile Ile
                325                 330                 335

Thr Ser Pro Phe Tyr Gly Asn Lys Ser Ser Glu Pro Val Gln Asn Leu
                340                 345                 350

Glu Phe Asn Gly Glu Lys Val Tyr Arg Ala Val Ala Asn Thr Asn Leu
                355                 360                 365

Ala Val Trp Pro Ser Ala Val Tyr Ser Gly Val Thr Lys Val Glu Phe
370                 375                 380

Ser Gln Tyr Asn Asp Gln Thr Asp Glu Ala Ser Thr Gln Thr Tyr Asp
385                 390                 395                 400

Ser Lys Arg Asn Val Gly Ala Val Ser Trp Asp Ser Ile Asp Gln Leu
                405                 410                 415

Pro Pro Glu Thr Thr Asp Glu Pro Leu Glu Lys Gly Tyr Ser His Gln
                420                 425                 430

Leu Asn Tyr Val Met Cys Phe Leu Met Gln Gly Ser Arg Gly Thr Ile
                435                 440                 445

Pro Val Leu Thr Trp Thr His Lys Ser Val Asp Phe Phe Asn Met Ile
                450                 455                 460

Asp Ser Lys Lys Ile Thr Gln Leu Pro Leu Thr Lys Ser Thr Asn Leu
465                 470                 475                 480

Gly Ser Gly Thr Ser Val Val Lys Gly Pro Gly Phe Thr Gly Gly Asp
                485                 490                 495
```

Ile Leu Arg Arg Thr Ser Pro Gly Gln Ile Ser Thr Leu Arg Val Asn
                500                 505                 510

Ile Thr Ala Pro Leu Ser Gln Arg Tyr Arg Val Arg Ile Arg Tyr Ala
            515                 520                 525

Ser Thr Thr Asn Leu Gln Phe His Thr Ser Ile Asp Gly Arg Pro Ile
        530                 535                 540

Asn Gly Gly Asn Phe Ser Ala Thr Met Ser Ser Gly Ser Asn Leu Gln
545                 550                 555                 560

Ser Gly Ser Phe Arg Thr Val Gly Phe Thr Thr Pro Phe Asn Phe Ser
                565                 570                 575

Asn Gly Ser Ser Val Phe Thr Leu Ser Ala His Val Phe Asn Ser Gly
            580                 585                 590

Asn Glu Val Tyr Ile Asp Arg Ile Glu Phe Val Pro Ala Glu Val Thr
        595                 600                 605

Phe Glu Ala Glu Tyr Asp Leu Glu Arg Ala Gln Lys Ala Val Asn Glu
610                 615                 620

Leu Phe Thr Ser Ser Asn Gln Ile Gly Leu Lys Thr Asp Val Thr Asp
625                 630                 635                 640

Tyr His Ile Asp Gln Val
                645

<210> SEQ ID NO 21
<211> LENGTH: 1845
<212> TYPE: DNA
<213> ORGANISM: Artificial Sequence
<220> FEATURE:
<223> OTHER INFORMATION: FR-cg-dm3 coding sequence

<400> SEQUENCE: 21

```
atgactagta acggccgcca gtgtgctggt attcgccctt atgacggccg acaacaacac     60
cgaggcctgg acagcagcac caccaaggac gtgatccaga agggcatcag cgtggtgggc    120
gacctgctgg gcgtggtggg cttccccttc ggcggcgccc tggtgagctt ctacaccaac    180
ttcctgaaca ccatctggcc cagcgaggac ccctggaagg ccttcatgga gcaggtggag    240
gccctgatgg accagaagat cgccgactac gccaagaaca aggcactggc cgagctacag    300
ggcctccaga caacgtggag ggactatgtg agcgccctga gcagctggca gaagaacccc    360
gtctcgagcc gcaaccccca gccagggc cgcatccgcg agctgttcag ccaggccgag    420
agccacttcc gcaacagcat gcccagcttc gccatcagcg ctacgaggt gctgttcctg    480
accacctacg cccaggccgc caacacccac ctgttcctgc tgaaggacgc caaatctac    540
ggagaggagt ggggctacga agaggaggac atcgccgagt ctacaagcg ccagctgaag    600
ctgacccagg agtacaccga ccactgcgtg aagtggtaca cgtgggtct agacaagctc    660
cgcggcagca gctacgagag ctgggtgaac ttcaaccgct accgccgcga tgaccctg    720
accgtgctgg acctgatcgc cctgttcccc ctgtacgacg tgcgcctgta ccccaaggag    780
gtgaagaccg agctgacccg cgacgtgctg accgacccca tcgtgggcgt gaacaacctg    840
cgcggctacg gcaccacctt cagcaacatc gagaactaca tccgcaagcc ccacctgttc    900
gactacctgc accgcatcca gttccacacg cgtttccagc cggctacta cggcaacgac    960
agcttcaact actggagcgg caactacgtg agcacccgcc ccagcatcgg cagcaacgac   1020
atcatcacca gccccttcta cggcaacaag agcagcgagc ccgtgcagaa ccttgagttc   1080
aacggcgaga aggtgtaccg cgccgtggct aacaccaacc tggccgtgtg gccctctgca   1140
```

-continued

```
gtgtacagcg gcgtgaccaa ggtggagttc agccagtaca acgaccagac cgacgaggcc    1200
agcacccaga cctacgacag caagcgcaac gtgggcgccg tgagctggga cagcatcgac    1260
cagctgcccc ccgagaccac cgacgagccc ctggagaagg gctacagcca ccagctgaac    1320
tacgtgatgt gcttcctgat gcagggcagc cgcggcacca tccccgtgct gacctggacc    1380
cacaagagcg tcgacttctt caacatgatc gacagcaaga agatcaccca gctgcccctg    1440
accaagagca ccaacctggg cagcggcacc agcgtggtga agggcccggg cttcaccggc    1500
ggcgacatcc tgcgccgcac cagccccggc cagatcagca ccctgcgcgt gaacatcacc    1560
gcccccctga ccagcgcta ccgcgtccgc atccgctacg ccagcaccac caacctgcag    1620
ttccacacca gcatcgacgg ccgccccatc aaccagggca cttcagcgc caccatgagc    1680 agcggcagca acctgcagag cggcagcttc gcaccgtgg gcttcaccac cccccttcaac    1740 ttcagcaacg gcagcagcgt gttcaccctg agcgcccacg tgttcaacag cggcaacgag    1800
gtgtacatcg accgcatcga gttcgtgccc gccgaggtga cctag                    1845
```

<210> SEQ ID NO 22
<211> LENGTH: 614
<212> TYPE: PRT
<213> ORGANISM: Artificial Sequence
<220> FEATURE:
<223> OTHER INFORMATION: FR-cg-dm3 protein

<400> SEQUENCE: 22

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
                20                  25                  30

Gln Lys Gly Ile Ser Val Val Gly Asp Leu Leu Gly Val Val Gly Phe
            35                  40                  45

Pro Phe Gly Gly Ala Leu Val Ser Phe Tyr Thr Asn Phe Leu Asn Thr
        50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Val Ser Ser Arg Asn Pro His Ser
        115                 120                 125

Gln Gly Arg Ile Arg Glu Leu Phe Ser Gln Ala Glu Ser His Phe Arg
    130                 135                 140

Asn Ser Met Pro Ser Phe Ala Ile Ser Gly Tyr Glu Val Leu Phe Leu
145                 150                 155                 160

Thr Thr Tyr Ala Gln Ala Ala Asn Thr His Leu Phe Leu Leu Lys Asp
                165                 170                 175

Ala Gln Ile Tyr Gly Glu Glu Trp Gly Tyr Glu Lys Glu Asp Ile Ala
            180                 185                 190

Glu Phe Tyr Lys Arg Gln Leu Lys Leu Thr Gln Glu Tyr Thr Asp His
        195                 200                 205

Cys Val Lys Trp Tyr Asn Val Gly Leu Asp Lys Leu Arg Gly Ser Ser
    210                 215                 220

Tyr Glu Ser Trp Val Asn Phe Asn Arg Tyr Arg Arg Glu Met Thr Leu
225                 230                 235                 240
```

```
Thr Val Leu Asp Leu Ile Ala Leu Phe Pro Leu Tyr Asp Val Arg Leu
                245                 250                 255

Tyr Pro Lys Glu Val Lys Thr Glu Leu Thr Arg Asp Val Leu Thr Asp
            260                 265                 270

Pro Ile Val Gly Val Asn Asn Leu Arg Gly Tyr Gly Thr Thr Phe Ser
        275                 280                 285

Asn Ile Glu Asn Tyr Ile Arg Lys Pro His Leu Phe Asp Tyr Leu His
    290                 295                 300

Arg Ile Gln Phe His Thr Arg Phe Gln Pro Tyr Tyr Gly Asn Asp
305                 310                 315                 320

Ser Phe Asn Tyr Trp Ser Gly Asn Tyr Val Ser Thr Arg Pro Ser Ile
                325                 330                 335

Gly Ser Asn Asp Ile Ile Thr Ser Pro Phe Tyr Gly Asn Lys Ser Ser
            340                 345                 350

Glu Pro Val Gln Asn Leu Glu Phe Asn Gly Glu Lys Val Tyr Arg Ala
        355                 360                 365

Val Ala Asn Thr Asn Leu Ala Val Trp Pro Ser Ala Val Tyr Ser Gly
    370                 375                 380

Val Thr Lys Val Glu Phe Ser Gln Tyr Asn Asp Gln Thr Asp Glu Ala
385                 390                 395                 400

Ser Thr Gln Thr Tyr Asp Ser Lys Arg Asn Val Gly Ala Val Ser Trp
                405                 410                 415

Asp Ser Ile Asp Gln Leu Pro Pro Glu Thr Thr Asp Glu Pro Leu Glu
            420                 425                 430

Lys Gly Tyr Ser His Gln Leu Asn Tyr Val Met Cys Phe Leu Met Gln
        435                 440                 445

Gly Ser Arg Gly Thr Ile Pro Val Leu Thr Trp Thr His Lys Ser Val
    450                 455                 460

Asp Phe Phe Asn Met Ile Asp Ser Lys Lys Ile Thr Gln Leu Pro Leu
465                 470                 475                 480

Thr Lys Ser Thr Asn Leu Gly Ser Gly Thr Ser Val Val Lys Gly Pro
                485                 490                 495

Gly Phe Thr Gly Gly Asp Ile Leu Arg Arg Thr Ser Pro Gly Gln Ile
            500                 505                 510

Ser Thr Leu Arg Val Asn Ile Thr Ala Pro Leu Ser Gln Arg Tyr Arg
        515                 520                 525

Val Arg Ile Arg Tyr Ala Ser Thr Thr Asn Leu Gln Phe His Thr Ser
    530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr
                565                 570                 575

Thr Pro Phe Asn Phe Ser Asn Gly Ser Ser Val Phe Thr Leu Ser Ala
            580                 585                 590

His Val Phe Asn Ser Gly Asn Glu Val Tyr Ile Asp Arg Ile Glu Phe
        595                 600                 605

Val Pro Ala Glu Val Thr
    610
```

<210> SEQ ID NO 23
<211> LENGTH: 1845
<212> TYPE: DNA
<213> ORGANISM: Artificial Sequence
<220> FEATURE:
<223> OTHER INFORMATION: 9F-cg-dm3 coding sequence

<400> SEQUENCE: 23

| | | | | | |
|---|---|---|---|---|---|
| atgactagta | acggccgcca | gtgtgctggt | attcgcccta | tgacggccga | caacaacacc | 60 |
| gaggccctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggag | gactatgtg | agcgccctga | gcagctggca | gaagaacccc | 360 |
| gtctcgagcc | gcaaccccca | cagccagggc | cgcatccgcg | agctgttcag | ccaggccgag | 420 |
| agccacttcc | gcaacagcat | gcccagcttc | gccatcagcg | gctacgaggt | gctgttcctg | 480 |
| accacctacg | cccaggccgc | caacacccac | ctgttcctgc | tgaaggacgc | caaatctac | 540 |
| ggagaggagt | ggggctacga | aaggaggac | atcgccgagt | tctacaagcg | ccagctgaag | 600 |
| ctgacccagg | agtacaccga | ccactgcgtg | aagtggtaca | cgtgggtct | agacaagctc | 660 |
| cgcggcagca | gctacgagag | ctgggtgaac | ttcaaccgct | accgccgcga | gatgaccctg | 720 |
| accgtgctgg | acctgatcgc | cctgttcccc | ctgtacgacg | tgcgcctgta | ccccaaggag | 780 |
| gtgaagaccg | agctgacccg | cgacgtgctg | accgacccca | tcgtgggcgt | gaacaacctg | 840 |
| cgcggctacg | caccaccttt | cagcaacatc | gagaactaca | tccgcaagcc | ccacctgttc | 900 |
| gactacctgc | accgcatcca | gttccacacg | cgtttccagc | ccggctacta | cggcaacgac | 960 |
| agcttcaact | actggagcgg | caactacgtg | agcaccgcc | ccagcatcgg | cagcaacgac | 1020 |
| atcatcacca | gccccttcta | cggcaacaag | agcagcgagc | ccgtgcagaa | ccttgagttc | 1080 |
| aacggcgaga | aggtgtaccg | cgccgtggct | aacaccaacc | tggccgtgtg | gccctctgca | 1140 |
| gtgtacagcg | gcgtgaccaa | ggtggagttc | agccagtaca | cgaccagac | cgacgaggcc | 1200 |
| agcacccaga | cctacgacag | caagcgcaac | gtgggcgccg | tgagctggga | cagcatcgac | 1260 |
| cagctgcccc | ccgagaccac | cgacgagccc | ctggagaagg | gctacagcca | ccagctgaac | 1320 |
| tacgtgatgt | gcttcctgat | gcagggcagc | cgcggcacca | tccccgtgct | gacctggacc | 1380 |
| cacaagagcg | tcgacttctt | caacatgatc | gacagcaaga | agatcaccca | gctgcccctg | 1440 |
| accaagagca | ccaacctggg | cagcggcacc | agcgtggtga | agggcccgg | cttcaccggc | 1500 |
| ggcgacatcc | tgcgccgcac | cagccccggc | cagatcagca | cctgcgcgt | gaacatcacc | 1560 |
| gcccccctga | ccagcgcta | ccgcgtccgc | atccgctacg | ccagcaccac | caacctgcag | 1620 |
| ttccacacca | gcatcgacgg | ccgccccatc | aaccagggca | acttcagcgc | caccatgagc | 1680 |
| agcggcagca | acctgcagag | cggcagcttc | cgcaccgtgg | gcttcaccac | ccccttcaac | 1740 |
| ttcagcaacg | gcagcagcgt | gttcaccctg | agcgcccacg | tgttcaacag | cggcaacgag | 1800 |
| gtgtacatcg | accgcatcga | gttcgtgccc | gccgaggtga | cctag | | 1845 |

<210> SEQ ID NO 24
<211> LENGTH: 614
<212> TYPE: PRT
<213> ORGANISM: Artificial Sequence
<220> FEATURE:
<223> OTHER INFORMATION: 9F-cg-dm3 protein

<400> SEQUENCE: 24

Met Thr Ser Asn Gly Arg Gln Cys Ala Gly Ile Arg Pro Met Thr Ala
1               5                   10                  15

Asp Asn Asn Thr Glu Ala Leu Asp Ser Ser Thr Thr Lys Asp Val Ile

-continued

```
                20                  25                  30
Gln Lys Gly Ile Ser Val Val Gly Asp Leu Leu Gly Val Val Gly Phe
            35                  40                  45
Pro Phe Gly Gly Ala Leu Val Ser Phe Tyr Thr Asn Phe Leu Asn Thr
    50                  55                  60
Ile Trp Pro Ser Glu Asp Pro Trp Lys Ala Phe Met Glu Gln Val Glu
65                  70                  75                  80
Ala Leu Met Asp Gln Lys Ile Ala Asp Tyr Ala Lys Asn Lys Ala Leu
                85                  90                  95
Ala Glu Leu Gln Gly Leu Gln Asn Asn Val Glu Asp Tyr Val Ser Ala
            100                 105                 110
Leu Ser Ser Trp Gln Lys Asn Pro Val Ser Ser Arg Asn Pro His Ser
        115                 120                 125
Gln Gly Arg Ile Arg Glu Leu Phe Ser Gln Ala Glu Ser His Phe Arg
    130                 135                 140
Asn Ser Met Pro Ser Phe Ala Ile Ser Gly Tyr Glu Val Leu Phe Leu
145                 150                 155                 160
Thr Thr Tyr Ala Gln Ala Ala Asn Thr His Leu Phe Leu Leu Lys Asp
                165                 170                 175
Ala Gln Ile Tyr Gly Glu Glu Trp Gly Tyr Glu Lys Glu Asp Ile Ala
            180                 185                 190
Glu Phe Tyr Lys Arg Gln Leu Lys Leu Thr Gln Glu Tyr Thr Asp His
        195                 200                 205
Cys Val Lys Trp Tyr Asn Val Gly Leu Asp Lys Leu Arg Gly Ser Ser
    210                 215                 220
Tyr Glu Ser Trp Val Asn Phe Asn Arg Tyr Arg Arg Glu Met Thr Leu
225                 230                 235                 240
Thr Val Leu Asp Leu Ile Ala Leu Phe Pro Leu Tyr Asp Val Arg Leu
                245                 250                 255
Tyr Pro Lys Glu Val Lys Thr Glu Leu Thr Arg Asp Val Leu Thr Asp
            260                 265                 270
Pro Ile Val Gly Val Asn Asn Leu Arg Gly Tyr Gly Thr Thr Phe Ser
        275                 280                 285
Asn Ile Glu Asn Tyr Ile Arg Lys Pro His Leu Phe Asp Tyr Leu His
    290                 295                 300
Arg Ile Gln Phe His Thr Arg Phe Gln Pro Gly Tyr Tyr Gly Asn Asp
305                 310                 315                 320
Ser Phe Asn Tyr Trp Ser Gly Asn Tyr Val Ser Thr Arg Pro Ser Ile
                325                 330                 335
Gly Ser Asn Asp Ile Ile Thr Ser Pro Phe Tyr Gly Asn Lys Ser Ser
            340                 345                 350
Glu Pro Val Gln Asn Leu Glu Phe Asn Gly Glu Lys Val Tyr Arg Ala
        355                 360                 365
Val Ala Asn Thr Asn Leu Ala Val Trp Pro Ser Ala Val Tyr Ser Gly
    370                 375                 380
Val Thr Lys Val Glu Phe Ser Gln Tyr Asn Asp Gln Thr Asp Glu Ala
385                 390                 395                 400
Ser Thr Gln Thr Tyr Asp Ser Lys Arg Asn Val Gly Ala Val Ser Trp
                405                 410                 415
Asp Ser Ile Asp Gln Leu Pro Pro Glu Thr Thr Asp Glu Pro Leu Glu
            420                 425                 430
Lys Gly Tyr Ser His Gln Leu Asn Tyr Val Met Cys Phe Leu Met Gln
        435                 440                 445
```

```
Gly Ser Arg Gly Thr Ile Pro Val Leu Thr Trp Thr His Lys Ser Val
    450                 455                 460
Asp Phe Phe Asn Met Ile Asp Ser Lys Lys Ile Thr Gln Leu Pro Leu
465                 470                 475                 480
Thr Lys Ser Thr Asn Leu Gly Ser Gly Thr Ser Val Val Lys Gly Pro
                485                 490                 495
Gly Phe Thr Gly Gly Asp Ile Leu Arg Arg Thr Ser Pro Gly Gln Ile
            500                 505                 510
Ser Thr Leu Arg Val Asn Ile Thr Ala Pro Leu Ser Gln Arg Tyr Arg
        515                 520                 525
Val Arg Ile Arg Tyr Ala Ser Thr Thr Asn Leu Gln Phe His Thr Ser
    530                 535                 540
Ile Asp Gly Arg Pro Ile Asn Gln Gly Asn Phe Ser Ala Thr Met Ser
545                 550                 555                 560
Ser Gly Ser Asn Leu Gln Ser Gly Ser Phe Arg Thr Val Gly Phe Thr
                565                 570                 575
Thr Pro Phe Asn Phe Ser Asn Gly Ser Ser Val Phe Thr Leu Ser Ala
            580                 585                 590
His Val Phe Asn Ser Gly Asn Glu Val Tyr Ile Asp Arg Ile Glu Phe
        595                 600                 605
Val Pro Ala Glu Val Thr
    610

<210> SEQ ID NO 25
<211> LENGTH: 1863
<212> TYPE: DNA
<213> ORGANISM: Artificial Sequence
<220> FEATURE:
<223> OTHER INFORMATION: B8a coding sequence

<400> SEQUENCE: 25
atgacggccg acaacaacac cgaggccctg gacagcagca ccaccaagga cgtgatccag      60
aagggcatca gcgtggtggg cgacctgctg ggcgtggtgg gcttccccct cggcggcgcc     120
ctggtgagct tctacaccaa cttcctgaac accatctggc ccagcgagga ccccctggaag    180 gccttcatgg agcaggtgga ggccctgatg accagaaga tcgccgacta cgccaagaac      240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480
ctgctgaagg acgcccaaat ctacggagag gagtggggct acgagaagga ggacatcgcc     540
gagttctaca gcgccagct gaagctgacc caggagtaca ccgaccactg cgtgaagtgg      600
tacaacgtgg gtctagacaa gctccgcggc agcagctacg agagctgggt gaacttcaac     660
cgctaccgcc gcgagatgac cctgaccgtg ctggacctga tcgccctgtt ccccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca agcccaccct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagccccct tctacggcaa caagagcagc    1020
gagcccgtgc agaaccttga gttcaacggc gagaaggtgt accgcgccgt ggctaacacc    1080
```

-continued

```
aacctggccg tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg ccccccgaga ccaccgacga gcccctggag    1260
aagggctaca gccaccagct gaactacgtg atgtgcttcc tgatgcaggg cagccgcggc    1320
accatccccg tgctgacctg gacccacaag agcgtcgact tcttcaacat gatcgacagc    1380
aagaagatca cccagctgcc cctggtgaag gccagcgagc tgcccagggg caccaccgtg    1440
gttcgcggcc ccggcttcac cggaggcgac atcctgcgac gcaccaacac cggcggcttc    1500
ggccccatcc gcgtgaccgt gaacggcccc ctgacccagc gctaccgcat cggcttccgc    1560
tacgccagca ccgtggactt cgacttcttc gtgagccgcg gcggcaccac cgtgaacaac    1620
ttccgcttcc tgcgcaccat gaacagcggc gacgagctga agtacggcaa cttcgtgcgc    1680
cgcgccttca ccaccccctt caccttcacc cagatccagg acatcatccg caccagcatc    1740
cagggcctga gcggcaacgg cgaggtgtac atcgacaaga tcgagatcat ccccgtgacc    1800
gccaccttcg aggccgagta cgacctagag cgcgcccagg aggccgtgaa cgccctgttc    1860
tag                                                                  1863
```

<210> SEQ ID NO 26
<211> LENGTH: 620
<212> TYPE: PRT
<213> ORGANISM: Artificial Sequence
<220> FEATURE:
<223> OTHER INFORMATION: B8a protein

<400> SEQUENCE: 26

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
```

```
            210                 215                 220
Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
                260                 265                 270

Thr Thr Phe Ser Asn Ile Glu Asn Tyr Ile Arg Lys Pro His Leu Phe
                275                 280                 285

Asp Tyr Leu His Arg Ile Gln Phe His Thr Arg Phe Gln Pro Gly Tyr
        290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
450                 455                 460

Gln Leu Pro Leu Val Lys Ala Ser Glu Leu Pro Gln Gly Thr Thr Val
465                 470                 475                 480

Val Arg Gly Pro Gly Phe Thr Gly Gly Asp Ile Leu Arg Arg Thr Asn
                485                 490                 495

Thr Gly Gly Phe Gly Pro Ile Arg Val Thr Val Asn Gly Pro Leu Thr
                500                 505                 510

Gln Arg Tyr Arg Ile Gly Phe Arg Tyr Ala Ser Thr Val Asp Phe Asp
                515                 520                 525

Phe Phe Val Ser Arg Gly Gly Thr Thr Val Asn Asn Phe Arg Phe Leu
        530                 535                 540

Arg Thr Met Asn Ser Gly Asp Glu Leu Lys Tyr Gly Asn Phe Val Arg
545                 550                 555                 560

Arg Ala Phe Thr Thr Pro Phe Thr Phe Thr Gln Ile Gln Asp Ile Ile
                565                 570                 575

Arg Thr Ser Ile Gln Gly Leu Ser Gly Asn Gly Glu Val Tyr Ile Asp
                580                 585                 590

Lys Ile Glu Ile Ile Pro Val Thr Ala Thr Phe Glu Ala Glu Tyr Asp
        595                 600                 605

Leu Glu Arg Ala Gln Glu Ala Val Asn Ala Leu Phe
        610                 615                 620

<210> SEQ ID NO 27
```

<211> LENGTH: 1902
<212> TYPE: DNA
<213> ORGANISM: Artificial Sequence
<220> FEATURE:
<223> OTHER INFORMATION: 5*B8a coding sequence

<400> SEQUENCE: 27

```
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtggag ggactatgtg agcgccctga gcagctggca gaagaacccc     360
gctgcaccgt tccgcaaccc ccacagccag ggccgcatcc gcgagctgtt cagccaggcc     420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa gcgccagctg     600
aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc ccatcgtggg cgtgaacaac     840
ctgcgcggct acggcaccac cttcagcaac atcgagaact acatccgcaa gccccacctg     900
ttcgactacc tgcaccgcat ccagttccac acgcgtttcc agcccggcta ctacggcaac     960
gacagcttca actactggag cggcaactac gtgagcaccc gccccagcat cggcagcaac    1020
gacatcatca ccagccccct ctacggcaac aagagcagcg agcccgtgca gaaccttgag    1080
ttcaacggcg agaaggtgta ccgcgccgtg gctaacacca acctggccgt gtggccctct    1140
gcagtgtaca gcggcgtgac caaggtggag ttcagccagt acaacgacca gaccgacgag    1200
gccagcaccc agacctacga cagcaagcgc aacgtgggcg ccgtgagctg ggacagcatc    1260
gaccagctgc cccccgagac caccgacgag cccctggaga agggctacag ccaccagctg    1320
aactacgtga tgtgcttcct gatgcagggc agccgcggca ccatcccgt gctgacctgg    1380
acccacaaga gcgtcgactt cttcaacatg atcgacagca agaagatcac ccagctgccc    1440
ctggtgaagg ccagcgagct gccccagggc accaccgtgg ttcgcggccc cggcttcacc    1500
ggaggcgaca tcctgcgacg caccaacacc ggcggcttcg cccccatccg cgtgaccgtg    1560
aacggccccc tgacccagcg ctaccgcatc ggcttccgct acgccagcac cgtggacttc    1620
gacttcttcg tgagccgcgg cggcaccacc gtgaacaact ccgcttcct gcgcaccatg    1680
aacagcggcg acgagctgaa gtacggcaac ttcgtgcgcc gcgccttcac caccccttc    1740
accttcaccc agatccagga catcatccgc accagcatcc agggcctgag cggcaacggc    1800
gaggtgtaca tcgacaagat cgagatcatc cccgtgaccg ccaccttcga ggccgagtac    1860
gacctagagc gcgcccagga ggccgtgaac gccctgttct ag                       1902
```

<210> SEQ ID NO 28
<211> LENGTH: 633
<212> TYPE: PRT
<213> ORGANISM: Artificial Sequence
<220> FEATURE:
<223> OTHER INFORMATION: 5*B8a Protein

<400> SEQUENCE: 28

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser

```
                    405                 410                 415
Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
    450                 455                 460

Val Asp Phe Phe Asn Met Ile Asp Ser Lys Lys Ile Thr Gln Leu Pro
465                 470                 475                 480

Leu Val Lys Ala Ser Glu Leu Pro Gln Gly Thr Thr Val Val Arg Gly
                485                 490                 495

Pro Gly Phe Thr Gly Gly Asp Ile Leu Arg Arg Thr Asn Thr Gly Gly
            500                 505                 510

Phe Gly Pro Ile Arg Val Thr Val Asn Gly Pro Leu Thr Gln Arg Tyr
        515                 520                 525

Arg Ile Gly Phe Arg Tyr Ala Ser Thr Val Asp Phe Asp Phe Phe Val
    530                 535                 540

Ser Arg Gly Gly Thr Thr Val Asn Asn Phe Arg Phe Leu Arg Thr Met
545                 550                 555                 560

Asn Ser Gly Asp Glu Leu Lys Tyr Gly Asn Phe Val Arg Arg Ala Phe
                565                 570                 575

Thr Thr Pro Phe Thr Phe Thr Gln Ile Gln Asp Ile Ile Arg Thr Ser
            580                 585                 590

Ile Gln Gly Leu Ser Gly Asn Gly Glu Val Tyr Ile Asp Lys Ile Glu
        595                 600                 605

Ile Ile Pro Val Thr Ala Thr Phe Glu Ala Glu Tyr Asp Leu Glu Arg
    610                 615                 620

Ala Gln Glu Ala Val Asn Ala Leu Phe
625                 630

<210> SEQ ID NO 29
<211> LENGTH: 1791
<212> TYPE: DNA
<213> ORGANISM: Artificial Sequence
<220> FEATURE:
<223> OTHER INFORMATION: V3A coding sequence

<400> SEQUENCE: 29
atgacggccg acaacaacac cgaggccctg gacagcagca ccaccaagga cgtgatccag      60
aagggcatca gcgtggtggg cgacctgctg ggcgtggtgg gcttccccct cggcggcgcc     120
ctggtgagct tctacaccaa cttcctgaac accatctggc cagcgagga ccctggaag       180 gccttcatgg agcaggtgga ggccctgatg accagaaga tcgccgacta cgccaagaac      240
aaggcactgg ccgagctaca gggcctccag aacaacgtgg aggactatgt gagcgccctg     300
agcagctggc agaagaaccc cgctgcaccg ttccgcaacc ccacagcca gggccgcatc      360 cgcgagctgt tcagccaggc cgagagccac ttccgcaaca gcatgccag cttcgccatc     420 agcggctacg aggtgctgtt cctgaccacc tacgcccagg ccgccaacac ccacctgttc     480
ctgctgaagg acgcccaaat ctacggagag gagtggggct acgagaagga ggacatcgcc    540
gagttctaca gcgccagct gaagctgacc caggagtaca ccgaccactg cgtgaagtgg     600
tacaacgtgg gtctagacaa gctccgcggc agcagctacg agagctgggt gaacttcaac    660
cgctaccgcc gcgagatgac cctgaccgtg ctggacatcg tgagcctgtt ccccaactac    720
gacagccgca cctacccat ccgcaccgtg agccagctga cccgcgagat ttacaccaac    780
```

```
cccgtgctgg agaacttcga cggcagcttc cgcggcagcg cccagggcat cgagggcagc    840
atccgcagcc cccacctgat ggacatcctg aacagcatca ccatctacac cgacgcccac    900
cgcggcgagt actactggag cggccaccag atcatggcca gccccgtcgg cttcagcggc    960
cccgagttca ccttccccct gtacggcacc atgggcaacg ctgcacctca gcagcgcatc   1020
gtggcacagc tgggccaggg agtgtaccgc accctgagca gcaccctgta ccgtcgacct   1080
ttcaacatcg gcatcaacaa ccagcagctg agcgtgctgg acggaccga gttcgcctac   1140
ggcaccagca gcaacctgcc cagcgccgtg taccgcaaga gcggcaccgt ggacagcctg   1200
gacgagatcc cccctcagaa caacaacgtg ccacctcgac agggcttcag ccaccgtctg   1260
agccacgtga gcatgttccg cagtggcttc agcaacagca gcgtgagcat catccgtgca   1320
cctatgttca gctggattca ccgcagtgcc gagttcaaca acatcatccc cagcagccag   1380
atcacccaga tcccctggt gaaggcctac aagctccaga gcggcgccag cgtggtggca   1440
ggccccgct tcaccggcgg cgacatcatc agtgcaccg agaacggcag cgccgccacc   1500
atctacgtga cccccgacgt gagctacagc cagaagtacc gcgcccgcat ccactacgcc   1560
agcaccagcc agatcacctt caccctgagc ctggacgggg cccccttcaa ccaatactac   1620
ttcgacaaga ccatcaacaa gggcgacacc ctgacctaca acagcttcaa cctggccagc   1680
ttcagcaccc ctttcgagct gagcggcaac aacctccaga tcggcgtgac cggcctgagc   1740
gccggcgaca aggtgtacat cgacaagatc gagttcatcc ccgtgaacta g            1791
```

<210> SEQ ID NO 30
<211> LENGTH: 596
<212> TYPE: PRT
<213> ORGANISM: Artificial Sequence
<220> FEATURE:
<223> OTHER INFORMATION: V3A protein

<400> SEQUENCE: 30

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
```

```
            180                 185                 190
Tyr Thr Asp His Cys Val Lys Trp Tyr Asn Val Gly Leu Asp Lys Leu
            195                 200                 205
Arg Gly Ser Ser Tyr Glu Ser Trp Val Asn Phe Asn Arg Tyr Arg Arg
            210                 215                 220
Glu Met Thr Leu Thr Val Leu Asp Ile Val Ser Leu Phe Pro Asn Tyr
225                 230                 235                 240
Asp Ser Arg Thr Tyr Pro Ile Arg Thr Val Ser Gln Leu Thr Arg Glu
            245                 250                 255
Ile Tyr Thr Asn Pro Val Leu Glu Asn Phe Asp Gly Ser Phe Arg Gly
            260                 265                 270
Ser Ala Gln Gly Ile Glu Gly Ser Ile Arg Ser Pro His Leu Met Asp
            275                 280                 285
Ile Leu Asn Ser Ile Thr Ile Tyr Thr Asp Ala His Arg Gly Glu Tyr
            290                 295                 300
Tyr Trp Ser Gly His Gln Ile Met Ala Ser Pro Val Gly Phe Ser Gly
305                 310                 315                 320
Pro Glu Phe Thr Phe Pro Leu Tyr Gly Thr Met Gly Asn Ala Ala Pro
            325                 330                 335
Gln Gln Arg Ile Val Ala Gln Leu Gly Gln Gly Val Tyr Arg Thr Leu
            340                 345                 350
Ser Ser Thr Leu Tyr Arg Arg Pro Phe Asn Ile Gly Ile Asn Asn Gln
            355                 360                 365
Gln Leu Ser Val Leu Asp Gly Thr Glu Phe Ala Tyr Gly Thr Ser Ser
            370                 375                 380
Asn Leu Pro Ser Ala Val Tyr Arg Lys Ser Gly Thr Val Asp Ser Leu
385                 390                 395                 400
Asp Glu Ile Pro Pro Gln Asn Asn Asn Val Pro Pro Arg Gln Gly Phe
            405                 410                 415
Ser His Arg Leu Ser His Val Ser Met Phe Arg Ser Gly Phe Ser Asn
            420                 425                 430
Ser Ser Val Ser Ile Ile Arg Ala Pro Met Phe Ser Trp Ile His Arg
            435                 440                 445
Ser Ala Glu Phe Asn Asn Ile Ile Pro Ser Ser Gln Ile Thr Gln Ile
            450                 455                 460
Pro Leu Val Lys Ala Tyr Lys Leu Gln Ser Gly Ala Ser Val Val Ala
465                 470                 475                 480
Gly Pro Arg Phe Thr Gly Gly Asp Ile Ile Gln Cys Thr Glu Asn Gly
            485                 490                 495
Ser Ala Ala Thr Ile Tyr Val Thr Pro Asp Val Ser Tyr Ser Gln Lys
            500                 505                 510
Tyr Arg Ala Arg Ile His Tyr Ala Ser Thr Ser Gln Ile Thr Phe Thr
            515                 520                 525
Leu Ser Leu Asp Gly Ala Pro Phe Asn Gln Tyr Tyr Phe Asp Lys Thr
            530                 535                 540
Ile Asn Lys Gly Asp Thr Leu Thr Tyr Asn Ser Phe Asn Leu Ala Ser
545                 550                 555                 560
Phe Ser Thr Pro Phe Glu Leu Ser Gly Asn Asn Leu Gln Ile Gly Val
            565                 570                 575
Thr Gly Leu Ser Ala Gly Asp Lys Val Tyr Ile Asp Lys Ile Glu Phe
            580                 585                 590
Ile Pro Val Asn
            595
```

<210> SEQ ID NO 31
<211> LENGTH: 1797
<212> TYPE: DNA
<213> ORGANISM: Artificial Sequence
<220> FEATURE:
<223> OTHER INFORMATION: V4F coding sequence

<400> SEQUENCE: 31

```
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc cagcgagga ccctggaag     180
gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgcccag cttcgccatc    420
agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca gcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca gccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg cccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcttcaacat gatcgacagc   1380
aagaagatca cccagctcgc cctgaccaag agcaccaacc tgggcagcgg caccagcgtg   1440
gtgaagggcc ccggcttcac cggcggcgac atcctgcgcc gcaccagccc cggccagatc   1500
agcaccctgc gcgtgaacat caccgccccc tgagccagc gctaccgcgt ccgcatccac   1560
tacgccagca ccagccagat caccttcacc ctgagcctgg acggggcccc cttcaaccaa   1620
tactacttcg acaagaccat caacaagggc gacaccctga cctacaacag cttcaacctg   1680
gccagcttca gcaccccttt cgagctgagc ggcaacaacc tccagatcgg cgtgaccggc   1740
ctgagcgccg cgacaaggt gtacatcgac aagatcgagt tcatccccgt gaactag       1797
```

<210> SEQ ID NO 32
<211> LENGTH: 598
<212> TYPE: PRT
<213> ORGANISM: Artificial Sequence
<220> FEATURE:
<223> OTHER INFORMATION: V4F protein

<400> SEQUENCE: 32

```
Met Thr Ala Asp Asn Asn Thr Glu Ala Leu Asp Ser Ser Thr Thr Lys
1               5                   10                  15
Asp Val Ile Gln Lys Gly Ile Ser Val Val Gly Asp Leu Leu Gly Val
            20                  25                  30
Val Gly Phe Pro Phe Gly Gly Ala Leu Val Ser Phe Tyr Thr Asn Phe
        35                  40                  45
Leu Asn Thr Ile Trp Pro Ser Glu Asp Pro Trp Lys Ala Phe Met Glu
    50                  55                  60
Gln Val Glu Ala Leu Met Asp Gln Lys Ile Ala Asp Tyr Ala Lys Asn
65                  70                  75                  80
Lys Ala Leu Ala Glu Leu Gln Gly Leu Gln Asn Asn Val Glu Asp Tyr
                85                  90                  95
Val Ser Ala Leu Ser Ser Trp Gln Lys Asn Pro Ala Ala Pro Phe Arg
            100                 105                 110
Asn Pro His Ser Gln Gly Arg Ile Arg Glu Leu Phe Ser Gln Ala Glu
        115                 120                 125
Ser His Phe Arg Asn Ser Met Pro Ser Phe Ala Ile Ser Gly Tyr Glu
    130                 135                 140
Val Leu Phe Leu Thr Thr Tyr Ala Gln Ala Ala Asn Thr His Leu Phe
145                 150                 155                 160
Leu Leu Lys Asp Ala Gln Ile Tyr Gly Glu Glu Trp Gly Tyr Glu Lys
                165                 170                 175
Glu Asp Ile Ala Glu Phe Tyr Lys Arg Gln Leu Lys Leu Thr Gln Glu
            180                 185                 190
Tyr Thr Asp His Cys Val Lys Trp Tyr Asn Val Gly Leu Asp Lys Leu
        195                 200                 205
Arg Gly Ser Ser Tyr Glu Ser Trp Val Asn Phe Asn Arg Tyr Arg Arg
    210                 215                 220
Glu Met Thr Leu Thr Val Leu Asp Leu Ile Ala Leu Phe Pro Leu Tyr
225                 230                 235                 240
Asp Val Arg Leu Tyr Pro Lys Glu Val Lys Thr Glu Leu Thr Arg Asp
                245                 250                 255
Val Leu Thr Asp Pro Ile Val Gly Val Asn Asn Leu Arg Gly Tyr Gly
            260                 265                 270
Thr Thr Phe Ser Asn Ile Glu Asn Tyr Ile Arg Lys Pro His Leu Phe
        275                 280                 285
Asp Tyr Leu His Arg Ile Gln Phe His Thr Arg Phe Gln Pro Gly Tyr
    290                 295                 300
Tyr Gly Asn Asp Ser Phe Asn Tyr Trp Ser Gly Asn Tyr Val Ser Thr
305                 310                 315                 320
Arg Pro Ser Ile Gly Ser Asn Asp Ile Ile Thr Ser Pro Phe Tyr Gly
                325                 330                 335
Asn Lys Ser Ser Glu Pro Val Gln Asn Leu Glu Phe Asn Gly Glu Lys
            340                 345                 350
Val Tyr Arg Ala Val Ala Asn Thr Asn Leu Ala Val Trp Pro Ser Ala
        355                 360                 365
Val Tyr Ser Gly Val Thr Lys Val Glu Phe Ser Gln Tyr Asn Asp Gln
    370                 375                 380
Thr Asp Glu Ala Ser Thr Gln Thr Tyr Asp Ser Lys Arg Asn Val Gly
385                 390                 395                 400
Ala Val Ser Trp Asp Ser Ile Asp Gln Leu Pro Pro Glu Thr Thr Asp
                405                 410                 415
```

```
Glu Pro Leu Glu Lys Gly Tyr Ser His Gln Leu Asn Tyr Val Met Cys
            420                 425                 430
Phe Leu Met Gln Gly Ser Arg Gly Thr Ile Pro Val Leu Thr Trp Thr
            435                 440                 445
His Lys Ser Val Asp Phe Phe Asn Met Ile Asp Ser Lys Lys Ile Thr
        450                 455                 460
Gln Leu Ala Leu Thr Lys Ser Thr Asn Leu Gly Ser Gly Thr Ser Val
465                 470                 475                 480
Val Lys Gly Pro Gly Phe Thr Gly Gly Asp Ile Leu Arg Arg Thr Ser
                485                 490                 495
Pro Gly Gln Ile Ser Thr Leu Arg Val Asn Ile Thr Ala Pro Leu Ser
            500                 505                 510
Gln Arg Tyr Arg Val Arg Ile His Tyr Ala Ser Thr Ser Gln Ile Thr
            515                 520                 525
Phe Thr Leu Ser Leu Asp Gly Ala Pro Phe Asn Gln Tyr Tyr Phe Asp
        530                 535                 540
Lys Thr Ile Asn Lys Gly Asp Thr Leu Thr Tyr Asn Ser Phe Asn Leu
545                 550                 555                 560
Ala Ser Phe Ser Thr Pro Phe Glu Leu Ser Gly Asn Asn Leu Gln Ile
                565                 570                 575
Gly Val Thr Gly Leu Ser Ala Gly Asp Lys Val Tyr Ile Asp Lys Ile
            580                 585                 590
Glu Phe Ile Pro Val Asn
        595

<210> SEQ ID NO 33
<211> LENGTH: 1836
<212> TYPE: DNA
<213> ORGANISM: Artificial Sequence
<220> FEATURE:
<223> OTHER INFORMATION: 5*V4F coding sequence

<400> SEQUENCE: 33
atgactagta acggccgcca gtgtgctggt attcgccctt atgacggccg acaacaacac    60
cgaggcctgg acagcagcac caccaaggac gtgatccaga agggcatcag cgtggtgggc   120
gacctgctgg gcgtggtggg cttccccttc ggcggcgccc tggtgagctt ctacaccaac   180
ttcctgaaca ccatctggcc cagcgaggac ccctggaagg ccttcatgga gcaggtggag   240
gccctgatgg accagaagat cgccgactac gccaagaaca aggcactggc cgagctacag   300
ggcctccaga caacgtgga ggactatgtg agcgccctga gcagctggca gaagaaccc    360 gctgcaccgt tccgcaaccc ccacagccag ggccgcatcc gcgagctgtt cagccaggcc   420
gagagccact tccgcaacag catgcccagc ttcgccatca gcggctacga ggtgctgttc   480
ctgaccacct acgcccaggc cgccaacacc cacctgttcc tgctgaagga cgcccaaatc   540 tacgagagg agtggggcta cgagaaggag gacatcgccg agttctacaa cgccagctg    600 aagctgaccc aggagtacac cgaccactgc gtgaagtggt acaacgtggg tctagacaag   660
ctccgcggca gcagctacga gagctgggtg aacttcaacc gctaccgccg cgagatgacc   720
ctgaccgtgc tggacctgat cgccctgttc cccctgtacg acgtgcgcct gtaccccaag   780
gaggtgaaga ccgagctgac ccgcgacgtg ctgaccgacc ccatcgtggg cgtgaacaac   840
ctgcgcggct acggcaccac cttcagcaac atcgagaact acatccgcaa gcccacctg    900 ttcgactacc tgcaccgcat ccagttccac acgcgtttcc agcccggcta ctacggcaac   960
```

-continued

```
gacagcttca actactggag cggcaactac gtgagcaccc gccccagcat cggcagcaac    1020
gacatcatca ccagccccett ctacggcaac aagagcagcg agcccgtgca gaaccttgag   1080
ttcaacggcg agaaggtgta ccgcgccgtg gctaacacca acctggccgt gtggccctct    1140
gcagtgtaca gcggcgtgac caaggtggag ttcagccagt acaacgacca gaccgacgag    1200
gccagcaccc agacctacga cagcaagcgc aacgtgggcg ccgtgagctg ggacagcatc    1260
gaccagctgc cccccgagac caccgacgag cccctggaga agggctacag ccaccagctg    1320
aactacgtga tgtgcttcct gatgcagggc agccgcggca ccatcccccgt gctgacctgg   1380 acccacaaga gcgtcgactt cttcaacatg atcgacagca agaagatcac ccagctcgcc    1440
ctgaccaaga gcaccaacct gggcagcggc accagcgtgg tgaagggccc cggcttcacc    1500
ggcggcgaca tcctgcgccg caccagcccc ggccagatca gcaccctgcg cgtgaacatc    1560
accgcccccc tgagccagcg ctaccgcgtc cgcatccact acgccagcac cagccagatc    1620
accttcaccc tgagcctgga cggggccccc ttcaaccaat actacttcga caagaccatc    1680
aacaagggcg acaccctgac ctacaacagc ttcaacctgg ccagcttcag caccccttc    1740 gagctgagcg gcaacaacct ccagatcggc gtgaccggcc tgagcgccgg cgacaaggtg    1800
tacatcgaca agatcgagtt catccccgtg aactag                              1836
```

<210> SEQ ID NO 34
<211> LENGTH: 611
<212> TYPE: PRT
<213> ORGANISM: Artificial Sequence
<220> FEATURE:
<223> OTHER INFORMATION: 5*V4F Protein

<400> SEQUENCE: 34

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205
```

```
His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Leu Arg Gly Tyr Gly Thr Thr Phe
                275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
                355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
                435                 440                 445

Gln Gly Ser Arg Gly Thr Ile Pro Val Leu Thr Trp Thr His Lys Ser
                450                 455                 460

Val Asp Phe Phe Asn Met Ile Asp Ser Lys Lys Ile Thr Gln Leu Ala
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
                500                 505                 510

Ile Ser Thr Leu Arg Val Asn Ile Thr Ala Pro Leu Ser Gln Arg Tyr
                515                 520                 525

Arg Val Arg Ile His Tyr Ala Ser Thr Ser Gln Ile Thr Phe Thr Leu
530                 535                 540

Ser Leu Asp Gly Ala Pro Phe Asn Gln Tyr Tyr Phe Asp Lys Thr Ile
545                 550                 555                 560

Asn Lys Gly Asp Thr Leu Thr Tyr Asn Ser Phe Asn Leu Ala Ser Phe
                565                 570                 575

Ser Thr Pro Phe Glu Leu Ser Gly Asn Asn Leu Gln Ile Gly Val Thr
                580                 585                 590

Gly Leu Ser Ala Gly Asp Lys Val Tyr Ile Asp Lys Ile Glu Phe Ile
                595                 600                 605

Pro Val Asn
610
```

<210> SEQ ID NO 35
<211> LENGTH: 1901
<212> TYPE: DNA
<213> ORGANISM: Artificial Sequence
<220> FEATURE:
<223> OTHER INFORMATION: 2OL-7 coding sequence

<400> SEQUENCE: 35

| | | | | | |
|---|---|---|---|---|---|
| atgacggccg | acaacaacac | cgaggccctg | acagcagca | ccaccaagga | cgtgatccag | 60 |
| aagggcatca | gcgtggtggg | cgacctgctg | ggcgtggtgg | gcttcccctt | cggcggcgcc | 120 |
| ctggtgagct | tctacaccaa | cttcctgaac | accatctggc | ccagcgagga | ccctggaag | 180 |
| gccttcatgg | agcaggtgga | ggccctgatg | accagaaga | tcgccgacta | cgccaagaac | 240 |
| aaggcactgg | ccgagctaca | gggcctccag | aacaacgtgg | aggactatgt | gagcgccctg | 300 |
| agcagctggc | agaagaaccc | cgctgcaccg | ttccgcaacc | ccacagcca | gggccgcatc | 360 |
| cgcgagctgt | tcagccaggc | cgagagccac | ttccgcaaca | gcatgcccag | cttcgccatc | 420 |
| agcggctacg | aggtgctgtt | cctgaccacc | tacgtgcagg | ccgccaacct | gcacctgagc | 480 |
| gtgctgcgcg | acgtcagcgt | gttcggccag | cgctgggct | cgacgccgc | caccatcaac | 540 |
| agccgctaca | cgacctgac | ccgcctgatc | ggcaactaca | ccgaccacgc | cgtgcgctgg | 600 |
| tacaacaccg | gcctggagcg | cgtgtggggt | cccgacagcc | gcgactggat | caggtacaac | 660 |
| cagttccgcc | gcgagctgac | cctgaccgtg | ctggacatcg | tgagcctgtt | ccccaactac | 720 |
| gacagccgca | cctaccccat | ccgcaccgtg | agccagctga | cccgcgagat | ttacaccaac | 780 |
| cccgtgctgg | agaacttcga | cggcagcttc | gcggcagcg | cccagggcat | cgagggcagc | 840 |
| atccgcagcc | cccacctgat | ggacatcctg | aacagcatca | ccatctacac | cgacgcccac | 900 |
| cgcggcgagt | actactggag | cggccaccag | atcatggcca | gccccgtcgg | cttcagcggc | 960 |
| cccgagttca | ccttccccct | gtacggcacc | atgggcaacg | ctgcacctca | gcagcgcatc | 1020 |
| gtggcacagc | tgggccaggg | agtgtaccgc | accctgagca | gcaccctgta | ccgtcgacct | 1080 |
| ttcaacatcg | gcatcaacaa | ccagcagctg | agcgtgctgg | acggcaccga | gttcgcctac | 1140 |
| ggcaccagca | gcaacctgcc | cagcgccgtg | taccgcaaga | gcggcaccgt | ggacagcctg | 1200 |
| gacgagatcc | cccctcagaa | caacaacgtg | ccacctcgac | agggcttcag | ccaccgtctg | 1260 |
| agccacgtga | gcatgttccg | cagtggcttc | agcaacagca | gcgtgagcat | catccgtgca | 1320 |
| cctatgttca | gctggattca | ccgcagtgcc | gagttcaaca | acatcatccc | cagcagccag | 1380 |
| atcacccaga | tcccctgac | caagagcacc | aacctgggca | gcggcaccag | cgtggtgaag | 1440 |
| ggccccggct | tcaccggcgg | cgacatcctg | cgccgcacca | gccccggcca | gatcagcacc | 1500 |
| ctgcgcgtga | acatcaccgc | ccccctgagc | cagcgctacc | gcgtccgcat | ccgctacgcc | 1560 |
| agcaccacca | acctgcagtt | ccacaccagc | atcgacggcc | gccccatcaa | ccagggcaac | 1620 |
| ttcagcgcca | ccatgagcag | cggcagcaac | ctgcagagcg | gcagcttccg | caccgtgggc | 1680 |
| ttcaccaccc | ccttcaactt | cagcaacggc | agcagcgtgt | tcaccctgag | cgcccacgtg | 1740 |
| ttcaacagcg | gcaacgaggt | gtacatcgac | cgcatcgagt | tcgtgcccgc | cgaggtgacc | 1800 |
| ttcgaggccg | agtacgacct | ggagagggct | cagaaggccg | tgaacgagct | gttcaccagc | 1860 |
| agcaaccaga | tcggcctgaa | gaccgacgtg | accgactacc | a | | 1901 |

<210> SEQ ID NO 36
<211> LENGTH: 633
<212> TYPE: PRT
<213> ORGANISM: Artificial Sequence
<220> FEATURE:

<223> OTHER INFORMATION: 2OL-7 protein

<400> SEQUENCE: 36

```
Met Thr Ala Asp Asn Asn Thr Glu Ala Leu Asp Ser Ser Thr Thr Lys
1               5                   10                  15
Asp Val Ile Gln Lys Gly Ile Ser Val Val Gly Asp Leu Leu Gly Val
            20                  25                  30
Val Gly Phe Pro Phe Gly Gly Ala Leu Val Ser Phe Tyr Thr Asn Phe
        35                  40                  45
Leu Asn Thr Ile Trp Pro Ser Glu Asp Pro Trp Lys Ala Phe Met Glu
    50                  55                  60
Gln Val Glu Ala Leu Met Asp Gln Lys Ile Ala Asp Tyr Ala Lys Asn
65                  70                  75                  80
Lys Ala Leu Ala Glu Leu Gln Gly Leu Gln Asn Asn Val Glu Asp Tyr
                85                  90                  95
Val Ser Ala Leu Ser Ser Trp Gln Lys Asn Pro Ala Ala Pro Phe Arg
            100                 105                 110
Asn Pro His Ser Gln Gly Arg Ile Arg Glu Leu Phe Ser Gln Ala Glu
        115                 120                 125
Ser His Phe Arg Asn Ser Met Pro Ser Phe Ala Ile Ser Gly Tyr Glu
    130                 135                 140
Val Leu Phe Leu Thr Thr Tyr Val Gln Ala Ala Asn Leu His Leu Ser
145                 150                 155                 160
Val Leu Arg Asp Val Ser Val Phe Gly Gln Arg Trp Gly Phe Asp Ala
                165                 170                 175
Ala Thr Ile Asn Ser Arg Tyr Asn Asp Leu Thr Arg Leu Ile Gly Asn
            180                 185                 190
Tyr Thr Asp His Ala Val Arg Trp Tyr Asn Thr Gly Leu Glu Arg Val
        195                 200                 205
Trp Gly Pro Asp Ser Arg Asp Trp Ile Arg Tyr Asn Gln Phe Arg Arg
    210                 215                 220
Glu Leu Thr Leu Thr Val Leu Asp Ile Val Ser Leu Phe Pro Asn Tyr
225                 230                 235                 240
Asp Ser Arg Thr Tyr Pro Ile Arg Thr Val Ser Gln Leu Thr Arg Glu
                245                 250                 255
Ile Tyr Thr Asn Pro Val Leu Glu Asn Phe Asp Gly Ser Phe Arg Gly
            260                 265                 270
Ser Ala Gln Gly Ile Glu Gly Ser Ile Arg Ser Pro His Leu Met Asp
        275                 280                 285
Ile Leu Asn Ser Ile Thr Ile Tyr Thr Asp Ala His Arg Gly Glu Tyr
    290                 295                 300
Tyr Trp Ser Gly His Gln Ile Met Ala Ser Pro Val Gly Phe Ser Gly
305                 310                 315                 320
Pro Glu Phe Thr Phe Pro Leu Tyr Gly Thr Met Gly Asn Ala Ala Pro
                325                 330                 335
Gln Gln Arg Ile Val Ala Gln Leu Gly Gln Gly Val Tyr Arg Thr Leu
            340                 345                 350
Ser Ser Thr Leu Tyr Arg Arg Pro Phe Asn Ile Gly Ile Asn Asn Gln
        355                 360                 365
Gln Leu Ser Val Leu Asp Gly Thr Glu Phe Ala Tyr Gly Thr Ser Ser
    370                 375                 380
Asn Leu Pro Ser Ala Val Tyr Arg Lys Ser Gly Thr Val Asp Ser Leu
385                 390                 395                 400
```

Asp Glu Ile Pro Pro Gln Asn Asn Asn Val Pro Pro Arg Gln Gly Phe
            405                 410                 415

Ser His Arg Leu Ser His Val Ser Met Phe Arg Ser Gly Phe Ser Asn
        420                 425                 430

Ser Ser Val Ser Ile Ile Arg Ala Pro Met Phe Ser Trp Ile His Arg
    435                 440                 445

Ser Ala Glu Phe Asn Asn Ile Ile Pro Ser Ser Gln Ile Thr Gln Ile
450                 455                 460

Pro Leu Thr Lys Ser Thr Asn Leu Gly Ser Gly Thr Ser Val Val Lys
465                 470                 475                 480

Gly Pro Gly Phe Thr Gly Gly Asp Ile Leu Arg Arg Thr Ser Pro Gly
                485                 490                 495

Gln Ile Ser Thr Leu Arg Val Asn Ile Thr Ala Pro Leu Ser Gln Arg
            500                 505                 510

Tyr Arg Val Arg Ile Arg Tyr Ala Ser Thr Thr Asn Leu Gln Phe His
        515                 520                 525

Thr Ser Ile Asp Gly Arg Pro Ile Asn Gln Gly Asn Phe Ser Ala Thr
    530                 535                 540

Met Ser Ser Gly Ser Asn Leu Gln Ser Gly Ser Phe Arg Thr Val Gly
545                 550                 555                 560

Phe Thr Thr Pro Phe Asn Phe Ser Asn Gly Ser Ser Val Phe Thr Leu
                565                 570                 575

Ser Ala His Val Phe Asn Ser Gly Asn Glu Val Tyr Ile Asp Arg Ile
            580                 585                 590

Glu Phe Val Pro Ala Glu Val Thr Phe Glu Ala Glu Tyr Asp Leu Glu
        595                 600                 605

Arg Ala Gln Lys Ala Val Asn Glu Leu Phe Thr Ser Ser Asn Gln Ile
    610                 615                 620

Gly Leu Lys Thr Asp Val Thr Asp Tyr
625                 630

<210> SEQ ID NO 37
<211> LENGTH: 1943
<212> TYPE: DNA
<213> ORGANISM: Artificial Sequence
<220> FEATURE:
<223> OTHER INFORMATION: T7-20L-7 coding sequence

<400> SEQUENCE: 37
atggctagca tgactggtgg acagcaaatg ggtcgcggat ccatgacggc cgacaacaac     60
accgaggccc tggacagcag caccaccaag gacgtgatcc agaagggcat cagcgtggtg    120
ggcgacctgc tgggcgtggt gggcttcccc ttcggcggcg ccctggtgag cttctacacc    180
aacttcctga caccatctg gcccagcgag gaccctggaa aggccttcat ggagcaggtg    240
gaggccctga tggaccagaa gatcgccgac tacgccaaga caaggcact ggccgagcta    300 cagggcctcc agaacaacgt ggaggactat gtgagcgccc tgagcagctg cagaagaac    360 cccgctgcac cgttccgcaa ccccacagc cagggccgca tccgcgagct gttcagccag    420
gccgagagcc acttccgcaa cagcatgccc agcttcgcca tcagcggcta cgaggtgctg    480
ttcctgacca cctacgtgca ggccgccaac ctgcacctga gcgtgctgcg cgacgtcagc    540
gtgttcggcc agcgctgggg cttcgacgcc gccaccatca cagccgcta caacgacctg    600 acccgcctga tcgcaacta caccgaccac gccgtgcgct ggtacaacac cggcctggag    660
cgcgtgtggg gtcccgacag ccgcgactgg atcaggtaca accagttccg ccgcgagctg    720

```
accctgaccg tgctggacat cgtgagcctg ttccccaact acgacagccg cacctacccc    780
atccgcaccg tgagccagct gacccgcgag atttacacca accccgtgct ggagaacttc    840
gacggcagct tccgcggcag cgcccagggc atcgagggca gcatccgcag ccccccacctg   900 atggacatcc tgaacagcat caccatctac accgacgccc accgcggcga gtactactgg    960
agcggccacc agatcatggc cagccccgtc ggcttcagcg gccccgagtt caccttcccc   1020
ctgtacggca ccatgggcaa cgctgcacct cagcagcgca tcgtggcaca gctgggccag   1080
ggagtgtacc gcaccctgag cagcaccctg taccgtcgac ctttcaacat cggcatcaac   1140
aaccagcagc tgagcgtgct ggacggcacc gagttcgcct acggcaccag cagcaacctg   1200
cccagcgccg tgtaccgcaa gagcggcacc gtggacagcc tggacgagat ccccccctcag  1260 aacaacaacg tgccacctcg acagggcttc agccaccgtc tgagccacgt gagcatgttc   1320
cgcagtggct tcagcaacag cagcgtgagc atcatccgtg cacctatgtt cagctggatt   1380
caccgcagtg ccgagttcaa caacatcatc cccagcagcc agatcaccca gatccccctg   1440
accaagagca ccaacctggg cagcggcacc agcgtggtga agggccccgg cttcaccggc   1500
ggcgacatcc tgcgccgcac cagccccggc cagatcagca ccctgcgcgt gaacatcacc   1560 gccccctga ccagcgcta ccgcgtccgc atccgctacg ccagcaccac caacctgcag    1620
ttccacacca gcatcgacgg ccgcccccatc aaccagggca acttcagcgc caccatgagc   1680
agcggcagca acctgcagag cggcagcttc cgcaccgtgg gcttcaccac ccccttcaac   1740
ttcagcaacg gcagcagcgt gttcacccctg agcgcccacg tgttcaacag cggcaacgag   1800
gtgtacatcg accgcatcga gttcgtgccc gccgaggtga ccttcgaggc cgagtacgac   1860
ctggagaggg ctcagaaggc cgtgaacgag ctgttcacca gcagcaacca gatcggcctg   1920
aagaccgacg tgaccgacta cca                                            1943
```

<210> SEQ ID NO 38
<211> LENGTH: 647
<212> TYPE: PRT
<213> ORGANISM: Artificial Sequence
<220> FEATURE:
<223> OTHER INFORMATION: T7-2OL-7 protein

<400> SEQUENCE: 38

```
Met Ala Ser Met Thr Gly Gly Gln Gln Met Gly Arg Gly Ser Met Thr
1               5                   10                  15

Ala Asp Asn Asn Thr Glu Ala Leu Asp Ser Ser Thr Thr Lys Asp Val
            20                  25                  30

Ile Gln Lys Gly Ile Ser Val Val Gly Asp Leu Leu Gly Val Val Gly
        35                  40                  45

Phe Pro Phe Gly Gly Ala Leu Val Ser Phe Tyr Thr Asn Phe Leu Asn
    50                  55                  60

Thr Ile Trp Pro Ser Glu Asp Pro Trp Lys Ala Phe Met Glu Gln Val
65                  70                  75                  80

Glu Ala Leu Met Asp Gln Lys Ile Ala Asp Tyr Ala Lys Asn Lys Ala
                85                  90                  95

Leu Ala Glu Leu Gln Gly Leu Gln Asn Asn Val Glu Asp Tyr Val Ser
            100                 105                 110

Ala Leu Ser Ser Trp Gln Lys Asn Pro Ala Ala Pro Phe Arg Asn Pro
        115                 120                 125

His Ser Gln Gly Arg Ile Arg Glu Leu Phe Ser Gln Ala Glu Ser His
    130                 135                 140
```

Phe Arg Asn Ser Met Pro Ser Phe Ala Ile Ser Gly Tyr Glu Val Leu
145                 150                 155                 160

Phe Leu Thr Thr Tyr Val Gln Ala Ala Asn Leu His Leu Ser Val Leu
        165                 170                 175

Arg Asp Val Ser Val Phe Gly Gln Arg Trp Gly Phe Asp Ala Ala Thr
            180                 185                 190

Ile Asn Ser Arg Tyr Asn Asp Leu Thr Arg Leu Ile Gly Asn Tyr Thr
        195                 200                 205

Asp His Ala Val Arg Trp Tyr Asn Thr Gly Leu Glu Arg Val Trp Gly
    210                 215                 220

Pro Asp Ser Arg Asp Trp Ile Arg Tyr Asn Gln Phe Arg Arg Glu Leu
225                 230                 235                 240

Thr Leu Thr Val Leu Asp Ile Val Ser Leu Phe Pro Asn Tyr Asp Ser
            245                 250                 255

Arg Thr Tyr Pro Ile Arg Thr Val Ser Gln Leu Thr Arg Glu Ile Tyr
            260                 265                 270

Thr Asn Pro Val Leu Glu Asn Phe Asp Gly Ser Phe Arg Gly Ser Ala
        275                 280                 285

Gln Gly Ile Glu Gly Ser Ile Arg Ser Pro His Leu Met Asp Ile Leu
    290                 295                 300

Asn Ser Ile Thr Ile Tyr Thr Asp Ala His Arg Gly Glu Tyr Tyr Trp
305                 310                 315                 320

Ser Gly His Gln Ile Met Ala Ser Pro Val Gly Phe Ser Gly Pro Glu
            325                 330                 335

Phe Thr Phe Pro Leu Tyr Gly Thr Met Gly Asn Ala Ala Pro Gln Gln
            340                 345                 350

Arg Ile Val Ala Gln Leu Gly Gln Gly Val Tyr Arg Thr Leu Ser Ser
        355                 360                 365

Thr Leu Tyr Arg Arg Pro Phe Asn Ile Gly Ile Asn Asn Gln Gln Leu
        370                 375                 380

Ser Val Leu Asp Gly Thr Glu Phe Ala Tyr Gly Thr Ser Ser Asn Leu
385                 390                 395                 400

Pro Ser Ala Val Tyr Arg Lys Ser Gly Thr Val Asp Ser Leu Asp Glu
            405                 410                 415

Ile Pro Pro Gln Asn Asn Asn Val Pro Pro Arg Gln Gly Phe Ser His
            420                 425                 430

Arg Leu Ser His Val Ser Met Phe Arg Ser Gly Phe Ser Asn Ser Ser
        435                 440                 445

Val Ser Ile Ile Arg Ala Pro Met Phe Ser Trp Ile His Arg Ser Ala
450                 455                 460

Glu Phe Asn Asn Ile Ile Pro Ser Ser Gln Ile Thr Gln Ile Pro Leu
465                 470                 475                 480

Thr Lys Ser Thr Asn Leu Gly Ser Gly Thr Ser Val Val Lys Gly Pro
            485                 490                 495

Gly Phe Thr Gly Gly Asp Ile Leu Arg Arg Thr Ser Pro Gly Gln Ile
            500                 505                 510

Ser Thr Leu Arg Val Asn Ile Thr Ala Pro Leu Ser Gln Arg Tyr Arg
        515                 520                 525

Val Arg Ile Arg Tyr Ala Ser Thr Thr Asn Leu Gln Phe His Thr Ser
        530                 535                 540

Ile Asp Gly Arg Pro Ile Asn Gln Gly Asn Phe Ser Ala Thr Met Ser
545                 550                 555                 560

Ser Gly Ser Asn Leu Gln Ser Gly Ser Phe Arg Thr Val Gly Phe Thr

```
                        565                 570                 575
Thr Pro Phe Asn Phe Ser Asn Gly Ser Ser Val Phe Thr Leu Ser Ala
                580                 585                 590

His Val Phe Asn Ser Gly Asn Glu Val Tyr Ile Asp Arg Ile Glu Phe
                595                 600                 605

Val Pro Ala Glu Val Thr Phe Glu Ala Glu Tyr Asp Leu Glu Arg Ala
            610                 615                 620

Gln Lys Ala Val Asn Glu Leu Phe Thr Ser Ser Asn Gln Ile Gly Leu
625                 630                 635                 640

Lys Thr Asp Val Thr Asp Tyr
                645

<210> SEQ ID NO 39
<211> LENGTH: 1940
<212> TYPE: DNA
<213> ORGANISM: Artificial Sequence
<220> FEATURE:
<223> OTHER INFORMATION: 5*20L-7 coding sequence

<400> SEQUENCE: 39
```

| | | | | | |
|---|---|---|---|---|---|
| atgactagta | acggccgcca | gtgtgctggt | attcgcccct | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggag | gactatgtg | agcgccctga | gcagctggca | gaagaacccc | 360 |
| gctgcaccgt | tccgcaaccc | cacagccag | ggccgcatcc | gcgagctgtt | cagccaggcc | 420 |
| gagagccact | tccgcaacag | catgcccagc | ttcgccatca | gcggctacga | ggtgctgttc | 480 |
| ctgaccacct | acgtgcaggc | cgccaacctg | cacctgagcg | tgctgcgcga | cgtcagcgtg | 540 |
| ttcggccagc | gctgggcgct | tcgacgccgcc | accatcaaca | gccgctacaa | cgacctgacc | 600 |
| cgcctgatcg | gcaactacac | cgaccacgcc | gtgcgctggt | acaacaccgg | cctggagcgc | 660 |
| gtgtggggtc | ccgacagccg | cgactggatc | aggtacaacc | agttccgccg | cgagctgacc | 720 |
| ctgaccgtgc | tggacatcgt | gagcctgttc | cccaactacg | acagccgcac | ctaccccatc | 780 |
| cgcaccgtga | gccagctgac | ccgcgagatt | tacaccaacc | ccgtgctgga | gaacttcgac | 840 |
| ggcagcttcc | gcggcagcgc | ccagggcatc | gagggcagca | tccgcagccc | ccacctgatg | 900 |
| gacatcctga | acagcatcac | catctacacc | gacgcccacc | gcggcgagta | ctactggagc | 960 |
| ggccaccaga | tcatggccag | ccccgtcggc | ttcagcggcc | ccgagttcac | cttccccctg | 1020 |
| tacggcacca | tgggcaacgc | tgcacctcag | cagcgcatcg | tggcacagct | gggccaggga | 1080 |
| gtgtaccgca | ccctgagcag | caccctgtac | cgtcgacctt | tcaacatcgg | catcaacaac | 1140 |
| cagcagctga | gcgtgctgga | cggcaccgag | ttcgcctacg | caccagcag | caacctgccc | 1200 |
| agcgccgtgt | accgcaagag | cggcaccgtg | gacagcctgg | acgagatccc | ccctcagaac | 1260 |
| aacaacgtgc | cacctcgaca | gggcttcagc | caccgtctga | gccacgtgag | catgttccgc | 1320 |
| agtggcttca | gcaacagcag | cgtgagcatc | atccgtgcac | ctatgttcag | ctggattcac | 1380 |
| cgcagtgccg | agttcaacaa | catcatcccc | agcagccaga | tcacccagat | ccccctgacc | 1440 |
| aagagcacca | acctgggcag | cggcaccagc | gtggtgaagg | ccccggcttc | accggcggc | 1500 |
| gacatcctgc | gccgcaccag | ccccggccag | atcagcaccc | tgcgcgtgaa | catcaccgcc | 1560 |

```
cccctgagcc agcgctaccg cgtccgcatc cgctacgcca gcaccaccaa cctgcagttc    1620
cacaccagca tcgacggccg ccccatcaac cagggcaact tcagcgccac catgagcagc    1680
ggcagcaacc tgcagagcgg cagcttccgc accgtgggct tcaccacccc cttcaacttc    1740
agcaacggca gcagcgtgtt caccctgagc gcccacgtgt tcaacagcgg caacgaggtg    1800
tacatcgacc gcatcgagtt cgtgcccgcc gaggtgacct tcgaggccga gtacgacctg    1860
gagagggctc agaaggccgt gaacgagctg ttcaccagca gcaaccagat cggcctgaag    1920
accgacgtga ccgactacca                                                1940
```

<210> SEQ ID NO 40
<211> LENGTH: 646
<212> TYPE: PRT
<213> ORGANISM: Artificial Sequence
<220> FEATURE:
<223> OTHER INFORMATION: 5*2OL-7 protein

<400> SEQUENCE: 40

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Val Gln Ala Ala Asn Leu His Leu Ser Val Leu Arg
                165                 170                 175

Asp Val Ser Val Phe Gly Gln Arg Trp Gly Phe Asp Ala Ala Thr Ile
            180                 185                 190

Asn Ser Arg Tyr Asn Asp Leu Thr Arg Leu Ile Gly Asn Tyr Thr Asp
        195                 200                 205

His Ala Val Arg Trp Tyr Asn Thr Gly Leu Glu Arg Val Trp Gly Pro
    210                 215                 220

Asp Ser Arg Asp Trp Ile Arg Tyr Asn Gln Phe Arg Arg Glu Leu Thr
225                 230                 235                 240

Leu Thr Val Leu Asp Ile Val Ser Leu Phe Pro Asn Tyr Asp Ser Arg
                245                 250                 255

Thr Tyr Pro Ile Arg Thr Val Ser Gln Leu Thr Arg Glu Ile Tyr Thr
            260                 265                 270

Asn Pro Val Leu Glu Asn Phe Asp Gly Ser Phe Arg Gly Ser Ala Gln
        275                 280                 285

Gly Ile Glu Gly Ser Ile Arg Ser Pro His Leu Met Asp Ile Leu Asn
```

Ser Ile Thr Ile Tyr Thr Asp Ala His Arg Gly Glu Tyr Tyr Trp Ser
305                 310                 315                 320

Gly His Gln Ile Met Ala Ser Pro Val Gly Phe Ser Gly Pro Glu Phe
            325                 330                 335

Thr Phe Pro Leu Tyr Gly Thr Met Gly Asn Ala Ala Pro Gln Gln Arg
            340                 345                 350

Ile Val Ala Gln Leu Gly Gln Gly Val Tyr Arg Thr Leu Ser Ser Thr
            355                 360                 365

Leu Tyr Arg Arg Pro Phe Asn Ile Gly Ile Asn Asn Gln Gln Leu Ser
370                 375                 380

Val Leu Asp Gly Thr Glu Phe Ala Tyr Gly Thr Ser Ser Asn Leu Pro
385                 390                 395                 400

Ser Ala Val Tyr Arg Lys Ser Gly Thr Val Asp Ser Leu Asp Glu Ile
            405                 410                 415

Pro Pro Gln Asn Asn Asn Val Pro Pro Arg Gln Gly Phe Ser His Arg
            420                 425                 430

Leu Ser His Val Ser Met Phe Arg Ser Gly Phe Ser Asn Ser Ser Val
            435                 440                 445

Ser Ile Ile Arg Ala Pro Met Phe Ser Trp Ile His Arg Ser Ala Glu
            450                 455                 460

Phe Asn Asn Ile Ile Pro Ser Ser Gln Ile Thr Gln Ile Pro Leu Thr
465                 470                 475                 480

Lys Ser Thr Asn Leu Gly Ser Gly Thr Ser Val Val Lys Gly Pro Gly
            485                 490                 495

Phe Thr Gly Gly Asp Ile Leu Arg Arg Thr Ser Pro Gly Gln Ile Ser
            500                 505                 510

Thr Leu Arg Val Asn Ile Thr Ala Pro Leu Ser Gln Arg Tyr Arg Val
            515                 520                 525

Arg Ile Arg Tyr Ala Ser Thr Thr Asn Leu Gln Phe His Thr Ser Ile
530                 535                 540

Asp Gly Arg Pro Ile Asn Gln Gly Asn Phe Ser Ala Thr Met Ser Ser
545                 550                 555                 560

Gly Ser Asn Leu Gln Ser Gly Ser Phe Arg Thr Val Gly Phe Thr Thr
            565                 570                 575

Pro Phe Asn Phe Ser Asn Gly Ser Ser Val Phe Thr Leu Ser Ala His
            580                 585                 590

Val Phe Asn Ser Gly Asn Glu Val Tyr Ile Asp Arg Ile Glu Phe Val
            595                 600                 605

Pro Ala Glu Val Thr Phe Glu Ala Glu Tyr Asp Leu Glu Arg Ala Gln
610                 615                 620

Lys Ala Val Asn Glu Leu Phe Thr Ser Ser Asn Gln Ile Gly Leu Lys
625                 630                 635                 640

Thr Asp Val Thr Asp Tyr
            645

<210> SEQ ID NO 41
<211> LENGTH: 1917
<212> TYPE: DNA
<213> ORGANISM: Artificial Sequence
<220> FEATURE:
<223> OTHER INFORMATION: 2OL-10 coding sequence

<400> SEQUENCE: 41
atgacggccg acaacaacac cgaggccctg gacagcagca ccaccaagga cgtgatccag    60

```
aagggcatca gcgtggtggg cgacctgctg ggcgtggtgg gcttccccctt cggcggcgcc      120 ctggtgagct tctacaccaa cttcctgaac accatctggc ccagcgagga ccccctggaag     180 gccttcatgg agcaggtgga ggccctgatg accagaaga tcgccgacta cgccaagaac       240
aaggcactgg ccgagctaca gggcctccag aacaacgtgg aggactatgt gagcgccctg      300
agcagctggc agaagaaccc cgctgcaccg ttccgcaacc cccacagcca gggccgcatc      360
cgcgagctgt tcagccaggc cgagagccac ttccgcaaca gcatgccag cttcgccatc       420 agcggctacg aggtgctgtt cctgaccacc tacgcccagg ccgccaacac ccacctgttc      480
ctgctgaagg acgcccaaat ctacggagag gagtggggct acgagaagga ggacatcgcc     540
gagttctaca gcgccagct gaagctgacc caggagtaca ccgaccactg cgtgaagtgg       600
tacaacgtgg gtctagacaa gctccgcggc agcagctacg agagctgggt gaacttcaac     660
cgctaccgcc gcgagatgac cctgaccgtg ctggacatcg tgagcctgtt ccccaactac     720
gacagccgca cctaccccat ccgcaccgtg agccagctga cccgcgagat ttacaccaac     780
cccgtgctgg agaacttcga cggcagcttc cgcggcagcg cccagggcat cgagggcagc    840
atccgcagcc cccaccctgat ggacatcctg aacagcatca ccatctacac cgacgcccac     900
cgcggcgagt actactggag cggccaccag atcatggcca gccccgtcgg cttcagcggc     960
cccgagttca ccttcccccct gtacggcacc atgggcaacg ctgcacctca gcagcgcatc   1020
gtggcacagc tgggccaggg agtgtaccgc accctgagca gcaccctgta ccgtcgacct   1080
ttcaacatcg gcatcaacaa ccagcagctg agcgtgctgg acggaccga gttcgcctac     1140 ggcaccagca gcaacctgcc cagcgccgtg taccgcaaga gcggcaccgt ggacagcctg   1200
gacgagatcc cccctcagaa caacaacgtg ccacctcgac agggcttcag ccaccgtctg   1260
agccacgtga gcatgttccg cagtggcttc agcaacagca gcgtgagcat catccgtgca   1320
cctatgttca gctggattca ccgcagtgcc gagttcaaca acatcatccc cagcagccag   1380
atcacccaga tcccctgac caagagcacc aacctgggca gcggcaccag cgtggtgaag    1440
ggccccggct tcaccggcgg cgacatcctg cgccgcacca gccccggcca gatcagcacc   1500
ctgcgcgtga acatcaccgc ccccctgagc cagcgctacc gcgtccgcat ccgctacgcc   1560
agcaccacca acctgcagtt ccacaccagc atcgacggcc gccccatcaa ccagggcaac   1620
ttcagcgcca ccatgagcag cggcagcaac ctgcagagcg cagcttccg caccgtgggc    1680 ttcaccaccc ccttcaactt cagcaacggc agcagcgtgt tcaccctgag cgcccacgtg   1740
ttcaacagcg gcaacgaggt gtacatcgac cgcatcgagt tcgtgcccgc cgaggtgacc   1800
ttcgaggccg agtacgacct ggagagggct cagaaggccg tgaacgagct gttcaccagc   1860
agcaaccaga tcggcctgaa gaccgacgtg accgactacc acatcgatca ggtgtag      1917
```

<210> SEQ ID NO 42
<211> LENGTH: 638
<212> TYPE: PRT
<213> ORGANISM: Artificial Sequence
<220> FEATURE:
<223> OTHER INFORMATION: 2OL-10 protein

<400> SEQUENCE: 42

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

```
Val Gly Phe Pro Phe Gly Gly Ala Leu Val Ser Phe Tyr Thr Asn Phe
         35                  40                  45

Leu Asn Thr Ile Trp Pro Ser Glu Asp Pro Trp Lys Ala Phe Met Glu
 50                  55                  60

Gln Val Glu Ala Leu Met Asp Gln Lys Ile Ala Asp Tyr Ala Lys Asn
 65                  70                  75                  80

Lys Ala Leu Ala Glu Leu Gln Gly Leu Gln Asn Asn Val Glu Asp Tyr
                 85                  90                  95

Val Ser Ala Leu Ser Ser Trp Gln Lys Asn Pro Ala Ala Pro Phe Arg
                100                 105                 110

Asn Pro His Ser Gln Gly Arg Ile Arg Glu Leu Phe Ser Gln Ala Glu
             115                 120                 125

Ser His Phe Arg Asn Ser Met Pro Ser Phe Ala Ile Ser Gly Tyr Glu
             130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                 165                 170                 175

Glu Asp Ile Ala Glu Phe Tyr Lys Arg Gln Leu Lys Leu Thr Gln Glu
             180                 185                 190

Tyr Thr Asp His Cys Val Lys Trp Tyr Asn Val Gly Leu Asp Lys Leu
             195                 200                 205

Arg Gly Ser Ser Tyr Glu Ser Trp Val Asn Phe Asn Arg Tyr Arg Arg
         210                 215                 220

Glu Met Thr Leu Thr Val Leu Asp Ile Val Ser Leu Phe Pro Asn Tyr
225                 230                 235                 240

Asp Ser Arg Thr Tyr Pro Ile Arg Thr Val Ser Gln Leu Thr Arg Glu
                 245                 250                 255

Ile Tyr Thr Asn Pro Val Leu Glu Asn Phe Asp Gly Ser Phe Arg Gly
             260                 265                 270

Ser Ala Gln Gly Ile Glu Gly Ser Ile Arg Ser Pro His Leu Met Asp
             275                 280                 285

Ile Leu Asn Ser Ile Thr Ile Tyr Thr Asp Ala His Arg Gly Glu Tyr
         290                 295                 300

Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
                 325                 330                 335

Gln Gln Arg Ile Val Ala Gln Leu Gly Gln Gly Val Tyr Arg Thr Leu
             340                 345                 350

Ser Ser Thr Leu Tyr Arg Arg Pro Phe Asn Ile Gly Ile Asn Asn Gln
             355                 360                 365

Gln Leu Ser Val Leu Asp Gly Thr Glu Phe Ala Tyr Gly Thr Ser Ser
         370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Val Pro Pro Arg Gln Gly Phe
                 405                 410                 415

Ser His Arg Leu Ser His Val Ser Met Phe Arg Ser Gly Phe Ser Asn
             420                 425                 430

Ser Ser Val Ser Ile Ile Arg Ala Pro Met Phe Ser Trp Ile His Arg
             435                 440                 445

Ser Ala Glu Phe Asn Asn Ile Ile Pro Ser Ser Gln Ile Thr Gln Ile
```

```
                450             455             460
Pro Leu Thr Lys Ser Thr Asn Leu Gly Ser Gly Thr Ser Val Val Lys
465                 470                 475                 480

Gly Pro Gly Phe Thr Gly Gly Asp Ile Leu Arg Arg Thr Ser Pro Gly
                485                 490                 495

Gln Ile Ser Thr Leu Arg Val Asn Ile Thr Ala Pro Leu Ser Gln Arg
            500                 505                 510

Tyr Arg Val Arg Ile Arg Tyr Ala Ser Thr Thr Asn Leu Gln Phe His
        515                 520                 525

Thr Ser Ile Asp Gly Arg Pro Ile Asn Gln Gly Asn Phe Ser Ala Thr
    530                 535                 540

Met Ser Ser Gly Ser Asn Leu Gln Ser Gly Ser Phe Arg Thr Val Gly
545                 550                 555                 560

Phe Thr Thr Pro Phe Asn Phe Ser Asn Gly Ser Ser Val Phe Thr Leu
                565                 570                 575

Ser Ala His Val Phe Asn Ser Gly Asn Glu Val Tyr Ile Asp Arg Ile
            580                 585                 590

Glu Phe Val Pro Ala Glu Val Thr Phe Glu Ala Glu Tyr Asp Leu Glu
        595                 600                 605

Arg Ala Gln Lys Ala Val Asn Glu Leu Phe Thr Ser Ser Asn Gln Ile
    610                 615                 620

Gly Leu Lys Thr Asp Val Thr Asp Tyr His Ile Asp Gln Val
625                 630                 635

<210> SEQ ID NO 43
<211> LENGTH: 1956
<212> TYPE: DNA
<213> ORGANISM: Artificial Sequence
<220> FEATURE:
<223> OTHER INFORMATION: 5*2OL-10 coding sequence

<400> SEQUENCE: 43
atgactagta acggccgcca gtgtgctggt attcgccctt atgacggccg acaacaacac        60
cgaggcctgg acagcagcac caccaaggac gtgatccaga agggcatcag cgtggtgggc       120
gacctgctgg gcgtggtggg cttccccttc ggcggcgccc tggtgagctt ctacaccaac       180
ttcctgaaca ccatctggcc cagcgaggac ccctggaagg ccttcatgga gcaggtggag       240
gccctgatgg accagaagat cgccgactac gccaagaaca aggcactggc cgagctacag       300
ggcctccaga caacgtggag gactatgtg agcgccctga gcagctggca gaagaacccc       360
gctgcaccgt ccgcaaccc ccacagccag ggccgcatcc gcgagctgtt cagccaggcc       420
gagagccact ccgcaacag catgcccagc ttcgccatca gcggctacga ggtgctgttc       480
ctgaccacct acgcccaggc cgccaacacc cacctgttcc tgctgaagga cgcccaaatc       540
tacggagagg agtggggcta cgagaaggag gacatcgccg agttctacaa cgccagctg       600 aagctgaccc aggagtacac cgaccactgc gtgaagtggt acaacgtggg tctagacaag       660
ctccgcggca gcagctacga gagctggtg aacttcaacc gctaccgccg cgagatgacc       720
ctgaccgtgc tggacatcgt gagcctgttc cccaactacg acagccgcac ctacccatc       780 cgcaccgtga gccagctgac ccgcgagatt tacaccaacc ccgtgctgga aacttcgac       840 ggcagcttcc gcggcagcgc ccagggcatc gagggcagca tccgcagccc ccacctgatg       900
gacatcctga acagcatcac catctacacc gacgcccacc gcggcgagta ctactggagc       960
ggccaccaga tcatggccag ccccgtcggc ttcagcggcc ccgagttcac cttccccctg      1020
```

```
tacggcacca tgggcaacgc tgcacctcag cagcgcatcg tggcacagct gggccaggga    1080
gtgtaccgca ccctgagcag caccctgtac cgtcgacctt caacatcgg catcaacaac     1140 cagcagctga gcgtgctgga cggcaccgag ttcgcctacg caccagcag caacctgccc     1200 agcgccgtgt accgcaagag cggcaccgtg acagcctgg acgagatccc cctcagaac     1260 aacaacgtgc acctcgaca gggcttcagc accgtctga ccacgtgag catgttccgc      1320 agtggcttca gcaacagcag cgtgagcatc atccgtgcac ctatgttcag ctggattcac    1380
cgcagtgccg agttcaacaa catcatcccc agcagccaga tcacccagat cccctgacc    1440 aagagcacca acctgggcag cggcaccagc gtggtgaagg ccccggctt caccggcggc     1500 gacatcctgc gccgcaccag ccccggccag atcagcaccc tgcgcgtgaa catcaccgcc   1560
cccctgagcc agcgctaccg cgtccgcatc cgctacgcca gcaccaccaa cctgcagttc   1620
cacaccagca tcgacggccg ccccatcaac agggcaact tcagcgccac catgagcagc    1680
ggcagcaacc tgcagagcgg cagcttccgc accgtgggct tcaccacccc cttcaacttc   1740
agcaacggca gcagcgtgtt cacccctgagc gcccacgtgt tcaacagcgg caacgaggtg   1800
tacatcgacc gcatcgagtt cgtgcccgcc gaggtgacct tcgaggccga gtacgacctg    1860
gagagggctc agaaggccgt gaacgagctg ttcaccagca gcaaccagat cggcctgaag   1920
accgacgtga ccgactacca catcgatcag gtgtag                              1956
```

<210> SEQ ID NO 44  
<211> LENGTH: 651  
<212> TYPE: PRT  
<213> ORGANISM: Artificial Sequnece  
<220> FEATURE:  
<223> OTHER INFORMATION: 5*2OL-10 protein

<400> SEQUENCE: 44

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
```

```
                195                 200                 205
    His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Ile Val Ser Leu Phe Pro Asn Tyr Asp Ser Arg
                    245                 250                 255

Thr Tyr Pro Ile Arg Thr Val Ser Gln Leu Thr Arg Glu Ile Tyr Thr
                    260                 265                 270

Asn Pro Val Leu Glu Asn Phe Asp Gly Ser Phe Arg Gly Ser Ala Gln
                    275                 280                 285

Gly Ile Glu Gly Ser Ile Arg Ser Pro His Leu Met Asp Ile Leu Asn
                    290                 295                 300

Ser Ile Thr Ile Tyr Thr Asp Ala His Arg Gly Glu Tyr Tyr Trp Ser
305                 310                 315                 320

Gly His Gln Ile Met Ala Ser Pro Val Gly Phe Ser Gly Pro Glu Phe
                    325                 330                 335

Thr Phe Pro Leu Tyr Gly Thr Met Gly Asn Ala Ala Pro Gln Gln Arg
                    340                 345                 350

Ile Val Ala Gln Leu Gly Gln Gly Val Tyr Arg Thr Leu Ser Ser Thr
                    355                 360                 365

Leu Tyr Arg Arg Pro Phe Asn Ile Gly Ile Asn Asn Gln Gln Leu Ser
                    370                 375                 380

Val Leu Asp Gly Thr Glu Phe Ala Tyr Gly Thr Ser Ser Asn Leu Pro
385                 390                 395                 400

Ser Ala Val Tyr Arg Lys Ser Gly Thr Val Asp Ser Leu Asp Glu Ile
                    405                 410                 415

Pro Pro Gln Asn Asn Asn Val Pro Pro Arg Gln Gly Phe Ser His Arg
                    420                 425                 430

Leu Ser His Val Ser Met Phe Arg Ser Gly Phe Ser Asn Ser Ser Val
                    435                 440                 445

Ser Ile Ile Arg Ala Pro Met Phe Ser Trp Ile His Arg Ser Ala Glu
                    450                 455                 460

Phe Asn Asn Ile Ile Pro Ser Ser Gln Ile Thr Gln Ile Pro Leu Thr
465                 470                 475                 480

Lys Ser Thr Asn Leu Gly Ser Gly Thr Ser Val Val Lys Gly Pro Gly
                    485                 490                 495

Phe Thr Gly Gly Asp Ile Leu Arg Arg Thr Ser Pro Gly Gln Ile Ser
                    500                 505                 510

Thr Leu Arg Val Asn Ile Thr Ala Pro Leu Ser Gln Arg Tyr Arg Val
                    515                 520                 525

Arg Ile Arg Tyr Ala Ser Thr Thr Asn Leu Gln Phe His Thr Ser Ile
                    530                 535                 540

Asp Gly Arg Pro Ile Asn Gln Gly Asn Phe Ser Ala Thr Met Ser Ser
545                 550                 555                 560

Gly Ser Asn Leu Gln Ser Gly Ser Phe Arg Thr Val Gly Phe Thr Thr
                    565                 570                 575

Pro Phe Asn Phe Ser Asn Gly Ser Ser Val Phe Thr Leu Ser Ala His
                    580                 585                 590

Val Phe Asn Ser Gly Asn Glu Val Tyr Ile Asp Arg Ile Glu Phe Val
                    595                 600                 605

Pro Ala Glu Val Thr Phe Glu Ala Glu Tyr Asp Leu Glu Arg Ala Gln
                    610                 615                 620
```

Lys Ala Val Asn Glu Leu Phe Thr Ser Ser Asn Gln Ile Gly Leu Lys
625                 630                 635                 640

Thr Asp Val Thr Asp Tyr His Ile Asp Gln Val
                645                 650

<210> SEQ ID NO 45
<211> LENGTH: 1821
<212> TYPE: DNA
<213> ORGANISM: Artificial Sequence
<220> FEATURE:
<223> OTHER INFORMATION: 2OL-12A coding sequence

<400> SEQUENCE: 45

| | | | | | |
|---|---|---|---|---|---|
| atggacaaca | accccaacat | caacgagtgc | atccoctaca | actgcctgag | caaccccgag | 60 |
| gtggaggtgc | tgggcggcga | gcgcatcgag | accggctaca | cccccatcga | catcagcctg | 120 |
| agcctgaccc | agttcctgct | gagcgagttc | gtgcccggcg | ccggcttcgt | gctgggcctg | 180 |
| gtggacatca | tctggggcat | cttcggcccc | agccagtggg | acgccttcct | ggtgcagatc | 240 |
| gagcagttga | taaaccaacg | catagaggaa | ttcgcccgca | accaggccat | cagccgcctg | 300 |
| gagggcctga | gcaacctgta | ccaaatctac | gccgagagct | tccgcgagtg | ggaggccgac | 360 |
| cccaccaacc | ccgccctgcg | cgaggagatg | cgcatccagt | tcaacgacat | gaacagcgcc | 420 |
| ctgaccaccg | ccatccccct | gttcgccgtg | cagaactacc | aggtgccoct | gctgagcgtg | 480 |
| tacgtgcagg | ccgccaacct | gcacctgagc | gtgctgcgcg | acgtcagcgt | gttcggccag | 540 |
| cgctggggct | tcgacgccgc | caccatcaac | agccgctaca | acgacctgac | cgcctgatc | 600 |
| ggcaactaca | ccgaccacgc | cgtgcgctgg | tacaacaccg | gcctggagcg | cgtgtggggt | 660 |
| cccgacagcc | gcgactggat | caggtacaac | cagttccgcc | gcgagctgac | cctgaccgtg | 720 |
| ctggacatcg | tgagcctgtt | ccccaactac | gacagccgca | cctaccccat | ccgcaccgtg | 780 |
| agccagctga | cccgcgagat | ttacaccaac | cccgtgctgg | agaacttcga | cggcagcttc | 840 |
| cgcggcagcg | cccagggcat | cgagggcagc | atccgcagcc | ccacctgat | ggacatcctg | 900 |
| aacagcatca | ccatctacac | cgacgcccac | cgcggcgagt | actactggag | cggccaccag | 960 |
| atcatggcca | gcccgtcgg | cttcagcggc | cccgagttca | ccttccccct | gtacggcacc | 1020 |
| atgggcaacg | ctgcacctca | gcagcgcatc | gtggcacagc | tgggccaggg | agtgtaccgc | 1080 |
| accctgagca | gcaccctgta | ccgtcgacct | ttcaacatcg | gcatcaacaa | ccagcagctg | 1140 |
| agcgtgctgg | acggcaccga | gttcgcctac | ggcaccagca | gcaacctgcc | cagcgccgtg | 1200 |
| taccgcaaga | gcggcaccgt | ggacagcctg | gacgagatcc | cccctcagaa | caacaacgtg | 1260 |
| ccacctcgac | agggcttcag | ccaccgtctg | agccacgtga | gcatgttccg | cagtggcttc | 1320 |
| agcaacagca | gcgtgagcat | catccgtgca | cctatgttca | gctggattca | ccgcagtgcc | 1380 |
| gagttcaaca | acatcatccc | cagcagccag | atcacccaga | tccccctggt | gaaggcctac | 1440 |
| aagctccaga | gcggcgccag | cgtggtggca | ggccccgct | tcaccggcgg | cgacatcatc | 1500 |
| cagtgcaccg | agaacggcag | cgccgccacc | atctacgtga | ccccgacgt | gagctacagc | 1560 |
| cagaagtacc | gcgcccgcat | ccactacgcc | agcaccagcc | agatcacctt | caccctgagc | 1620 |
| ctggacgggg | cccccttcaa | ccaatactac | ttcgacaaga | ccatcaacaa | gggcgacacc | 1680 |
| ctgacctaca | acagcttcaa | cctggccagc | ttcagcaccc | ctttcgagct | gagcggcaac | 1740 |
| aacctccaga | tcgccgtgac | cggcctgagc | gccggcgaca | aggtgtacat | cgacaagatc | 1800 |
| gagttcatcc | ccgtgaacta | g | | | | 1821 |

```
<210> SEQ ID NO 46
<211> LENGTH: 606
<212> TYPE: PRT
<213> ORGANISM: Artificial Sequence
<220> FEATURE:
<223> OTHER INFORMATION: 2OL-12A protein

<400> SEQUENCE: 46

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365
```

```
Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Val Lys Ala Tyr
465                 470                 475                 480

Lys Leu Gln Ser Gly Ala Ser Val Val Ala Gly Pro Arg Phe Thr Gly
                485                 490                 495

Gly Asp Ile Ile Gln Cys Thr Glu Asn Gly Ser Ala Ala Thr Ile Tyr
                500                 505                 510

Val Thr Pro Asp Val Ser Tyr Ser Gln Lys Tyr Arg Ala Arg Ile His
            515                 520                 525

Tyr Ala Ser Thr Ser Gln Ile Thr Phe Thr Leu Ser Leu Asp Gly Ala
530                 535                 540

Pro Phe Asn Gln Tyr Tyr Phe Asp Lys Thr Ile Asn Lys Gly Asp Thr
545                 550                 555                 560

Leu Thr Tyr Asn Ser Phe Asn Leu Ala Ser Phe Ser Thr Pro Phe Glu
                565                 570                 575

Leu Ser Gly Asn Asn Leu Gln Ile Gly Val Thr Gly Leu Ser Ala Gly
                580                 585                 590

Asp Lys Val Tyr Ile Asp Lys Ile Glu Phe Ile Pro Val Asn
            595                 600                 605

<210> SEQ ID NO 47
<211> LENGTH: 1791
<212> TYPE: DNA
<213> ORGANISM: Artificial Sequence
<220> FEATURE:
<223> OTHER INFORMATION: 2OL-13 coding sequence

<400> SEQUENCE: 47
atgacggccg acaacaacac cgaggccctg acagcagca ccaccaagga cgtgatccag    60
aagggcatca gcgtggtggg cgacctgctg ggcgtggtgg gcttcccctt cggcggcgcc   120
ctggtgagct tctacaccaa cttcctgaac accatctggc cagcgagga ccctggaag    180 gccttcatgg gcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc ccacagcca gggccgcatc    360 cgcgagctgt tcagccaggc cgagagccac ttccgcaaca gcatgcccag cttcgccatc    420
agcggctacg aggtgctgtt cctgaccacc tacgcccagg ccgccaacac ccacctgagc    480
gtgctgcgcg acgtcagcgt gttcggccag cgctggggct cgacgccgc caccatcaac    540 agccgctaca cgacctgac cgcctgatc ggcaactaca ccgaccacgc cgtgcgctgg    600
tacaacaccg ccctggagcg cgtgtggggt cccgacagcc gcgactggat caggtacaac    660
cagttccgcc gcgagctgac cctgaccgtg ctggacatcg tgagcctgtt ccccaactac    720
```

```
gacagccgca cctaccccat ccgcaccgtg agccagctga cccgcgagat ttacaccaac    780
cccgtgctgg agaacttcga cggcagcttc cgcggcagcg cccagggcat cgagggcagc    840
atccgcagcc cccacctgat ggacatcctg aacagcatca ccatctacac cgacgcccac    900
cgcggcgagt actactggag cggccaccag atcatggcca gccccgtcgg cttcagcggc    960
cccgagttca ccttccccct gtacggcacc atgggcaacg ctgcacctca gcagcgcatc   1020
gtggcacagc tgggccaggg agtgtaccgc accctgagca gcaccctgta ccgtcgacct   1080
ttcaacatcg gcatcaacaa ccagcagctg agcgtgctgg acggcaccga gttcgcctac   1140
ggcaccagca gcaacctgcc cagcgccgtg taccgcaaga gcggcaccgt ggacagcctg   1200
gacgagatcc cccctcagaa caacaacgtg ccacctcgac agggcttcag ccaccgtctg   1260
agccacgtga gcatgttccg cagtggcttc agcaacagca gcgtgagcat catccgtgca   1320
cctatgttca gctggattca ccgcagtgcc gagttcaaca acatcatccc cagcagccag   1380
atcacccaga tcccctgac caagagcacc aacctgggca gcggcaccag cgtggtgaag   1440
```

```
Ala Thr Ile Asn Ser Arg Tyr Asn Asp Leu Thr Arg Leu Ile Gly Asn
            180                 185                 190

Tyr Thr Asp His Ala Val Arg Trp Tyr Asn Thr Gly Leu Glu Arg Val
        195                 200                 205

Trp Gly Pro Asp Ser Arg Asp Trp Ile Arg Tyr Asn Gln Phe Arg Arg
    210                 215                 220

Glu Leu Thr Leu Thr Val Leu Asp Ile Val Ser Leu Phe Pro Asn Tyr
225                 230                 235                 240

Asp Ser Arg Thr Tyr Pro Ile Arg Thr Val Ser Gln Leu Thr Arg Glu
                245                 250                 255

Ile Tyr Thr Asn Pro Val Leu Glu Asn Phe Asp Gly Ser Phe Arg Gly
            260                 265                 270

Ser Ala Gln Gly Ile Glu Gly Ser Ile Arg Ser Pro His Leu Met Asp
        275                 280                 285

Ile Leu Asn Ser Ile Thr Ile Tyr Thr Asp Ala His Arg Gly Glu Tyr
    290                 295                 300

Tyr Trp Ser Gly His Gln Ile Met Ala Ser Pro Val Gly Phe Ser Gly
305                 310                 315                 320

Pro Glu Phe Thr Phe Pro Leu Tyr Gly Thr Met Gly Asn Ala Ala Pro
                325                 330                 335

Gln Gln Arg Ile Val Ala Gln Leu Gly Gln Gly Val Tyr Arg Thr Leu
            340                 345                 350

Ser Ser Thr Leu Tyr Arg Arg Pro Phe Asn Ile Gly Ile Asn Asn Gln
        355                 360                 365

Gln Leu Ser Val Leu Asp Gly Thr Glu Phe Ala Tyr Gly Thr Ser Ser
    370                 375                 380

Asn Leu Pro Ser Ala Val Tyr Arg Lys Ser Gly Thr Val Asp Ser Leu
385                 390                 395                 400

Asp Glu Ile Pro Pro Gln Asn Asn Asn Val Pro Pro Arg Gln Gly Phe
                405                 410                 415

Ser His Arg Leu Ser His Val Ser Met Phe Arg Ser Gly Phe Ser Asn
            420                 425                 430

Ser Ser Val Ser Ile Ile Arg Ala Pro Met Phe Ser Trp Ile His Arg
        435                 440                 445

Ser Ala Glu Phe Asn Asn Ile Ile Pro Ser Ser Gln Ile Thr Gln Ile
450                 455                 460

Pro Leu Thr Lys Ser Thr Asn Leu Gly Ser Gly Thr Ser Val Val Lys
465                 470                 475                 480

Gly Pro Gly Phe Thr Gly Gly Asp Ile Leu Arg Arg Thr Ser Pro Gly
                485                 490                 495

Gln Ile Ser Thr Leu Arg Val Asn Ile Thr Ala Pro Leu Ser Gln Arg
            500                 505                 510

Tyr Arg Ala Arg Ile His Tyr Ala Ser Thr Ser Gln Ile Thr Phe Thr
        515                 520                 525

Leu Ser Leu Asp Gly Ala Pro Phe Asn Gln Tyr Tyr Phe Asp Lys Thr
    530                 535                 540

Ile Asn Lys Gly Asp Thr Leu Thr Tyr Asn Ser Phe Asn Leu Ala Ser
545                 550                 555                 560

Phe Ser Thr Pro Phe Glu Leu Ser Gly Asn Asn Leu Gln Ile Gly Val
                565                 570                 575

Thr Gly Leu Ser Ala Gly Asp Lys Val Tyr Ile Asp Lys Ile Glu Phe
            580                 585                 590

Ile Pro Val Asn
```

<210> SEQ ID NO 49
<211> LENGTH: 1923
<212> TYPE: DNA
<213> ORGANISM: Artificial Sequence
<220> FEATURE:
<223> OTHER INFORMATION: V5&6 coding sequence

<400> SEQUENCE: 49

```
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaaag     180
gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgccag cttcgccatc     420
agcggctacg aggtgctgtt cctgaccacc tacgcccagg ccgccaacac ccacctgttc     480
ctgctgaagg acgcccaaat ctacggagag agtggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacctga tcgccctgtt cccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca gccccaccct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagccct tctacggcaa caagagcagc    1020
gagcccgtgc agaaccttga gttcaacggc gagaaggtgt accgcgccgt ggctaacacc    1080
aacctggccg tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg cccccgaga ccaccgacga gccctggag    1260
aagggctaca gccaccagct gaactacgtg atgtgcttcc tgatgcaggg cagccgcggc    1320
accatccccg tgctgacctg gacccacaag agcgtcgact cttcaacat gatcgacagc    1380
aagaagatca cccagctgcc cctggtgaag gcctacaagc tccagagcgg cgccagcgtg    1440
gtggcaggcc ccgcttcac cggcggcgac atcatccagt gcaccgagaa cggcagcgcc    1500
gccaccatct acgtgacccc cgacgtgagc tacagccaga agtaccgcgc ccgcatccac    1560
tacgccagca ccaccaacct gcagttccac accagcatcg acggccgccc catcaaccag    1620
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca cagcggcaa cgaggtgtac atcgaccgca tcgagttcgt gcccgccgag    1800
gtgaccttcg aggccgagta cgacctggag agggctcaga aggccgtgaa cgagctgttc    1860
accagcagca accagatcgg cctgaagacc gacgtgaccg actaccacat cgatcaggtg    1920
tag                                                                  1923
```

```
<210> SEQ ID NO 50
<211> LENGTH: 640
<212> TYPE: PRT
<213> ORGANISM: Artificial Sequence
<220> FEATURE:
<223> OTHER INFORMATION: V5&6 protein

<400> SEQUENCE: 50

Met Thr Ala Asp Asn Asn Thr Glu Ala Leu Asp Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65              70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
```

```
              370                 375                 380
Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
            435                 440                 445

His Lys Ser Val Asp Phe Phe Asn Met Ile Asp Ser Lys Lys Ile Thr
450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
                500                 505                 510

Gln Lys Tyr Arg Ala Arg Ile His Tyr Ala Ser Thr Thr Asn Leu Gln
            515                 520                 525

Phe His Thr Ser Ile Asp Gly Arg Pro Ile Asn Gln Gly Asn Phe Ser
        530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
        595                 600                 605

Leu Glu Arg Ala Gln Lys Ala Val Asn Glu Leu Phe Thr Ser Ser Asn
    610                 615                 620

Gln Ile Gly Leu Lys Thr Asp Val Thr Asp Tyr His Ile Asp Gln Val
625                 630                 635                 640
```

<210> SEQ ID NO 51
<211> LENGTH: 1962
<212> TYPE: DNA
<213> ORGANISM: Artificial Sequence
<220> FEATURE:
<223> OTHER INFORMATION: 5*V5&6 coding sequence

<400> SEQUENCE: 51

```
atgactagta acggccgcca gtgtgctggt attcgccctt atgacggccg acaacaacac        60
cgaggcctgg acagcagcac caccaaggac gtgatccaga agggcatcag cgtggtgggc       120
gacctgctgg gcgtggtggg cttccccttc ggcggcgccc tggtgagctt ctacaccaac       180
ttcctgaaca ccatctggcc cagcgaggac ccctggaagg ccttcatgga gcaggtggag       240
gccctgatgg accagaagat cgccgactac gccaagaaca ggcactggc cgagctacag        300
ggcctccaga caacgtgga ggactatgtg agcgccctga gcagtggca gaagaacccc         360
gctgcaccgt tccgcaaccc ccacagccag ggccgcatcc gcgagctgtt cagccaggcc       420
gagagccact tccgcaacag catgcccagc ttcgccatca gcggctacga ggtgctgttc       480
ctgaccacct acgcccaggc cgccaacacc cacctgttcc tgctgaagga cgcccaaatc       540
tacggagagg agtggggcta cgagaaggag gacatcgccg agttctacaa gcgccagctg       600
```

```
aagctgaccc aggagtacac cgaccactgc gtgaagtggt acaacgtggg tctagacaag    660
ctccgcggca gcagctacga gagctgggtg aacttcaacc gctaccgccg cgagatgacc    720
ctgaccgtgc tggacctgat cgccctgttc cccctgtacg acgtgcgcct gtaccccaag    780
gaggtgaaga ccgagctgac ccgcgacgtg ctgaccgacc ccatcgtggg cgtgaacaac    840
ctgcgcggct acggcaccac cttcagcaac atcgagaact acatccgcaa gccccacctg    900
ttcgactacc tgcaccgcat ccagttccac acgcgtttcc agcccggcta ctacggcaac    960
gacagcttca actactggag cggcaactac gtgagcaccc gccccagcat cggcagcaac   1020
gacatcatca ccagcccctt ctacggcaac aagagcagcg agcccgtgca gaaccttgag   1080
ttcaacggcg agaaggtgta ccgcgccgtg gctaacacca acctggccgt gtggccctct   1140
gcagtgtaca gcgcgtgac caaggtggag ttcagccagt acaacgacca gaccgacgag   1200
gccagcaccc agacctacga cagcaagcgc aacgtgggcg ccgtgagctg ggacagcatc   1260
gaccagctgc cccccgagac caccgacgag cccctggaga agggctacag ccaccagctg   1320
aactacgtga tgtgcttcct gatgcagggc agccgcggca ccatccccgt gctgacctgg   1380
acccacaaga gcgtcgactt cttcaacatg atcgacagca agaagatcac ccagctgccc   1440
ctggtgaagg cctacaagct ccagagcggc gccagcgtgg tggcaggccc ccgcttcacc   1500
ggcggcgaca tcatccagtg caccgagaac ggcagcgccg ccaccatcta cgtgaccccc   1560
gacgtgagct acagccagaa gtaccgcgcc cgcatccact acgccagcac caccaacctg   1620
cagttccaca ccagcatcga cggccgcccc atcaaccagg caacttcag cgccaccatg   1680
agcagcggca gcaacctgca gagcggcagc ttccgcaccg tgggcttcac cacccccttc   1740
aacttcagca acggcagcag cgtgttcacc ctgagcgccc acgtgttcaa cagcggcaac   1800
gaggtgtaca tcgaccgcat cgagttcgtg cccgccgagg tgaccttcga ggccgagtac   1860
gacctggaga gggctcagaa ggccgtgaac gagctgttca ccagcagcaa ccagatcggc   1920
ctgaagaccg acgtgaccga ctaccacatc gatcaggtgt ag                      1962
```

<210> SEQ ID NO 52
<211> LENGTH: 653
<212> TYPE: PRT
<213> ORGANISM: Artificial Sequence
<220> FEATURE:
<223> OTHER INFORMATION: 5*V5&6 protein

<400> SEQUENCE: 52

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
```

```
                115                 120                 125
Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Asn Thr His Leu Phe Leu Leu Lys
                165                 170                 175

Asp Ala Gln Ile Tyr Gly Glu Glu Trp Gly Tyr Glu Lys Glu Asp Ile
                180                 185                 190

Ala Glu Phe Tyr Lys Arg Gln Leu Lys Leu Thr Gln Glu Tyr Thr Asp
                195                 200                 205

His Cys Val Lys Trp Tyr Asn Val Gly Leu Asp Lys Leu Arg Gly Ser
                210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Asn Leu Arg Gly Tyr Gly Thr Thr Phe
                275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
                355                 360                 365

Ala Val Ala Asn Thr Asn Leu Ala Val Trp Pro Ser Ala Val Tyr Ser
                370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
                435                 440                 445

Gln Gly Ser Arg Gly Thr Ile Pro Val Leu Thr Trp Thr His Lys Ser
                450                 455                 460

Val Asp Phe Phe Asn Met Ile Asp Ser Lys Lys Ile Thr Gln Leu Pro
465                 470                 475                 480

Leu Val Lys Ala Tyr Lys Leu Gln Ser Gly Ala Ser Val Val Ala Gly
                485                 490                 495

Pro Arg Phe Thr Gly Gly Asp Ile Ile Gln Cys Thr Glu Asn Gly Ser
                500                 505                 510

Ala Ala Thr Ile Tyr Val Thr Pro Asp Val Ser Tyr Ser Gln Lys Tyr
                515                 520                 525

Arg Ala Arg Ile His Tyr Ala Ser Thr Thr Asn Leu Gln Phe His Thr
                530                 535                 540
```

```
Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
            565                 570                 575

Thr Thr Pro Phe Asn Phe Ser Asn Gly Ser Ser Val Phe Thr Leu Ser
        580                 585                 590

Ala His Val Phe Asn Ser Gly Asn Glu Val Tyr Ile Asp Arg Ile Glu
            595                 600                 605

Phe Val Pro Ala Glu Val Thr Phe Glu Ala Glu Tyr Asp Leu Glu Arg
610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650
```

<210> SEQ ID NO 53
<211> LENGTH: 1845
<212> TYPE: DNA
<213> ORGANISM: Artificial Sequence
<220> FEATURE:
<223> OTHER INFORMATION: 88A-dm3 coding sequence

<400> SEQUENCE: 53

```
atgactagta acggccgcca gtgtgctggt attcgccctt atgacggccg acaacaacac    60
cgaggcctgg acagcagcac caccaaggac gtgatccaga agggcatcag cgtggtgggc   120
gacctgctgg gcgtggtggg cttccccttc ggcggcgccc tggtgagctt ctacaccaac   180
ttcctgaaca ccatctggcc cagcgaggac ccctggaagg ccttcatgga gcaggtggag   240
gccctgatgg accagaagat cgccgactac gccaagaaca aggcactggc cgagctacag   300
ggcctccaga caacgtggag gactatgtg agcgccctga gcagctggca agaaccccc    360
gctgcaccgt tccgcaaccc ccacagccag gccgcatcc gcgagctgtt cagccaggcc   420
gagagccact tccgcaacag catgcccagc ttcgccatca gcggctacga ggtgctgttc   480
ctgaccacct acgcccaggc cgccaacacc cacctgttcc tgctgaagga cgcccaaatc   540
tacggagagg agtggggcta cgagaaggag gacatcgccg agttctacaa cgccagctg    600
aagctgaccc aggagtacac cgaccactgc gtgaagtggt acaacgtggg tctagacaag   660
ctccgcggca gcagctacga gagctgggtg aacttcaacc gctaccgccg cgagatgacc   720
ctgaccgtgc tggacctgat cgccctgttc cccctgtacg acgtgcgcct gtaccccaag   780
gaggtgaaga ccgagctgac ccgcgacgtg ctgaccgacc ccatcgtggg cgtgaacaac   840
ctgcgcggct acggcaccac cttcagcaac atcgagaact acatccgcaa gcccacctg    900
ttcgactacc tgcaccgcat ccagttccac acgcgtttcc agcccggcta ctacggcaac   960
gacagcttca actactggag cggcaactac gtgagcaccc gccccagcat cggcagcaac  1020
gacatcatca ccagcccctt ctacggcaac aagagcagca gcccgtgca gaaccttgag   1080
ttcaacggcg agaaggtgta ccgcgccgtg gctaacacca acctggccgt gtggccctct   1140
gcagtgtaca gcggcgtgac caaggtggag ttcagccagt acaacgacca gaccgacgag  1200
gccagcaccc agacctacga cagcaagcgc aacgtgggcg ccgtgagctg ggacagcatc  1260
gaccagctgc cccccgagac caccgacgag cccctggaga agggctacag ccaccagctg  1320
aactacgtga tgtgcttcct gatgcagggc agccgcggca ccatcccgt gctgacctgg  1380
acccacaaga gcgtcgactt cttcaacatg atcgacagca agaagatcac ccagctgccc  1440
```

```
ctggtaaagg gagacatgtt atatctaggg ggttccgtag tacagggtcc tggatttaca    1500
ggaggagata tattaaaaag aaccaatcct agcatattag ggacctttgc ggttacagta    1560
aatgggtcgt tatcacaaag atatcgtgta agaattcgct atgcctctac aacagatttt    1620
gaatttactc tataccttgg cgacacaata gaaaaaata gatttaacaa aactatggat    1680 aatgggcat ctttaacgta tgaaacattt aaattcgcaa gtttcattac tgatttccaa    1740
ttcagagaaa cacaagataa aatactccta tccatgggtg attttagctc cggtcaagaa    1800
gtttatatag accgaatcga attcatccca gtagatgaga catag                    1845
```

<210> SEQ ID NO 54
<211> LENGTH: 614
<212> TYPE: PRT
<213> ORGANISM: Artificial Sequence
<220> FEATURE:
<223> OTHER INFORMATION: 88A-dm3 protein

<400> SEQUENCE: 54

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285
```

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Val Lys Gly Asp Met Leu Tyr Leu Gly Gly Ser Val Val Gln Gly
                485                 490                 495

Pro Gly Phe Thr Gly Gly Asp Ile Leu Lys Arg Thr Asn Pro Ser Ile
            500                 505                 510

Leu Gly Thr Phe Ala Val Thr Val Asn Gly Ser Leu Ser Gln Arg Tyr
        515                 520                 525

Arg Val Arg Ile Arg Tyr Ala Ser Thr Thr Asp Phe Glu Phe Thr Leu
530                 535                 540

Tyr Leu Gly Asp Thr Ile Glu Lys Asn Arg Phe Asn Lys Thr Met Asp
545                 550                 555                 560

Asn Gly Ala Ser Leu Thr Tyr Glu Thr Phe Lys Phe Ala Ser Phe Ile
                565                 570                 575

Thr Asp Phe Gln Phe Arg Glu Thr Gln Asp Lys Ile Leu Leu Ser Met
            580                 585                 590

Gly Asp Phe Ser Ser Gly Gln Glu Val Tyr Ile Asp Arg Ile Glu Phe
        595                 600                 605

Ile Pro Val Asp Glu Thr
    610

<210> SEQ ID NO 55
<211> LENGTH: 1986
<212> TYPE: DNA
<213> ORGANISM: Artificial Sequence
<220> FEATURE:
<223> OTHER INFORMATION: FR(1Fa) coding sequence

<400> SEQUENCE: 55
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttcccctt ggcggcgccc tggtgagctt ctacaccaac      180

|                                                                                      |      |
|--------------------------------------------------------------------------------------|------|
| ttcctgaaca ccatctggcc cagcgaggac ccctggaagg ccttcatgga gcaggtggag                    | 240  |
| gccctgatgg accagaagat cgccgactac gccaagaaca aggcactggc cgagctacag                    | 300  |
| ggcctccaga acaacgtgga ggactatgtg agcgccctga gcagctggca gaagaacccc                    | 360  |
| gctgcaccgt tccgcaaccc ccacagccag ggccgcatcc gcgagctgtt cagccaggcc                    | 420  |
| gagagccact tccgcaacag catgcccagc ttcgccatca gcggctacga ggtgctgttc                    | 480  |
| ctgaccacct acgcccaggc cgccaacacc cacctgttcc tgctgaagga cgcccaaatc                    | 540  |
| tacggagagg agtggggcta cgagaaggag gacatcgccg agttctacaa cgccagctg                     | 600  |
| aagctgaccc aggagtacac cgaccactgc gtgaagtggt acaacgtggg tctagacaag                    | 660  |
| ctccgcggca gcagctacga gagctgggtg aacttcaacc gctaccgccg cgagatgacc                    | 720  |
| ctgaccgtgc tggacctgat cgccctgttc cccctgtacg acgtgcgcct gtaccccaag                    | 780  |
| gaggtgaaga ccgagctgac ccgcgacgtg ctgaccgacc ccatcgtggg cgtgaacaac                    | 840  |
| ctgcgcggct acggcaccac cttcagcaac atcgagaact acatccgcaa gccccacctg                    | 900  |
| ttcgactacc tgcaccgcat ccagttccac acgcgtttcc agcccggcta ctacggcaac                    | 960  |
| gacagcttca actactggag cggcaactac gtgagcaccc gccccagcat cggcagcaac                    | 1020 |
| gacatcatca ccagcccctt ctacggcaac aagagcagcg agcccgtgca gaaccttgag                    | 1080 |
| ttcaacggcg agaaggtgta ccgcgccgtg gctaacacca acctggccgt gtggccctct                    | 1140 |
| gcagtgtaca cgcggcgtgac caaggtggag ttcagccagt acaacgacca gaccgacgag                   | 1200 |
| gccagcaccc agacctacga cagcaagcgc aacgtgggcg ccgtgagctg ggacagcatc                    | 1260 |
| gaccagctgc ccccgagac caccgacgag ccctggaga agggctacag ccaccagctg                      | 1320 |
| aactacgtga tgtgcttcct gatgcagggc agccgcggca ccatccccgt gctgacctgg                    | 1380 |
| acccacaaga gcgtcgactt cttcaacatg atcgacagca gaagatcac ccagctgccc                     | 1440 |
| ctggtgaagg cccacaccct ccagtccggc accaccgtgg tgcgcggccc gggcttcacc                    | 1500 |
| ggcgcgaca tcctccgccg cacctccggc ggccgttcg cctacaccat cgtgaacatc                      | 1560 |
| aacggccagc tcccgcagcg ctaccgcgcc cgcatccgct acgcctccac caccaacctc                    | 1620 |
| cgcatctacg tgaccgtggc cggcgagcgc atcttcgccg ccagttcaa caagaccatg                     | 1680 |
| gacaccggcg acccgctcac cttccagtcc ttctcctacg ccaccatcaa caccgccttc                    | 1740 |
| accttcccga tgtcccagtc ctccttcacc gtgggcgccg acaccttctc ctccggcaac                    | 1800 |
| gaggtgtaca tcgaccgctt cgagctgatc ccggtgaccg ccaccttcga ggccgagtac                    | 1860 |
| gacctggagc gcgcccagaa ggccgtgaac gccctcttca cctccatcaa ccagatcggc                    | 1920 |
| atcaagaccg acgtgaccga ctaccacatc gaccaggtgt ccaacctcgt ggactgctta                    | 1980 |
| agctag                                                                               | 1986 |

<210> SEQ ID NO 56
<211> LENGTH: 661
<212> TYPE: PRT
<213> ORGANISM: Artificial Sequence
<220> FEATURE:
<223> OTHER INFORMATION: FR(1Fa) protein

<400> SEQUENCE: 56

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe

```
                35                  40                  45
Pro Phe Gly Gly Ala Leu Val Ser Phe Tyr Thr Asn Phe Leu Asn Thr
 50                  55                  60

Ile Trp Pro Ser Glu Asp Pro Trp Lys Ala Phe Met Glu Gln Val Glu
 65                  70                  75                  80

Ala Leu Met Asp Gln Lys Ile Ala Asp Tyr Ala Lys Asn Lys Ala Leu
                 85                  90                  95

Ala Glu Leu Gln Gly Leu Gln Asn Asn Val Glu Asp Tyr Val Ser Ala
                100                 105                 110

Leu Ser Ser Trp Gln Lys Asn Pro Ala Ala Pro Phe Arg Asn Pro His
            115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
                180                 185                 190

Ala Glu Phe Tyr Lys Arg Gln Leu Lys Leu Thr Gln Glu Tyr Thr Asp
            195                 200                 205

His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
450                 455                 460
```

Val Asp Phe Phe Asn Met Ile Asp Ser Lys Lys Ile Thr Gln Leu Pro
465                 470                 475                 480

Leu Val Lys Ala His Thr Leu Gln Ser Gly Thr Val Val Arg Gly
                485                 490                 495

Pro Gly Phe Thr Gly Gly Asp Ile Leu Arg Arg Thr Ser Gly Gly Pro
            500                 505                 510

Phe Ala Tyr Thr Ile Val Asn Ile Asn Gly Gln Leu Pro Gln Arg Tyr
            515                 520                 525

Arg Ala Arg Ile Arg Tyr Ala Ser Thr Thr Asn Leu Arg Ile Tyr Val
            530                 535                 540

Thr Val Ala Gly Glu Arg Ile Phe Ala Gly Gln Phe Asn Lys Thr Met
545                 550                 555                 560

Asp Thr Gly Asp Pro Leu Thr Phe Gln Ser Phe Ser Tyr Ala Thr Ile
                565                 570                 575

Asn Thr Ala Phe Thr Phe Pro Met Ser Gln Ser Ser Phe Thr Val Gly
            580                 585                 590

Ala Asp Thr Phe Ser Ser Gly Asn Glu Val Tyr Ile Asp Arg Phe Glu
            595                 600                 605

Leu Ile Pro Val Thr Ala Thr Phe Glu Ala Glu Tyr Asp Leu Glu Arg
610                 615                 620

Ala Gln Lys Ala Val Asn Ala Leu Phe Thr Ser Ile Asn Gln Ile Gly
625                 630                 635                 640

Ile Lys Thr Asp Val Thr Asp Tyr His Ile Asp Gln Val Ser Asn Leu
                645                 650                 655

Val Asp Cys Leu Ser
            660

<210> SEQ ID NO 57
<211> LENGTH: 1842
<212> TYPE: DNA
<213> ORGANISM: Artificial Sequence
<220> FEATURE:
<223> OTHER INFORMATION: FR(1Ac) coding sequence

<400> SEQUENCE: 57
atgactagta acggccgcca gtgtgctggt attcgccctt atgacggccg acaacaacac      60
cgaggcctgg acagcagcac caccaaggac gtgatccaga agggcatcag cgtggtgggc     120
gacctgctgg gcgtggtggg cttccccttc ggcggcgccc tggtgagctt ctacaccaac     180
ttcctgaaca ccatctggcc cagcgaggac ccctggaagg ccttcatgga gcaggtggag     240
gccctgatgg accagaagat cgccgactac gccaagaaca aggcactggc cgagctacag     300
ggcctccaga caacgtgga ggactatgtg agcgccctga gcagctggca gaagaacccc     360
gctgcaccgt tccgcaaccc ccacagccag gccgcatcc gcgagctgtt cagccaggcc     420
gagagccact tccgcaacag catgcccagc ttcgccatca gcggctacga ggtgctgttc     480
ctgaccacct acgcccaggc cgccaacacc cacctgttcc tgctgaagga cgcccaaatc     540
tacggagagg agtggggcta cgagaaggag gacatcgccg agttctacaa cgccagctg     600 aagctgaccc aggagtacac cgaccactgc gtgaagtggt acaacgtggg tctagacaag     660
ctccgcggca gcagctacga gagctgggtg aacttcaacc gctaccgccg cgagatgacc     720
ctgaccgtgc tggacctgat cgccctgttc cccctgtacg acgtgcgcct gtaccccaag     780
gaggtgaaga ccgagctgac ccgcgacgtg ctgaccgacc catcgtgggc cgtgaacaac     840
ctgcgcggct acggcaccac cttcagcaac atcgagaact acatccgcaa gccccacctg     900

```
ttcgactacc tgcaccgcat ccagttccac acgcgtttcc agcccggcta ctacggcaac      960
gacagcttca actactggag cggcaactac gtgagcaccc gccccagcat cggcagcaac     1020
gacatcatca ccagccccct ctacggcaac aagagcagcg agcccgtgca gaaccttgag     1080
ttcaacggcg agaaggtgta ccgcgccgtg gctaacacca acctggccgt gtggccctct     1140
gcagtgtaca gcggcgtgac caaggtggag ttcagccagt acaacgacca gaccgacgag     1200
gccagcaccc agacctacga cagcaagcgc aacgtgggcg ccgtgagctg ggacagcatc     1260
gaccagctgc cccccgagac accgacgagc ccctggagaa agggctacag ccaccagctg     1320
aactacgtga tgtgcttcct gatgcagggc agccgcggca ccatcccccgt gctgacctgg     1380 acccacaaga gcgtcgactt cttcaacatg atcgacagca agaagatcac ccagctgccc     1440
ctggtgaagg aaactttct ttttaatggt tctgtaattt caggaccagg atttactggt       1500
ggggacttag ttagattaaa tagtagtgga ataacattc agaatagagg gtatattgaa       1560
gttccaattc acttcccatc gacatctacc agatatcgag ttcgtgtacg gtatgcttct     1620
gtaaccccga ttcacctcaa cgttaattgg ggtaattcat ccattttttc caatacagta    1680
ccagctacag ctacgtcatt agataatcta caatcaagtg attttggtta ttttgaaagt    1740
gccaatgctt ttacatcttc attaggtaat atagtaggtg ttagaaattt tagtgggact    1800
gcaggagtga taatagacag atttgaattt attccagttt ag                       1842
```

<210> SEQ ID NO 58
<211> LENGTH: 613
<212> TYPE: PRT
<213> ORGANISM: Artificial Sequence
<220> FEATURE:
<223> OTHER INFORMATION: FR(1Ac) protein

<400> SEQUENCE: 58

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190
```

```
Ala Glu Phe Tyr Lys Arg Gln Leu Lys Leu Thr Gln Glu Tyr Thr Asp
            195                 200                 205

His Cys Val Lys Trp Tyr Asn Val Gly Leu Asp Lys Leu Arg Gly Ser
210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
            275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
            370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Val Lys Gly Asn Phe Leu Phe Asn Gly Ser Val Ile Ser Gly Pro
                485                 490                 495

Gly Phe Thr Gly Gly Asp Leu Val Arg Leu Asn Ser Ser Gly Asn Asn
            500                 505                 510

Ile Gln Asn Arg Gly Tyr Ile Glu Val Pro Ile His Phe Pro Ser Thr
515                 520                 525

Ser Thr Arg Tyr Arg Val Arg Val Arg Tyr Ala Ser Val Thr Pro Ile
530                 535                 540

His Leu Asn Val Asn Trp Gly Asn Ser Ser Ile Phe Ser Asn Thr Val
545                 550                 555                 560

Pro Ala Thr Ala Thr Ser Leu Asp Asn Leu Gln Ser Ser Asp Phe Gly
                565                 570                 575

Tyr Phe Glu Ser Ala Asn Ala Phe Thr Ser Ser Leu Gly Asn Ile Val
            580                 585                 590

Gly Val Arg Asn Phe Ser Gly Thr Ala Gly Val Ile Ile Asp Arg Phe
            595                 600                 605

Glu Phe Ile Pro Val
```

610

<210> SEQ ID NO 59
<211> LENGTH: 2067
<212> TYPE: DNA
<213> ORGANISM: Artificial Sequence
<220> FEATURE:
<223> OTHER INFORMATION: FR(1Ia) coding sequence

<400> SEQUENCE: 59

| | | | | | |
|---|---|---|---|---|---|
| atgactagta | acggccgcca | gtgtgctggt | attcgccctt | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttccccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggag | gactatgtg | agcgccctga | gcagctggca | gaagaacccc | 360 |
| gctgcaccgt | tccgcaaccc | ccacagccag | gccgcatcc | gcgagctgtt | cagccaggcc | 420 |
| gagagccact | tccgcaacag | catgcccagc | ttcgccatca | gcggctacga | ggtgctgttc | 480 |
| ctgaccacct | acgcccaggc | cgccaacacc | cacctgttcc | tgctgaagga | cgcccaaatc | 540 |
| tacggagagg | agtggggcta | cgagaaggag | gacatcgccg | agttctacaa | cgccagctg | 600 |
| aagctgaccc | aggagtacac | cgaccactgc | gtgaagtggt | acaacgtggg | tctagacaag | 660 |
| ctccgcggca | gcagctacga | gagctgggtg | aacttcaacc | gctaccgccg | cgagatgacc | 720 |
| ctgaccgtgc | tggacctgat | cgccctgttc | ccctgtacg | acgtgcgcct | gtaccccaag | 780 |
| gaggtgaaga | ccgagctgac | ccgcgacgtg | ctgaccgacc | ccatcgtggg | cgtgaacaac | 840 |
| ctgcgcggct | acggcaccac | cttcagcaac | atcgagaact | acatccgcaa | gccccacctg | 900 |
| ttcgactacc | tgcaccgcat | ccagttccac | acgcgtttcc | agcccggcta | ctacggcaac | 960 |
| gacagcttca | actactggag | cggcaactac | gtgagcaccc | gccccagcat | cggcagcaac | 1020 |
| gacatcatca | ccagcccctt | ctacggcaac | aagagcagcg | agcccgtgca | gaaccttgag | 1080 |
| ttcaacggcg | agaaggtgta | ccgcgccgtg | gctaacacca | acctggccgt | gtggccctct | 1140 |
| gcagtgtaca | gcggcgtgac | caaggtggag | ttcagccagt | acaacgacca | gaccgacgag | 1200 |
| gccagcaccc | agacctacga | cagcaagcgc | aacgtgggcg | ccgtgagctg | ggacagcatc | 1260 |
| gaccagctgc | ccccgagac | caccgacgag | ccctggaga | agggctacag | ccaccagctg | 1320 |
| aactacgtga | tgtgcttcct | gatgcagggc | agccgcggca | ccatccccgt | gctgacctgg | 1380 |
| acccacaaga | gcgtcgactt | cttcaacatg | atcgacagca | gaagatcac | ccagctgccc | 1440 |
| ctggtaaaag | ctttcaatct | gtcttcaggt | gccgctgtag | tgagaggacc | aggatttaca | 1500 |
| ggtggggata | tccttcgaag | aacgaatact | ggtacatttg | gggatatacg | agtaaatatt | 1560 |
| aatccaccat | ttgcacaaag | atatcgcgtg | aggattcgct | atgcttctac | cacagattta | 1620 |
| caattccata | cgtcaattaa | cggtaaagct | attaatcaag | gtaattttc | agcaactatg | 1680 |
| aatagaggag | aggacttaga | ctataaaacc | tttagaactg | taggctttac | cactccattt | 1740 |
| agctttttag | atgtacaaag | tacattcaca | ataggtgctt | ggaacttctc | ttcaggtaac | 1800 |
| gaagtttata | tagatagaat | tgaatttgtt | ccggtagaag | taacatatga | ggcagaatat | 1860 |
| gattttgaaa | aagcgcaaga | gaaggttact | gcactgttta | catctacgaa | tccaagagga | 1920 |
| ttaaaaacag | atgtaaagga | ttatcatatt | gaccaggtat | caaatttagt | agagtctcta | 1980 |
| tcagatgaat | tctatcttga | tgaaaagaga | gaattattcg | agatagttaa | atacgcgaag | 2040 | caactccata ttgagcgtaa catgtag 2067

<210> SEQ ID NO 60
<211> LENGTH: 688
<212> TYPE: PRT
<213> ORGANISM: Artificial Sequence
<220> FEATURE:
<223> OTHER INFORMATION: FR(IIa) protein

<400> SEQUENCE: 60

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350
```

Ser Glu Pro Val Gln Asn Leu Glu Phe Asn Gly Glu Lys Val Tyr Arg
355                 360                 365

Ala Val Ala Asn Thr Asn Leu Ala Val Trp Pro Ser Ala Val Tyr Ser
370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Val Lys Ala Phe Asn Leu Ser Ser Gly Ala Ala Val Val Arg Gly
                485                 490                 495

Pro Gly Phe Thr Gly Gly Asp Ile Leu Arg Arg Thr Asn Thr Gly Thr
            500                 505                 510

Phe Gly Asp Ile Arg Val Asn Ile Asn Pro Pro Phe Ala Gln Arg Tyr
            515                 520                 525

Arg Val Arg Ile Arg Tyr Ala Ser Thr Thr Asp Leu Gln Phe His Thr
530                 535                 540

Ser Ile Asn Gly Lys Ala Ile Asn Gln Gly Asn Phe Ser Ala Thr Met
545                 550                 555                 560

Asn Arg Gly Glu Asp Leu Asp Tyr Lys Thr Phe Arg Thr Val Gly Phe
                565                 570                 575

Thr Thr Pro Phe Ser Phe Leu Asp Val Gln Ser Thr Phe Thr Ile Gly
            580                 585                 590

Ala Trp Asn Phe Ser Ser Gly Asn Glu Val Tyr Ile Asp Arg Ile Glu
            595                 600                 605

Phe Val Pro Val Glu Val Thr Tyr Glu Ala Glu Tyr Asp Phe Glu Lys
610                 615                 620

Ala Gln Glu Lys Val Thr Ala Leu Phe Thr Ser Thr Asn Pro Arg Gly
625                 630                 635                 640

Leu Lys Thr Asp Val Lys Asp Tyr His Ile Asp Gln Val Ser Asn Leu
                645                 650                 655

Val Glu Ser Leu Ser Asp Glu Phe Tyr Leu Asp Glu Lys Arg Glu Leu
            660                 665                 670

Phe Glu Ile Val Lys Tyr Ala Lys Gln Leu His Ile Glu Arg Asn Met
            675                 680                 685

<210> SEQ ID NO 61
<211> LENGTH: 1962
<212> TYPE: DNA
<213> ORGANISM: Artificial Sequence
<220> FEATURE:
<223> OTHER INFORMATION: DM23A coding sequence

<400> SEQUENCE: 61
atgactagta acggccgcca gtgtgctggt attcgccctt atgacggccg acaacaacac     60
cgaggcctgg acagcagcac caccaaggac gtgatccaga agggcatcag cgtggtgggc    120
gacctgctgg gcgtggtggg cttccccttc ggcggcgccc tggtgagctt ctacaccaac    180

```
ttcctgaaca ccatctggcc cagcgaggac ccctggaagg ccttcatgga gcaggtggag      240
gccctgatgg accagaagat cgccgactac gccaagaaca aggcactggc cgagctacag      300
ggcctccaga caacgtgga ggactatgtg agcgccctga gcagctggca agaaccccc        360 gctgcaccgt ccgcaaccc ccacagccag ggccgcatcc gcgagctgtt cagccaggcc       420
gagagccact tccgcaacag catgcccagc ttcgccatca gcggctacga ggtgctgttc      480
ctgaccacct acgcccaggc cgccaacacc cacctgttcc tgctgaagga cgcccaaatc      540
tacggagagg agtggggcta cgagaaggag gacatcgccg agttctacaa cgccagctg      600 aagctgaccc aggagtacac cgaccactgc gtgaagtggt acaacgtggg tctagacaag      660
ctccgcggca gcagctacga gagctgggtg aacttcaacc gctaccgccg cgagatgacc      720
ctgaccgtgc tggacctgat cgccctgttc ccctgtacg acgtgcgcct gtaccccaag      780
gaggtgaaga ccgagctgac ccgcgacgtg ctgaccgacc ccatcgtggg cgtgaacaac      840
ctgcgcggct acggcaccac cttcagcaac atcgagaact acatccgcaa gccccacctg      900
ttcgactacc tgcaccgcat ccagttccac acgcgtttcc agcccggcta ctacggcaac      960
gacagcttca actactggag cggcaactac gtgagcaccc gccccagcat cggcagcaac     1020
gacatcatca ccagcccctt ctacggcaac aagagcagca gcccgtgca gaaccttgag     1080 ttcaacggcg agaaggtgta ccgcgccgtg gctaacacca acctggccgt gtggccctct     1140
gcagtgtaca cgcggtgac caaggtggag ttcagccagt acaacgacca gaccgacgag     1200
gccagcaccc agacctacga cagcaagcgc aacgtgggcg ccgtgagctg gacagcatc     1260 gaccagctgc ccccgagac caccgacgag ccctggaga agggctacag ccaccagctg     1320
aactacgtga tgtgcttcct gatgcagggc agccgcggca ccatccccgt gctgacctgg     1380
acccacaaga gcgccgagtt caacaacatc atccccagca gccagatcac ccagatcccc     1440
ctgaccaaga gcaccaacct gggcagcggc accagcgtgg tgaagggccc cggcttcacc     1500
ggcggcgaca tcctgcgccg caccagcccc ggccagatca gcaccctgcg cgtgaacatc     1560
accgcccccc tgagccagcg ctaccgcgtc cgcatccgct acgccagcac caccaacctg     1620
cagttccaca ccagcatcga cggccgcccc atcaaccagg caacttcag cgccaccatg     1680 agcagcggca gcaacctgca gagcggcagc ttccgcaccg tgggcttcac cacccccttc     1740
aacttcagca acggcagcag cgtgttcacc ctgagcgccc acgtgttcaa cagcggcaac     1800
gaggtgtaca tcgaccgcat cgagttcgtg cccgccgagg tgaccttcga ggccgagtac     1860
gacctggaga gggctcagaa ggccgtgaac gagctgttca ccagcagcaa ccagatcggc     1920
ctgaagaccg acgtgaccga ctaccacatc gatcaggtgt ag                        1962
```

<210> SEQ ID NO 62
<211> LENGTH: 653
<212> TYPE: PRT
<213> ORGANISM: Artificial Sequence
<220> FEATURE:
<223> OTHER INFORMATION: DM23A protein

<400> SEQUENCE: 62

```
Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45
```

```
Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
    450                 455                 460

Ala Glu Phe Asn Asn Ile Ile Pro Ser Ser Gln Ile Thr Gln Ile Pro
```

```
                465                 470                 475                 480
Leu Thr Lys Ser Thr Asn Leu Gly Ser Gly Thr Ser Val Val Lys Gly
                    485                 490                 495
Pro Gly Phe Thr Gly Gly Asp Ile Leu Arg Arg Thr Ser Pro Gly Gln
                500                 505                 510
Ile Ser Thr Leu Arg Val Asn Ile Thr Ala Pro Leu Ser Gln Arg Tyr
            515                 520                 525
Arg Val Arg Ile Arg Tyr Ala Ser Thr Thr Asn Leu Gln Phe His Thr
        530                 535                 540
Ser Ile Asp Gly Arg Pro Ile Asn Gln Gly Asn Phe Ser Ala Thr Met
545                 550                 555                 560
Ser Ser Gly Ser Asn Leu Gln Ser Gly Ser Phe Arg Thr Val Gly Phe
                    565                 570                 575
Thr Thr Pro Phe Asn Phe Ser Asn Gly Ser Ser Val Phe Thr Leu Ser
                580                 585                 590
Ala His Val Phe Asn Ser Gly Asn Glu Val Tyr Ile Asp Arg Ile Glu
            595                 600                 605
Phe Val Pro Ala Glu Val Thr Phe Glu Ala Glu Tyr Asp Leu Glu Arg
        610                 615                 620
Ala Gln Lys Ala Val Asn Glu Leu Phe Thr Ser Ser Asn Gln Ile Gly
625                 630                 635                 640
Leu Lys Thr Asp Val Thr Asp Tyr His Ile Asp Gln Val
                    645                 650

<210> SEQ ID NO 63
<211> LENGTH: 1923
<212> TYPE: DNA
<213> ORGANISM: Artificial Sequence
<220> FEATURE:
<223> OTHER INFORMATION: 8AF coding sequence

<400> SEQUENCE: 63
atgacggccg acaacaacac cgaggccctg gacagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaag     180 gccttcatgg agcaggtgga ggccctgatg accagaaga tcgccgacta cgccaagaac     240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgccag cttcgccatc     420 agcggctacg aggtgctgtt cctgaccacc tacgcccagg ccgccaacac ccacctgttc     480
ctgctgaagg acgcccaaat ctacggagag gagtgggggct acgagaagga ggacatcgcc     540
gagttctaca gcgccagct gaagctgacc caggagtaca ccgaccactg cgtgaagtgg     600
tacaacgtgg gtctagacaa gctccgcggc agcagctacg agagctgggt gaacttcaac     660
cgctaccgcc gcgagatgac cctgaccgtg ctggacctga tcgccctgtt ccccctgtac     720
gacgtgcgcc tgtaccccaa ggaggtgaag accgagctga cccgcgacgt gctgaccgac     780
cccatcgtgg gcgtgaacaa cctgcgcggc tacggcacca ccttcagcaa catcgagaac     840
tacatccgca agcccacct gttcgactac ctgcaccgca tccagttcca cacgcgtttc     900
cagcccggct actacggcaa cgacagcttc aactactgga gcggcaacta cgtgagcacc     960
cgccccagca tcggcagcaa cgacatcatc accagcccct ctacggcaa caagagcagc    1020
```

```
gagcccgtgc agaaccttga gttcaacggc gagaaggtgt accgcgccgt ggctaacacc    1080
aacctggccg tgtggccctc tgcagtgtac agcggcgtga ccaaggtgga gttcagccag    1140
tacaacgacc agaccgacga ggccagcacc cagacctacg acagcaagcg caacgtgggc    1200
gccgtgagct gggacagcat cgaccagctg ccccccgaga ccaccgacga gcccctggag    1260
aagggctaca gccaccagct gaactacgtg atgtgcttcc tgatgcaggg cagccgcggc    1320
accatccccg tgctgacctg gacccacaag agcgtcgact tcttcaacat gatcgacagc    1380
aagaagatca cccagctgcc cctgaccaag agcaccaacc tgggcagcgg caccagcgtg    1440
gtgaagggcc ccggcttcac cggcggcgac atcctgcgcc gcaccagccc cggccagatc    1500
agcaccctgc gcgtgaacat caccgccccc ctgagccagc gctaccgcgt ccgcatccgc    1560
tacgccagca ccaccaacct gcagttccac accagcatcg acggccgccc catcaaccag    1620
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca cagcggcaa cgaggtgtac atcgaccgca tcgagttcgt gcccgccgag    1800
gtgaccttcg aggccgagta cgacctggag agggctcaga aggccgtgaa cgagctgttc    1860
accagcagca accagatcgg cctgaagacc gacgtgaccg actaccacat cgatcaggtg    1920
tag                                                                  1923
```

<210> SEQ ID NO 64
<211> LENGTH: 640
<212> TYPE: PRT
<213> ORGANISM: Artificial Sequence
<220> FEATURE:
<223> OTHER INFORMATION: 8AF protein

<400> SEQUENCE: 64

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
```

-continued

```
            195                 200                 205
Arg Gly Ser Ser Tyr Glu Ser Trp Val Asn Phe Asn Arg Tyr Arg Arg
210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
                260                 265                 270

Thr Thr Phe Ser Asn Ile Glu Asn Tyr Ile Arg Lys Pro His Leu Phe
                275                 280                 285

Asp Tyr Leu His Arg Ile Gln Phe His Thr Arg Phe Gln Pro Gly Tyr
                290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
                355                 360                 365

Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
                435                 440                 445

His Lys Ser Val Asp Phe Phe Asn Met Ile Asp Ser Lys Lys Ile Thr
                450                 455                 460

Gln Leu Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
                500                 505                 510

Gln Arg Tyr Arg Val Arg Ile Arg Tyr Ala Ser Thr Thr Asn Leu Gln
                515                 520                 525

Phe His Thr Ser Ile Asp Gly Arg Pro Ile Asn Gln Gly Asn Phe Ser
                530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
                580                 585                 590

Arg Ile Glu Phe Val Pro Ala Glu Val Thr Phe Glu Ala Glu Tyr Asp
                595                 600                 605

Leu Glu Arg Ala Gln Lys Ala Val Asn Glu Leu Phe Thr Ser Ser Asn
                610                 615                 620
```

Gln Ile Gly Leu Lys Thr Asp Val Thr Asp Tyr His Ile Asp Gln Val
625                 630                 635                 640

<210> SEQ ID NO 65
<211> LENGTH: 1836
<212> TYPE: DNA
<213> ORGANISM: Artificial Sequence
<220> FEATURE:
<223> OTHER INFORMATION: 5*cry3A055 coding sequence

<400> SEQUENCE: 65

```
atgactagta acggccgcca gtgtgctgga attcgcccctt atgacggccg acaacaacac    60
cgaggcctgg acagcagcac caccaaggac gtgatccaga agggcatcag cgtggtgggc   120
gacctgctgg gcgtggtggg cttccccttc ggcggcgccc tggtgagctt ctacaccaac   180
ttcctgaaca ccatctggcc cagcgaggac ccctggaagg ccttcatgga gcaggtggag   240
gccctgatgg accagaagat cgccgactac gccaagaaca aggcactggc cgagctacag   300
ggcctccaga caacgtgga ggactatgtg agcgccctga gcagctggca agaaccc       360
gctgcaccgt tccgcaaccc ccacagccag ggccgcatcc gcgagctgtt cagccaggcc   420
gagagccact tccgcaacag catgcccagc ttcgccatca gcggctacga ggtgctgttc   480
ctgaccacct acgcccaggc cgccaacacc cacctgttcc tgctgaagga cgcccaaatc   540
tacggagagg agtggggcta cgagaaggag gacatcgccg agttctacaa cgccagctg   600
aagctgaccc aggagtacac cgaccactgc gtgaagtggt acaacgtggg tctagacaag   660
ctccgcggca gcagctacga gagctgggtg aacttcaacc gctaccgccg cgagatgacc   720
ctgaccgtgc tggacctgat cgccctgttc cccctgtacg acgtgcgcct gtaccccaag   780
gaggtgaaga ccgagctgac ccgcgacgtg ctgaccgacc ccatcgtggg cgtgaacaac   840
ctgcgcggct acggcaccac cttcagcaac atcgagaact acatccgcaa gccccacctg   900
ttcgactacc tgcaccgcat ccagttccac acgcgttttcc agcccggcta ctacggcaac   960
gacagcttca actactggag cggcaactac gtgagcaccc gccccagcat cggcagcaac  1020
gacatcatca ccagccccatt ctacggcaac aagagcagcg agcccgtgca gaaccttgag  1080
ttcaacggcg agaaggtgta ccgcgccgtg gctaacacca acctggccgt gtggcccatct  1140
gcagtgtaca cgcgcgtgac caaggtggag ttcagccagt acaacgacca gaccgacgag  1200
gccagcaccc agacctacga cagcaagcgc aacgtgggcg ccgtgagctg ggacagcatc  1260
gaccagctgc cccccgagac caccgacgag ccccctggaga agggctacag ccaccagctg  1320
aactacgtga tgtgcttcct gatgcagggc agccgcggca ccatccccgt gctgacctgg  1380
acccacaaga gcgtcgactt cttcaacatg atcgacagca agaagatcac ccagctgccc  1440
ctggtgaagg cctacaagct ccagagcggc gccagcgtgg tggcaggccc ccgcttcacc  1500
ggcggcgaca tcatccagtg caccgagaac ggcagcgccg ccaccatcta cgtgaccccc  1560
gacgtgagct acagccagaa gtaccgcgcc cgcatccact acgccagcac cagccagatc  1620
accttcaccc tgagcctgga cggggccccc ttcaaccaat actacttcga caagaccatc  1680
aacaagggcg acaccctgac ctacaacagc ttcaacctgg ccagcttcag caccccttttc  1740
gagctgagcg gcaacaacct ccagatcggc gtgaccggcc tgagcgccgg cgacaaggtg  1800
tacatcgaca agatcgagtt catccccgtg aactag                             1836
```

<210> SEQ ID NO 66
<211> LENGTH: 611

```
<212> TYPE: PRT
<213> ORGANISM: Artificial Sequence
<220> FEATURE:
<223> OTHER INFORMATION: 5*Cry3A055 protein

<400> SEQUENCE: 66
```

| | | | | | | | | | | | | | | |
|---|---|---|---|---|---|---|---|---|---|---|---|---|---|---|
| Met | Thr | Ser | Asn | Gly | Arg | Gln | Cys | Ala | Gly | Ile | Arg | Pro | Tyr | Asp | Gly |
| 1 | | | | 5 | | | | | 10 | | | | | 15 | |

Arg Gln Gln His Arg Gly Leu Asp Ser Ser Thr Thr Lys Asp Val Ile
                20                  25                  30

Gln Lys Gly Ile Ser Val Val Gly Asp Leu Leu Gly Val Val Gly Phe
            35                  40                  45

Pro Phe Gly Gly Ala Leu Val Ser Phe Tyr Thr Asn Phe Leu Asn Thr
        50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
                100                 105                 110

Leu Ser Ser Trp Gln Lys Asn Pro Ala Ala Pro Phe Arg Asn Pro His
                115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
                180                 185                 190

Ala Glu Phe Tyr Lys Arg Gln Leu Lys Leu Thr Gln Glu Tyr Thr Asp
                195                 200                 205

His Cys Val Lys Trp Tyr Asn Val Gly Leu Asp Lys Leu Arg Gly Ser
                210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Asn Leu Arg Gly Tyr Gly Thr Thr Phe
                275                 280                 285

Ser Asn Ile Glu Asn Tyr Ile Arg Lys Pro His Leu Phe Asp Tyr Leu
                290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
                355                 360                 365

Ala Val Ala Asn Thr Asn Leu Ala Val Trp Pro Ser Ala Val Tyr Ser
                370                 375                 380

| | | | | | | | | | | | |
|---|---|---|---|---|---|---|---|---|---|---|---|
|Gly|Val|Thr|Lys|Val|Glu|Phe|Ser|Gln|Tyr|Asn|Asp|Gln|Thr|Asp|Glu|
|385| | | | |390| | | | |395| | | | |400|

Ala Ser Thr Gln Thr Tyr Asp Ser Lys Arg Asn Val Gly Ala Val Ser
            405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
450                 455                 460

Val Asp Phe Phe Asn Met Ile Asp Ser Lys Lys Ile Thr Gln Leu Pro
465                 470                 475                 480

Leu Val Lys Ala Tyr Lys Leu Gln Ser Gly Ala Ser Val Val Ala Gly
            485                 490                 495

Pro Arg Phe Thr Gly Gly Asp Ile Ile Gln Cys Thr Glu Asn Gly Ser
            500                 505                 510

Ala Ala Thr Ile Tyr Val Thr Pro Asp Val Ser Tyr Ser Gln Lys Tyr
            515                 520                 525

Arg Ala Arg Ile His Tyr Ala Ser Thr Ser Gln Ile Thr Phe Thr Leu
530                 535                 540

Ser Leu Asp Gly Ala Pro Phe Asn Gln Tyr Tyr Phe Asp Lys Thr Ile
545                 550                 555                 560

Asn Lys Gly Asp Thr Leu Thr Tyr Asn Ser Phe Asn Leu Ala Ser Phe
            565                 570                 575

Ser Thr Pro Phe Glu Leu Ser Gly Asn Asn Leu Gln Ile Gly Val Thr
            580                 585                 590

Gly Leu Ser Ala Gly Asp Lys Val Tyr Ile Asp Lys Ile Glu Phe Ile
            595                 600                 605

Pro Val Asn
610

<210> SEQ ID NO 67
<211> LENGTH: 1803
<212> TYPE: DNA
<213> ORGANISM: Artificial Sequence
<220> FEATURE:
<223> OTHER INFORMATION: mocry3A coding sequence

<400> SEQUENCE: 67

```
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc ccagcgagga ccctggaag     180
gccttcatgg agcaggtgga ggccctgatg gaccagaaga tcgccgacta cgccaagaac    240
aaggcactgg ccgagctaca gggcctccag aacaacgtgg aggactatgt gagcgccctg    300
agcagctggc agaagaaccc cgtctcgagc cgcaaccccc acagccaggg ccgcatccgc    360
gagctgttca gccaggccga gccacttc gcaacagca tgcccagctt cgccatcagc       420
ggctacgagg tgctgttcct gaccacctac gcccaggccg ccaacaccca cctgttcctg    480
ctgaaggacg cccaaatcta cggagaggag tggggctacg agaaggagga catcgccgag    540
ttctacaagc gccagctgaa gctgacccag gagtacaccg accactgcgt gaagtggtac    600
aacgtgggtc tagacaagct ccgcggcagc agctacgaga ctgggtgaa cttcaaccgc     660
taccgccgcg agatgaccct gaccgtgctg gacctgatcg ccctgttccc cctgtacgac    720
```

```
gtgcgcctgt accccaagga ggtgaagacc gagctgaccc cgacgtgct gaccgacccc    780
atcgtgggcg tgaacaacct cgcggctac ggcaccacct tcagcaacat cgagaactac    840
atccgcaagc ccacctgtt cgactacctg caccgcatcc agttccacac gcgtttccag    900
cccggctact acggcaacga cagcttcaac tactggagcg caactacgt gagcacccgc    960
cccagcatcg gcagcaacga catcatcacc agccccttct acggcaacaa gagcagcgag   1020
cccgtgcaga accttgagtt caacggcgag aaggtgtacc gcgccgtggc taacaccaac   1080
ctggccgtgt ggccctctgc agtgtacagc ggcgtgacca aggtggagtt cagccagtac   1140
aacgaccaga ccgacgaggc cagcacccag acctacgaca gcaagcgcaa cgtgggcgcc   1200
gtgagctggg acagcatcga ccagctgccc cccgagacca ccgacgagcc cctggagaag   1260
ggctacagcc accagctgaa ctacgtgatg tgcttcctga tgcagggcag ccgcggcacc   1320
atccccgtgc tgacctggac ccacaagagc gtcgacttct tcaacatgat cgacagcaag   1380
aagatcaccc agctgcccct ggtgaaggcc tacaagctcc agagcggcgc cagcgtggtg   1440
gcaggccccc gcttcaccgg cggcgacatc atccagtgca ccgagaacgg cagcgccgcc   1500
accatctacg tgaccccga cgtgagctac agccagaagt accgcgcccg catccactac   1560
gccagcacca gccagatcac cttcaccctg agcctggacg ggcccccctt caaccaatac   1620
tacttcgaca agaccatcaa caagggcgac accctgacct acaacagctt caacctggcc   1680
agcttcagca cccctttcga gctgagcggc aacaacctcc agatcggcgt gaccggcctg   1740
agcgccggcg acaaggtgta catcgacaag atcgagttca tccccgtgaa ctagatctga   1800
gct                                                                 1803
```

<210> SEQ ID NO 68
<211> LENGTH: 597
<212> TYPE: PRT
<213> ORGANISM: Bacillus thuringiensis
<220> FEATURE:
<223> OTHER INFORMATION: moCry3A

<400> SEQUENCE: 68

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140

Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
```

```
            165                 170                 175
Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
            195                 200                 205

Gly Ser Ser Tyr Glu Ser Trp Val Asn Phe Asn Arg Tyr Arg Arg Glu
            210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                    245                 250                 255

Leu Thr Asp Pro Ile Val Gly Val Asn Asn Leu Arg Gly Tyr Gly Thr
                260                 265                 270

Thr Phe Ser Asn Ile Glu Asn Tyr Ile Arg Lys Pro His Leu Phe Asp
            275                 280                 285

Tyr Leu His Arg Ile Gln Phe His Thr Arg Phe Gln Pro Gly Tyr Tyr
            290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                    325                 330                 335

Lys Ser Ser Glu Pro Val Gln Asn Leu Glu Phe Asn Gly Glu Lys Val
                340                 345                 350

Tyr Arg Ala Val Ala Asn Thr Asn Leu Ala Val Trp Pro Ser Ala Val
            355                 360                 365

Tyr Ser Gly Val Thr Lys Val Glu Phe Ser Gln Tyr Asn Asp Gln Thr
370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                    405                 410                 415

Pro Leu Glu Lys Gly Tyr Ser His Gln Leu Asn Tyr Val Met Cys Phe
                420                 425                 430

Leu Met Gln Gly Ser Arg Gly Thr Ile Pro Val Leu Thr Trp Thr His
            435                 440                 445

Lys Ser Val Asp Phe Phe Asn Met Ile Asp Ser Lys Lys Ile Thr Gln
            450                 455                 460

Leu Pro Leu Val Lys Ala Tyr Lys Leu Gln Ser Gly Ala Ser Val Val
465                 470                 475                 480

Ala Gly Pro Arg Phe Thr Gly Gly Asp Ile Ile Gln Cys Thr Glu Asn
                    485                 490                 495

Gly Ser Ala Ala Thr Ile Tyr Val Thr Pro Asp Val Ser Tyr Ser Gln
                500                 505                 510

Lys Tyr Arg Ala Arg Ile His Tyr Ala Ser Thr Ser Gln Ile Thr Phe
            515                 520                 525

Thr Leu Ser Leu Asp Gly Ala Pro Phe Asn Gln Tyr Tyr Phe Asp Lys
            530                 535                 540

Thr Ile Asn Lys Gly Asp Thr Leu Thr Tyr Asn Ser Phe Asn Leu Ala
545                 550                 555                 560

Ser Phe Ser Thr Pro Phe Glu Leu Ser Gly Asn Asn Leu Gln Ile Gly
                    565                 570                 575

Val Thr Gly Leu Ser Ala Gly Asp Lys Val Tyr Ile Asp Lys Ile Glu
                580                 585                 590
```

Phe Ile Pro Val Asn
      595

<210> SEQ ID NO 69
<211> LENGTH: 1807
<212> TYPE: DNA
<213> ORGANISM: Artificial Sequence
<220> FEATURE:
<223> OTHER INFORMATION: cry3A055 coding sequence

<400> SEQUENCE: 69

| | | | | | | |
|---|---|---|---|---|---|---|
| atgacggccg | acaacaacac | cgaggccctg | acagcagca | ccaccaagga | cgtgatccag | 60 |
| aagggcatca | gcgtggtggg | cgacctgctg | ggcgtggtgg | gcttcccctt | cggcggcgcc | 120 |
| ctggtgagct | tctacaccaa | cttcctgaac | accatctggc | cagcgagga | cccctggaag | 180 |
| gccttcatgg | agcaggtgga | ggccctgatg | gaccagaaga | tcgccgacta | cgccaagaac | 240 |
| aaggcactgg | ccgagctaca | gggcctccag | aacaacgtgg | aggactatgt | gagcgccctg | 300 |
| agcagctggc | agaagaaccc | cgctgcaccg | ttccgcaacc | ccacagcca | gggccgcatc | 360 |
| cgcgagctgt | tcagccaggc | cgagagccac | ttccgcaaca | gcatgccag | cttcgccatc | 420 |
| agcggctacg | aggtgctgtt | cctgaccacc | tacgcccagg | ccgccaacac | ccacctgttc | 480 |
| ctgctgaagg | acgcccaaat | ctacggagag | gagtggggct | acgagaagga | ggacatcgcc | 540 |
| gagttctaca | agcgccagct | gaagctgacc | aggagtaca | ccgaccactg | cgtgaagtgg | 600 |
| tacaacgtgg | gtctagacaa | gctccgcggc | agcagctacg | agagctgggt | gaacttcaac | 660 |
| cgctaccgcc | gcgagatgac | cctgaccgtg | ctggacctga | tcgccctgtt | cccctgtac | 720 |
| gacgtgcgcc | tgtaccccaa | ggaggtgaag | accgagctga | cccgcgacgt | gctgaccgac | 780 |
| cccatcgtgg | gcgtgaacaa | cctgcgcggc | tacggcacca | ccttcagcaa | catcgagaac | 840 |
| tacatccgca | agcccacct | gttcgactac | ctgcaccgca | tccagttcca | cacgcgtttc | 900 |
| cagcccggct | actacggcaa | cgacagcttc | aactactgga | gcggcaacta | cgtgagcacc | 960 |
| cgccccagca | tcggcagcaa | cgacatcatc | accagcccct | tctacggcaa | caagagcagc | 1020 |
| gagcccgtgc | agaaccttga | gttcaacggc | gagaaggtgt | accgcgccgt | ggctaacacc | 1080 |
| aacctggccg | tgtggcctc | tgcagtgtac | agcggcgtga | ccaaggtgga | gttcagccag | 1140 |
| tacaacgacc | agaccgacga | ggccagcacc | cagacctacg | acagcaagcg | caacgtgggc | 1200 |
| gccgtgagct | gggacagcat | cgaccagctg | ccccccgaga | ccaccgacga | gccctggag | 1260 |
| aagggctaca | gccaccagct | gaactacgtg | atgtgcttcc | tgatgcaggg | cagccgcggc | 1320 |
| accatccccg | tgctgacctg | gacccacaag | agcgtcgact | tcttcaacat | gatcgacagc | 1380 |
| aagaagatca | cccagctgcc | cctggtgaag | gcctacaagc | tccagagcgg | cgccagcgtg | 1440 |
| gtggcaggcc | ccgcgcttcac | cggcggcgac | atcatccagt | gcaccgagaa | cggcagcgcc | 1500 |
| gccaccatct | acgtgacccc | cgacgtgagc | tacagccaga | gtaccgcgc | ccgcatccac | 1560 |
| tacgccagca | ccagccagat | caccttcacc | ctgagcctgg | acggggcccc | cttcaaccaa | 1620 |
| tactacttcg | acaagaccat | caacaagggc | gacacctga | cctacaacag | cttcaacctg | 1680 |
| gccagcttca | gcaccccttt | cgagctgagc | ggcaacaacc | tccagatcgg | cgtgaccggc | 1740 |
| ctgagcgccg | gcgacaaggt | gtacatcgac | aagatcgagt | tcatccccgt | gaactagatc | 1800 |
| tgagctc | | | | | | 1807 |

<210> SEQ ID NO 70
<211> LENGTH: 598

<212> TYPE: PRT
<213> ORGANISM: Artificial Sequence
<220> FEATURE:
<223> OTHER INFORMATION: Cry3A055 protein

<400> SEQUENCE: 70

| | | | | | | | | | | | | | | |
|---|---|---|---|---|---|---|---|---|---|---|---|---|---|---|
| Met | Thr | Ala | Asp | Asn | Asn | Thr | Glu | Ala | Leu | Asp | Ser | Ser | Thr | Thr | Lys |
| 1 | | | | 5 | | | | | 10 | | | | | 15 | |
| Asp | Val | Ile | Gln | Lys | Gly | Ile | Ser | Val | Val | Gly | Asp | Leu | Leu | Gly | Val |
| | | | 20 | | | | | 25 | | | | | 30 | | |
| Val | Gly | Phe | Pro | Phe | Gly | Gly | Ala | Leu | Val | Ser | Phe | Tyr | Thr | Asn | Phe |
| | | | 35 | | | | | 40 | | | | | 45 | | |
| Leu | Asn | Thr | Ile | Trp | Pro | Ser | Glu | Asp | Pro | Trp | Lys | Ala | Phe | Met | Glu |
| | 50 | | | | | 55 | | | | | 60 | | | | |
| Gln | Val | Glu | Ala | Leu | Met | Asp | Gln | Lys | Ile | Ala | Asp | Tyr | Ala | Lys | Asn |
| 65 | | | | | 70 | | | | | 75 | | | | | 80 |
| Lys | Ala | Leu | Ala | Glu | Leu | Gln | Gly | Leu | Gln | Asn | Asn | Val | Glu | Asp | Tyr |
| | | | | 85 | | | | | 90 | | | | | 95 | |
| Val | Ser | Ala | Leu | Ser | Ser | Trp | Gln | Lys | Asn | Pro | Ala | Ala | Pro | Phe | Arg |
| | | | 100 | | | | | 105 | | | | | 110 | | |
| Asn | Pro | His | Ser | Gln | Gly | Arg | Ile | Arg | Glu | Leu | Phe | Ser | Gln | Ala | Glu |
| | | | 115 | | | | | 120 | | | | | 125 | | |
| Ser | His | Phe | Arg | Asn | Ser | Met | Pro | Ser | Phe | Ala | Ile | Ser | Gly | Tyr | Glu |
| | 130 | | | | | 135 | | | | | 140 | | | | |
| Val | Leu | Phe | Leu | Thr | Thr | Tyr | Ala | Gln | Ala | Ala | Asn | Thr | His | Leu | Phe |
| 145 | | | | | 150 | | | | | 155 | | | | | 160 |
| Leu | Leu | Lys | Asp | Ala | Gln | Ile | Tyr | Gly | Glu | Glu | Trp | Gly | Tyr | Glu | Lys |
| | | | | 165 | | | | | 170 | | | | | 175 | |
| Glu | Asp | Ile | Ala | Glu | Phe | Tyr | Lys | Arg | Gln | Leu | Lys | Leu | Thr | Gln | Glu |
| | | | 180 | | | | | 185 | | | | | 190 | | |
| Tyr | Thr | Asp | His | Cys | Val | Lys | Trp | Tyr | Asn | Val | Gly | Leu | Asp | Lys | Leu |
| | | | 195 | | | | | 200 | | | | | 205 | | |
| Arg | Gly | Ser | Ser | Tyr | Glu | Ser | Trp | Val | Asn | Phe | Asn | Arg | Tyr | Arg | Arg |
| | 210 | | | | | 215 | | | | | 220 | | | | |
| Glu | Met | Thr | Leu | Thr | Val | Leu | Asp | Leu | Ile | Ala | Leu | Phe | Pro | Leu | Tyr |
| 225 | | | | | 230 | | | | | 235 | | | | | 240 |
| Asp | Val | Arg | Leu | Tyr | Pro | Lys | Glu | Val | Lys | Thr | Glu | Leu | Thr | Arg | Asp |
| | | | | 245 | | | | | 250 | | | | | 255 | |
| Val | Leu | Thr | Asp | Pro | Ile | Val | Gly | Val | Asn | Asn | Leu | Arg | Gly | Tyr | Gly |
| | | | 260 | | | | | 265 | | | | | 270 | | |
| Thr | Thr | Phe | Ser | Asn | Ile | Glu | Asn | Tyr | Ile | Arg | Lys | Pro | His | Leu | Phe |
| | | | 275 | | | | | 280 | | | | | 285 | | |
| Asp | Tyr | Leu | His | Arg | Ile | Gln | Phe | His | Thr | Arg | Phe | Gln | Pro | Gly | Tyr |
| | 290 | | | | | 295 | | | | | 300 | | | | |
| Tyr | Gly | Asn | Asp | Ser | Phe | Asn | Tyr | Trp | Ser | Gly | Asn | Tyr | Val | Ser | Thr |
| 305 | | | | | 310 | | | | | 315 | | | | | 320 |
| Arg | Pro | Ser | Ile | Gly | Ser | Asn | Asp | Ile | Ile | Thr | Ser | Pro | Phe | Tyr | Gly |
| | | | | 325 | | | | | 330 | | | | | 335 | |
| Asn | Lys | Ser | Ser | Glu | Pro | Val | Gln | Asn | Leu | Glu | Phe | Asn | Gly | Glu | Lys |
| | | | 340 | | | | | 345 | | | | | 350 | | |
| Val | Tyr | Arg | Ala | Val | Ala | Asn | Thr | Asn | Leu | Ala | Val | Trp | Pro | Ser | Ala |
| | | | 355 | | | | | 360 | | | | | 365 | | |
| Val | Tyr | Ser | Gly | Val | Thr | Lys | Val | Glu | Phe | Ser | Gln | Tyr | Asn | Asp | Gln |
| | 370 | | | | | 375 | | | | | 380 | | | | |

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
            405                 410                 415

Glu Pro Leu Glu Lys Gly Tyr Ser His Gln Leu Asn Tyr Val Met Cys
        420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
            485                 490                 495

Asn Gly Ser Ala Ala Thr Ile Tyr Val Thr Pro Asp Val Ser Tyr Ser
        500                 505                 510

Gln Lys Tyr Arg Ala Arg Ile His Tyr Ala Ser Thr Ser Gln Ile Thr
        515                 520                 525

Phe Thr Leu Ser Leu Asp Gly Ala Pro Phe Asn Gln Tyr Tyr Phe Asp
    530                 535                 540

Lys Thr Ile Asn Lys Gly Asp Thr Leu Thr Tyr Asn Ser Phe Asn Leu
545                 550                 555                 560

Ala Ser Phe Ser Thr Pro Phe Glu Leu Ser Gly Asn Asn Leu Gln Ile
            565                 570                 575

Gly Val Thr Gly Leu Ser Ala Gly Asp Lys Val Tyr Ile Asp Lys Ile
        580                 585                 590

Glu Phe Ile Pro Val Asn
        595

<210> SEQ ID NO 71
<211> LENGTH: 1947
<212> TYPE: DNA
<213> ORGANISM: Artificial Sequence
<220> FEATURE:
<223> OTHER INFORMATION: mocry1Ab coding sequence

<400> SEQUENCE: 71
atggacaaca accccaacat caacgagtgc atcccctaca actgcctgag caaccccgag      60
gtggaggtgc tgggcggcga gcgcatcgag accggctaca ccccatcga catcagcctg     120 agcctgaccc agttcctgct gagcgagttc gtgcccggcg ccggcttcgt gctgggcctg     180
gtggacatca tctggggcat cttcggcccc agccagtggg acgccttcct ggtgcagatc     240
gagcagttga taaaccaacg catagaggaa ttcgcccgca accaggccat cagccgcctg     300
gagggcctga gcaacctgta ccaaatctac gccgagagct ccgcgagtg ggaggccgac     360 cccaccaacc ccgccctgcg cgaggagatg cgcatccagt tcaacgacat gaacagcgcc     420
ctgaccaccg ccatccccct gttcgccgtg cagaactacc aggtgcccct gctgagcgtg     480
tacgtgcagg ccgccaacct gcacctgagc gtgctgcgcg acgtcagcgt gttcggccag     540
cgctggggct cgacgccgc caccatcaac agccgctaca acgacctgac cgcctgatc      600 ggcaactaca ccgaccacgc cgtgcgctgg tacaacaccg gcctggagcg cgtgtgggt     660 cccgacagcc gcgactggat caggtacaac cagttccgcc gcgagctgac cctgaccgtg     720
ctggacatcg tgagcctgtt ccccaactac gacagccgca cctaccccat ccgcaccgtg     780
agccagctga cccgcgagat ttacaccaac cccgtgctgg agaacttcga cggcagcttc     840

```
cgcggcagcg cccagggcat cgagggcagc atccgcagcc cccacctgat ggacatcctg    900
aacagcatca ccatctacac cgacgccac cgcggcgagt actactggag cggccaccag    960
atcatggcca gccccgtcgg cttcagcggc cccgagttca ccttcccct gtacggcacc   1020 atgggcaacg ctgcacctca gcagcgcatc gtggcacagc tgggccaggg agtgtaccgc   1080
accctgagca gcaccctgta ccgtcgacct ttcaacatcg gcatcaacaa ccagcagctg   1140
agcgtgctgg acggcaccga gttcgcctac ggcaccagca gcaacctgcc cagcgccgtg   1200
taccgcaaga gcggcaccgt ggacagcctg gacgagatcc cccctcagaa caacaacgtg   1260
ccacctcgac agggcttcag ccaccgtctg agccacgtga gcatgttccg cagtggcttc   1320
agcaacagca gcgtgagcat catccgtgca cctatgttca gctggattca ccgcagtgcc   1380
gagttcaaca acatcatccc cagcagccag atcacccaga tcccctgac aagagcacc    1440 aacctgggca gcggcaccag cgtggtgaag ggccccggct tcaccggcgg cgacatcctg   1500
cgccgcacca gccccggcca gatcagcacc ctgcgcgtga acatcaccgc cccccctgagc   1560 cagcgctacc gcgtccgcat ccgctacgcc agcaccacca acctgcagtt ccacaccagc   1620
atcgacggcc gccccatcaa ccagggcaac ttcagcgcca ccatgagcag cggcagcaac   1680
ctgcagagcg gcagcttccg caccgtgggc ttcaccaccc ccttcaactt cagcaacggc   1740
agcagcgtgt tcaccctgag cgcccacgtg ttcaacagcg gcaacgaggt gtacatcgac   1800
cgcatcgagt tcgtgcccgc cgaggtgacc ttcgaggccg agtacgacct ggagagggct   1860
cagaaggccg tgaacgagct gttcaccagc agcaaccaga tcggcctgaa gaccgacgtg   1920
accgactacc acatcgatca ggtgtag                                       1947

<210> SEQ ID NO 72
<211> LENGTH: 648
<212> TYPE: PRT
<213> ORGANISM: Bacillus thuringiensis
<220> FEATURE:
<223> OTHER INFORMATION: Cry1Ab protein

<400> SEQUENCE: 72

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160
```

-continued

```
Tyr Val Gln Ala Ala Asn Leu His Leu Ser Val Leu Arg Asp Val Ser
            165                 170                 175

Val Phe Gly Gln Arg Trp Gly Phe Asp Ala Ala Thr Ile Asn Ser Arg
        180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
        210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
            245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
        290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
        450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
            485                 490                 495

Gly Asp Ile Leu Arg Arg Thr Ser Pro Gly Gln Ile Ser Thr Leu Arg
        500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
            565                 570                 575

Phe Ser Asn Gly Ser Ser Val Phe Thr Leu Ser Ala His Val Phe Asn
```

```
            580              585              590
Ser Gly Asn Glu Val Tyr Ile Asp Arg Ile Glu Phe Val Pro Ala Glu
                     595              600              605

Val Thr Phe Glu Ala Glu Tyr Asp Leu Glu Arg Ala Gln Lys Ala Val
            610              615              620

Asn Glu Leu Phe Thr Ser Ser Asn Gln Ile Gly Leu Lys Thr Asp Val
625              630              635              640

Thr Asp Tyr His Ile Asp Gln Val
                645
```

<210> SEQ ID NO 73
<211> LENGTH: 1971
<212> TYPE: DNA
<213> ORGANISM: Artificial Sequence
<220> FEATURE:
<223> OTHER INFORMATION: mocry1Ba coding sequence

<400> SEQUENCE: 73

| | |
|---|---:|
| atgaccagca accgcaagaa cgagaacgag atcatcaacg ccgtgagcaa ccacagcgcc | 60 |
| cagatggacc tgctgcccga cgcccgcatc gaggacagcc tgtgcatcgc cgagggcaac | 120 |
| aacatcgacc ccttcgtgag cgctagcacc gtgcagaccg tatcaacat cgctggccgc | 180 |
| atcctgggcg tgctgggcgt gcccttcgcc ggccagctgg ctagcttcta cagcttcctg | 240 |
| gtcggtgagc tgtggccacg cggccgcgac cagtgggaaa tcttcctgga gcacgtggag | 300 |
| cagctgatca ccagcagat caccgagaac gcccgcaaca ccgctcttgc ccgcctgcag | 360 |
| ggtctgggcg acagcttccg cgcctaccag cagagcctgg aggactggct ggagaaccgc | 420 |
| gacgacgccc gcacccgcag cgtgctgtac acccagtaca tcgccctgga gctggacttc | 480 |
| ctgaacgcca tgcccctgtt cgccattcga accaggagg tgcccctgct gatggtgtac | 540 |
| gcccaggccg ccaacctgca cctgctgctg ctgcgcgacg ccagcctgtt cggcagcgag | 600 |
| ttcggcctga ccagcagga gatccagcgg tactacgagc gccaggtgga gcgcacccgc | 660 |
| gactacagcg actactgcgt ggagtggtac aacaccggcc tgaacagctt aaggggcacc | 720 |
| aacgccgcca gctgggtgcg ctacaaccag ttccgccgcg acctgaccct gggcgtgctg | 780 |
| gacctggtgg ccctgttccc cagctacgac accgcacct accccatcaa caccagcgcc | 840 |
| cagctgaccc gcgaggtgta caccgacgcc atcggcgcca ccggcgtgaa catgccagc | 900 |
| atgaactggt acaacaacaa cgccccagc ttcagcgcca tcgaggccgc cgccatccgc | 960 |
| agcccccacc tgctggactt cctggagcag ctgaccatct tcagtgccag cagccgctgg | 1020 |
| agcaacaccc gccacatgac ctactggcgc ggccacacca tccagtctag acccatcggc | 1080 |
| ggcggcctga acaccagcac ccacggcgcc accaacacca gcatcaaccc cgtgaccctg | 1140 |
| cgcttcgcct cccgagacgt ctaccgcacc gagagctacg ccggcgtgct gctgtggggc | 1200 |
| atctacctgg agcccatcca tggcgtgccc accgtgcgct tcaacttcac caaccccag | 1260 |
| aacatcagcg accgcggcac cgccaactac agccagccct acgagagccc cgggttgcag | 1320 |
| ctgaaggaca gcgagaccga gctgccccc gagaccaccg agcgcccaa ctacgagagc | 1380 |
| tacagccacc gcctgagcca catcggcatc atcttgcaga gcgcgtgaa cgtgcccgtg | 1440 |
| tacagctgga cccaccgcag cgccgaccgc accaacacca tcggccccaa ccgcatcacc | 1500 |
| cagatcccca tggtgaaggc cagcgagctg cccagggca ccaccgtggt tcgcggcccc | 1560 |
| ggcttcaccg gagcgacat cctgcgacgc accaacaccg cggcttcgg ccccatccgc | 1620 |
| gtgaccgtga acggcccct gacccagcgc taccgcatcg gcttccgcta cgccagcacc | 1680 |

```
gtggacttcg acttcttcgt gagccgcggc ggcaccaccg tgaacaactt ccgcttcctg   1740
cgcaccatga acagcggcga cgagctgaag tacggcaact tcgtgcgccg cgccttcacc   1800
accccctcca ccttcaccca gatccaggac atcatccgca ccagcatcca gggcctgagc   1860
ggcaacggcg aggtgtacat cgacaagatc gagatcatcc ccgtgaccgc caccttcgag   1920
gccgagtacg acctagagcg cgcccaggag gccgtgaacg ccctgttcta g            1971
```

<210> SEQ ID NO 74
<211> LENGTH: 656
<212> TYPE: PRT
<213> ORGANISM: Bacillus thuringiensis
<220> FEATURE:
<223> OTHER INFORMATION: Cry1B protein

<400> SEQUENCE: 74

```
Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
```

```
                305                 310                 315                 320
Ser Pro His Leu Leu Asp Phe Leu Glu Gln Leu Thr Ile Phe Ser Ala
                    325                 330                 335
Ser Ser Arg Trp Ser Asn Thr Arg His Met Thr Tyr Trp Arg Gly His
                340                 345                 350
Thr Ile Gln Ser Arg Pro Ile Gly Gly Leu Asn Thr Ser Thr His
            355                 360                 365
Gly Ala Thr Asn Thr Ser Ile Asn Pro Val Thr Leu Arg Phe Ala Ser
370                 375                 380
Arg Asp Val Tyr Arg Thr Glu Ser Tyr Ala Gly Val Leu Leu Trp Gly
385                 390                 395                 400
Ile Tyr Leu Glu Pro Ile His Gly Val Pro Thr Val Arg Phe Asn Phe
                405                 410                 415
Thr Asn Pro Gln Asn Ile Ser Asp Arg Gly Thr Ala Asn Tyr Ser Gln
                420                 425                 430
Pro Tyr Glu Ser Pro Gly Leu Gln Leu Lys Asp Ser Glu Thr Glu Leu
            435                 440                 445
Pro Pro Glu Thr Thr Glu Arg Pro Asn Tyr Glu Ser Tyr Ser His Arg
450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Met Val Lys Ala Ser Glu Leu Pro Gln
                500                 505                 510
Gly Thr Thr Val Val Arg Gly Pro Gly Phe Thr Gly Gly Asp Ile Leu
            515                 520                 525
Arg Arg Thr Asn Thr Gly Gly Phe Gly Pro Ile Arg Val Thr Val Asn
545                 530                 535                 540
Gly Pro Leu Thr Gln Arg Tyr Arg Ile Gly Phe Arg Tyr Ala Ser Thr
545                 550                 555                 560
Val Asp Phe Asp Phe Phe Val Ser Arg Gly Gly Thr Thr Val Asn Asn
                565                 570                 575
Phe Arg Phe Leu Arg Thr Met Asn Ser Gly Asp Glu Leu Lys Tyr Gly
                580                 585                 590
Asn Phe Val Arg Arg Ala Phe Thr Thr Pro Phe Thr Phe Thr Gln Ile
                595                 600                 605
Gln Asp Ile Ile Arg Thr Ser Ile Gln Gly Leu Ser Gly Asn Gly Glu
            610                 615                 620
Val Tyr Ile Asp Lys Ile Glu Ile Ile Pro Val Thr Ala Thr Phe Glu
625                 630                 635                 640
Ala Glu Tyr Asp Leu Glu Arg Ala Gln Glu Ala Val Asn Ala Leu Phe
                    645                 650                 655

<210> SEQ ID NO 75
<211> LENGTH: 1950
<212> TYPE: DNA
<213> ORGANISM: Artificial Sequence
<220> FEATURE:
<223> OTHER INFORMATION: mocry1Fa coding sequence

<400> SEQUENCE: 75
atggagaaca acatccagaa ccagtgcgtg ccgtacaact gcctcaacaa cccggaggtg      60
gagatcctca cgaggagcg ctccaccggc cgcctcccgc tcgacatctc cctctcccctc    120
```

```
acccgcttcc tcctctccga gttcgtgccg ggcgtgggcg tggccttcgg cctcttcgac    180
ctcatctggg gcttcatcac cccgtccgac tggtccctct cctcctcca gatcgagcag    240
ctcatcgagc agcgcatcga gaccctggag cgcaaccgcg ccatcaccac cctccgcggc    300
ctcgccgact cctacgaaat ctacatcgag gccctccgcg agtgggaggc caacccgaac    360
aacgcccagc tccgcgagga cgtgcgcatc cgcttcgcca caccgacga cgccctcatc     420
accgccatca caacttcac cctcacctcc ttcgagatcc cgctcctctc cgtgtacgtg     480
caggccgcca acctccacct ctccctcctc cgcgacgccg tgtccttcgg ccagggctgg    540
ggcctcgaca tcgccaccgt gaacaaccac tacaaccgcc tcatcaacct catccaccgc    600
tacaccaagc actgcctcga cacctacaac cagggcctgg agaacctccg cggcaccaac    660
acccgccagt gggcccgctt caaccagttc cgccgcgacc tcaccctcac cgtgctcgac    720
atcgtggccc tcttcccgaa ctacgacgtg cgcacctacc cgatccagac ctcctcccag    780
ctcacccgcg aaatctacac ctcctccgtg atcgaggact cccggtgtc cgccaacatc    840
ccgaacggct tcaaccgcgc cgagttcggc gtgcgcccgc gcacctcat ggacttcatg     900
aactccctct tcgtgaccgc cgagaccgtg cgctcccaga ccgtgtgggg cggccacctc   960
gtgtcctccc gcaacaccgc cggcaaccgc atcaacttcc gtcctacgg cgtgttcaac    1020
ccgggcggcg ccatctggat cgccgacgag gacccgcgcc cgttctaccg caccctctcc    1080
gacccggtgt tcgtgcgcgg cggcttcggc aacccgcact acgtgctcgg cctccgcggc    1140
gtggccttcc agcagaccgg caccaaccac acccgcacct tccgcaactc cggcaccatc    1200
gactccctcg acgagatccc gccgcaggac aactccggcg ccccgtggaa cgactactcc    1260
cacgtgctca ccacgtgac cttcgtgcgc tggccgggcg agatatccgg ctccgactcc    1320
tggcgtgcac cgatgttctc ctggaccac cgctccgcca cccgaccaa caccatcgac     1380
ccggagcgca tcacccagat cccgctcgtg aaggcccaca ccctccagtc cggcaccacc   1440
gtggtgcgcg gccgggcctt caccggcggc gacatcctcc gccgcacctc cggcggcccg    1500
ttcgcctaca ccatcgtgaa catcaacggc cagctcccgc agcgctaccg cgcccgcatc    1560
cgctacgcct ccaccaccaa cctccgcatc tacgtgaccg tggccggcga gcgcatcttc   1620
gccggccagt tcaacaagac catggacacc ggcgaccgc tcaccttcca gtccttctcc    1680
tacgccacca tcaacaccgc cttcaccttc ccgatgtccc agtcctcctt caccgtgggc    1740
gccgacacct tctcctccgg caacgaggtg tacatcgacc gcttcgagct gatcccggtg    1800
accgccacct tcgaggccga gtacgacctg gagcgcgccc agaaggccgt gaacgccctc    1860
ttcacctcca tcaaccagat cggcatcaag accgacgtga ccgactacca catcgaccag    1920
gtgtccaacc tcgtggactg cttaagctag                                     1950
```

<210> SEQ ID NO 76
<211> LENGTH: 649
<212> TYPE: PRT
<213> ORGANISM: Bacillus thguringiensis
<220> FEATURE:
<223> OTHER INFORMATION: Cry1F protein

<400> SEQUENCE: 76

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe

```
            35                  40                  45
Val Pro Gly Val Gly Val Ala Phe Gly Leu Phe Asp Leu Ile Trp Gly
 50                  55                  60

Phe Ile Thr Pro Ser Asp Trp Ser Leu Phe Leu Gln Ile Glu Gln
65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
                100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Ala Leu Ile Thr Ala Ile Asn
            130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
                180                 185                 190

Arg Leu Ile Asn Leu Ile His Arg Tyr Thr Lys His Cys Leu Asp Thr
            195                 200                 205

Tyr Asn Gln Gly Leu Glu Asn Leu Arg Gly Thr Asn Thr Arg Gln Trp
210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
            275                 280                 285

Phe Gly Val Arg Pro Pro His Leu Met Asp Phe Met Asn Ser Leu Phe
290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
                340                 345                 350

Arg Pro Phe Tyr Arg Thr Leu Ser Asp Pro Val Phe Val Arg Gly Gly
            355                 360                 365

Phe Gly Asn Pro His Tyr Val Leu Gly Leu Arg Gly Val Ala Phe Gln
            370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
                420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
            450                 455                 460
```

```
Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605

Asp Leu Glu Arg Ala Gln Lys Ala Val Asn Ala Leu Phe Thr Ser Ile
    610                 615                 620

Asn Gln Ile Gly Ile Lys Thr Asp Val Thr Asp Tyr His Ile Asp Gln
625                 630                 635                 640

Val Ser Asn Leu Val Asp Cys Leu Ser
                645
```

<210> SEQ ID NO 77
<211> LENGTH: 3469
<212> TYPE: DNA
<213> ORGANISM: Bacillus thuringiensis
<220> FEATURE:
<221> NAME/KEY: misc_feature
<222> LOCATION: (1)..(3469)
<223> OTHER INFORMATION: cry8Aa coding sequence

<400> SEQUENCE: 77

```
atgagtccaa ataatcaaaa tgaatatgaa attatagatg cgacaccttc tacatctgta      60
tccagtgatt ctaacagata cccttttgcg aatgagccaa cagatgcgtt acaaaatatg     120
aattataaag attatctgaa aatgtctggg ggagagaatc ctgaattatt tggaaatccg     180
gagacgttta ttagttcatc cacgattcaa actggaattg gcattgttgg tcgaatacta     240
ggagctttag ggttccatt tgctagtcag atagctagtt tctatagttt cattgttggt      300
caattatggc cgtcaaagag cgtagatata tggggagaaa ttatggaacg agtggaagaa     360
ctcgttgatc aaaaaataga aaaatatgta aaagataagg ctcttgctga attaaaaggg     420
ctaggaaatg ctttggatgt atatcagcag tcacttgaag attggctgga aaatcgcaat     480
gatgcaagaa ctagaagtgt tgtttctaat caatttatag ctttagatct taactttgtt     540
agttcaattc catcttttgc agtatccgga cacgaagtac tattattagc agtatatgca     600
caggctgtga acctacattt attgttatta agagatgctt ctatttttgg agaagagtgg     660
ggatttacac caggtgaaat ttctagattt tataatcgtc aagtgcaact taccgctgaa     720
tattcagact attgtgtaaa gtggtataaa atcggcttag ataaattgaa aggtaccact     780
tctaaaagtt ggctgaatta tcatcagttc cgtagagaga tgacattact ggtattagat     840
ttggtggcgt tatttccaaa ctatgacaca catatgtatc caatcgaaac aacagctcaa     900
```

```
cttacacggg atgtgtatac agatccgata gcatttaaca tagtgacaag tactggattc    960
tgcaacccct tggtcaaccca cagtggtatt cttttttatg aagttgaaaa caacgtaatt   1020
cgtccgccac acttgtttga tatactcagc tcagtagaaa ttaatacaag tagaggggt    1080
attacgttaa ataatgatgc atatataaac tactggtcag gacataccct aaaatatcgt   1140
agaacagctg attcgaccgt aacatacaca gctaattacg gtcgaatcac ttcagaaaag   1200
aattcatttg cacttgagga tagggatatt tttgaaatta attcaactgt ggcaaaccta   1260
gctaattact accaaaaggc atatggtgtg ccgggatctt ggttccatat ggtaaaaagg   1320
ggaacctcat caacaacagc gtatttatat tcaaaaacac atacagctct ccaagggtgt   1380
acacaggttt atgaatcaag tgatgaaata cctctagata gaactgtacc ggtagctgaa   1440
agctatagtc atagattatc tcatattacc tcccattctt tctctaaaaa tgggagtgca   1500
tactatggga gtttccctgt atttgtttgg acacatacta gtgcggattt aaataataca   1560
atatattcag ataaaatcac tcaaattcca gcggtaaagg gagacatgtt atatctaggg   1620
ggttccgtag tacagggtcc tggatttaca ggaggagata tattaaaaag aaccaatcct   1680
agcatattag ggacctttgc ggttacagta atgggtcgt tatcacaaag atatcgtgta    1740
agaattcgct atgcctctac aacagatttt gaatttactc tataccttgg cgacacaata   1800
gaaaaaaata gatttaacaa aactatggat aatggggcat ctttaacgta tgaaacattt   1860
aaaattcgcaa gtttcattac tgatttccaa ttcagagaaa cacaagataa aatactccta   1920
tccatgggtg attttagctc cggtcaagaa gtttatatag accgaatcga attcatccca   1980
gtagatgaga catatgaggc ggaacaagat ttagaagcgg cgaagaaagc agtgaatgcc   2040
ttgtttacga atacaaaaga tggcttacga ccaggtgtaa cggattatga agtaaatcaa   2100
gcggcaaact tagtggaatg cctatcggat gatttatatc caaatgaaaa acgattgtta   2160
tttgatgcgg tgagagaggc aaaacgcctc agtggggcac gtaacttact acaagatcca   2220
gatttccaag agataaacgg agaaaatgga tgggcggcaa gtacgggaat tgagattgta   2280
gaagggatg ctgtatttaa aggacgttat ctacgcctac caggtgcacg agaaattgat    2340
acggaaacgt atccaacgta tctgtatcaa aaagtagagg aaggtgtatt aaaaccatac   2400
acaagatata gactgagagg gtttgtggga gtagtcaag gattagaaat ttatacgata    2460
cgtcaccaaa cgaatcgaat tgtaaagaat gtaccagatg atttattgcc agatgtatct   2520
cctgtaaaact ctgatggcag tatcaatcga tgcagcgaac aaaagtatgt gaatagccgt   2580
ttagaaggag aaaaccgttc tggtgatgca catgagttct cgctccctat cgatatagga   2640
gagctggatt acaatgaaaa tgcaggaata tgggttggat ttaagattac ggacccagag   2700
ggatacgcaa cacttggaaa tcttgaatta gtcgaagagg gacctttgtc aggagacgca   2760
ttagagcgct tgcaaagaga agaacaacag tggaagattc aaatgacaag aagacgtgaa   2820
gagacagata gaagatacat ggcatcgaaa caagcggtag atcgtttata tgccgattat   2880
caggatcaac aactgaatcc tgatgtagag attacagatc ttactgcggc tcaagatctg   2940
atacagtcca ttccttacgt atataacgaa atgttcccag aaataccagg gatgaactat   3000
acgaagttta cagaattaac agatcgactc caacaagcgt ggaatttgta tgatcagcga   3060
aatgccatac caaatggtga ttttcgaaat gggttaagta attggaatgc aacgcctggc   3120
gtagaagtac aacaaatcaa tcatacatct gtccttgtga ttccaaactg ggatgaacaa   3180
gtttcacaac agtttacagt tcaaccgaat caaagatatg tattacgagt tactgcaaga   3240
aaagaagggg taggaaatgg atatgtaagt attcgtgatg gtggaaatca atcagaaacg   3300
```

-continued

```
cttactttta gtgcaagcga ttatgataca aatggtgtgt ataatgacca aaccggctat    3360
atcacaaaaa cagtgacatt catcccgtat acagatcaaa tgtggattga aataagtgaa    3420
acagaaggta cgttctatat agaaagtgta gaattgattg tagacgtag                3469
```

<210> SEQ ID NO 78
<211> LENGTH: 1156
<212> TYPE: PRT
<213> ORGANISM: Bacillus thuringiensis
<220> FEATURE:
<221> NAME/KEY: MISC_FEATURE
<222> LOCATION: (1)..(1156)
<223> OTHER INFORMATION: Cry8Aa protein

<400> SEQUENCE: 78

```
Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
            20                  25                  30

Pro Thr Asp Ala Leu Gln Asn Met Asn Tyr Lys Asp Tyr Leu Lys Met
        35                  40                  45

Ser Gly Gly Glu Asn Pro Glu Leu Phe Gly Asn Pro Glu Thr Phe Ile
    50                  55                  60

Ser Ser Ser Thr Ile Gln Thr Gly Ile Gly Ile Val Gly Arg Ile Leu
65                  70                  75                  80

Gly Ala Leu Gly Val Pro Phe Ala Ser Gln Ile Ala Ser Phe Tyr Ser
                85                  90                  95

Phe Ile Val Gly Gln Leu Trp Pro Ser Lys Ser Val Asp Ile Trp Gly
            100                 105                 110

Glu Ile Met Glu Arg Val Glu Glu Leu Val Asp Gln Lys Ile Glu Lys
        115                 120                 125

Tyr Val Lys Asp Lys Ala Leu Ala Glu Leu Lys Gly Leu Gly Asn Ala
    130                 135                 140

Leu Asp Val Tyr Gln Gln Ser Leu Glu Asp Trp Leu Glu Asn Arg Asn
145                 150                 155                 160

Asp Ala Arg Thr Arg Ser Val Val Ser Asn Gln Phe Ile Ala Leu Asp
                165                 170                 175

Leu Asn Phe Val Ser Ser Ile Pro Ser Phe Ala Val Ser Gly His Glu
            180                 185                 190

Val Leu Leu Leu Ala Val Tyr Ala Gln Ala Val Asn Leu His Leu Leu
        195                 200                 205

Leu Leu Arg Asp Ala Ser Ile Phe Gly Glu Glu Trp Gly Phe Thr Pro
    210                 215                 220

Gly Glu Ile Ser Arg Phe Tyr Asn Arg Gln Val Gln Leu Thr Ala Glu
225                 230                 235                 240

Tyr Ser Asp Tyr Cys Val Lys Trp Tyr Lys Ile Gly Leu Asp Lys Leu
                245                 250                 255

Lys Gly Thr Thr Ser Lys Ser Trp Leu Asn Tyr His Gln Phe Arg Arg
            260                 265                 270

Glu Met Thr Leu Leu Val Leu Asp Leu Val Ala Leu Phe Pro Asn Tyr
        275                 280                 285

Asp Thr His Met Tyr Pro Ile Glu Thr Thr Ala Gln Leu Thr Arg Asp
    290                 295                 300

Val Tyr Thr Asp Pro Ile Ala Phe Asn Ile Val Thr Ser Thr Gly Phe
305                 310                 315                 320
```

```
Cys Asn Pro Trp Ser Thr His Ser Gly Ile Leu Phe Tyr Glu Val Glu
            325                 330                 335

Asn Asn Val Ile Arg Pro Pro His Leu Phe Asp Ile Leu Ser Ser Val
            340                 345                 350

Glu Ile Asn Thr Ser Arg Gly Gly Ile Thr Leu Asn Asn Asp Ala Tyr
            355                 360                 365

Ile Asn Tyr Trp Ser Gly His Thr Leu Lys Tyr Arg Arg Thr Ala Asp
            370                 375                 380

Ser Thr Val Thr Tyr Thr Ala Asn Tyr Gly Arg Ile Thr Ser Glu Lys
385                 390                 395                 400

Asn Ser Phe Ala Leu Glu Asp Arg Asp Ile Phe Glu Ile Asn Ser Thr
                405                 410                 415

Val Ala Asn Leu Ala Asn Tyr Tyr Gln Lys Ala Tyr Gly Val Pro Gly
                420                 425                 430

Ser Trp Phe His Met Val Lys Arg Gly Thr Ser Ser Thr Thr Ala Tyr
                435                 440                 445

Leu Tyr Ser Lys Thr His Thr Ala Leu Gln Gly Cys Thr Gln Val Tyr
    450                 455                 460

Glu Ser Ser Asp Glu Ile Pro Leu Asp Arg Thr Val Pro Val Ala Glu
465                 470                 475                 480

Ser Tyr Ser His Arg Leu Ser His Ile Thr Ser His Ser Phe Ser Lys
                485                 490                 495

Asn Gly Ser Ala Tyr Tyr Gly Ser Phe Pro Val Phe Val Trp Thr His
                500                 505                 510

Thr Ser Ala Asp Leu Asn Asn Thr Ile Tyr Ser Asp Lys Ile Thr Gln
                515                 520                 525

Ile Pro Ala Val Lys Gly Asp Met Leu Tyr Leu Gly Gly Ser Val Val
    530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
                580                 585                 590

Thr Leu Tyr Leu Gly Asp Thr Ile Glu Lys Asn Arg Phe Asn Lys Thr
    595                 600                 605

Met Asp Asn Gly Ala Ser Leu Thr Tyr Glu Thr Phe Lys Phe Ala Ser
    610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
                660                 665                 670

Ala Ala Lys Lys Ala Val Asn Ala Leu Phe Thr Asn Thr Lys Asp Gly
                675                 680                 685

Leu Arg Pro Gly Val Thr Asp Tyr Glu Val Asn Gln Ala Ala Asn Leu
    690                 695                 700

Val Glu Cys Leu Ser Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gly Trp Ala
```

```
                740                 745                 750
Ala Ser Thr Gly Ile Glu Ile Val Glu Gly Asp Ala Val Phe Lys Gly
            755                 760                 765

Arg Tyr Leu Arg Leu Pro Gly Ala Arg Glu Ile Asp Thr Glu Thr Tyr
        770                 775                 780

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Gln Gly Leu Glu
                805                 810                 815

Ile Tyr Thr Ile Arg His Gln Thr Asn Arg Ile Val Lys Asn Val Pro
            820                 825                 830

Asp Asp Leu Leu Pro Asp Val Ser Pro Val Asn Ser Asp Gly Ser Ile
            835                 840                 845

Asn Arg Cys Ser Glu Gln Lys Tyr Val Asn Ser Arg Leu Glu Gly Glu
        850                 855                 860

Asn Arg Ser Gly Asp Ala His Glu Phe Ser Leu Pro Ile Asp Ile Gly
865                 870                 875                 880

Glu Leu Asp Tyr Asn Glu Asn Ala Gly Ile Trp Val Gly Phe Lys Ile
                885                 890                 895

Thr Asp Pro Glu Gly Tyr Ala Thr Leu Gly Asn Leu Glu Leu Val Glu
            900                 905                 910

Glu Gly Pro Leu Ser Gly Asp Ala Leu Glu Arg Leu Gln Arg Glu Glu
            915                 920                 925

Gln Gln Trp Lys Ile Gln Met Thr Arg Arg Glu Glu Thr Asp Arg
        930                 935                 940

Arg Tyr Met Ala Ser Lys Gln Ala Val Asp Arg Leu Tyr Ala Asp Tyr
945                 950                 955                 960

Gln Asp Gln Gln Leu Asn Pro Asp Val Glu Ile Thr Asp Leu Thr Ala
                965                 970                 975

Ala Gln Asp Leu Ile Gln Ser Ile Pro Tyr Val Tyr Asn Glu Met Phe
            980                 985                 990

Pro Glu Ile Pro Gly Met Asn Tyr Thr Lys Phe Thr Glu Leu Thr Asp
            995                 1000                1005

Arg Leu Gln Gln Ala Trp Asn Leu Tyr Asp Gln Arg Asn Ala Ile
        1010                1015                1020

Pro Asn Gly Asp Phe Arg Asn Gly Leu Ser Asn Trp Asn Ala Thr
    1025                1030                1035

Pro Gly Val Glu Val Gln Gln Ile Asn His Thr Ser Val Leu Val
    1040                1045                1050

Ile Pro Asn Trp Asp Glu Gln Val Ser Gln Gln Phe Thr Val Gln
    1055                1060                1065

Pro Asn Gln Arg Tyr Val Leu Arg Val Thr Ala Arg Lys Glu Gly
    1070                1075                1080

Val Gly Asn Gly Tyr Val Ser Ile Arg Asp Gly Gly Asn Gln Ser
    1085                1090                1095

Glu Thr Leu Thr Phe Ser Ala Ser Asp Tyr Asp Thr Asn Gly Val
    1100                1105                1110

Tyr Asn Asp Gln Thr Gly Tyr Ile Thr Lys Thr Val Thr Phe Ile
    1115                1120                1125

Pro Tyr Thr Asp Gln Met Trp Ile Glu Ile Ser Glu Thr Glu Gly
    1130                1135                1140

Thr Phe Tyr Ile Glu Ser Val Glu Leu Ile Val Asp Val
    1145                1150                1155
```

<210> SEQ ID NO 79
<211> LENGTH: 3537
<212> TYPE: DNA
<213> ORGANISM: Bacillus thuringiensis
<220> FEATURE:
<221> NAME/KEY: misc_feature
<222> LOCATION: (1)..(3537)
<223> OTHER INFORMATION: cry1Ac coding sequence

<400> SEQUENCE: 79

```
atggataaca atccgaacat caatgaatgc attccttata attgtttaag taaccctgaa     60
gtagaagtat taggtggaga aagaatagaa actggttaca ccccaatcga tatttccttg    120
tcgctaacgc aatttctttt gagtgaattt gttcccggtg ctggatttgt gttaggacta    180
gttgatataa tatggggaat ttttggtccc tctcaatggg acgcatttct tgtacaaatt    240
gaacagttaa ttaaccaaag aatagaagaa ttcgctagga accaagccat ttctagatta    300
gaaggactaa gcaatcttta tcaaatttac gcagaatctt ttagagagtg ggaagcagat    360
cctactaatc cagcattaag agaagagatg cgtattcaat tcaatgacat gaacagtgcc    420
cttacaaccg ctattcctct tttgcagtt caaaattatc aagttcctct tttatcagta    480
tatgttcaag ctgcaaattt acatttatca gttttgagag atgtttcagt gtttggacaa    540
aggtggggat ttgatgccgc gactatcaat agtcgttata atgatttaac taggcttatt    600
ggcaactata cagattatgc tgtacgctgg tacaatacgg gattagaacg tgtatgggga    660
ccggattcta gagattgggt aaggtataat caatttagaa gagaattaac actaactgta    720
ttagatatcg ttgctctgtt cccgaattat gatagtagaa gatatccaat tcgaacagtt    780
tcccaattaa caagagaaat ttatacaaac ccagtattag aaaattttga tggtagtttt    840
cgaggctcgg ctcagggcat agaaagaagt attaggagtc cacatttgat ggatatactt    900
aacagtataa ccatctatac ggatgctcat aggggttatt attattggtc agggcatcaa    960
ataatggctt ctcctgtagg gttttcgggg ccagaattca cttttccgct atatggaact   1020
atgggaaatg cagctccaca acaacgtatt gttgctcaac taggtcaggg cgtgtataga   1080
acattatcgt ccactttata tagaagacct tttaatatag ggataaataa tcaacaacta   1140
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attactcaaa tccctgcagt gaagggaaac   1440
tttcttttta atggttctgt aatttcagga ccaggattta ctggtgggga cttagttaga   1500
ttaaatagta gtggaaataa cattcagaat agagggtata ttgaagttcc aattcacttc   1560
ccatcgacat ctaccagata tcgagttcgt gtacggtatg cttctgtaac cccgattcac   1620
ctcaacgtta attggggtaa ttcatccatt ttttccaata cagtaccagc tacagctacg   1680
tcattagata atctacaatc aagtgatttt ggttattttg aaagtgccaa tgcttttaca   1740
tcttcattag gtaatatagt aggtgttaga aattttagtg ggactgcagg agtgataata   1800
gacagatttg aatttattcc agttactgca acactcgagg ctgaatataa tctggaaaga   1860
gcgcagaagg cggtgaatgc gctgtttacg tctacaaacc aactagggct aaaaaacaaat   1920
gtaacggatt atcatattga tcaagtgtcc aatttagtta cgtatttatc ggatgaattt   1980
```

-continued

```
tgtctggatg aaaagcgaga attgtccgag aaagtcaaac atgcgaagcg actcagtgat    2040
gaacgcaatt tactccaaga ttcaaatttc aaagacatta ataggcaacc agaacgtggg    2100
tggggcggaa gtacagggat taccatccaa ggaggggatg acgtatttaa agaaaattac    2160
gtcacactat caggtacctt tgatgagtgc tatccaacat atttgtatca aaaaatcgat    2220
gaatcaaaat taaaagcctt tacccgttat caattaagag ggtatatcga agatagtcaa    2280
gacttagaaa tctatttaat tcgctacaat gcaaaacatg aaacagtaaa tgtgccaggt    2340
acgggttcct tatggccgct ttcagcccaa agtccaatcg aaagtgtggg agagccgaat    2400
cgatgcgcgc cacaccttga atggaatcct gacttagatt gttcgtgtag ggatggagaa    2460
aagtgtgccc atcattcgca tcatttctcc ttagacattg atgtaggatg tacagactta    2520
aatgaggacc taggtgtatg ggtgatcttt aagattaaga cgcaagatgg gcacgcaaga    2580
ctagggaatc tagagtttct cgaagagaaa ccattagtag gagaagcgct agctcgtgtg    2640
aaaagagcgg agaaaaaatg gagagacaaa cgtgaaaaat tggaatggga aacaaatatc    2700
gtttataaag aggcaaaaga atctgtagat gctttatttg taaactctca atatgatcaa    2760
ttacaagcgg atacgaatat tgccatgatt catgcggcag ataaacgtgt tcatagcatt    2820
cgagaagctt atctgcctga gctgtctgtg attccgggtg tcaatgcggc tatttttgaa    2880
gaattagaag ggcgtatttt cactgcattc tccctatatg atgcgagaaa tgtcattaaa    2940
aatggtgatt ttaataatgg cttatcctgc tggaacgtga agggcatgt agatgtgaaa    3000 gaacaaaaca accaacgttc ggtccttgtt gttccggaat gggaagcaga agtgtcacaa    3060
gaagttcgtg tctgtccggg tcgtggctat atccttcgtg tcacagcgta caaggaggga    3120
tatggagaag gttgcgtaac cattcatgag atcgagaaca atacagacga actgaagttt    3180
agcaactgcg tagaagagga aatctatcca aataacacgg taacgtgtaa tgattatact    3240
gtaaatcaag aagaatacgg aggtgcgtac acttctcgta atcgaggata taacgaagct    3300
ccttccgtac cagctgatta tgcgtcagtc tatgaagaaa aatcgtatac agatggacga    3360
agagagaatc cttgtgaatt taacagaggg tatagggatt acacgccact accagttggt    3420
tatgtgacaa agaattaga atacttccca gaaaccgata aggtatggat tgagattgga    3480
gaaacggaag gaacatttat cgtggacagc gtggaattac tccttatgga ggaatag      3537
```

<210> SEQ ID NO 80
<211> LENGTH: 1178
<212> TYPE: PRT
<213> ORGANISM: Bacillus thuringiensis
<220> FEATURE:
<221> NAME/KEY: MISC_FEATURE
<222> LOCATION: (1)..(1178)
<223> OTHER INFORMATION: Cry1Ac protein

<400> SEQUENCE: 80

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80
```

-continued

```
Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
            370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
```

```
                500             505             510
Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
            610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
            645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
            690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
            770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
            805                 810                 815

Arg Asp Gly Glu Lys Cys Ala His His Ser His His Phe Ser Leu Asp
            820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
            850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
            885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925
```

```
Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
                980                 985                 990

Val Lys Gly His Val Asp Val Glu Glu Gln Asn Asn Gln Arg Ser Val
                995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

Asn Thr Asp Glu Leu Lys Phe Ser Asn Cys Val Glu Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 81
<211> LENGTH: 2160
<212> TYPE: DNA
<213> ORGANISM: Bacillus thuringiensis
<220> FEATURE:
<221> NAME/KEY: misc_feature
<222> LOCATION: (1)..(2160)
<223> OTHER INFORMATION: cry1Ia coding sequence

<400> SEQUENCE: 81
atgaaactaa agaatcaaga taagcatcaa agtttttcta gcaatgcgaa agtagataaa        60
atctctacgg attcactaaa aaatgaaaca gatatagaat acaaaacat taatcatgaa       120 gattgtttga aaatgtctga gtatgaaaat gtagagccgt tgttagtgc atcaacaatt       180 caaacaggta ttggtattgc gggtaaaata cttggtaccc taggcgttcc ttttgcagga       240
caagtagcta gtctttatag tttatcttta ggtgagctat ggcctaaggg gaaaaatcaa       300
tgggaaatct ttatggaaca tgtagaagag attattaatc aaaaaatatc aacttatgca       360
agaaataaag cacttacaga cttgaaagga ttaggagatg ccttagctgt ctaccatgat       420
tcgcttgaaa gttgggttgg aaatcgtaat aacacaaggg ctaggagtgt tgtcaagagc       480
```

```
caatatatcg cattagaatt gatgttcgtt cagaaactac cttcttttgc agtgtctgga      540
gaggaggtac cattattacc gatatatgcc caagctgcaa atttacattt gttgctatta      600
agagatgcat ctattttgg aaaagagtgg ggattatcat cttcagaaat ttcaacattt       660
tataaccgtc aagtcgaacg agcaggagat tattcctacc attgtgtgaa atggtatagc      720
acaggtctaa ataacttgag gggtacaaat gccgaaagtt gggtacgata taatcaattc      780
cgtagagaca tgactttaat ggtactagat ttagtggcac tatttccaag ctatgataca      840
caaatgtatc caattaaaac tacagcccaa cttacaagag aagtatatac agacgcaatt      900
gggacagtac atccgcatcc aagttttaca agtacgactt ggtataataa taatgcacct      960
tcgttctctg ccatagaggc tgctgttgtt cgaaacccgc atctactcga ttttctagaa     1020
caagttacaa tttacagctt attaagtcga tggagtaaca ctcagtatat gaatatgtgg     1080
ggaggacata aactagaatt ccgaacaata ggaggaacgt taaatatctc aacacaagga     1140
tctactaata cttctattaa tcctgtaaca ttaccgttca cttctcgaga cgtctatagg     1200
actgaatcat tggcagggct gaatctattt ttaactcaac tgttaatgg agtacctagg      1260 gttgattttc attggaaatt cgtcacacat ccgatcgcat ctgataattt ctattatcca     1320
gggtatgctg gaattgggac gcaattacag gattcagaaa atgaattacc acctgaagca     1380
acaggacagc caaattatga atcttatagt catagattat ctcatatagg actcatttca     1440
gcatcacatg tgaaagcatt ggtatattct tggacgcatc gtagtgcaga tcgtacaaat     1500
acaattgagc caaatagcat tacacaaata ccattagtaa aagctttcaa tctgtcttca     1560
ggtgccgctg tagtgagagg accaggattt acaggtgggg atatccttcg aagaacgaat     1620
actggtacat ttggggatat acgagtaaat attaatccac catttgcaca agatatcgc      1680 gtgaggattc gctatgcttc taccacagat ttacaattcc atacgtcaat taacggtaaa     1740
gctattaatc aaggtaattt ttcagcaact atgaatagag gagaggactt agactataaa     1800
acctttagaa ctgtaggctt taccactcca tttagctttt tagatgtaca aagtacattc     1860
acaataggtg cttggaactt ctcttcaggt aacgaagttt atatagatag aattgaattt     1920
gttccggtag aagtaacata tgaggcagaa tatgattttg aaaaagcgca agagaaggtt     1980
actgcactgt ttcatctac gaatccaaga ggattaaaaa cagatgtaaa ggattatcat     2040
attgaccagg tatcaaattt agtagagtct ctatcagatg aattctatct tgatgaaaag     2100
agagaattat tcgagatagt taaatacgcg aagcaactcc atattgagcg taacatgtag     2160
```

<210> SEQ ID NO 82
<211> LENGTH: 719
<212> TYPE: PRT
<213> ORGANISM: Bacillus thuringiensis
<220> FEATURE:
<221> NAME/KEY: MISC_FEATURE
<222> LOCATION: (1)..(719)
<223> OTHER INFORMATION: Cry1Ia protein

<400> SEQUENCE: 82

Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile

```
            50                  55                  60
Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
                     85                  90                  95

Gly Lys Asn Gln Trp Glu Ile Phe Met Glu His Val Glu Glu Ile Ile
                100                 105                 110

Asn Gln Lys Ile Ser Thr Tyr Ala Arg Asn Lys Ala Leu Thr Asp Leu
            115                 120                 125

Lys Gly Leu Gly Asp Ala Leu Ala Val Tyr His Asp Ser Leu Glu Ser
        130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
                180                 185                 190

Ala Asn Leu His Leu Leu Leu Arg Asp Ala Ser Ile Phe Gly Lys
            195                 200                 205

Glu Trp Gly Leu Ser Ser Ser Glu Ile Ser Thr Phe Tyr Asn Arg Gln
210                 215                 220

Val Glu Arg Ala Gly Asp Tyr Ser Tyr His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
                260                 265                 270

Ala Leu Phe Pro Ser Tyr Asp Thr Gln Met Tyr Pro Ile Lys Thr Thr
            275                 280                 285

Ala Gln Leu Thr Arg Glu Val Tyr Thr Asp Ala Ile Gly Thr Val His
        290                 295                 300

Pro His Pro Ser Phe Thr Ser Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
                340                 345                 350

Asn Thr Gln Tyr Met Asn Met Trp Gly Gly His Lys Leu Glu Phe Arg
            355                 360                 365

Thr Ile Gly Gly Thr Leu Asn Ile Ser Thr Gln Gly Ser Thr Asn Thr
        370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
                420                 425                 430

Ala Ser Asp Asn Phe Tyr Tyr Pro Gly Tyr Ala Gly Ile Gly Thr Gln
            435                 440                 445

Leu Gln Asp Ser Glu Asn Glu Leu Pro Pro Glu Ala Thr Gly Gln Pro
        450                 455                 460

Asn Tyr Glu Ser Tyr Ser His Arg Leu Ser His Ile Gly Leu Ile Ser
465                 470                 475                 480
```

```
Ala Ser His Val Lys Ala Leu Val Tyr Ser Trp Thr His Arg Ser Ala
            485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Arg Gly Pro
            515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
            595                 600                 605

Thr Pro Phe Ser Phe Leu Asp Val Gln Ser Thr Phe Thr Ile Gly Ala
            610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
            675                 680                 685

Glu Ser Leu Ser Asp Glu Phe Tyr Leu Asp Glu Lys Arg Glu Leu Phe
            690                 695                 700

Glu Ile Val Lys Tyr Ala Lys Gln Leu His Ile Glu Arg Asn Met
705                 710                 715

<210> SEQ ID NO 83
<211> LENGTH: 34
<212> TYPE: DNA
<213> ORGANISM: Artificial Sequence
<220> FEATURE:
<223> OTHER INFORMATION: 53A-1-bam

<400> SEQUENCE: 83
ccggatccat gacggccgac aacaacaccg aggc                                34

<210> SEQ ID NO 84
<211> LENGTH: 20
<212> TYPE: DNA
<213> ORGANISM: Artificial Sequence
<220> FEATURE:
<223> OTHER INFORMATION: C3-3a-6 primer

<400> SEQUENCE: 84
caggggcagc tgggtgatct                                                20

<210> SEQ ID NO 85
<211> LENGTH: 20
<212> TYPE: DNA
<213> ORGANISM: Artificial Sequence
<220> FEATURE:
<223> OTHER INFORMATION: C3-1Ab-3 primer
<220> FEATURE:
<221> NAME/KEY: misc_feature
```

```
<222> LOCATION: (1)..(20)
<223> OTHER INFORMATION: 1ab-3 primer

<400> SEQUENCE: 85
agatcaccca gatcccctg                                                      20

<210> SEQ ID NO 86
<211> LENGTH: 39
<212> TYPE: DNA
<213> ORGANISM: Artificial Sequence
<220> FEATURE:
<223> OTHER INFORMATION: 1Ab-6-sac primer

<400> SEQUENCE: 86
ccgagctcag ctcctacacc tgatcgatgt ggtagtcgg                                 39

<210> SEQ ID NO 87
<211> LENGTH: 56
<212> TYPE: DNA
<213> ORGANISM: Artificial Sequence
<220> FEATURE:
<223> OTHER INFORMATION: 8a-atg-delri primer

<400> SEQUENCE: 87
ccggatccac catgactagt aacggccgcc agtgtgctgg tattcgccct tatgac             56

<210> SEQ ID NO 88
<211> LENGTH: 20
<212> TYPE: DNA
<213> ORGANISM: Artificial Sequence
<220> FEATURE:
<223> OTHER INFORMATION: C2-3A-4 primer

<400> SEQUENCE: 88
gtccagcacg gtcagggtca                                                     20

<210> SEQ ID NO 89
<211> LENGTH: 20
<212> TYPE: DNA
<213> ORGANISM: Artificial Sequence
<220> FEATURE:
<223> OTHER INFORMATION: reverse primer

<400> SEQUENCE: 89
gcgtgcagtc aagtcagatc                                                     20

<210> SEQ ID NO 90
<211> LENGTH: 38
<212> TYPE: DNA
<213> ORGANISM: Artificial Sequence
<220> FEATURE:
<223> OTHER INFORMATION: FR8a-OL-1 primer

<400> SEQUENCE: 90
ggtgttgttg tcggccgtca tagggcgaat accagcac                                 38

<210> SEQ ID NO 91
<211> LENGTH: 39
<212> TYPE: DNA
<213> ORGANISM: Artificial Sequence
<220> FEATURE:
<223> OTHER INFORMATION: FR8a-OL-2 primer

<400> SEQUENCE: 91
gccgacaaca acaccgaggc cctggacagc agcaccacc                                39
```

<210> SEQ ID NO 92
<211> LENGTH: 27
<212> TYPE: DNA
<213> ORGANISM: Artificial Sequence
<220> FEATURE:
<223> OTHER INFORMATION: C1-3a-2 primer

<400> SEQUENCE: 92
caggtgggtg ttggcggcct gggcgta                                27

<210> SEQ ID NO 93
<211> LENGTH: 21
<212> TYPE: DNA
<213> ORGANISM: Artificial Sequence
<220> FEATURE:
<223> OTHER INFORMATION: 5'FR8a primer

<400> SEQUENCE: 93
ggatccacca tgactagtaa c                                      21

<210> SEQ ID NO 94
<211> LENGTH: 36
<212> TYPE: DNA
<213> ORGANISM: Artificial Sequence
<220> FEATURE:
<223> OTHER INFORMATION: 5'fr8a-12aa primer

<400> SEQUENCE: 94
ccggatccac catgtatgac ggccgacaac aacacc                      36

<210> SEQ ID NO 95
<211> LENGTH: 20
<212> TYPE: DNA
<213> ORGANISM: Artificial Sequence
<220> FEATURE:
<223> OTHER INFORMATION: C2-3A-3 primer

<400> SEQUENCE: 95
tgaccctgac cgtgctggac                                        20

<210> SEQ ID NO 96
<211> LENGTH: 27
<212> TYPE: DNA
<213> ORGANISM: Artificial Sequence
<220> FEATURE:
<223> OTHER INFORMATION: 3'1Ab-dm3 primer

<400> SEQUENCE: 96
gagctcctag gtcacctcgg cgggcac                                27

<210> SEQ ID NO 97
<211> LENGTH: 32
<212> TYPE: DNA
<213> ORGANISM: Artificial Sequence
<220> FEATURE:
<223> OTHER INFORMATION: 5'FR-del6 primer

<400> SEQUENCE: 97
ggatccacca tgtgtgctgg tattcgccct at                          32

<210> SEQ ID NO 98
<211> LENGTH: 32
<212> TYPE: DNA
<213> ORGANISM: Artificial Sequence
<220> FEATURE:
<223> OTHER INFORMATION: 5'1Ab-bam primer

<400> SEQUENCE: 98
ccggatccat ggacaacaac cccaacatca ac                                   32

<210> SEQ ID NO 99
<211> LENGTH: 20
<212> TYPE: DNA
<213> ORGANISM: Artificial Sequence
<220> FEATURE:
<223> OTHER INFORMATION: C3-3a-7 primer
<220> FEATURE:
<221> NAME/KEY: misc_feature
<222> LOCATION: (1)..(20)
<223> OTHER INFORMATION: C3-3a-7 primer

<400> SEQUENCE: 99
gcttcaccgg cggcgacatc                                                 20

<210> SEQ ID NO 100
<211> LENGTH: 20
<212> TYPE: DNA
<213> ORGANISM: Artificial Sequence
<220> FEATURE:
<223> OTHER INFORMATION: C3-3a-8 primer

<400> SEQUENCE: 100
gatgtcgccg ccggtgaagc                                                 20

<210> SEQ ID NO 101
<211> LENGTH: 23
<212> TYPE: DNA
<213> ORGANISM: Artificial Sequence
<220> FEATURE:
<223> OTHER INFORMATION: C4-3a-9 primer

<400> SEQUENCE: 101
ccgcatccac tacgccagca cca                                             23

<210> SEQ ID NO 102
<211> LENGTH: 23
<212> TYPE: DNA
<213> ORGANISM: Artificial Sequence
<220> FEATURE:
<223> OTHER INFORMATION: C4-3a-10 primer

<400> SEQUENCE: 102
tggtgctggc gtagtggatg cgg                                             23

<210> SEQ ID NO 103
<211> LENGTH: 44
<212> TYPE: DNA
<213> ORGANISM: Artificial Sequence
<220> FEATURE:
<223> OTHER INFORMATION: 3a-12-sac primer

<400> SEQUENCE: 103
ccgagctcag ctcagatcta gttcacgggg atgaactcga tctt                      44

<210> SEQ ID NO 104
<211> LENGTH: 27
<212> TYPE: DNA
<213> ORGANISM: Artificial Sequence
<220> FEATURE:
<223> OTHER INFORMATION: 3a-22 primer

<400> SEQUENCE: 104

```
ggccttcacc aggggcagct gggtgat                                              27

<210> SEQ ID NO 105
<211> LENGTH: 31
<212> TYPE: DNA
<213> ORGANISM: Artificial Sequence
<220> FEATURE:
<223> OTHER INFORMATION: 1B-5 primer

<400> SEQUENCE: 105
ccgccgcgac ctgaccctgg gcgtgctgga c                                         31

<210> SEQ ID NO 106
<211> LENGTH: 27
<212> TYPE: DNA
<213> ORGANISM: Artificial Sequence
<220> FEATURE:
<223> OTHER INFORMATION: 1B-7 primer

<400> SEQUENCE: 106
atcacccaga tccccatggt gaaggcc                                              27

<210> SEQ ID NO 107
<211> LENGTH: 26
<212> TYPE: DNA
<213> ORGANISM: Artificial Sequence
<220> FEATURE:
<223> OTHER INFORMATION: 1B-10 primer

<400> SEQUENCE: 107
ccgagctcct agaacagggc gttcac                                               26

<210> SEQ ID NO 108
<211> LENGTH: 20
<212> TYPE: DNA
<213> ORGANISM: Artificial Sequence
<220> FEATURE:
<223> OTHER INFORMATION: C3-1Ab-2 primer

<400> SEQUENCE: 108 caggggatc tgggtgatct                                                       20

<210> SEQ ID NO 109
<211> LENGTH: 20
<212> TYPE: DNA
<213> ORGANISM: Artificial Sequence
<220> FEATURE:
<223> OTHER INFORMATION: C3-3A-5 primer

<400> SEQUENCE: 109
agatcaccca gctgcccctg                                                      20

<210> SEQ ID NO 110
<211> LENGTH: 27
<212> TYPE: DNA
<213> ORGANISM: Artificial Sequence
<220> FEATURE:
<223> OTHER INFORMATION: C1-1Ab-1 primer

<400> SEQUENCE: 110
tacgtgcagg ccgccaacct gcacctg                                              27

<210> SEQ ID NO 111
<211> LENGTH: 42
<212> TYPE: DNA
<213> ORGANISM: Artificial Sequence
```

```
<220> FEATURE:
<223> OTHER INFORMATION: 5'8Aa-dm3 primer

<400> SEQUENCE: 111
agatcaccca gctgcccctg gtaaagggag acatgttata tc                         42

<210> SEQ ID NO 112
<211> LENGTH: 30
<212> TYPE: DNA
<213> ORGANISM: Artificial Sequence
<220> FEATURE:
<223> OTHER INFORMATION: 3'8Aa-dm3 primer

<400> SEQUENCE: 112
gagctcctat gtctcatcta ctgggatgaa                                       30

<210> SEQ ID NO 113
<211> LENGTH: 33
<212> TYPE: DNA
<213> ORGANISM: Artificial Sequence
<220> FEATURE:
<223> OTHER INFORMATION: Tant-OL-1 primer

<400> SEQUENCE: 113
acccagctgc ccctggtgaa ggcccacacc ctc                                   33

<210> SEQ ID NO 114
<211> LENGTH: 33
<212> TYPE: DNA
<213> ORGANISM: Artificial Sequence
<220> FEATURE:
<223> OTHER INFORMATION: Tant-OL-2 primer

<400> SEQUENCE: 114
gagggtgtgg gccttcacca ggggcagctg ggt                                   33

<210> SEQ ID NO 115
<211> LENGTH: 29
<212> TYPE: DNA
<213> ORGANISM: Artificial Sequence
<220> FEATURE:
<223> OTHER INFORMATION: Tant-3'sac primer

<400> SEQUENCE: 115
gagctctagc ttaagcagtc cacgaggtt                                        29

<210> SEQ ID NO 116
<211> LENGTH: 37
<212> TYPE: DNA
<213> ORGANISM: Artificial Sequence
<220> FEATURE:
<223> OTHER INFORMATION: 1Ac-OL-1 primer

<400> SEQUENCE: 116
acccagctgc ccctggtgaa gggaaacttt cttttta                               37

<210> SEQ ID NO 117
<211> LENGTH: 37
<212> TYPE: DNA
<213> ORGANISM: Artificial Sequence
<220> FEATURE:
<223> OTHER INFORMATION: 1Ac-OL-2 primer

<400> SEQUENCE: 117
taaaaagaaa gtttcccttc accaggggca gctgggt                               37
```

<210> SEQ ID NO 118
<211> LENGTH: 30
<212> TYPE: DNA
<213> ORGANISM: Artificial Sequnce
<220> FEATURE:
<223> OTHER INFORMATION: 1Ac-3'sac primer

<400> SEQUENCE: 118
gagctcctat gttgcagtaa ctggaataaa                              30

<210> SEQ ID NO 119
<211> LENGTH: 38
<212> TYPE: DNA
<213> ORGANISM: Artificial Sequence
<220> FEATURE:
<223> OTHER INFORMATION: 1Ia-OL-1 primer

<400> SEQUENCE: 119
acccagctgc ccctgagtaa aagctttcaa tctgtctt                     38

<210> SEQ ID NO 120
<211> LENGTH: 38
<212> TYPE: DNA
<213> ORGANISM: Artificial Sequence
<220> FEATURE:
<223> OTHER INFORMATION: 1Ia-OL-2 primer

<400> SEQUENCE: 120
aagacagatt gaaagctttt actcaggggc agctgggt                     38

<210> SEQ ID NO 121
<211> LENGTH: 31
<212> TYPE: DNA
<213> ORGANISM: Artificial Sequence
<220> FEATURE:
<223> OTHER INFORMATION: 1Ia-3'sac primer

<400> SEQUENCE: 121
gagctcctac atgttacgct caatatggag t                            31

<210> SEQ ID NO 122
<211> LENGTH: 33
<212> TYPE: DNA
<213> ORGANISM: Artificial Sequence
<220> FEATURE:
<223> OTHER INFORMATION: FR-1Ab-1 primer

<400> SEQUENCE: 122
tggacccaca agagcgccga gttcaacaac atc                          33

<210> SEQ ID NO 123
<211> LENGTH: 33
<212> TYPE: DNA
<213> ORGANISM: Artificial Sequence
<220> FEATURE:
<223> OTHER INFORMATION: FR-1Ab-2 primer

<400> SEQUENCE: 123
gatgttgttg aactcggcgc tcttgtgggt cca                          33

<210> SEQ ID NO 124
<211> LENGTH: 40
<212> TYPE: DNA
<213> ORGANISM: Artificial Sequence
<220> FEATURE:
<223> OTHER INFORMATION: FR-1Ab-3 primer

<400> SEQUENCE: 124
ccacaagagc gtcgacttca acacatcatc cccagcagcc                40

<210> SEQ ID NO 125
<211> LENGTH: 41
<212> TYPE: DNA
<213> ORGANISM: Artificial Sequence
<220> FEATURE:
<223> OTHER INFORMATION: FR-1Ab-4 primer

<400> SEQUENCE: 125
ggctcgtggg gatgatgttg ttgaagtcga cgctcttgtg g              41

<210> SEQ ID NO 126
<211> LENGTH: 35
<212> TYPE: PRT
<213> ORGANISM: Artificial Sequence
<220> FEATURE:
<223> OTHER INFORMATION: Peptidyl fragment 1
<220> FEATURE:
<221> NAME/KEY: MISC_FEATURE
<222> LOCATION: (1)..(14)
<223> OTHER INFORMATION: Derived from pET21a
<220> FEATURE:
<221> NAME/KEY: MISC_FEATURE
<222> LOCATION: (15)..(26)
<223> OTHER INFORMATION: Derived from pCR2.1-TOPO
<220> FEATURE:
<221> NAME/KEY: MISC_FEATURE
<222> LOCATION: (27)..(35)
<223> OTHER INFORMATION: Derived from cry3A055 frame shift.

<400> SEQUENCE: 126

Met Ala Ser Met Thr Gly Gly Gln Gln Met Gly Arg Gly Ser Thr Ser
1               5                   10                  15

Asn Gly Arg Gln Cys Ala Gly Ile Arg Pro Tyr Asp Gly Arg Gln Gln
            20                  25                  30

His Arg Gly
        35

<210> SEQ ID NO 127
<211> LENGTH: 22
<212> TYPE: PRT
<213> ORGANISM: Artificial Sequence
<220> FEATURE:
<223> OTHER INFORMATION: Peptidyl Fragment 2

<400> SEQUENCE: 127

Met Thr Ser Asn Gly Arg Gln Cys Ala Gly Ile Arg Pro Tyr Asp Gly
1               5                   10                  15

Arg Gln Gln His Arg Gly
            20

<210> SEQ ID NO 128
<211> LENGTH: 10
<212> TYPE: PRT
<213> ORGANISM: Artificial Sequence
<220> FEATURE:
<223> OTHER INFORMATION: Peptidyl Fragment 3

<400> SEQUENCE: 128

Met Tyr Asp Gly Arg Gln Gln His Arg Gly
1               5                   10

<210> SEQ ID NO 129

```
<211> LENGTH: 13
<212> TYPE: PRT
<213> ORGANISM: Artificial Sequence
<220> FEATURE:
<223> OTHER INFORMATION: Peptidyl Fragment 4

<400> SEQUENCE: 129

Met Thr Ser Asn Gly Arg Gln Cys Ala Gly Ile Arg Pro
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Peptidyl fragment 5

<400> SEQUENCE: 130

Met Cys Ala Gly Ile Arg Pro
1               5

<210> SEQ ID NO 131
<211> LENGTH: 55
<212> TYPE: PRT
<213> ORGANISM: Artificial Sequence
<220> FEATURE:
<223> OTHER INFORMATION: Peptidyl fragment 6

<400> SEQUENCE: 131

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Asp Ile Gly
            20                  25                  30

Ser Thr Thr Ser Asn Gly Arg Gln Cys Ala Gly Ile Arg Pro Tyr Asp
        35                  40                  45

Gly Arg Gln Gln His Arg Gly
    50                  55

<210> SEQ ID NO 132
<211> LENGTH: 14
<212> TYPE: PRT
<213> ORGANISM: Artificial Sequence
<220> FEATURE:
<223> OTHER INFORMATION: Chemically synthesized peptidyl fragment 7

<400> SEQUENCE: 132

Met Ala Ser Met Thr Gly Gly Gln Gln Met Gly Arg Gly Ser
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Peptidyl fragment 8

<400> SEQUENCE: 133

Tyr Asp Gly Arg Gln Gln His Arg Gly
1               5

<210> SEQ ID NO 134
<211> LENGTH: 12
<212> TYPE: PRT
<213> ORGANISM: Artificial Sequence
<220> FEATURE:
<223> OTHER INFORMATION: Peptidyl fragment 9
```

<400> SEQUENCE: 134

Thr Ser Asn Gly Arg Gln Cys Ala Gly Ile Arg Pro
1               5                   10

<210> SEQ ID NO 135
<211> LENGTH: 644
<212> TYPE: PRT
<213> ORGANISM: Bacillus thuringiensis
<220> FEATURE:
<223> OTHER INFORMATION: Full-length Cry3A protein

<400> SEQUENCE: 135

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
        450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 136
<211> LENGTH: 31
<212> TYPE: DNA
<213> ORGANISM: Artificial Sequence
<220> FEATURE:
<223> OTHER INFORMATION: Chemically synthesized CMS94 primer

<400> SEQUENCE: 136
ggcgcgccac catggctagc atgactggtg g        31

<210> SEQ ID NO 137
<211> LENGTH: 20
<212> TYPE: DNA
<213> ORGANISM: Artificial Sequence
<220> FEATURE:
<223> OTHER INFORMATION: Chemically synthesized CMS95 primer -continued

<400> SEQUENCE: 137
gcaggaacag gtgggtgttg                                                      20

<210> SEQ ID NO 138
<211> LENGTH: 20
<212> TYPE: DNA
<213> ORGANISM: Artificial sequence
<220> FEATURE:
<223> OTHER INFORMATION: Chemically synthesized CMS96 primer

<400> SEQUENCE: 138
cctgaacacc atctggccca                                                      20

<210> SEQ ID NO 139
<211> LENGTH: 39
<212> TYPE: DNA
<213> ORGANISM: Artificial Sequence
<220> FEATURE:
<223> OTHER INFORMATION: Chemically synthesized CMS97 primer

<400> SEQUENCE: 139
ctggctgctg gggatgatgt tgttgaagtc gacgctctt                                 39

<210> SEQ ID NO 140
<211> LENGTH: 21
<212> TYPE: DNA
<213> ORGANISM: Artificial Sequence
<220> FEATURE:
<223> OTHER INFORMATION: Chemically synthesized CMS98 primer

<400> SEQUENCE: 140
gagctcttag gtcacctcgg c                                                    21

<210> SEQ ID NO 141
<211> LENGTH: 39
<212> TYPE: DNA
<213> ORGANISM: Artificial Sequence
<220> FEATURE:
<223> OTHER INFORMATION: Chemically synthesized CMS99 primer

<400> SEQUENCE: 141
aagagcgtcg acttcaacaa catcatcccc agcagccag                                 39

<210> SEQ ID NO 142
<211> LENGTH: 40
<212> TYPE: DNA
<213> ORGANISM: Artificial Sequence
<220> FEATURE:
<223> OTHER INFORMATION: Chemically synthesized CMS100 primer

<400> SEQUENCE: 142
gaagtaccgc gcccgcatcc gctacgccag caccaccaac                                40

<210> SEQ ID NO 143
<211> LENGTH: 40
<212> TYPE: DNA
<213> ORGANISM: Artificial Sequence
<220> FEATURE:
<223> OTHER INFORMATION: Chemically synthesized CMS101 primer

<400> SEQUENCE: 143
gttggtggtg ctggcgtagc ggatgcgggc gcggtacttc                                40

<210> SEQ ID NO 144
<211> LENGTH: 1966

<212> TYPE: DNA
<213> ORGANISM: Artificial Sequence
<220> FEATURE:
<223> OTHER INFORMATION: T7-8AF coding sequence

<400> SEQUENCE: 144

```
atggctagca tgactggtgg acagcaaatg ggtcgcggat ccatgacggc cgacaacaac      60
accgaggccc tggacagcag caccaccaag gacgtgatcc agaagggcat cagcgtggtg     120
ggcgacctgc tgggcgtggt gggcttcccc ttcggcggcg ccctggtgag cttctacacc     180
aacttcctga caccatctg gcccagcgag gaccccgga aggccttcat ggagcaggtg      240
gaggccctga tggaccagaa gatcgccgac tacgccaaga caaggcact ggccgagcta     300
cagggcctcc agaacaacgt ggaggactat gtgagcgccc tgagcagctg cagaagaac     360
cccgctgcac cgttccgcaa ccccacagc cagggccgca tccgcgagct gttcagccag     420
gccgagagcc acttccgcaa cagcatgccc agcttcgcca tcagcggcta cgaggtgctg     480
ttcctgacca cctacgccca ggccgccaac acccacctgt cctgctgaa ggacgcccaa     540
atctacggag aggagtgggg ctacgagaag gaggacatcg ccgagttcta caagcgccag     600
ctgaagctga cccaggagta caccgaccac tgcgtgaagt ggtacaacgt gggtctagac     660
aagctccgcg gcagcagcta cgagagctgg gtgaacttca ccgctaccg ccgcgagatg     720
accctgaccg tgctggacct gatcgccctg ttcccctgt acgacgtgcg cctgtacccc     780
aaggaggtga agaccgagct gaccgcgac gtgctgaccg accccatcgt gggcgtgaac     840
aacctgcgcg gctacggcac caccttcagc aacatcgaga actacatccg caagccccac     900
ctgttcgact acctgcaccg catccagttc cacacgcgtt ccagcccgg ctactacggc     960
aacgacagct tcaactactg gagcggcaac tacgtgagca cccgcccag catcggcagc    1020
aacgacatca tcaccagccc cttctacggc aacaagagca gcgagcccgt gcagaacctt    1080
gagttcaacg gcgagaaggt gtaccgcgcc gtggctaaca ccaacctggc cgtgtggccc    1140
tctgcagtgt acagcggcgt gaccaaggtg gagttcagcc agtacaacga ccagaccgac    1200
gaggccagca cccagaccta cgacagcaag cgcaacgtgg cgccgtgag ctggacagc     1260
atcgaccagc tgccccccga gaccaccgac gagcccctgg agaagggcta cagccaccag    1320
ctgaactacg tgatgtgctt cctgatgcag ggcagccgcg gcaccatccc cgtgctgacc    1380
tggacccaca gagcgtcga cttcttcaac atgatcgaca gcaagaagat cacccagctg    1440
cccctgacca gagcaccaa cctgggcagc ggcaccagcg tggtgaaggg ccccggcttc    1500
accggcggcg acatcctgcg ccgcaccagc cccggccaga tcagcaccct gcgcgtgaac    1560
atcaccgccc ccctgagcca gcgctaccgc gtccgcatcc gctacgccag caccaccaac    1620
ctgcagttcc acaccagcat cgacggccgc cccatcaacc agggcaactt cagcgccacc    1680
atgagcagcg gcagcaacct gcagagcggc agcttccgca ccgtgggctt caccaccccc    1740
ttcaacttca gcaacggcag cagcgtgttc accctgagcg cccacgtgtt caacagcggc    1800
aacgaggtgt acatcgaccg catcgagttc gtgcccgccg aggtgacctt cgaggccgag    1860
tacgacctgg agagggctca gaaggccgtg aacgagctgt tcaccagcag caaccagatc    1920
ggcctgaaga ccgacgtgac cgactaccac atcgatcagg tgtagg              1966
```

<210> SEQ ID NO 145
<211> LENGTH: 654
<212> TYPE: PRT
<213> ORGANISM: Artificial Sequence
<220> FEATURE:

<223> OTHER INFORMATION: T7-8AF protein

<400> SEQUENCE: 145

```
Met Ala Ser Met Thr Gly Gly Gln Gln Met Gly Arg Gly Ser Met Thr
1               5                   10                  15

Ala Asp Asn Asn Thr Glu Ala Leu Asp Ser Ser Thr Thr Lys Asp Val
            20                  25                  30

Ile Gln Lys Gly Ile Ser Val Val Gly Asp Leu Leu Gly Val Val Gly
        35                  40                  45

Phe Pro Phe Gly Gly Ala Leu Val Ser Phe Tyr Thr Asn Phe Leu Asn
    50                  55                  60

Thr Ile Trp Pro Ser Glu Asp Pro Trp Lys Ala Phe Met Glu Gln Val
65                  70                  75                  80

Glu Ala Leu Met Asp Gln Lys Ile Ala Asp Tyr Ala Lys Asn Lys Ala
                85                  90                  95

Leu Ala Glu Leu Gln Gly Leu Gln Asn Asn Val Glu Asp Tyr Val Ser
            100                 105                 110

Ala Leu Ser Ser Trp Gln Lys Asn Pro Ala Ala Pro Phe Arg Asn Pro
        115                 120                 125

His Ser Gln Gly Arg Ile Arg Glu Leu Phe Ser Gln Ala Glu Ser His
    130                 135                 140

Phe Arg Asn Ser Met Pro Ser Phe Ala Ile Ser Gly Tyr Glu Val Leu
145                 150                 155                 160

Phe Leu Thr Thr Tyr Ala Gln Ala Ala Asn Thr His Leu Phe Leu Leu
                165                 170                 175

Lys Asp Ala Gln Ile Tyr Gly Glu Glu Trp Gly Tyr Glu Lys Glu Asp
            180                 185                 190

Ile Ala Glu Phe Tyr Lys Arg Gln Leu Lys Leu Thr Gln Glu Tyr Thr
        195                 200                 205

Asp His Cys Val Lys Trp Tyr Asn Val Gly Leu Asp Lys Leu Arg Gly
    210                 215                 220

Ser Ser Tyr Glu Ser Trp Val Asn Phe Asn Arg Tyr Arg Arg Glu Met
225                 230                 235                 240

Thr Leu Thr Val Leu Asp Leu Ile Ala Leu Phe Pro Leu Tyr Asp Val
                245                 250                 255

Arg Leu Tyr Pro Lys Glu Val Lys Thr Glu Leu Thr Arg Asp Val Leu
            260                 265                 270

Thr Asp Pro Ile Val Gly Val Asn Asn Leu Arg Gly Tyr Gly Thr Thr
        275                 280                 285

Phe Ser Asn Ile Glu Asn Tyr Ile Arg Lys Pro His Leu Phe Asp Tyr
    290                 295                 300

Leu His Arg Ile Gln Phe His Thr Arg Phe Gln Pro Gly Tyr Tyr Gly
305                 310                 315                 320

Asn Asp Ser Phe Asn Tyr Trp Ser Gly Asn Tyr Val Ser Thr Arg Pro
                325                 330                 335

Ser Ile Gly Ser Asn Asp Ile Ile Thr Ser Pro Phe Tyr Gly Asn Lys
            340                 345                 350

Ser Ser Glu Pro Val Gln Asn Leu Glu Phe Asn Gly Glu Lys Val Tyr
        355                 360                 365

Arg Ala Val Ala Asn Thr Asn Leu Ala Val Trp Pro Ser Ala Val Tyr
    370                 375                 380

Ser Gly Val Thr Lys Val Glu Phe Ser Gln Tyr Asn Asp Gln Thr Asp
385                 390                 395                 400
```

Glu Ala Ser Thr Gln Thr Tyr Asp Ser Lys Arg Asn Val Gly Ala Val
            405                 410                 415

Ser Trp Asp Ser Ile Asp Gln Leu Pro Pro Glu Thr Thr Asp Glu Pro
        420                 425                 430

Leu Glu Lys Gly Tyr Ser His Gln Leu Asn Tyr Val Met Cys Phe Leu
            435                 440                 445

Met Gln Gly Ser Arg Gly Thr Ile Pro Val Leu Thr Trp Thr His Lys
        450                 455                 460

Ser Val Asp Phe Phe Asn Met Ile Asp Ser Lys Lys Ile Thr Gln Leu
465                 470                 475                 480

Pro Leu Thr Lys Ser Thr Asn Leu Gly Ser Gly Thr Ser Val Val Lys
                485                 490                 495

Gly Pro Gly Phe Thr Gly Gly Asp Ile Leu Arg Arg Thr Ser Pro Gly
            500                 505                 510

Gln Ile Ser Thr Leu Arg Val Asn Ile Thr Ala Pro Leu Ser Gln Arg
        515                 520                 525

Tyr Arg Val Arg Ile Arg Tyr Ala Ser Thr Thr Asn Leu Gln Phe His
    530                 535                 540

Thr Ser Ile Asp Gly Arg Pro Ile Asn Gln Gly Asn Phe Ser Ala Thr
545                 550                 555                 560

Met Ser Ser Gly Ser Asn Leu Gln Ser Gly Ser Phe Arg Thr Val Gly
                565                 570                 575

Phe Thr Thr Pro Phe Asn Phe Ser Asn Gly Ser Ser Val Phe Thr Leu
            580                 585                 590

Ser Ala His Val Phe Asn Ser Gly Asn Glu Val Tyr Ile Asp Arg Ile
        595                 600                 605

Glu Phe Val Pro Ala Glu Val Thr Phe Glu Ala Glu Tyr Asp Leu Glu
    610                 615                 620

Arg Ala Gln Lys Ala Val Asn Glu Leu Phe Thr Ser Ser Asn Gln Ile
625                 630                 635                 640

Gly Leu Lys Thr Asp Val Thr Asp Tyr His Ile Asp Gln Val
                645                 650

<210> SEQ ID NO 146
<211> LENGTH: 1920
<212> TYPE: DNA
<213> ORGANISM: Artificial Sequence
<220> FEATURE:
<223> OTHER INFORMATION: -catG8AF coding sequence

<400> SEQUENCE: 146
atgacggccg acaacaacac cgaggccctg gacagcagca ccaccaagga cgtgatccag      60
aagggcatca gcgtggtggg cgacctgctg ggcgtggtgg gcttccccct cggcggcgcc     120
ctggtgagct tctacaccaa cttcctgaac accatctggc ccagcgagga cccctggaag     180
gccttcatgg agcaggtgga ggccctgatg accagaagag tcgccgacta cgccaagaac     240
aaggcactgg ccgagctaca gggcctccag aacaacgtgg aggactatgt gagcgccctg     300
agcagctggc agaagaaccc cgtctcgagc cgcaacccca cagccaggg ccgcatccgc     360 gagctgttca gccaggccga gccacttc gcaacagca tgcccagctt cgccatcagc     420
ggctacgagg tgctgttcct gaccacctac gcccaggccg ccaacaccca cctgttcctg     480
ctgaaggacg cccaaatcta cggagaggag tggggctacg agaaggagga catcgccgag     540
ttctacaagc gccagctgaa gctgacccag gagtacaccg accactgcgt gaagtggtac     600
aacgtgggtc tagacaagct ccgcggcagc agctacgaga gctgggtgaa cttcaaccgc     660

```
taccgccgcg agatgaccct gaccgtgctg gacctgatcg ccctgttccc cctgtacgac    720
gtgcgcctgt accccaagga ggtgaagacc gagctgaccc gcgacgtgct gaccgacccc    780
atcgtgggcg tgaacaacct gcgcggctac ggcaccacct tcagcaacat cgagaactac    840
atccgcaagc cccacctgtt cgactacctg caccgcatcc agttccacac gcgtttccag    900
cccggctact acggcaacga cagcttcaac tactggagcg gcaactacgt gagcacccgc    960
cccagcatcg gcagcaacga catcatcacc agccccttct acggcaacaa gagcagcgag   1020
cccgtgcaga accttgagtt caacggcgag aaggtgtacc gcgccgtggc taacaccaac   1080
ctggccgtgt ggccctctgc agtgtacagc ggcgtgacca aggtggagtt cagccagtac   1140
aacgaccaga ccgacgaggc cagcacccag acctacgaca gcaagcgcaa cgtgggcgcc   1200
gtgagctggg acagcatcga ccagctgccc ccgagacca ccgacgagcc cctggagaag   1260
ggctacagcc accagctgaa ctacgtgatg tgcttcctga tgcagggcag ccgcggcacc   1320
atccccgtgc tgacctggac ccacaagagc gtcgacttct tcaacatgat cgacagcaag   1380
aagatcaccc agctgcccct gaccaagagc accaacctgg gcagcggcac cagcgtggtg   1440
aagggccccg gcttcaccgg cggcgacatc ctgcgccgca ccagccccgg ccagatcagc   1500
accctgcgcg tgaacatcac cgcccccctg agccagcgct accgcgtccg catccgctac   1560
gccagcacca ccaacctgca gttccacacc agcatcgacg gccgcccat caaccagggc   1620
aacttcagcg ccaccatgag cagcggcagc aacctgcaga gcggcagctt ccgcaccgtg   1680
ggcttcacca ccccccttcaa cttcagcaac ggcagcagcg tgttcacccc tgagcgccac   1740
gtgttcaaca gcggcaacga ggtgtacatc gaccgcatcg agttcgtgcc cgccgaggtg   1800
accttcgagg ccgagtacga cctggagagg gctcagaagg ccgtgaacga gctgttcacc   1860
agcagcaacc agatcggcct gaagaccgac gtgaccgact accacatcga tcaggtgtag   1920
```

<210> SEQ ID NO 147
<211> LENGTH: 639
<212> TYPE: PRT
<213> ORGANISM: Artificial Sequence
<220> FEATURE:
<223> OTHER INFORMATION: -catG8AF protein

<400> SEQUENCE: 147

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Val Ser Ser Arg Asn
            100                 105                 110

Pro His Ser Gln Gly Arg Ile Arg Glu Leu Phe Ser Gln Ala Glu Ser
        115                 120                 125

His Phe Arg Asn Ser Met Pro Ser Phe Ala Ile Ser Gly Tyr Glu Val
    130                 135                 140
```

```
Leu Phe Leu Thr Thr Tyr Ala Gln Ala Ala Asn Thr His Leu Phe Leu
145                 150                 155                 160

Leu Lys Asp Ala Gln Ile Tyr Gly Glu Glu Trp Gly Tyr Glu Lys Glu
                165                 170                 175

Asp Ile Ala Glu Phe Tyr Lys Arg Gln Leu Lys Leu Thr Gln Glu Tyr
            180                 185                 190

Thr Asp His Cys Val Lys Trp Tyr Asn Val Gly Leu Asp Lys Leu Arg
        195                 200                 205

Gly Ser Ser Tyr Glu Ser Trp Val Asn Phe Asn Arg Tyr Arg Arg Glu
    210                 215                 220

Met Thr Leu Thr Val Leu Asp Leu Ile Ala Leu Phe Pro Leu Tyr Asp
225                 230                 235                 240

Val Arg Leu Tyr Pro Lys Glu Val Lys Thr Glu Leu Thr Arg Asp Val
                245                 250                 255

Leu Thr Asp Pro Ile Val Gly Val Asn Asn Leu Arg Gly Tyr Gly Thr
            260                 265                 270

Thr Phe Ser Asn Ile Glu Asn Tyr Ile Arg Lys Pro His Leu Phe Asp
        275                 280                 285

Tyr Leu His Arg Ile Gln Phe His Thr Arg Phe Gln Pro Gly Tyr Tyr
    290                 295                 300

Gly Asn Asp Ser Phe Asn Tyr Trp Ser Gly Asn Tyr Val Ser Thr Arg
305                 310                 315                 320

Pro Ser Ile Gly Ser Asn Asp Ile Ile Thr Ser Pro Phe Tyr Gly Asn
                325                 330                 335

Lys Ser Ser Glu Pro Val Gln Asn Leu Glu Phe Asn Gly Glu Lys Val
            340                 345                 350

Tyr Arg Ala Val Ala Asn Thr Asn Leu Ala Val Trp Pro Ser Ala Val
        355                 360                 365

Tyr Ser Gly Val Thr Lys Val Glu Phe Ser Gln Tyr Asn Asp Gln Thr
    370                 375                 380

Asp Glu Ala Ser Thr Gln Thr Tyr Asp Ser Lys Arg Asn Val Gly Ala
385                 390                 395                 400

Val Ser Trp Asp Ser Ile Asp Gln Leu Pro Pro Glu Thr Thr Asp Glu
                405                 410                 415

Pro Leu Glu Lys Gly Tyr Ser His Gln Leu Asn Tyr Val Met Cys Phe
            420                 425                 430

Leu Met Gln Gly Ser Arg Gly Thr Ile Pro Val Leu Thr Trp Thr His
        435                 440                 445

Lys Ser Val Asp Phe Phe Asn Met Ile Asp Ser Lys Lys Ile Thr Gln
    450                 455                 460

Leu Pro Leu Thr Lys Ser Thr Asn Leu Gly Ser Gly Thr Ser Val Val
465                 470                 475                 480

Lys Gly Pro Gly Phe Thr Gly Gly Asp Ile Leu Arg Arg Thr Ser Pro
                485                 490                 495

Gly Gln Ile Ser Thr Leu Arg Val Asn Ile Thr Ala Pro Leu Ser Gln
            500                 505                 510

Arg Tyr Arg Val Arg Ile Arg Tyr Ala Ser Thr Thr Asn Leu Gln Phe
        515                 520                 525

His Thr Ser Ile Asp Gly Arg Pro Ile Asn Gln Gly Asn Phe Ser Ala
    530                 535                 540

Thr Met Ser Ser Gly Ser Asn Leu Gln Ser Gly Ser Phe Arg Thr Val
545                 550                 555                 560
```

```
Gly Phe Thr Thr Pro Phe Asn Phe Ser Asn Gly Ser Ser Val Phe Thr
                565                 570                 575

Leu Ser Ala His Val Phe Asn Ser Gly Asn Glu Val Tyr Ile Asp Arg
            580                 585                 590

Ile Glu Phe Val Pro Ala Glu Val Thr Phe Glu Ala Glu Tyr Asp Leu
        595                 600                 605

Glu Arg Ala Gln Lys Ala Val Asn Glu Leu Phe Thr Ser Ser Asn Gln
    610                 615                 620

Ile Gly Leu Lys Thr Asp Val Thr Asp Tyr His Ile Asp Gln Val
625                 630                 635
```

<210> SEQ ID NO 148
<211> LENGTH: 1809
<212> TYPE: DNA
<213> ORGANISM: Artificial Sequence
<220> FEATURE:
<223> OTHER INFORMATION: 8AFdm3 coding sequence

<400> SEQUENCE: 148

```
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc cagcgagga cccctggaag    180
gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgcccag cttcgccatc    420
agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca gcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct ctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcaacaacat catccccagc   1380
agccagatca cccagatccc cctgaccaag agcaccaacc tgggcagcgg caccagcgtg   1440
gtgaagggcc ccggcttcac cggcggcgac atcctgcgcc gcaccagccc cggccagatc   1500
agcaccctgc gcgtgaacat caccgccccc ctgagccagc gctaccgcgt ccgcatccgc   1560
tacgccagca ccaccaacct gcagttccac accagcatcg acggccgccc catcaaccag   1620
```

-continued

```
ggcaacttca gcgccaccat gagcagcggc agcaacctgc agagcggcag cttccgcacc    1680
gtgggcttca ccaccccctt caacttcagc aacggcagca gcgtgttcac cctgagcgcc    1740
cacgtgttca acagcggcaa cgaggtgtac atcgaccgca tcgagttcgt gcccgccgag    1800
gtgacctaa                                                            1809
```

<210> SEQ ID NO 149
<211> LENGTH: 602
<212> TYPE: PRT
<213> ORGANISM: Artificial Sequence
<220> FEATURE:
<223> OTHER INFORMATION: 8AFdm3 protein

<400> SEQUENCE: 149

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
```

|     |     |     |     | 325 |     |     |     | 330 |     |     |     | 335 |     |     |
| --- | --- | --- | --- | --- | --- | --- | --- | --- | --- | --- | --- | --- | --- | --- |
| Asn | Lys | Ser | Ser | Glu | Pro | Val | Gln | Asn | Leu | Glu | Phe | Asn | Gly | Glu | Lys |
|     |     |     | 340 |     |     |     | 345 |     |     |     | 350 |     |     |     |     |
| Val | Tyr | Arg | Ala | Val | Ala | Asn | Thr | Asn | Leu | Ala | Val | Trp | Pro | Ser | Ala |
|     |     | 355 |     |     |     | 360 |     |     |     | 365 |     |     |     |     |     |
| Val | Tyr | Ser | Gly | Val | Thr | Lys | Val | Glu | Phe | Ser | Gln | Tyr | Asn | Asp | Gln |
|     | 370 |     |     |     | 375 |     |     |     | 380 |     |     |     |     |     |     |
| Thr | Asp | Glu | Ala | Ser | Thr | Gln | Thr | Tyr | Asp | Ser | Lys | Arg | Asn | Val | Gly |
| 385 |     |     |     | 390 |     |     |     | 395 |     |     |     | 400 |     |     |     |
| Ala | Val | Ser | Trp | Asp | Ser | Ile | Asp | Gln | Leu | Pro | Pro | Glu | Thr | Thr | Asp |
|     |     |     | 405 |     |     |     | 410 |     |     |     | 415 |     |     |     |     |
| Glu | Pro | Leu | Glu | Lys | Gly | Tyr | Ser | His | Gln | Leu | Asn | Tyr | Val | Met | Cys |
|     |     |     | 420 |     |     |     | 425 |     |     |     | 430 |     |     |     |     |
| Phe | Leu | Met | Gln | Gly | Ser | Arg | Gly | Thr | Ile | Pro | Val | Leu | Thr | Trp | Thr |
|     |     | 435 |     |     |     | 440 |     |     |     | 445 |     |     |     |     |     |
| His | Lys | Ser | Val | Asp | Phe | Asn | Asn | Ile | Ile | Pro | Ser | Ser | Gln | Ile | Thr |
|     | 450 |     |     |     | 455 |     |     |     | 460 |     |     |     |     |     |     |
| Gln | Ile | Pro | Leu | Thr | Lys | Ser | Thr | Asn | Leu | Gly | Ser | Gly | Thr | Ser | Val |
| 465 |     |     |     | 470 |     |     |     | 475 |     |     |     | 480 |     |     |     |
| Val | Lys | Gly | Pro | Gly | Phe | Thr | Gly | Gly | Asp | Ile | Leu | Arg | Arg | Thr | Ser |
|     |     |     | 485 |     |     |     | 490 |     |     |     | 495 |     |     |     |     |
| Pro | Gly | Gln | Ile | Ser | Thr | Leu | Arg | Val | Asn | Ile | Thr | Ala | Pro | Leu | Ser |
|     |     |     | 500 |     |     |     | 505 |     |     |     | 510 |     |     |     |     |
| Gln | Arg | Tyr | Arg | Val | Arg | Ile | Arg | Tyr | Ala | Ser | Thr | Thr | Asn | Leu | Gln |
|     |     | 515 |     |     |     | 520 |     |     |     | 525 |     |     |     |     |     |
| Phe | His | Thr | Ser | Ile | Asp | Gly | Arg | Pro | Ile | Asn | Gln | Gly | Asn | Phe | Ser |
|     | 530 |     |     |     | 535 |     |     |     | 540 |     |     |     |     |     |     |
| Ala | Thr | Met | Ser | Ser | Gly | Ser | Asn | Leu | Gln | Ser | Gly | Ser | Phe | Arg | Thr |
| 545 |     |     |     | 550 |     |     |     | 555 |     |     |     | 560 |     |     |     |
| Val | Gly | Phe | Thr | Thr | Pro | Phe | Asn | Phe | Ser | Asn | Gly | Ser | Ser | Val | Phe |
|     |     |     | 565 |     |     |     | 570 |     |     |     | 575 |     |     |     |     |
| Thr | Leu | Ser | Ala | His | Val | Phe | Asn | Ser | Gly | Asn | Glu | Val | Tyr | Ile | Asp |
|     |     |     | 580 |     |     |     | 585 |     |     |     | 590 |     |     |     |     |
| Arg | Ile | Glu | Phe | Val | Pro | Ala | Glu | Val | Thr |     |     |     |     |     |     |
|     |     | 595 |     |     |     | 600 |     |     |     |     |     |     |     |     |     |

<210> SEQ ID NO 150
<211> LENGTH: 1809
<212> TYPE: DNA
<213> ORGANISM: Artificial Sequence
<220> FEATURE:
<223> OTHER INFORMATION: 8AFlomgdm3 coding sequence

<400> SEQUENCE: 150

| | |
|---|---|
| atgacggccg acaacaacac cgaggccctg gacagcagca ccaccaagga cgtgatccag | 60 |
| aagggcatca gcgtggtggg cgacctgctg ggcgtggtgg gcttcccctt cggcggcgcc | 120 |
| ctggtgagct tctacaccaa cttcctgaac accatctggc ccagcgagga ccctggaag | 180 |
| gccttcatgg agcaggtgga ggccctgatg accagaagaa tcgccgacta cgccaagaac | 240 |
| aaggcactgg ccgagctaca gggcctccag aacaacgtgg aggactatgt gagcgccctg | 300 |
| agcagctggc agaagaaccc cgctgcaccg ttccgcaacc cccacagcca gggccgcatc | 360 |
| cgcgagctgt tcagccaggc cgagagccac ttccgcaaca gcatgccag cttcgccatc | 420 |
| agcggctacg aggtgctgtt cctgaccacc tacgcccagg ccgccaacac ccacctgttc | 480 |

```
ctgctgaagg acgcccaaat ctacggagag gagtggggct acgagaagga ggacatcgcc    540
gagttctaca agcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcgcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gccctggag   1260 aagggctaca gccaccagct gaactacgtg atgtgcttcc tgatgcaggg cagccgcggc   1320
accatccccg tgctgacctg gacccacaag agcgtcgact tcttcaacat gatcgacagc   1380
aagaagatca cccagctgcc cctggtgaag gcctacaagc tccagagcgg cgccagcgtg   1440
gtggcaggcc cccgcttcac cggcggcgac atcatccagt gcaccgagaa cggcagcgcc   1500
gccaccatct acgtgacccc cgacgtgagc tacagccaga agtaccgcgc ccgcatccgc   1560
tacgccagca ccaccaacct gcagttccac accagcatcg acggccgccc catcaaccag   1620
ggcaacttca gcgccaccat gagcagcggc agcaacctgc agagcggcag cttccgcacc   1680
gtgggcttca ccaccccctt caacttcagc aacggcagca gcgtgttcac cctgagcgcc   1740
cacgtgttca acagcggcaa cgaggtgtac atcgaccgca tcgagttcgt gcccgccgag   1800
gtgacctaa                                                            1809
```

<210> SEQ ID NO 151
<211> LENGTH: 602
<212> TYPE: PRT
<213> ORGANISM: Artificial Sequence
<220> FEATURE:
<223> OTHER INFORMATION: 8AFlongdm3 protein

<400> SEQUENCE: 151

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125
```

```
Ser His Phe Arg Asn Ser Met Pro Ser Phe Ala Ile Ser Gly Tyr Glu
        130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
    370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile Arg Tyr Ala Ser Thr Thr Asn Leu Gln
        515                 520                 525

Phe His Thr Ser Ile Asp Gly Arg Pro Ile Asn Gln Gly Asn Phe Ser
    530                 535                 540
```

```
Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr
            595                 600
```

<210> SEQ ID NO 152
<211> LENGTH: 1848
<212> TYPE: DNA
<213> ORGANISM: Artificial Sequence
<220> FEATURE:
<223> OTHER INFORMATION: cap8AFdm3 coding sequence

<400> SEQUENCE: 152

| | | | | |
|---|---|---|---|---|
| atgactagta | acggccgcca | gtgtgctggt | attcgccctt | atgacggccg | acaacaacac | 60 |
| cgaggcctgg | acagcagcac | caccaaggac | gtgatccaga | agggcatcag | cgtggtgggc | 120 |
| gacctgctgg | gcgtggtggg | cttcccttc | ggcggcgccc | tggtgagctt | ctacaccaac | 180 |
| ttcctgaaca | ccatctggcc | cagcgaggac | ccctggaagg | ccttcatgga | gcaggtggag | 240 |
| gccctgatgg | accagaagat | cgccgactac | gccaagaaca | aggcactggc | cgagctacag | 300 |
| ggcctccaga | caacgtggga | ggactatgtg | agcgccctga | gcagctggca | gaagaacccc | 360 |
| gctgcaccgt | tccgcaaccc | ccacagccag | ggccgcatcc | gcgagctgtt | cagccaggcc | 420 |
| gagagccact | tccgcaacag | catgcccagc | ttcgccatca | gcggctacga | ggtgctgttc | 480 |
| ctgaccacct | acgcccaggc | cgccaacacc | acctgttcc | tgctgaagga | cgcccaaatc | 540 |
| tacggagagg | agtggggcta | cgagaaggag | gacatcgccg | agttctacaa | cgccagctg | 600 |
| aagctgaccc | aggagtacac | cgaccactgc | gtgaagtggt | acaacgtggg | tctagacaag | 660 |
| ctccgcggca | gcagctacga | gagctggtg | aacttcaacc | gctaccgccg | cgagatgacc | 720 |
| ctgaccgtgc | tggacctgat | cgccctgttc | cccctgtacg | acgtgcgcct | gtaccccaag | 780 |
| gaggtgaaga | ccgagctgac | ccgcgacgtg | ctgaccgacc | ccatcgtggg | cgtgaacaac | 840 |
| ctgcgcggct | acggcaccac | cttcagcaac | atcgagaact | acatccgcaa | gccccacctg | 900 |
| ttcgactacc | tgcaccgcat | ccagttccac | acgcgtttcc | agcccggcta | ctacggcaac | 960 |
| gacagcttca | actactggag | cggcaactac | gtgagcaccc | gccccagcat | cggcagcaac | 1020 |
| gacatcatca | ccagccccctt | ctacggcaac | aagagcagcg | agcccgtgca | gaaccttgag | 1080 |
| ttcaacggcg | agaaggtgta | ccgcgccgtg | gctaacacca | acctggccgt | gtggccctct | 1140 |
| gcagtgtaca | gcggcgtgac | caaggtggag | ttcagccagt | acaacgacca | gaccgacgag | 1200 |
| gccagcaccc | agacctacga | cagcaagcgc | aacgtgggcg | ccgtgagctg | ggacagcatc | 1260 |
| gaccagctgc | cccccgagac | caccgacgag | cccctggaga | agggctacag | ccaccagctg | 1320 |
| aactacgtga | tgtgcttcct | gatgcagggc | agccgcggca | ccatccccgt | gctgacctgg | 1380 |
| acccacaaga | gcgtcgactt | caacaacatc | atccccagca | gccagatcac | ccagatcccc | 1440 |
| ctgaccaaga | gcaccaacct | gggcagcggc | accagcgtgg | tgaagggccc | cggcttcacc | 1500 |
| ggcggcgaca | tcctgcgccg | caccagcccc | ggccagatca | gcaccctgcg | cgtgaacatc | 1560 |
| accgccccc | tgagccagcg | ctaccgcgtc | cgcatccgct | acgccagcac | caccaacctg | 1620 |
| cagttccaca | ccagcatcga | cggccgcccc | atcaaccagg | gcaacttcag | cgccaccatg | 1680 |
| agcagcggca | gcaacctgca | gagcggcagc | ttccgcaccg | tgggcttcac | caccccccttc | 1740 | aacttcagca acggcagcag cgtgttcacc ctgagcgccc acgtgttcaa cagcggcaac    1800 gaggtgtaca tcgaccgcat cgagttcgtg cccgccgagg tgacctag    1848

<210> SEQ ID NO 153
<211> LENGTH: 615
<212> TYPE: PRT
<213> ORGANISM: Artificial Sequence
<220> FEATURE:
<223> OTHER INFORMATION: cap8AFdm3 protein

<400> SEQUENCE: 153

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser

|  |  |  | 340 |  |  |  | 345 |  |  |  | 350 |
|---|---|---|---|---|---|---|---|---|---|---|---|

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
            405                 410                 415

Trp Asp Ser Ile Asp Gln Leu Pro Pro Glu Thr Thr Asp Glu Pro Leu
            420                 425                 430

Glu Lys Gly Tyr Ser His Gln Leu Asn Tyr Val Met Cys Phe Leu Met
        435                 440                 445

Gln Gly Ser Arg Gly Thr Ile Pro Val Leu Thr Trp Thr His Lys Ser
        450                 455                 460

Val Asp Phe Asn Asn Ile Ile Pro Ser Ser Gln Ile Thr Gln Ile Pro
465                 470                 475                 480

Leu Thr Lys Ser Thr Asn Leu Gly Ser Gly Thr Ser Val Val Lys Gly
            485                 490                 495

Pro Gly Phe Thr Gly Gly Asp Ile Leu Arg Arg Thr Ser Pro Gly Gln
        500                 505                 510

Ile Ser Thr Leu Arg Val Asn Ile Thr Ala Pro Leu Ser Gln Arg Tyr
        515                 520                 525

Arg Val Arg Ile Arg Tyr Ala Ser Thr Thr Asn Leu Gln Phe His Thr
    530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
            565                 570                 575

Thr Thr Pro Phe Asn Phe Ser Asn Gly Ser Ser Val Phe Thr Leu Ser
        580                 585                 590

Ala His Val Phe Asn Ser Gly Asn Glu Val Tyr Ile Asp Arg Ile Glu
        595                 600                 605

Phe Val Pro Ala Glu Val Thr
        610                 615

<210> SEQ ID NO 154
<211> LENGTH: 1923
<212> TYPE: DNA
<213> ORGANISM: Artificial Sequence
<220> FEATURE:
<223> OTHER INFORMATION: 8AFdm3 T coding sequence

<400> SEQUENCE: 154
atgacggccg acaacaacac cgaggccctg acagcagca ccaccaagga cgtgatccag      60
aagggcatca gcgtggtggg cgacctgctg ggcgtggtgg gcttcccctt cggcggcgcc     120
ctggtgagct tctacaccaa cttcctgaac accatctggc ccagcgagga ccctggaag     180 gccttcatgg agcaggtgga ggccctgatg accagaaga tcgccgacta cgccaagaac      240
aaggcactgg ccgagctaca gggcctccag aacaacgtgg aggactatgt gagcgccctg     300
agcagctggc agaagaaccc cgctgcaccg ttccgcaacc cccacagcca gggccgcatc     360
cgcgagctgt tcagccaggc cgagagccac ttccgcaaca gcatgcccag cttcgccatc     420
agcggctacg aggtgctgtt cctgaccacc tacgcccagg ccgccaacac ccacctgttc     480

```
ctgctgaagg acgcccaaat ctacggagag gagtggggct acgagaagga ggacatcgcc    540
gagttctaca agcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca agccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcgcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcaacaacat catccccagc   1380
agccagatca cccagatccc cctgaccaag agcaccaacc tgggcagcgg caccagcgtg   1440
gtgaagggcc ccggcttcac cggcggcgac atcctgcgcc gcaccagccc cggccagatc   1500
agcaccctgc gcgtgaacat caccgccccc ctgagccagc gctaccgcgt ccgcatccgc   1560
tacgccagca ccaccaacct gcagttccac accagcatcg acggccgccc catcaaccag   1620
ggcaacttca gcgccaccat gagcagcggc agcaacctgc agagcggcag cttccgcacc   1680
gtgggcttca ccacccccgtt caacttcagc aacggcagca gcgtgttcac cctgagcgcc   1740
cacgtgttca acagcggcaa cgaggtgtac atcgaccgca tcgagttcgt gcccgccgag   1800
gtgaccttcg aggccgagta cgacctggag agggctcaga aggccgtgaa cgagctgttc   1860
accagcagca accagatcgg cctgaagacc gacgtgaccg actaccacat cgatcaggtg   1920
tag                                                                 1923
```

<210> SEQ ID NO 155
<211> LENGTH: 640
<212> TYPE: PRT
<213> ORGANISM: Artificial Sequence
<220> FEATURE:
<223> OTHER INFORMATION: 8AFdm3 T protein

<400> SEQUENCE: 155

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
            20                  25                  30

Val Gly Phe Pro Phe Gly Gly Ala Leu Val Ser Phe Tyr Thr Asn Phe
        35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
```

-continued

```
                100                 105                 110
Asn Pro His Ser Gln Gly Arg Ile Arg Glu Leu Phe Ser Gln Ala Glu
            115                 120                 125

Ser His Phe Arg Asn Ser Met Pro Ser Phe Ala Ile Ser Gly Tyr Glu
        130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
        210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
        290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
            340                 345                 350

Val Tyr Arg Ala Val Ala Asn Thr Asn Leu Ala Val Trp Pro Ser Ala
        355                 360                 365

Val Tyr Ser Gly Val Thr Lys Val Glu Phe Ser Gln Tyr Asn Asp Gln
        370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Asn Asn Ile Ile Pro Ser Ser Gln Ile Thr
        450                 455                 460

Gln Ile Pro Leu Thr Lys Ser Thr Asn Leu Gly Ser Gly Thr Ser Val
465                 470                 475                 480

Val Lys Gly Pro Gly Phe Thr Gly Gly Asp Ile Leu Arg Arg Thr Ser
                485                 490                 495

Pro Gly Gln Ile Ser Thr Leu Arg Val Asn Ile Thr Ala Pro Leu Ser
            500                 505                 510

Gln Arg Tyr Arg Val Arg Ile Arg Tyr Ala Ser Thr Thr Asn Leu Gln
        515                 520                 525
```

Phe His Thr Ser Ile Asp Gly Arg Pro Ile Asn Gln Gly Asn Phe Ser
    530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
            580                 585                 590

Arg Ile Glu Phe Val Pro Ala Glu Val Thr Phe Glu Ala Glu Tyr Asp
        595                 600                 605

Leu Glu Arg Ala Gln Lys Ala Val Asn Glu Leu Phe Thr Ser Ser Asn
    610                 615                 620

Gln Ile Gly Leu Lys Thr Asp Val Thr Asp Tyr His Ile Asp Gln Val
625                 630                 635                 640

<210> SEQ ID NO 156
<211> LENGTH: 1923
<212> TYPE: DNA
<213> ORGANISM: Artificial Sequence
<220> FEATURE:
<223> OTHER INFORMATION: 8AFlongdm3T coding sequence

<400> SEQUENCE: 156
atgacggccg acaacaacac cgaggccctg acagcagca ccaccaagga cgtgatccag      60
aagggcatca gcgtggtggg cgacctgctg ggcgtggtgg gcttcccctt cggcggcgcc    120
ctggtgagct tctacaccaa cttcctgaac accatctggc cagcgagga ccctggaag     180 gccttcatgg agcaggtgga ggccctgatg accagaaga tcgccgacta cgccaagaac    240
aaggcactgg ccgagctaca gggcctccag aacaacgtgg aggactatgt gagcgccctg    300
agcagctggc agaagaaccc cgctgcaccg ttccgcaacc cccacagcca gggccgcatc    360
cgcgagctgt tcagccaggc cgagagccac ttccgcaaca gcatgcccag cttcgccatc    420
agcggctacg aggtgctgtt cctgaccacc tacgcccagg ccgccaacac ccacctgttc    480
ctgctgaagg acgcccaaat ctacggagag gagtggggct acgagaagga ggacatcgcc    540
gagttctaca gcgccagct gaagctgacc caggagtaca ccgaccactg cgtgaagtgg    600
tacaacgtgg gtctagacaa gctccgcggc agcagctacg agagctgggt gaacttcaac    660
cgctaccgcc gcgagatgac cctgaccgtg ctggacctga tcgccctgtt ccccctgtac    720
gacgtgcgcc tgtaccccaa ggaggtgaag accgagctga cccgcgacgt gctgaccgac    780
cccatcgtgg gcgtgaacaa cctgcgcggc tacggcacca ccttcagcaa catcgagaac    840
tacatccgca gccccacct gttcgactac ctgcaccgca tccagttcca cacgcgtttc    900
cagcccggct actacggcaa cgacagcttc aactactgga gcggcaacta cgtgagcacc    960
cgccccagca tcggcagcaa cgacatcatc accagcccct tctacggcaa caagagcagc   1020
gagcccgtgc agaaccttga gttcaacggc gagaaggtgt accgcgccgt ggctaacacc   1080
aacctggccg tgtggccctc tgcagtgtac agcggcgtga ccaaggtgga gttcagccag   1140
tacaacgacc agaccgacga ggccagcacc cagacctacg acagcaagcg caacgtgggc   1200
gccgtgagct gggacagcat cgaccagctg ccccccgaga ccaccgacga gcccctggag   1260
aagggctaca gccaccagct gaactacgtg atgtgcttcc tgatgcaggg cagccgcggc   1320
accatccccg tgctgacctg gacccacaag agcgtcgact tcttcaacat gatcgacagc   1380
aagaagatca cccagctgcc cctggtgaag gcctacaagc tccagagcgg cgccagcgtg   1440

```
gtggcaggcc cccgcttcac cggcggcgac atcatccagt gcaccgagaa cggcagcgcc   1500
gccaccatct acgtgacccc cgacgtgagc tacagcgcgc ccgcatccgc             1560
tacgccagca ccaccaacct gcagttccac accagcatcg acggccgccc catcaaccag  1620
ggcaacttca gcgccaccat gagcagcggc agcaacctgc agagcggcag cttccgcacc  1680
gtgggcttca ccaccccctt caacttcagc aacggcagca gcgtgttcac cctgagcgcc  1740
cacgtgttca cagcggcaa cgaggtgtac atcgaccgca tcgagttcgt gcccgccgag  1800
gtgaccttcg aggccgagta cgacctggag agggctcaga aggccgtgaa cgagctgttc  1860
accagcagca accagatcgg cctgaagacc gacgtgaccg actaccacat cgatcaggtg  1920
tag                                                                1923
```

<210> SEQ ID NO 157
<211> LENGTH: 640
<212> TYPE: PRT
<213> ORGANISM: Artificial Sequence
<220> FEATURE:
<223> OTHER INFORMATION: 8AFlongdm3T protein

<400> SEQUENCE: 157

```
Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
    50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270
```

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
290                 295                 300

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
                325                 330                 335

Asn Lys Ser Ser Glu Pro Val Gln Asn Leu Glu Phe Asn Gly Glu Lys
                340                 345                 350

Val Tyr Arg Ala Val Ala Asn Thr Asn Leu Ala Val Trp Pro Ser Ala
                355                 360                 365

Val Tyr Ser Gly Val Thr Lys Val Glu Phe Ser Gln Tyr Asn Asp Gln
                370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
                420                 425                 430

Phe Leu Met Gln Gly Ser Arg Gly Thr Ile Pro Val Leu Thr Trp Thr
                435                 440                 445

His Lys Ser Val Asp Phe Phe Asn Met Ile Asp Ser Lys Lys Ile Thr
                450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
                500                 505                 510

Gln Lys Tyr Arg Ala Arg Ile Arg Tyr Ala Ser Thr Thr Asn Leu Gln
                515                 520                 525

Phe His Thr Ser Ile Asp Gly Arg Pro Ile Asn Gln Gly Asn Phe Ser
                530                 535                 540

Ala Thr Met Ser Ser Gly Ser Asn Leu Gln Ser Gly Ser Phe Arg Thr
545                 550                 555                 560

Val Gly Phe Thr Thr Pro Phe Asn Phe Ser Asn Gly Ser Ser Val Phe
                565                 570                 575

Thr Leu Ser Ala His Val Phe Asn Ser Gly Asn Glu Val Tyr Ile Asp
                580                 585                 590

Arg Ile Glu Phe Val Pro Ala Glu Val Thr Phe Glu Ala Glu Tyr Asp
                595                 600                 605

Leu Glu Arg Ala Gln Lys Ala Val Asn Glu Leu Phe Thr Ser Ser Asn
610                 615                 620

Gln Ile Gly Leu Lys Thr Asp Val Thr Asp Tyr His Ile Asp Gln Val
625                 630                 635                 640

<210> SEQ ID NO 158
<211> LENGTH: 1962
<212> TYPE: DNA
<213> ORGANISM: Artificial Sequence
<220> FEATURE:
<223> OTHER INFORMATION: cap8AFdm3T coding serquence

<400> SEQUENCE: 158

```
atgactagta acggccgcca gtgtgctggt attcgcccctt atgacggccg acaacaacac       60
cgaggcctgg acagcagcac caccaaggac gtgatccaga agggcatcag cgtggtgggc      120
gacctgctgg gcgtggtggg cttcccttc ggcggcgccc tggtgagctt ctacaccaac      180
ttcctgaaca ccatctggcc cagcgaggac ccctggaagg ccttcatgga gcaggtggag      240
gccctgatgg accagaagat cgccgactac gccaagaaca aggcactggc cgagctacag      300
ggcctccaga caacgtggag ggactatgtg agcgccctga gcagctggca gaagaacccc      360
gctgcaccgt tccgcaaccc ccacagccag ggccgcatcc gcgagctgtt cagccaggcc      420
gagagccact tccgcaacag catgcccagc ttcgccatca gcggctacga ggtgctgttc      480
ctgaccacct acgcccaggc cgccaacacc cacctgttcc tgctgaagga cgcccaaatc      540
tacggagagg agtggggcta cgagaaggag gacatcgccg agttctacaa cgccagctg      600 aagctgaccc aggagtacac cgaccactgc gtgaagtggt acaacgtggg tctagacaag      660
ctccgcggca gcagctacga gagctgggtg aacttcaacc gctaccgccg cgagatgacc      720
ctgaccgtgc tggacctgat cgccctgttc cccctgtacg acgtgcgcct gtaccccaag      780
gaggtgaaga ccgagctgac ccgcgacgtg ctgaccgacc ccatcgtggg cgtgaacaac      840
ctgcgcggct acggcaccac cttcagcaac atcgagaact acatccgcaa gccccacctg      900
ttcgactacc tgcaccgcat ccagttccac acgcgtttcc agcccggcta ctacggcaac      960
gacagcttca actactggag cggcaactac gtgagcaccc gccccagcat cggcagcaac     1020
gacatcatca ccagcccctt ctacggcaac aagagcagcg agcccgtgca gaaccttgag     1080
ttcaacggcg agaaggtgta ccgcgccgtg gctaacacca acctggccgt gtgggccctct    1140 gcagtgtaca gcggcgtgac caaggtggag ttcagccagt acaacgacca gaccgacgag     1200
gccagcaccc agacctacga cagcaagcgc aacgtgggcg ccgtgagctg ggacagcatc     1260
gaccagctgc cccccgagac caccgacgag cccctggaga agggctacag ccaccagctg     1320
aactacgtga tgtgcttcct gatgcagggc agccgcggca ccatccccgt gctgacctgg     1380
acccacaaga gcgtcgactt caacaacatc atccccagca gccagatcac ccagatcccc     1440
ctgaccaaga gcaccaacct gggcagcggc accagcgtgg tgaagggccc cggcttcacc     1500
ggcggcgaca tcctgcgccg caccagcccc ggccagatca gcaccctgcg cgtgaacatc     1560 accgccccc tgagccagcg ctaccgcgtc cgcatccgct acgccagcac caccaacctg     1620
cagttccaca ccagcatcga cggccgcccc atcaaccagg gcaacttcag cgccaccatg     1680
agcagcggca gcaacctgca gagcggcagc ttccgcaccg tgggcttcac caccccttc     1740 aacttcagca acggcagcag cgtgttcacc ctgagcgccc acgtgttcaa cagcggcaac     1800
gaggtgtaca tcgaccgcat cgagttcgtg cccgccgagg tgaccttcga ggccgagtac     1860
gacctggaga gggctcagaa ggccgtgaac gagctgttca ccagcagcaa ccagatcggc     1920
ctgaagaccg acgtgaccga ctaccacatc gatcaggtgt ag                        1962
```

<210> SEQ ID NO 159
<211> LENGTH: 653
<212> TYPE: PRT
<213> ORGANISM: Artificial Sequence
<220> FEATURE:
<223> OTHER INFORMATION: cap8AFdm3T protein

<400> SEQUENCE: 159

Met Thr Ser Asn Gly Arg Gln Cys Ala Gly Ile Arg Pro Tyr Asp Gly
1               5                   10                  15

```
Arg Gln Gln His Arg Gly Leu Asp Ser Ser Thr Thr Lys Asp Val Ile
             20                  25                  30

Gln Lys Gly Ile Ser Val Val Gly Asp Leu Leu Gly Val Val Gly Phe
         35                  40                  45

Pro Phe Gly Gly Ala Leu Val Ser Phe Tyr Thr Asn Phe Leu Asn Thr
 50                  55                  60

Ile Trp Pro Ser Glu Asp Pro Trp Lys Ala Phe Met Glu Gln Val Glu
 65                  70                  75                  80

Ala Leu Met Asp Gln Lys Ile Ala Asp Tyr Ala Lys Asn Lys Ala Leu
                 85                  90                  95

Ala Glu Leu Gln Gly Leu Gln Asn Asn Val Asp Tyr Val Ser Ala
            100                 105                 110

Leu Ser Ser Trp Gln Lys Asn Pro Ala Ala Pro Phe Arg Asn Pro His
            115                 120                 125

Ser Gln Gly Arg Ile Arg Glu Leu Phe Ser Gln Ala Glu Ser His Phe
130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
        195                 200                 205

His Cys Val Lys Trp Tyr Asn Val Gly Leu Asp Lys Leu Arg Gly Ser
    210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
            260                 265                 270

Asp Pro Ile Val Gly Val Asn Asn Leu Arg Gly Tyr Gly Thr Thr Phe
        275                 280                 285

Ser Asn Ile Glu Asn Tyr Ile Arg Lys Pro His Leu Phe Asp Tyr Leu
    290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
            340                 345                 350

Ser Glu Pro Val Gln Asn Leu Glu Phe Asn Gly Glu Lys Val Tyr Arg
        355                 360                 365

Ala Val Ala Asn Thr Asn Leu Ala Val Trp Pro Ser Ala Val Tyr Ser
    370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
            420                 425                 430
```

```
Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
        450                 455                 460

Val Asp Phe Asn Asn Ile Ile Pro Ser Ser Gln Ile Thr Gln Ile Pro
465                 470                 475                 480

Leu Thr Lys Ser Thr Asn Leu Gly Ser Gly Thr Ser Val Val Lys Gly
            485                 490                 495

Pro Gly Phe Thr Gly Gly Asp Ile Leu Arg Arg Thr Ser Pro Gly Gln
            500                 505                 510

Ile Ser Thr Leu Arg Val Asn Ile Thr Ala Pro Leu Ser Gln Arg Tyr
        515                 520                 525

Arg Val Arg Ile Arg Tyr Ala Ser Thr Thr Asn Leu Gln Phe His Thr
    530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
            565                 570                 575

Thr Thr Pro Phe Asn Phe Ser Asn Gly Ser Ser Val Phe Thr Leu Ser
            580                 585                 590

Ala His Val Phe Asn Ser Gly Asn Glu Val Tyr Ile Asp Arg Ile Glu
        595                 600                 605

Phe Val Pro Ala Glu Val Thr Phe Glu Ala Glu Tyr Asp Leu Glu Arg
    610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
            645                 650

<210> SEQ ID NO 160
<211> LENGTH: 687
<212> TYPE: PRT
<213> ORGANISM: Artificial Sequence
<220> FEATURE:
<223> OTHER INFORMATION: FR8a+34 protein

<400> SEQUENCE: 160

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Asp Ile Gly
            20                  25                  30

Ser Thr Met Thr Ser Asn Gly Arg Gln Cys Ala Gly Ile Arg Pro Tyr
        35                  40                  45

Asp Gly Arg Gln Gln His Arg Gly Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
            85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140
```

```
Ser Ala Leu Ser Ser Trp Gln Lys Asn Pro Ala Ala Pro Phe Arg Asn
145                 150                 155                 160

Pro His Ser Gln Gly Arg Ile Arg Glu Leu Phe Ser Gln Ala Glu Ser
                165                 170                 175

His Phe Arg Asn Ser Met Pro Ser Phe Ala Ile Ser Gly Tyr Glu Val
            180                 185                 190

Leu Phe Leu Thr Thr Tyr Ala Gln Ala Asn Thr His Leu Phe Leu
        195                 200                 205

Leu Lys Asp Ala Gln Ile Tyr Gly Glu Glu Trp Gly Tyr Glu Lys Glu
    210                 215                 220

Asp Ile Ala Glu Phe Tyr Lys Arg Gln Leu Lys Leu Thr Gln Glu Tyr
225                 230                 235                 240

Thr Asp His Cys Val Lys Trp Tyr Asn Val Gly Leu Asp Lys Leu Arg
                245                 250                 255

Gly Ser Ser Tyr Glu Ser Trp Val Asn Phe Asn Arg Tyr Arg Arg Glu
            260                 265                 270

Met Thr Leu Thr Val Leu Asp Leu Ile Ala Leu Phe Pro Leu Tyr Asp
        275                 280                 285

Val Arg Leu Tyr Pro Lys Glu Val Lys Thr Glu Leu Thr Arg Asp Val
    290                 295                 300

Leu Thr Asp Pro Ile Val Gly Val Asn Asn Leu Arg Gly Tyr Gly Thr
305                 310                 315                 320

Thr Phe Ser Asn Ile Glu Asn Tyr Ile Arg Lys Pro His Leu Phe Asp
                325                 330                 335

Tyr Leu His Arg Ile Gln Phe His Thr Arg Phe Gln Pro Gly Tyr Tyr
            340                 345                 350

Gly Asn Asp Ser Phe Asn Tyr Trp Ser Gly Asn Tyr Val Ser Thr Arg
        355                 360                 365

Pro Ser Ile Gly Ser Asn Asp Ile Ile Thr Ser Pro Phe Tyr Gly Asn
370                 375                 380

Lys Ser Ser Glu Pro Val Gln Asn Leu Glu Phe Asn Gly Glu Lys Val
385                 390                 395                 400

Tyr Arg Ala Val Ala Asn Thr Asn Leu Ala Val Trp Pro Ser Ala Val
                405                 410                 415

Tyr Ser Gly Val Thr Lys Val Glu Phe Ser Gln Tyr Asn Asp Gln Thr
            420                 425                 430

Asp Glu Ala Ser Thr Gln Thr Tyr Asp Ser Lys Arg Asn Val Gly Ala
        435                 440                 445

Val Ser Trp Asp Ser Ile Asp Gln Leu Pro Pro Glu Thr Thr Asp Glu
450                 455                 460

Pro Leu Glu Lys Gly Tyr Ser His Gln Leu Asn Tyr Val Met Cys Phe
465                 470                 475                 480

Leu Met Gln Gly Ser Arg Gly Thr Ile Pro Val Leu Thr Trp Thr His
                485                 490                 495

Lys Ser Val Asp Phe Phe Asn Met Ile Asp Ser Lys Lys Ile Thr Gln
            500                 505                 510

Leu Pro Leu Thr Lys Ser Thr Asn Leu Gly Ser Gly Thr Ser Val Val
        515                 520                 525

Lys Gly Pro Gly Phe Thr Gly Gly Asp Ile Leu Arg Arg Thr Ser Pro
530                 535                 540

Gly Gln Ile Ser Thr Leu Arg Val Asn Ile Thr Ala Pro Leu Ser Gln
545                 550                 555                 560

Arg Tyr Arg Val Arg Ile Arg Tyr Ala Ser Thr Thr Asn Leu Gln Phe
```

```
                    565                 570                 575
His Thr Ser Ile Asp Gly Arg Pro Ile Asn Gln Gly Asn Phe Ser Ala
            580                 585                 590

Thr Met Ser Ser Gly Ser Asn Leu Gln Ser Gly Ser Phe Arg Thr Val
        595                 600                 605

Gly Phe Thr Thr Pro Phe Asn Phe Ser Asn Gly Ser Ser Val Phe Thr
    610                 615                 620

Leu Ser Ala His Val Phe Asn Ser Gly Asn Glu Val Tyr Ile Asp Arg
625                 630                 635                 640

Ile Glu Phe Val Pro Ala Glu Val Thr Phe Glu Ala Glu Tyr Asp Leu
                645                 650                 655

Glu Arg Ala Gln Lys Ala Val Asn Glu Leu Phe Thr Ser Ser Asn Gln
                660                 665                 670

Ile Gly Leu Lys Thr Asp Val Thr Asp Tyr His Ile Asp Gln Val
            675                 680                 685
```

What is claimed is:

1. An engineered hybrid insecticidal protein comprising the amino acid sequence of SEQ ID NO:4.

2. A nucleic acid comprising a coding sequence that encodes the engineered hybrid insecticidal protein of claim 1.

3. The nucleic acid of claim 2, wherein the coding sequence comprises SEQ ID NO:3.

4. An expression cassette comprising a heterologous promoter sequence operably linked to the nucleic acid molecule of claim 2.

5. A vector comprising the expression cassette of claim 4.

6. A transgenic host cell comprising the engineered hybrid insecticidal protein of claim 1.

7. A transgenic host cell comprising the expression cassette of claim 4.

8. The transgenic host cell of claim 7, wherein the transgenic host cell is a plant cell.

9. The transgenic host cell of claim 8, wherein the plant cell is a monocot cell.

10. The transgenic host cell of claim 9, wherein the plant cell is a maize cell.

11. A transgenic plant comprising the engineered hybrid insecticidal protein of claim 1.

12. The transgenic plant of claim 11, wherein the plant is a monocot.

13. The transgenic plant of claim 12, wherein the plant is a maize plant.

14. A seed of the transgenic plant of claim 11, wherein the seed comprises the engineered hybrid insecticidal protein.

15. A seed of the transgenic plant of claim 12, wherein the seed comprises the engineered hybrid insecticidal protein.

16. A seed of the transgenic plant of claim 13, wherein the seed comprises the engineered hybrid insecticidal protein.

17. An insecticidal composition comprising the engineered hybrid insecticidal protein of claim 1.

18. A method of producing an insect-resistant transgenic plant, comprising:
    (a) introducing the expression cassette according to claim 4 into a plant genome thus producing a transgenic plant; and
    (b) expressing the engineered hybrid insecticidal protein in an effective amount to control insects.

19. A method of controlling a coleopteran pest comprising delivering to the pest the engineered hybrid insecticidal protein of claim 1.

20. The method of claim 19, wherein the engineered hybrid insecticidal protein is delivered by feeding.

* * * * *